US011692014B2

(12) United States Patent
Anantha et al.

(10) Patent No.: US 11,692,014 B2
(45) Date of Patent: Jul. 4, 2023

(54) TUBERCULOSIS COMPOSITIONS AND METHODS OF TREATING OR PREVENTING TUBERCULOSIS

(71) Applicant: International AIDS Vaccine Initiative, Inc., New York, NY (US)

(72) Inventors: Ravi P. Anantha, Rockville, MD (US); Thomas G. Evans, Rockville, MD (US); Aurelio M. Bonavia, Rockville, MD (US)

(73) Assignee: International AIDS Vaccine Initiative, Inc., New York, NY (US)

( * ) Notice: Subject to any disclaimer, the term of this patent is extended or adjusted under 35 U.S.C. 154(b) by 0 days.

(21) Appl. No.: 16/541,518

(22) Filed: Aug. 15, 2019

(65) Prior Publication Data

US 2020/0181209 A1 Jun. 11, 2020

Related U.S. Application Data

(63) Continuation of application No. 15/624,853, filed on Jun. 16, 2017, now Pat. No. 10,428,122.

(60) Provisional application No. 62/350,837, filed on Jun. 16, 2016.

(51) Int. Cl.

| | |
|---|---|
| ***C07K 14/35*** | (2006.01) |
| ***A61P 31/06*** | (2006.01) |
| ***A61K 39/04*** | (2006.01) |
| ***A61K 39/00*** | (2006.01) |

(52) U.S. Cl.

CPC .............. *C07K 14/35* (2013.01); *A61K 39/04* (2013.01); *A61P 31/06* (2018.01); *A61K 2039/53* (2013.01); *A61K 2039/55561* (2013.01); *C07K 2319/00* (2013.01)

(58) Field of Classification Search

CPC ..... A61K 39/04; C07K 2319/00; C07K 14/35

See application file for complete search history.

(56) References Cited

U.S. PATENT DOCUMENTS

| | | | | |
|---|---|---|---|---|
| 5,593,972 | A | 1/1997 | Weiner et al. | |
| 5,962,428 | A | 10/1999 | Carrano | |
| 7,670,609 | B2 | 3/2010 | Shafferman | |
| 8,703,151 | B2 * | 4/2014 | Aagaard ................ | C07K 14/35 424/248.1 |
| 2009/0136534 | A1 | 5/2009 | Shafferman et al. | |
| 2009/0304750 | A1 | 12/2009 | Hone et al. | |
| 2011/0117133 | A1 | 5/2011 | Shafferman et al. | |

(Continued)

FOREIGN PATENT DOCUMENTS

| | | |
|---|---|---|
| CN | 101289496 | 10/2008 |
| CN | 104474538 | 4/2015 |

(Continued)

OTHER PUBLICATIONS

Commandeur et al., (Vaccine. vol. 32, Issue 29, Jun. 17, 2014, pp. 3580-3588) (Year: 2014).*

(Continued)

*Primary Examiner* — Jana A Hines

(74) *Attorney, Agent, or Firm* — Armstrong Teasdale LLP

(57) ABSTRACT

The present disclosure provides fusion proteins comprising *Mycobacterium tuberculosis* (Mtb) antigens, nucleic acid molecules encoding the same, vectors comprising nucleic acid molecules, compositions comprising the same, and methods of eliciting an immune response against tuberculosis.

13 Claims, 4 Drawing Sheets

Specification includes a Sequence Listing.

(56) References Cited

U.S. PATENT DOCUMENTS

| | | | | |
|---|---|---|---|---|
| 2012/0003256 | A1 | 1/2012 | Han et al. | |
| 2012/0219582 | A1 | 8/2012 | Yasutomi et al. | |
| 2012/0244173 | A1 | 9/2012 | Wu et al. | |
| 2012/0294882 | A1 | 11/2012 | Blais et al. | |
| 2013/0142800 | A1 | 6/2013 | Carroll et al. | |
| 2014/0377300 | A1* | 12/2014 | Anantha | A61P 37/04<br>424/190.1 |

FOREIGN PATENT DOCUMENTS

| | | |
|---|---|---|
| JP | 2013517783 | 5/2013 |
| NO | 2014210018 | 12/2014 |
| WO | 94016737 | 8/1994 |
| WO | 2007058663 | 5/2007 |
| WO | 2008124647 | 10/2008 |
| WO | 2009070700 | 6/2009 |
| WO | 2011045612 | 4/2011 |
| WO | 2014009438 | 1/2014 |

OTHER PUBLICATIONS

Millington et al., (Proc Natl Acad Sci U S A. Apr. 5, 2011;108(14):5730-5). (Year: 2011).*

Shein et al., Cell & Mol. Immuno. vol. 4, No. 2. Apr. 2007: pp. 113-120 (Year: 2007).*

Ma et al., "*Mycobacterium tuberculosis* multistage antigens confer comprehensive protection against pre- and post-exposure infections by driving Th1 type T cell immunity", Oncotarget, 2016, 7(39), pp. 63804-63815.

Mir et al., "A Multicistronic DNA Vaccine Induces Significant Protection against Tuberculosis in Mice and Offers Flexibility in the Expressed Antigen Repertoire", Clin Vaccine Immunol, 2009, 16(10), p. 1467-1475.

Reece et al., "Improved long-term protection against *Mycobacterium tuberculosis* Beijing/W in mice after intra-dermal inoculation of recombinant BCG expressing latency associated antigens", Vaccine, 2011, 29(47), pp. 8740-8744.

Geluk et al., "A multistage-polyepitope vaccine protects against *Mycobacterium tuberculosis* infection in HLA-DR3 transgenic mice", Vaccine, 2012, 30(52), pp. 7513-7521.

De Sousa et al., "Immunogenicity of a Fusion Protein Containing Immunodominant Epitopes of Ag85C, MPT51, and HspX from *Mycobacterium tuberculosis* in Mice and Active TB Infection", Plos ONE, 2012, 7(10), e47781.

Luo et al., "Fusion Protein Ag85B-MPT64(190-198)-Mtb8.4 Has Higher Immunogenicity Than Ag85B With Capacity to Boost BCG-primed Immunity Against *Mycobacterium tuberculosis* in Mice", Vaccine, 2009, 27, pp. 6179-6185.

Office Action dated Mar. 31, 2020 in related U.S. Appl. No. 16/289,919.

Notice of Allowance dated Jan. 22, 2021 in related U.S. Appl. No. 16/289,919.

Kaufmann, S. et al., "Tuberculosis Vaccines: Time to think about the next generation", 2013, Seminars in Immunology, 25(2), pp. 172-181.

Cruse et al., Illustrated Dict of Immunology, 2003, 2nd ed, CRC Press, p. 46.

McGuinness et al., "Class 1 outer membrane protein of Neisseria meningitidis: epitope analysis of the antigenic diversity between strains, implications for subtype definitions and molecular epidemiology", 1993, Mol Microbiol, 7, pp. 505-514.

Moudallal et al., "Monoclonal antibodies as probes of the antigenic structure of tobacco mosaic virus", 1982, EMBO Journal, 1, pp. 1005-1010.

Abaza et al., "Effects of amino acid substitutions outside an antigenic site on protein binding to monoclonal antibodies of predetermined specificity obtained by peptide immunization: Demonstration with region 94-100 (antigenic site 3) of myoglobin", 1992, J Prot Chem, 11, pp. 433-444.

Notice of Allowance dated Dec. 4, 2018 in related U.S. Appl. No. 14/313,694.

Commandeur et al., "The in vivo expressed *Mycobacterium tuberculosis* (IVE-TB) antigen Rv2034 induces CD4+ T-cells that protect against pulmonary infection in HLA-DR transgenic mice and guinea pigs", Vaccine, 2014, 32(29), pp. 3580-3588.

Millington et al., "Rv3615c is highly immunodominant RD1 (Region of Difference 1)-dependent secreted antigen specific for *Mycobacterium tuberculosis* infection", PNAS, 2011, 108(14), pp. 5730-5735.

Non-Final Office Action dated Aug. 31, 2022 in related U.S. Appl. No. 17/236,409.

Final Office Action dated Dec. 14, 2020 in related U.S. Appl. No. 16/289,919.

* cited by examiner

SEQUENCE LISTING

<160> NUMBER OF SEQ ID NOS: 75

<210> SEQ ID NO 1
<211> LENGTH: 1089
<212> TYPE: DNA
<213> ORGANISM: Mycobacterium tuberculosis
<220> FEATURE:
<223> OTHER INFORMATION: Rv1009

<400> SEQUENCE: 1
atgttgcgcc tggtagtcgg tgcgctgctg ctggtgttgg cgttcgccgg tggctatgcg 60
gtcgccgcat gcaaaacggt gacgttgacc gtcgacggaa ccgcgatgcg ggtgaccacg 120
atgaaatcgc gggtgatcga catcgtcgaa gagaacgggt tctcagtcga cgaccgcgac 180
gacctgtatc ccgcggccgg cgtgcaggtc catgacgccg acaccatcgt gctgcggcgt 240
agccgtccgc tgcagatctc gctggatggt cacgacgcta agcaggtgtg gacgaccgcg 300
tcgacggtgg acgaggcgct ggcccaactc gcgatgaccg acacggcgcc ggccgcggct 360
tctcgcgcca gccgcgtccc gctgtccggg atggcgctac cggtcgtcag cgccaagacg 420
gtgcagctca acgacggcgg gttggtgcgc acggtgcact tgccggcccc caatgtcgcg 480
gggctgctga gtgcggccgg cgtgccgctg ttgcaaagcg accacgtggt gcccgccgcg 540
acggccccga tcgtcgaagg catgcagatc caggtgaccc gcaatcggat caagaaggtc 600
accgagcggc tgccgctgcc gccgaacgcg cgtcgtgtcg aggacccgga gatgaacatg 660
agccgggagg tcgtcgaaga cccgggggtt ccggggaccc aggatgtgac gttcgcggta 720
gctgaggtca acggcgtcga gaccggccgt ttgcccgtcg ccaacgtcgt ggtgaccccg 780
gcccacgaag ccgtggtgcg ggtgggcacc aagcccggta ccgaggtgcc cccggtgatc 840
gacggaagca tctgggacgc gatcgccggc tgtgaggccg gtggcaactg ggcgatcaac 900
accggcaacg ggtattacgg tggtgtgcag tttgaccagg gcacctggga ggccaacggc 960
gggctgcggt atgcaccccg cgctgacctc gccacccgcg aagagcagat cgccgttgcc 1020
gaggtgaccc gactgcgtca aggttggggc gcctggccgg tatgtgctgc acgagcgggt 1080
gcgcgctga 1089

<210> SEQ ID NO 2
<211> LENGTH: 362
<212> TYPE: PRT
<213> ORGANISM: Mycobacterium tuberculosis
<220> FEATURE:
<223> OTHER INFORMATION: Rv1009

<400> SEQUENCE: 2

Met Leu Arg Leu Val Val Gly Ala Leu Leu Leu Val Leu Ala Phe Ala
1 5 10 15

Gly Gly Tyr Ala Val Ala Ala Cys Lys Thr Val Thr Leu Thr Val Asp
20 25 30

Gly Thr Ala Met Arg Val Thr Thr Met Lys Ser Arg Val Ile Asp Ile
35 40 45

Val Glu Glu Asn Gly Phe Ser Val Asp Asp Arg Asp Asp Leu Tyr Pro
50 55 60

Ala Ala Gly Val Gln Val His Asp Ala Asp Thr Ile Val Leu Arg Arg
65 70 75 80

Ser Arg Pro Leu Gln Ile Ser Leu Asp Gly His Asp Ala Lys Gln Val
85 90 95

Trp Thr Thr Ala Ser Thr Val Asp Glu Ala Leu Ala Gln Leu Ala Met

-continued

```
            100                 105                 110

Thr Asp Thr Ala Pro Ala Ala Ala Ser Arg Ala Ser Arg Val Pro Leu
        115                 120                 125

Ser Gly Met Ala Leu Pro Val Val Ser Ala Lys Thr Val Gln Leu Asn
    130                 135                 140

Asp Gly Gly Leu Val Arg Thr Val His Leu Pro Ala Pro Asn Val Ala
145                 150                 155                 160

Gly Leu Leu Ser Ala Ala Gly Val Pro Leu Leu Gln Ser Asp His Val
                165                 170                 175

Val Pro Ala Ala Thr Ala Pro Ile Val Glu Gly Met Gln Ile Gln Val
            180                 185                 190

Thr Arg Asn Arg Ile Lys Lys Val Thr Glu Arg Leu Pro Leu Pro Pro
        195                 200                 205

Asn Ala Arg Arg Val Glu Asp Pro Glu Met Asn Met Ser Arg Glu Val
    210                 215                 220

Val Glu Asp Pro Gly Val Pro Gly Thr Gln Asp Val Thr Phe Ala Val
225                 230                 235                 240

Ala Glu Val Asn Gly Val Glu Thr Gly Arg Leu Pro Val Ala Asn Val
                245                 250                 255

Val Val Thr Pro Ala His Glu Ala Val Val Arg Val Gly Thr Lys Pro
            260                 265                 270

Gly Thr Glu Val Pro Pro Val Ile Asp Gly Ser Ile Trp Asp Ala Ile
        275                 280                 285

Ala Gly Cys Glu Ala Gly Gly Asn Trp Ala Ile Asn Thr Gly Asn Gly
    290                 295                 300

Tyr Tyr Gly Gly Val Gln Phe Asp Gln Gly Thr Trp Glu Ala Asn Gly
305                 310                 315                 320

Gly Leu Arg Tyr Ala Pro Arg Ala Asp Leu Ala Thr Arg Glu Glu Gln
                325                 330                 335

Ile Ala Val Ala Glu Val Thr Arg Leu Arg Gln Gly Trp Gly Ala Trp
            340                 345                 350

Pro Val Cys Ala Ala Arg Ala Gly Ala Arg
        355                 360


<210> SEQ ID NO 3
<211> LENGTH: 1023
<212> TYPE: DNA
<213> ORGANISM: Mycobacterium tuberculosis
<220> FEATURE:
<223> OTHER INFORMATION: Rv1009 without signal sequence

<400> SEQUENCE: 3

gcatgcaaaa cggtgacgtt gaccgtcgac ggaaccgcga tgcgggtgac cacgatgaaa      60

tcgcgggtga tcgacatcgt cgaagagaac gggttctcag tcgacgaccg cgacgacctg     120

tatcccgcgg ccggcgtgca ggtccatgac gccgacacca tcgtgctgcg gcgtagccgt     180

ccgctgcaga tctcgctgga tggtcacgac gctaagcagg tgtggacgac cgcgtcgacg     240

gtggacgagg cgctggccca actcgcgatg accgacacgg cgccggccgc ggcttctcgc     300

gccagccgcg tcccgctgtc cgggatggcg ctaccggtcg tcagcgccaa gacggtgcag     360

ctcaacgacg gcgggttggt gcgcacggtg cacttgccgg cccccaatgt cgcggggctg     420

ctgagtgcgg ccggcgtgcc gctgttgcaa agcgaccacg tggtgcccgc cgcgacggcc     480

ccgatcgtcg aaggcatgca gatccaggtg acccgcaatc ggatcaagaa ggtcaccgag     540

cggctgccgc tgccgccgaa cgcgcgtcgt gtcgaggacc cggagatgaa catgagccgg     600
```

-continued

```
gaggtcgtcg aagacccggg ggttccgggg acccaggatg tgacgttcgc ggtagctgag    660

gtcaacggcg tcgagaccgg ccgtttgccc gtcgccaacg tcgtggtgac cccggcccac    720

gaagccgtgg tgcgggtggg caccaagccc ggtaccgagg tgcccccggt gatcgacgga    780

agcatctggg acgcgatcgc cggctgtgag gccggtggca actgggcgat caacaccggc    840

aacgggtatt acggtggtgt gcagtttgac cagggcacct gggaggccaa cggcgggctg    900

cggtatgcac cccgcgctga cctcgccacc cgcgaagagc agatcgccgt tgccgaggtg    960

acccgactgc gtcaaggttg gggcgcctgg ccggtatgtg ctgcacgagc gggtgcgcgc   1020

tga                                                                 1023
```

```
<210> SEQ ID NO 4
<211> LENGTH: 340
<212> TYPE: PRT
<213> ORGANISM: Mycobacterium tuberculosis
<220> FEATURE:
<223> OTHER INFORMATION: Rv1009 without signal sequence

<400> SEQUENCE: 4

Ala Cys Lys Thr Val Thr Leu Thr Val Asp Gly Thr Ala Met Arg Val
1               5                   10                  15

Thr Thr Met Lys Ser Arg Val Ile Asp Ile Val Glu Glu Asn Gly Phe
            20                  25                  30

Ser Val Asp Asp Arg Asp Asp Leu Tyr Pro Ala Ala Gly Val Gln Val
        35                  40                  45

His Asp Ala Asp Thr Ile Val Leu Arg Arg Ser Arg Pro Leu Gln Ile
    50                  55                  60

Ser Leu Asp Gly His Asp Ala Lys Gln Val Trp Thr Thr Ala Ser Thr
65                  70                  75                  80

Val Asp Glu Ala Leu Ala Gln Leu Ala Met Thr Asp Thr Ala Pro Ala
                85                  90                  95

Ala Ala Ser Arg Ala Ser Arg Val Pro Leu Ser Gly Met Ala Leu Pro
            100                 105                 110

Val Val Ser Ala Lys Thr Val Gln Leu Asn Asp Gly Gly Leu Val Arg
        115                 120                 125

Thr Val His Leu Pro Ala Pro Asn Val Ala Gly Leu Leu Ser Ala Ala
    130                 135                 140

Gly Val Pro Leu Leu Gln Ser Asp His Val Val Pro Ala Ala Thr Ala
145                 150                 155                 160

Pro Ile Val Glu Gly Met Gln Ile Gln Val Thr Arg Asn Arg Ile Lys
                165                 170                 175

Lys Val Thr Glu Arg Leu Pro Leu Pro Pro Asn Ala Arg Arg Val Glu
            180                 185                 190

Asp Pro Glu Met Asn Met Ser Arg Glu Val Val Glu Asp Pro Gly Val
        195                 200                 205

Pro Gly Thr Gln Asp Val Thr Phe Ala Val Ala Glu Val Asn Gly Val
    210                 215                 220

Glu Thr Gly Arg Leu Pro Val Ala Asn Val Val Val Thr Pro Ala His
225                 230                 235                 240

Glu Ala Val Val Arg Val Gly Thr Lys Pro Gly Thr Glu Val Pro Pro
                245                 250                 255

Val Ile Asp Gly Ser Ile Trp Asp Ala Ile Ala Gly Cys Glu Ala Gly
            260                 265                 270

Gly Asn Trp Ala Ile Asn Thr Gly Asn Gly Tyr Tyr Gly Gly Val Gln
```

-continued

```
        275                 280                 285

Phe Asp Gln Gly Thr Trp Glu Ala Asn Gly Gly Leu Arg Tyr Ala Pro
    290                 295                 300

Arg Ala Asp Leu Ala Thr Arg Glu Glu Gln Ile Ala Val Ala Glu Val
305                 310                 315                 320

Thr Arg Leu Arg Gln Gly Trp Gly Ala Trp Pro Val Cys Ala Ala Arg
                325                 330                 335

Ala Gly Ala Arg
            340


<210> SEQ ID NO 5
<211> LENGTH: 1143
<212> TYPE: DNA
<213> ORGANISM: Mycobacterium tuberculosis
<220> FEATURE:
<223> OTHER INFORMATION: Rv3136

<400> SEQUENCE: 5

atggatttcg cactgttacc accggaagtc aactccgccc ggatgtacac cggccctggg     60

gcaggatcgc tgttggctgc cgcgggcggc tgggattcgc tggccgccga gttggccacc    120

acagccgagg catatggatc ggtgctgtcc ggactggccg ccttgcattg gcgtggaccg    180

gcagcggaat cgatggcggt gacggccgct ccctatatcg gttggctgta cacgaccgcc    240

gaaaagacac agcaaacagc gatccaagcc agggcggcag cgctggcctt cgagcaagca    300

tacgcaatga ccctgccgcc accggtggta gcggccaacc ggatacagct gctagcactg    360

atcgcgacga acttcttcgg ccagaacact gcggcgatcg cggccaccga ggcacagtac    420

gccgagatgt gggcccagga cgccgccgcg atgtacggtt acgccaccgc ctcagcggct    480

gcggccctgc tgacaccgtt ctccccgccg cggcagacca ccaacccggc cggcctgacc    540

gctcaggccg ccgcggtcag ccaggccacc gacccactgt cgctgctgat tgagacggtg    600

acccaagcgc tgcaagcgct gacgattccg agcttcatcc ctgaggactt caccttcctt    660

gacgccatat tcgctggata tgccacggta ggtgtgacgc aggatgtcga gtcctttgtt    720

gccgggacca tcggggccga gagcaaccta ggccttttga acgtcggcga cgagaatccc    780

gcggaggtga caccgggcga ctttgggatc ggcgagttgg tttccgcgac cagtcccggc    840

ggtggggtgt ctgcgtcggg tgccggcggt gcggcgagcg tcggcaacac ggtgctcgcg    900

agtgtcggcc gggcaaactc gattgggcaa ctatcggtcc caccgagctg ggccgcgccc    960

tcgacgcgcc ctgtctcggc attgtcgccc gccggcctga ccacactccc ggggaccgac   1020

gtggccgagc acgggatgcc aggtgtaccg ggggtgccag tggcagcagg gcgagcctcc   1080

ggcgtcctac ctcgatacgg ggttcggctc acggtgatgg cccacccacc cgcggcaggg   1140

taa                                                                 1143


<210> SEQ ID NO 6
<211> LENGTH: 1146
<212> TYPE: DNA
<213> ORGANISM: Mycobacterium tuberculosis

<400> SEQUENCE: 6

atggattttg cgctgctgcc gccggaagtg aacagcgcgc gcatgtatac cggcccgggc     60

gcgggcagcc tgctggcggc ggcgggcggc tgggatagcc tggcggcgga actggcgacc    120

accgcggaag cgtatggcag cgtgctgagc ggcctggcgg cgctgcattg gcgcggcccg    180

gcggcggaaa gcatggcggt gaccgcggcg ccgtatattg gctggctgta taccaccgcg    240
```

```
gaaaaaaccc agcagaccgc gattcaggcg cgcgcggcgg cgctggcgtt tgaacaggcg    300
tatgcgatga ccctgccgcc gccggtggtg gcggcgaacc gcattcagct gctggcgctg    360
attgcgacca actttttgg ccagaacacc gcggcgattg cggcgaccga agcgcagtat     420
gcggaaatgt gggcgcagga tgcggcggcg atgtatggct atgcgaccgc gagcgcggcg    480
gcggcgctgc tgaccccgtt tagcccgccg cgccagacca ccaacccggc gggcctgacc    540
gcgcaggcgg cggcggtgag ccaggcgacc gatccgctga gcctgctgat tgaaaccgtg    600
acccaggcgc tgcaggcgct gaccattccg agctttattc cggaagattt tacctttctg    660
gatgcgattt ttgcgggcta tgcgaccgtg ggcgtgaccc aggatgtgga aagctttgtg    720
gcgggcacca ttggcgcgga aagcaacctg ggcctgctga acgtgggcga tgaaaacccg    780
gcggaagtga ccccgggcga ttttggcatt ggcgaactgg tgagcgcgac cagcccgggc    840
ggcggcgtga gcgcgagcgg cgcgggcggc gcggcgagcg tgggcaacac cgtgctggcg    900
agcgtgggcc gcgcgaacag cattggccag ctgagcgtgc cgccgagctg ggcggcgccg    960
agcacccgcc cggtgagcgc gctgagcccg gcgggcctga ccaccctgcc gggcaccgat   1020
gtggcggaac atggcatgcc gggcgtgccg ggcgtgccgg tggcggcggg ccgcgcgagc   1080
ggcgtgctgc cgcgctatgg cgtgcgcctg accgtgatgg cgcatccgcc ggcggcgggc   1140
gaattt                                                              1146
```

<210> SEQ ID NO 7
<211> LENGTH: 1143
<212> TYPE: DNA
<213> ORGANISM: Mycobacterium tuberculosis
<220> FEATURE:
<223> OTHER INFORMATION: Rv3136

<400> SEQUENCE: 7

```
atggatttcg ctctgctccc ccccgaggtg aatagcgcta ggatgtacac aggacccgga     60
gctggaagcc tcctggctgc tgctggagga tgggactccc tggctgccga gctcgctaca    120
accgctgagg cttacggaag cgtgctctcc ggcctggctg ctctccattg gagaggccct    180
gctgccgagt ccatggctgt cacagccgct ccctacattg gatggctgta caccaccgcc    240
gagaagaccc agcaaaccgc tattcaggcc agagctgccg ccctggcctt cgaacaggcc    300
tacgctatga cactcccccc ccctgtcgtg gctgccaata ggatccagct cctggccctc    360
atcgccacca acttcttcgg ccaaaacacc gctgccatcg ctgccaccga agcccagtac    420
gccgaaatgt gggcccagga tgccgctgct atgtacggct atgccacagc tagcgctgcc    480
gctgctctgc tcacaccctt cagccccccc aggcaaacaa ccaaccctgc cggactgaca    540
gcccaagctg ctgccgtcag ccaagctacc gacccccctga gcctcctgat cgaaaccgtg    600
acacaggccc tgcaggccct gaccattccc agctttatcc ccgaggactt cacctttctg    660
gacgctatct tcgctggcta cgccaccgtg ggcgtgacac aagacgtcga gtccttcgtc    720
gccggcacaa tcggagccga gtccaacctc ggactcctca acgtcggcga cgaaaatccc    780
gccgaagtga cacctggaga cttcggcatt ggagaactcg tcagcgccac atcccctggc    840
ggaggagtga gcgcttccgg agctggagga gctgcttccg tgggcaatac cgtgctggcc    900
agcgtgggaa gggccaactc cattggccag ctcagcgtcc ccccttcctg ggctgcccct    960
tccacaaggc ctgtgtccgc tctcagccct gctggactga ccacactccc tggcacagac   1020
gtggctgagc atggcatgcc cggagtgcct ggagtccctg tggctgctgg cagagcttcc   1080
```

ggagtcctcc ctaggtatgg cgtgaggctg acagtgatgg ctcatccccc cgctgccgga 1140
taa 1143

<210> SEQ ID NO 8
<211> LENGTH: 380
<212> TYPE: PRT
<213> ORGANISM: Mycobacterium tuberculosis
<220> FEATURE:
<223> OTHER INFORMATION: Rv3136

<400> SEQUENCE: 8

Met Asp Phe Ala Leu Leu Pro Pro Glu Val Asn Ser Ala Arg Met Tyr
1 5 10 15

Thr Gly Pro Gly Ala Gly Ser Leu Leu Ala Ala Ala Gly Gly Trp Asp
20 25 30

Ser Leu Ala Ala Glu Leu Ala Thr Thr Ala Glu Ala Tyr Gly Ser Val
35 40 45

Leu Ser Gly Leu Ala Ala Leu His Trp Arg Gly Pro Ala Ala Glu Ser
50 55 60

Met Ala Val Thr Ala Ala Pro Tyr Ile Gly Trp Leu Tyr Thr Thr Ala
65 70 75 80

Glu Lys Thr Gln Gln Thr Ala Ile Gln Ala Arg Ala Ala Ala Leu Ala
85 90 95

Phe Glu Gln Ala Tyr Ala Met Thr Leu Pro Pro Pro Val Val Ala Ala
100 105 110

Asn Arg Ile Gln Leu Leu Ala Leu Ile Ala Thr Asn Phe Phe Gly Gln
115 120 125

Asn Thr Ala Ala Ile Ala Ala Thr Glu Ala Gln Tyr Ala Glu Met Trp
130 135 140

Ala Gln Asp Ala Ala Ala Met Tyr Gly Tyr Ala Thr Ala Ser Ala Ala
145 150 155 160

Ala Ala Leu Leu Thr Pro Phe Ser Pro Pro Arg Gln Thr Thr Asn Pro
165 170 175

Ala Gly Leu Thr Ala Gln Ala Ala Ala Val Ser Gln Ala Thr Asp Pro
180 185 190

Leu Ser Leu Leu Ile Glu Thr Val Thr Gln Ala Leu Gln Ala Leu Thr
195 200 205

Ile Pro Ser Phe Ile Pro Glu Asp Phe Thr Phe Leu Asp Ala Ile Phe
210 215 220

Ala Gly Tyr Ala Thr Val Gly Val Thr Gln Asp Val Glu Ser Phe Val
225 230 235 240

Ala Gly Thr Ile Gly Ala Glu Ser Asn Leu Gly Leu Leu Asn Val Gly
245 250 255

Asp Glu Asn Pro Ala Glu Val Thr Pro Gly Asp Phe Gly Ile Gly Glu
260 265 270

Leu Val Ser Ala Thr Ser Pro Gly Gly Gly Val Ser Ala Ser Gly Ala
275 280 285

Gly Gly Ala Ala Ser Val Gly Asn Thr Val Leu Ala Ser Val Gly Arg
290 295 300

Ala Asn Ser Ile Gly Gln Leu Ser Val Pro Pro Ser Trp Ala Ala Pro
305 310 315 320

Ser Thr Arg Pro Val Ser Ala Leu Ser Pro Ala Gly Leu Thr Thr Leu
325 330 335

Pro Gly Thr Asp Val Ala Glu His Gly Met Pro Gly Val Pro Gly Val
340 345 350

```
Pro Val Ala Ala Gly Arg Ala Ser Gly Val Leu Pro Arg Tyr Gly Val
        355                 360                 365

Arg Leu Thr Val Met Ala His Pro Pro Ala Ala Gly
    370                 375                 380


<210> SEQ ID NO 9
<211> LENGTH: 312
<212> TYPE: DNA
<213> ORGANISM: Mycobacterium tuberculosis
<220> FEATURE:
<223> OTHER INFORMATION: Rv3615c

<400> SEQUENCE: 9

atgacggaaa acttgaccgt ccagcccgag cgtctcggtg tactggcgtc gcaccatgac     60

aacgcggcgg tcgatgcctc ctcgggcgtc gaagctgccg ctggcctagg cgaatctgtg    120

gcgatcactc acggtccgta ctgctcacag ttcaacgaca cgttaaatgt gtacttgact    180

gcccacaatg ccctgggctc gtccttgcat acggccggtg tcgatctcgc caaaagtctt    240

cgaattgcgg cgaagatata tagcgaggcc gacgaagcgt ggcgcaaggc tatcgacggg    300

ttgtttacct ga                                                        312


<210> SEQ ID NO 10
<211> LENGTH: 312
<212> TYPE: DNA
<213> ORGANISM: Mycobacterium tuberculosis
<220> FEATURE:
<223> OTHER INFORMATION: Rv3615c

<400> SEQUENCE: 10

atgaccgaga acctgaccgt gcagcctgag aggctgggag tgctggccag ccaccacgac     60

aacgctgccg tggacgcttc cagcggagtg gaggctgctg ctggactggg agagagcgtg    120

gccatcaccc acggacccta ctgcagccag ttcaacgaca ccctgaacgt gtacctgaca    180

gcccacaacg ccctgggaag cagcctgcat acagccggcg tggacctggc taagtccctg    240

aggatcgccg ccaagatcta cagcgaggcc gacgaggcct ggaggaaagc catcgacggc    300

ctgttcacct aa                                                        312


<210> SEQ ID NO 11
<211> LENGTH: 103
<212> TYPE: PRT
<213> ORGANISM: Mycobacterium tuberculosis
<220> FEATURE:
<223> OTHER INFORMATION: Rv3615c

<400> SEQUENCE: 11

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
            20                  25                  30

Ala Ala Gly Leu Gly Glu Ser Val Ala Ile Thr His Gly Pro Tyr Cys
        35                  40                  45

Ser Gln Phe Asn Asp Thr Leu Asn Val Tyr Leu Thr Ala His Asn Ala
    50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95
```

```
Ala Ile Asp Gly Leu Phe Thr
            100


<210> SEQ ID NO 12
<211> LENGTH: 363
<212> TYPE: DNA
<213> ORGANISM: Mycobacterium tuberculosis
<220> FEATURE:
<223> OTHER INFORMATION: Rv2628

<400> SEQUENCE: 12

atgtccacgc aacgaccgag gcactccggt attcgggctg ttggccccta cgcatgggcc      60

ggccgatgtg gtcggatagg caggtggggg gtgcaccagg aggcgatgat gaatctagcg     120

atatggcacc cgcgcaaggt gcaatccgcc accatctatc aggtgaccga tcgctcgcac     180

gacgggcgca cagcacgggt gcctggtgac gagatcacta gcaccgtgtc cggttggttg     240

tcggagttgg gcacccaaag cccgttggcc gatgagcttg cgcgtgcggt gcggatcggc     300

gactggcccg ctgcgtacgc aatcggtgag cacctgtccg ttgagattgc cgttgcggtc     360

taa                                                                   363


<210> SEQ ID NO 13
<211> LENGTH: 363
<212> TYPE: DNA
<213> ORGANISM: Mycobacterium tuberculosis
<220> FEATURE:
<223> OTHER INFORMATION: Rv2628

<400> SEQUENCE: 13

atgagcaccc agagacccag gcacagcggc attagggccg tgggacctta tgcttgggcc      60

ggcagatgcg gaaggatcgg cagatggggc gtgcaccaag aggccatgat gaacctggcc     120

atctggcacc ccaggaaggt gcagagcgcc accatctacc aggtgaccga caggagccat     180

gacggaagga ccgccagagt gcccggcgat gagatcacca gcaccgtgag cggctggctg     240

agcgaactgg gcacccaatc ccccctggct gatgaactgg ccagggctgt gaggatcggc     300

gattggcctg ccgcctatgc catcggcgag catctgagcg tggagatcgc cgtggccgtg     360

taa                                                                   363


<210> SEQ ID NO 14
<211> LENGTH: 120
<212> TYPE: PRT
<213> ORGANISM: Mycobacterium tuberculosis
<220> FEATURE:
<223> OTHER INFORMATION: Rv2628

<400> SEQUENCE: 14

Met Ser Thr Gln Arg Pro Arg His Ser Gly Ile Arg Ala Val Gly Pro
1               5                   10                  15

Tyr Ala Trp Ala Gly Arg Cys Gly Arg Ile Gly Arg Trp Gly Val His
            20                  25                  30

Gln Glu Ala Met Met Asn Leu Ala Ile Trp His Pro Arg Lys Val Gln
        35                  40                  45

Ser Ala Thr Ile Tyr Gln Val Thr Asp Arg Ser His Asp Gly Arg Thr
    50                  55                  60

Ala Arg Val Pro Gly Asp Glu Ile Thr Ser Thr Val Ser Gly Trp Leu
65                  70                  75                  80

Ser Glu Leu Gly Thr Gln Ser Pro Leu Ala Asp Glu Leu Ala Arg Ala
                85                  90                  95
```

-continued

Val Arg Ile Gly Asp Trp Pro Ala Ala Tyr Ala Ile Gly Glu His Leu
            100                 105                 110

Ser Val Glu Ile Ala Val Ala Val
        115                 120

<210> SEQ ID NO 15
<211> LENGTH: 324
<212> TYPE: DNA
<213> ORGANISM: Mycobacterium tuberculosis
<220> FEATURE:
<223> OTHER INFORMATION: Rv2034

<400> SEQUENCE: 15
gtgtccactt acagatcacc ggatcgcgct tggcaggcgc tggcggacgg cactcgccgg 60
gccatcgtgg agcggctggc gcacggcccg ctggccgtcg gcgagttggc ccgcgacctg 120
cccgtcagcc gacccgcggt gtcacagcac ctcaaagtgc tcaagaccgc caggctggtg 180
tgcgaccgcc ccgcgggaac acgccgcgtc taccagctcg acccgacagg ccttgcggca 240
ttgcgcaccg acctcgaccg gttctggaca cgcgccctga ctggctacgc gcagctcatc 300
gactccgaag gagacgacac atga 324

<210> SEQ ID NO 16
<211> LENGTH: 107
<212> TYPE: PRT
<213> ORGANISM: Mycobacterium tuberculosis
<220> FEATURE:
<223> OTHER INFORMATION: Rv2034

<400> SEQUENCE: 16

Val Ser Thr Tyr Arg Ser Pro Asp Arg Ala Trp Gln Ala Leu Ala Asp
1               5                   10                  15

Gly Thr Arg Arg Ala Ile Val Glu Arg Leu Ala His Gly Pro Leu Ala
            20                  25                  30

Val Gly Glu Leu Ala Arg Asp Leu Pro Val Ser Arg Pro Ala Val Ser
        35                  40                  45

Gln His Leu Lys Val Leu Lys Thr Ala Arg Leu Val Cys Asp Arg Pro
    50                  55                  60

Ala Gly Thr Arg Arg Val Tyr Gln Leu Asp Pro Thr Gly Leu Ala Ala
65                  70                  75                  80

Leu Arg Thr Asp Leu Asp Arg Phe Trp Thr Arg Ala Leu Thr Gly Tyr
                85                  90                  95

Ala Gln Leu Ile Asp Ser Glu Gly Asp Asp Thr
            100                 105

<210> SEQ ID NO 17
<211> LENGTH: 540
<212> TYPE: DNA
<213> ORGANISM: Mycobacterium tuberculosis
<220> FEATURE:
<223> OTHER INFORMATION: Rv3136 N-terminus

<400> SEQUENCE: 17
atggatttcg cactgttacc accggaagtc aactccgccc ggatgtacac cggccctggg 60
gcaggatcgc tgttggctgc cgcgggcggc tgggattcgc tggccgccga gttggccacc 120
acagccgagg catatggatc ggtgctgtcc ggactggccg ccttgcattg gcgtggaccg 180
gcagcggaat cgatggcggt gacggccgct ccctatatcg gttggctgta cacgaccgcc 240
gaaaagacac agcaaacagc gatccaagcc agggcggcag cgctggcctt cgagcaagca 300
tacgcaatga ccctgccgcc accggtggta gcggccaacc ggatacagct gctagcactg 360
atcgcgacga acttcttcgg ccagaacact gcggcgatcg cggccaccga ggcacagtac 420
gccgagatgt gggcccagga cgccgccgcg atgtacggtt acgccaccgc ctcagcggct 480
gcggccctgc tgacaccgtt ctccccgccg cggcagacca ccaacccggc cggcctgacc 540

<210> SEQ ID NO 18
<211> LENGTH: 180
<212> TYPE: PRT
<213> ORGANISM: Mycobacterium tuberculosis
<220> FEATURE:
<223> OTHER INFORMATION: Rv3136 N-terminus

<400> SEQUENCE: 18

Met Asp Phe Ala Leu Leu Pro Pro Glu Val Asn Ser Ala Arg Met Tyr
1 5 10 15

Thr Gly Pro Gly Ala Gly Ser Leu Leu Ala Ala Ala Gly Gly Trp Asp
20 25 30

Ser Leu Ala Ala Glu Leu Ala Thr Thr Ala Glu Ala Tyr Gly Ser Val
35 40 45

Leu Ser Gly Leu Ala Ala Leu His Trp Arg Gly Pro Ala Ala Glu Ser
50 55 60

Met Ala Val Thr Ala Ala Pro Tyr Ile Gly Trp Leu Tyr Thr Thr Ala
65 70 75 80

Glu Lys Thr Gln Gln Thr Ala Ile Gln Ala Arg Ala Ala Ala Leu Ala
85 90 95

Phe Glu Gln Ala Tyr Ala Met Thr Leu Pro Pro Pro Val Val Ala Ala
100 105 110

Asn Arg Ile Gln Leu Leu Ala Leu Ile Ala Thr Asn Phe Phe Gly Gln
115 120 125

Asn Thr Ala Ala Ile Ala Ala Thr Glu Ala Gln Tyr Ala Glu Met Trp
130 135 140

Ala Gln Asp Ala Ala Ala Met Tyr Gly Tyr Ala Thr Ala Ser Ala Ala
145 150 155 160

Ala Ala Leu Leu Thr Pro Phe Ser Pro Pro Arg Gln Thr Thr Asn Pro
165 170 175

Ala Gly Leu Thr
180

<210> SEQ ID NO 19
<211> LENGTH: 1017
<212> TYPE: DNA
<213> ORGANISM: Mycobacterium tuberculosis
<220> FEATURE:
<223> OTHER INFORMATION: Ag85A

<400> SEQUENCE: 19
atgcagcttg ttgacagggt tcgtggcgcc gtcacgggta tgtcgcgtcg actcgtggtc 60
ggggccgtcg gcgcggccct agtgtcgggt ctggtcggcg ccgtcggtgg cacggcgacc 120
gcgggggcat tttcccggcc gggcttgccg gtggagtacc tgcaggtgcc gtcgccgtcg 180
atgggccgtg acatcaaggt ccaattccaa agtggtggtg ccaactcgcc cgccctgtac 240
ctgctcgacg gcctgcgcgc gcaggacgac ttcagcggct gggacatcaa cacccccggcg 300 ttcgagtggt acgaccagtc gggcctgtcg gtggtcatgc cggtgggtgg ccagtcaagc 360
ttctactccg actggtacca gcccgcctgc ggcaaggccg gttgccagac ttacaagtgg 420
gagaccttcc tgaccagcga gctgccgggg tggctgcagg ccaacaggca cgtcaagccc 480

-continued

```
accggaagcg ccgtcgtcgg tctttcgatg gctgcttctt cggcgctgac gctggcgatc    540

tatcaccccc agcagttcgt ctacgcggga gcgatgtcgg gcctgttgga cccctcccag    600

gcgatgggtc ccaccctgat cggcctggcg atgggtgacg ctggcggcta caaggcctcc    660

gacatgtggg gcccgaagga ggacccggcg tggcagcgca acgacccgct gttgaacgtc    720

gggaagctga tcgccaacaa cacccgcgtc tgggtgtact gcggcaacgg caagccgtcg    780

gatctgggtg gcaacaacct gccggccaag ttcctcgagg gcttcgtgcg gaccagcaac    840

atcaagttcc aagacgccta caacgccggt ggcggccaca acggcgtgtt cgacttcccg    900

gacagcggta cgcacagctg ggagtactgg ggcgcgcagc tcaacgctat gaagcccgac    960

ctgcaacggg cactgggtgc cacgcccaac accgggcccg cgccccaggg cgcctag      1017
```

<210> SEQ ID NO 20
<211> LENGTH: 338
<212> TYPE: PRT
<213> ORGANISM: Mycobacterium tuberculosis
<220> FEATURE:
<223> OTHER INFORMATION: Ag85A

<400> SEQUENCE: 20

```
Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30

Gly Ala Val Gly Gly Thr Ala Thr Ala Gly Ala Phe Ser Arg Pro Gly
        35                  40                  45

Leu Pro Val Glu Tyr Leu Gln Val Pro Ser Pro Ser Met Gly Arg Asp
    50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270
```

-continued

```
Glu Gly Phe Val Arg Thr Ser Asn Ile Lys Phe Gln Asp Ala Tyr Asn
        275                 280                 285

Ala Gly Gly Gly His Asn Gly Val Phe Asp Phe Pro Asp Ser Gly Thr
    290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala
```

```
<210> SEQ ID NO 21
<211> LENGTH: 977
<212> TYPE: DNA
<213> ORGANISM: Mycobacterium tuberculosis
<220> FEATURE:
<223> OTHER INFORMATION: Ag85B

<400> SEQUENCE: 21

atgacagacg tgagccgaaa gattcgagct tggggacgcc gattgatgat cggcacggca      60

gcggctgtag tccttccggg cctggtgggg cttgccgcgg agcggcaacc gcgggcgcgt     120

tctcccggcc ggggctgccg gtcgagtacc tgcaggtgcc gtcgccgtcg atgggccgcg     180

acatcaaggt tcagttccag agcggtggga acaactcacc tgcggtttat ctgctcgacg     240

gcctgcgcgc ccaagacgac tacaacggct gggatatcaa caccccggcg ttcgagtggt     300

actaccagtc gggactgtcg atagtcatgc cggtcggcgg gcagtccagc ttctacagcg     360

actggtacag cccggcctgc ggtaaggctg gctgccagac ttacaagtgg gaaaccttcc     420

tgaccagcga gctgccgcaa tggttgtccg ccaacagggc cgtgaagccc accggcagcg     480

ctgcaatcgg cttgtcgatg gccggctcgt cggcaatgat cttggccgcc taccaccccc     540

agcagttcat ctacgccggc tcgctgtcgg ccctgctgga cccctctcag gggatggggc     600

ctagcctgat cggcctcgcg atgggtgacg ccggcggtta caaggccgca gacatgtggg     660

gtccctcgag tgacccggca tgggagcgca acgaccctac gcagcagatc cccaagctgg     720

tcgcaaacaa cacccggcta tgggtttatt gcgggaacgg caccccgaac gagttgggcg     780

gtgccaacat acccgccgag ttcttggaga acttcgttcg tagcagcaac ctgaagttcc     840

aggatgcgta caacgccgcg ggcgggcaca acgccgtgtt caacttcccg cccaacggca     900

cgcacagctg ggagtactgg ggcgctcagc tcaacgccat gaagggtgac ctgcagagtt     960

cgttaggcgc cggctga                                                    977
```

```
<210> SEQ ID NO 22
<211> LENGTH: 858
<212> TYPE: DNA
<213> ORGANISM: Mycobacterium tuberculosis
<220> FEATURE:
<223> OTHER INFORMATION: Ag85B

<400> SEQUENCE: 22

atgtttagcc gtcctggcct gccagttgaa tacctgcaag ttccgagccc gtccatgggt      60

cgtgacatta aggtgcagtt ccagagcggc ggtaacaata gcccggctgt gtacctgctg     120

gacggtctgc gtgcgcagga tgattacaac ggctgggaca tcaatacccc ggcatttgag     180

tggtattacc agtcgggtct gagcattgtg atgccggttg gcggtcaaag cagcttctat     240

agcgattggt acagcccggc atgcggcaag gctggttgcc aaacctacaa gtgggaaact     300
```

ttcttgacca gcgagctgcc gcaatggttg agcgccaacc gtgcggtcaa accgaccggt 360
agcgctgcta ttggcctgtc catggccggc agcagcgcga tgatcttggc ggcataccat 420
ccgcagcagt ttatctacgc cggtagcctg agcgcattgc tggacccgag ccaaggcatg 480
ggtccgagcc tgattggtct ggcaatgggt gacgcaggtg gttacaaagc ggccgatatg 540
tggggcccat ctagcgaccc ggcatgggag cgtaatgacc cgacccagca aattccgaaa 600
ctggtggcga ataacacgcg cctgtgggtc tactgtggca atggtacgcc gaacgagctg 660
ggtggcgcga atatccctgc ggagtttctg gaaaactttg ttcgcagcag caacctgaaa 720
ttccaggacg cgtataacgc agccggtggt cacaatgcgg ttttcaattt cccgccaaat 780
ggcactcata gctgggagta ctggggtgcg cagttgaacg caatgaaagg cgatctgcaa 840
tcctctctgg gtgcgggc 858

<210> SEQ ID NO 23
<211> LENGTH: 858
<212> TYPE: DNA
<213> ORGANISM: Mycobacterium tuberculosis
<220> FEATURE:
<223> OTHER INFORMATION: Ag85B

<400> SEQUENCE: 23
atgttctcca ggcccggcct gcctgtcgag tatctgcagg tcccctcccc ctccatgggc 60
agagacatca aggtgcagtt ccaatccgga ggcaacaaca gccccgccgt gtatctcctc 120
gacggcctga gggctcagga cgactacaac ggctgggaca tcaacacccc cgccttcgag 180
tggtactacc agtccggact gagcatcgtc atgcccgtgg gcggccagag ctccttctac 240
agcgactggt atagccctgc ctgcggcaaa gccggatgcc agacctacaa gtgggagacc 300
tttctgacca gcgaactgcc ccagtggctg tccgccaata gggccgtcaa acctaccggc 360
tccgctgcca tcggactcag catggccgga agctccgcta tgatcctggc cgcctaccac 420
ccccagcaat ttatctacgc tggcagcctg tccgctctgc tggatcctag ccaaggcatg 480
ggccctagcc tcattggcct ggccatgggc gatgctggcg gctataaggc cgccgatatg 540
tggggcccta gctccgatcc tgcctgggag aggaatgacc ccacccagca gatccccaag 600
ctggtggcca acaacacaag gctctgggtg tactgcggca atggcacccc caacgaactg 660
ggcggagcca acattcccgc cgagttcctg gagaacttcg tcaggagcag caacctgaag 720
ttccaggacg cctacaatgc cgccggaggc cacaacgctg tgttcaactt ccctcccaac 780
ggcacccaca gctgggagta ttggggcgct cagctgaacg ccatgaaagg cgacctccag 840
agctccctgg gagctgga 858

<210> SEQ ID NO 24
<211> LENGTH: 325
<212> TYPE: PRT
<213> ORGANISM: Mycobacterium tuberculosis
<220> FEATURE:
<223> OTHER INFORMATION: Ag85B

<400> SEQUENCE: 24

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

```
Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325


<210> SEQ ID NO 25
<211> LENGTH: 286
<212> TYPE: PRT
<213> ORGANISM: Mycobacterium tuberculosis
<220> FEATURE:
<223> OTHER INFORMATION: Ag85B

<400> SEQUENCE: 25

Met Phe Ser Arg Pro Gly Leu Pro Val Glu Tyr Leu Gln Val Pro Ser
1               5                   10                  15

Pro Ser Met Gly Arg Asp Ile Lys Val Gln Phe Gln Ser Gly Gly Asn
            20                  25                  30

Asn Ser Pro Ala Val Tyr Leu Leu Asp Gly Leu Arg Ala Gln Asp Asp
        35                  40                  45

Tyr Asn Gly Trp Asp Ile Asn Thr Pro Ala Phe Glu Trp Tyr Tyr Gln
    50                  55                  60

Ser Gly Leu Ser Ile Val Met Pro Val Gly Gly Gln Ser Ser Phe Tyr
65                  70                  75                  80
```

```
Ser Asp Trp Tyr Ser Pro Ala Cys Gly Lys Ala Gly Cys Gln Thr Tyr
                85                  90                  95

Lys Trp Glu Thr Phe Leu Thr Ser Glu Leu Pro Gln Trp Leu Ser Ala
            100                 105                 110

Asn Arg Ala Val Lys Pro Thr Gly Ser Ala Ala Ile Gly Leu Ser Met
        115                 120                 125

Ala Gly Ser Ser Ala Met Ile Leu Ala Ala Tyr His Pro Gln Gln Phe
    130                 135                 140

Ile Tyr Ala Gly Ser Leu Ser Ala Leu Leu Asp Pro Ser Gln Gly Met
145                 150                 155                 160

Gly Pro Ser Leu Ile Gly Leu Ala Met Gly Asp Ala Gly Gly Tyr Lys
                165                 170                 175

Ala Ala Asp Met Trp Gly Pro Ser Ser Asp Pro Ala Trp Glu Arg Asn
            180                 185                 190

Asp Pro Thr Gln Gln Ile Pro Lys Leu Val Ala Asn Asn Thr Arg Leu
        195                 200                 205

Trp Val Tyr Cys Gly Asn Gly Thr Pro Asn Glu Leu Gly Gly Ala Asn
    210                 215                 220

Ile Pro Ala Glu Phe Leu Glu Asn Phe Val Arg Ser Ser Asn Leu Lys
225                 230                 235                 240

Phe Gln Asp Ala Tyr Asn Ala Ala Gly Gly His Asn Ala Val Phe Asn
                245                 250                 255

Phe Pro Pro Asn Gly Thr His Ser Trp Glu Tyr Trp Gly Ala Gln Leu
            260                 265                 270

Asn Ala Met Lys Gly Asp Leu Gln Ser Ser Leu Gly Ala Gly
        275                 280                 285


<210> SEQ ID NO 26
<211> LENGTH: 300
<212> TYPE: DNA
<213> ORGANISM: Mycobacterium tuberculosis
<220> FEATURE:
<223> OTHER INFORMATION: Rv3407

<400> SEQUENCE: 26

atgcgtgcta ccgttgggct tgtggaggca atcggaatcc gagaactaag acagcacgca      60

tcgcgatacc tcgcccgggt tgaagccggc gaggaacttg gcgtcaccaa caaaggaaga     120

cttgtggccc gactcatccc ggtgcaggcc gcggagcgtt ctcgcgaagc cctgattgaa     180

tcaggtgtcc tgattccggc tcgtcgtcca caaaaccttc tcgacgtcac cgccgaaccg     240

gcgcgcggcc gcaagcgcac cctgtccgat gttctcaacg aaatgcgcga cgagcagtga     300


<210> SEQ ID NO 27
<211> LENGTH: 99
<212> TYPE: PRT
<213> ORGANISM: Mycobacterium tuberculosis
<220> FEATURE:
<223> OTHER INFORMATION: Rv3407

<400> SEQUENCE: 27

Met Arg Ala Thr Val Gly Leu Val Glu Ala Ile Gly Ile Arg Glu Leu
1               5                   10                  15

Arg Gln His Ala Ser Arg Tyr Leu Ala Arg Val Glu Ala Gly Glu Glu
            20                  25                  30

Leu Gly Val Thr Asn Lys Gly Arg Leu Val Ala Arg Leu Ile Pro Val
        35                  40                  45

Gln Ala Ala Glu Arg Ser Arg Glu Ala Leu Ile Glu Ser Gly Val Leu
```

```
    50                  55                  60

Ile Pro Ala Arg Arg Pro Gln Asn Leu Leu Asp Val Thr Ala Glu Pro
65                  70                  75                  80

Ala Arg Gly Arg Lys Arg Thr Leu Ser Asp Val Leu Asn Glu Met Arg
                85                  90                  95

Asp Glu Gln


<210> SEQ ID NO 28
<211> LENGTH: 633
<212> TYPE: DNA
<213> ORGANISM: Mycobacterium tuberculosis
<220> FEATURE:
<223> OTHER INFORMATION: Rv1733

<400> SEQUENCE: 28

atgatcgcca caacccgcga tcgtgaagga gccaccatga tcacgtttag gctgcgcttg      60

ccgtgccgga cgatactgcg ggtgttcagc cgcaatccgc tggtgcgtgg gacggatcga     120

ctcgaggcgg tcgtcatgct gctggccgtc acggtctcgc tgctgactat cccgttcgcc     180

gccgcggccg gcaccgcagt ccaggattcc cgcagccacg tctatgccca ccaggcccag     240

acccgccatc ccgcaaccgc gaccgtgatc gatcacgagg gggtgatcga cagcaacacg     300

accgccacgt cagcgccgcc gcgcacgaag atcaccgtgc ctgcccgatg ggtcgtgaac     360

ggaatagaac gcagcggtga ggtcaacgcg aagccgggaa ccaaatccgg tgaccgcgtc     420

ggcatttggg tcgacagtgc cggtcagctg gtcgatgaac cagctccgcc ggcccgtgcc     480

attgcggatg cggccctggc cgccttggga ctctggttga gcgtcgccgc ggttgcgggc     540

gccctgctgg cgctcactcg ggcgattctg atccgcgttc gcaacgccag ttggcaacac     600

gacatcgaca gcctgttctg cacgcagcgg tga                                  633


<210> SEQ ID NO 29
<211> LENGTH: 210
<212> TYPE: PRT
<213> ORGANISM: Mycobacterium tuberculosis
<220> FEATURE:
<223> OTHER INFORMATION: Rv1733

<400> SEQUENCE: 29

Met Ile Ala Thr Thr Arg Asp Arg Glu Gly Ala Thr Met Ile Thr Phe
1               5                   10                  15

Arg Leu Arg Leu Pro Cys Arg Thr Ile Leu Arg Val Phe Ser Arg Asn
            20                  25                  30

Pro Leu Val Arg Gly Thr Asp Arg Leu Glu Ala Val Val Met Leu Leu
        35                  40                  45

Ala Val Thr Val Ser Leu Leu Thr Ile Pro Phe Ala Ala Ala Ala Gly
    50                  55                  60

Thr Ala Val Gln Asp Ser Arg Ser His Val Tyr Ala His Gln Ala Gln
65                  70                  75                  80

Thr Arg His Pro Ala Thr Ala Thr Val Ile Asp His Glu Gly Val Ile
                85                  90                  95

Asp Ser Asn Thr Thr Ala Thr Ser Ala Pro Pro Arg Thr Lys Ile Thr
            100                 105                 110

Val Pro Ala Arg Trp Val Val Asn Gly Ile Glu Arg Ser Gly Glu Val
        115                 120                 125

Asn Ala Lys Pro Gly Thr Lys Ser Gly Asp Arg Val Gly Ile Trp Val
    130                 135                 140
```

-continued

```
Asp Ser Ala Gly Gln Leu Val Asp Glu Pro Ala Pro Pro Ala Arg Ala
145                 150                 155                 160

Ile Ala Asp Ala Ala Leu Ala Ala Leu Gly Leu Trp Leu Ser Val Ala
                165                 170                 175

Ala Val Ala Gly Ala Leu Leu Ala Leu Thr Arg Ala Ile Leu Ile Arg
            180                 185                 190

Val Arg Asn Ala Ser Trp Gln His Asp Ile Asp Ser Leu Phe Cys Thr
        195                 200                 205

Gln Arg
    210


<210> SEQ ID NO 30
<211> LENGTH: 432
<212> TYPE: DNA
<213> ORGANISM: Mycobacterium tuberculosis
<220> FEATURE:
<223> OTHER INFORMATION: Rv2626c

<400> SEQUENCE: 30

atgaccaccg cacgcgacat catgaacgca ggtgtgacct gtgttggcga acacgagacg      60

ctaaccgctg ccgctcaata catgcgtgag cacgacatcg gcgcgttgcc gatctgcggg     120

gacgacgacc ggctgcacgg catgctcacc gaccgcgaca ttgtgatcaa aggcctggct     180

gcgggcctag acccgaatac cgccacggct ggcgagttgg cccgggacag catctactac     240

gtcgatgcga acgcaagcat ccaggagatg ctcaacgtca tggaagaaca tcaggtccgc     300

cgtgttccgg tcatctcaga gcaccgcttg gtcggaatcg tcaccgaagc cgacatcgcc     360

cgacacctgc ccgagcacgc cattgtgcag ttcgtcaagg caatctgctc gcccatggcc     420

ctcgccagct ag                                                         432


<210> SEQ ID NO 31
<211> LENGTH: 143
<212> TYPE: PRT
<213> ORGANISM: Mycobacterium tuberculosis
<220> FEATURE:
<223> OTHER INFORMATION: Rv2626c

<400> SEQUENCE: 31

Met Thr Thr Ala Arg Asp Ile Met Asn Ala Gly Val Thr Cys Val Gly
1               5                   10                  15

Glu His Glu Thr Leu Thr Ala Ala Ala Gln Tyr Met Arg Glu His Asp
            20                  25                  30

Ile Gly Ala Leu Pro Ile Cys Gly Asp Asp Asp Arg Leu His Gly Met
        35                  40                  45

Leu Thr Asp Arg Asp Ile Val Ile Lys Gly Leu Ala Ala Gly Leu Asp
    50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
            100                 105                 110

Ile Val Thr Glu Ala Asp Ile Ala Arg His Leu Pro Glu His Ala Ile
        115                 120                 125

Val Gln Phe Val Lys Ala Ile Cys Ser Pro Met Ala Leu Ala Ser
    130                 135                 140
```

<210> SEQ ID NO 32
<211> LENGTH: 1224
<212> TYPE: DNA
<213> ORGANISM: Mycobacterium tuberculosis
<220> FEATURE:
<223> OTHER INFORMATION: RpfA

<400> SEQUENCE: 32
atgagtggac gccaccgtaa gcccaccaca tccaacgtca gcgtcgccaa gatcgccttt 60
accggcgcag tactcggtgg cggcggcatc gccatggccg ctcaggcgac cgcggccacc 120
gacggggaat gggatcaggt ggcccgctgc gagtcgggcg gcaactggtc gatcaacacc 180
ggcaacggtt acctcggtgg cttgcagttc actcaaagca cctgggccgc acatggtggc 240
ggcgagttcg ccccgtcggc tcagctggcc agccgggagc agcagattgc cgtcggtgag 300
cgggtgctgg ccacccaggg tcgcggcgcc tggccggtgt gcggccgcgg gttatcgaac 360
gcaacacccc gcgaagtgct tcccgcttcg gcagcgatgg acgctccgtt ggacgcggcc 420
gcggtcaacg gcgaaccagc accgctggcc ccgccgcccg ccgacccggc gccacccgtg 480
gaacttgccg ctaacgacct gcccgcaccg ctgggtgaac ccctcccggc agctcccgcc 540
gacccggcac cacccgccga cctggcacca cccgcgcccg ccgacgtcgc gccacccgtg 600
gaacttgccg taaacgacct gcccgcaccg ctgggtgaac ccctcccggc agctcccgcc 660
gacccggcac cacccgccga cctggcacca cccgcgcccg ccgacctggc gccacccgcg 720
cccgccgacc tggcgccacc cgcgcccgcc gacctggcac cacccgtgga acttgccgta 780
aacgacctgc ccgcgccgct gggtgaaccc ctcccggcag ctcccgccga actggcgcca 840
cccgccgatc tggcacccgc gtccgccgac ctggcgccac ccgcgcccgc cgacctggcg 900
ccacccgcgc ccgccgaact ggcgccaccc gcgcccgccg acctggcacc acccgctgcg 960
gtgaacgagc aaaccgcgcc gggcgatcag cccgccacag ctccaggcgg cccggttggc 1020
cttgccaccg atttggaact ccccgagccc gacccccaac cagctgacgc accgccgccc 1080
ggcgacgtca ccgaggcgcc cgccgaaacg ccccaagtct cgaacatcgc ctatacgaag 1140
aagctgtggc aggcgattcg ggcccaggac gtctgcggca acgatgcgct ggactcgctc 1200
gcacagccgt acgtcatcgg ctga 1224

<210> SEQ ID NO 33
<211> LENGTH: 407
<212> TYPE: PRT
<213> ORGANISM: Mycobacterium tuberculosis
<220> FEATURE:
<223> OTHER INFORMATION: RpfA

<400> SEQUENCE: 33

Met Ser Gly Arg His Arg Lys Pro Thr Thr Ser Asn Val Ser Val Ala
1 5 10 15

Lys Ile Ala Phe Thr Gly Ala Val Leu Gly Gly Gly Gly Ile Ala Met
20 25 30

Ala Ala Gln Ala Thr Ala Ala Thr Asp Gly Glu Trp Asp Gln Val Ala
35 40 45

Arg Cys Glu Ser Gly Gly Asn Trp Ser Ile Asn Thr Gly Asn Gly Tyr
50 55 60

Leu Gly Gly Leu Gln Phe Thr Gln Ser Thr Trp Ala Ala His Gly Gly
65 70 75 80

Gly Glu Phe Ala Pro Ser Ala Gln Leu Ala Ser Arg Glu Gln Gln Ile
85 90 95

```
Ala Val Gly Glu Arg Val Leu Ala Thr Gln Gly Arg Gly Ala Trp Pro
            100                 105                 110

Val Cys Gly Arg Gly Leu Ser Asn Ala Thr Pro Arg Glu Val Leu Pro
        115                 120                 125

Ala Ser Ala Ala Met Asp Ala Pro Leu Asp Ala Ala Ala Val Asn Gly
    130                 135                 140

Glu Pro Ala Pro Leu Ala Pro Pro Pro Ala Asp Pro Ala Pro Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Pro Ala Asp Leu Ala Pro Pro Ala
            180                 185                 190

Pro Ala Asp Val Ala Pro Pro Val Glu Leu Ala Val Asn Asp Leu Pro
        195                 200                 205

Ala Pro Leu Gly Glu Pro Leu Pro Ala Ala Pro Ala Asp Pro Ala Pro
    210                 215                 220

Pro Ala Asp Leu Ala Pro Pro Ala Pro Ala Asp Leu Ala Pro Pro Ala
225                 230                 235                 240

Pro Ala Asp Leu Ala Pro Pro Ala Pro Ala Asp Leu Ala Pro Pro Val
                245                 250                 255

Glu Leu Ala Val Asn Asp Leu Pro Ala Pro Leu Gly Glu Pro Leu Pro
            260                 265                 270

Ala Ala Pro Ala Glu Leu Ala Pro Pro Ala Asp Leu Ala Pro Ala Ser
        275                 280                 285

Ala Asp Leu Ala Pro Pro Ala Pro Ala Asp Leu Ala Pro Pro Ala Pro
    290                 295                 300

Ala Glu Leu Ala Pro Pro Ala Pro Ala Asp Leu Ala Pro Pro Ala Ala
305                 310                 315                 320

Val Asn Glu Gln Thr Ala Pro Gly Asp Gln Pro Ala Thr Ala Pro Gly
                325                 330                 335

Gly Pro Val Gly Leu Ala Thr Asp Leu Glu Leu Pro Glu Pro Asp Pro
            340                 345                 350

Gln Pro Ala Asp Ala Pro Pro Pro Gly Asp Val Thr Glu Ala Pro Ala
        355                 360                 365

Glu Thr Pro Gln Val Ser Asn Ile Ala Tyr Thr Lys Lys Leu Trp Gln
    370                 375                 380

Ala Ile Arg Ala Gln Asp Val Cys Gly Asn Asp Ala Leu Asp Ser Leu
385                 390                 395                 400

Ala Gln Pro Tyr Val Ile Gly
                405


<210> SEQ ID NO 34
<211> LENGTH: 531
<212> TYPE: DNA
<213> ORGANISM: Mycobacterium tuberculosis
<220> FEATURE:
<223> OTHER INFORMATION: RpfC

<400> SEQUENCE: 34

gtgcatcctt tgccggccga ccacggccgg tcgcggtgca atagacaccc gatctcacca      60

ctctctctaa tcggtaacgc ttcggccact tccggcgata tgtcgagcat gacaagaatc     120

gccaagccgc tcatcaagtc cgccatggcc gcaggactcg tcacggcatc catgtcgctc     180

tccaccgccg ttgcccacgc cggtcccagc ccgaactggg acgccgtcgc gcagtgcgaa     240

tccgggggca actgggcggc caacaccgga aacggcaaat acggcggact gcagttcaag     300
```

-continued

```
ccggccacct gggccgcatt cggcggtgtc ggcaacccag cagctgcctc tcgggaacaa    360

caaatcgcag ttgccaatcg ggttctcgcc gaacagggat tggacgcgtg gccgacgtgc    420

ggcgccgcct ctggccttcc gatcgcactg tggtcgaaac ccgcgcaggg catcaagcaa    480

atcatcaacg agatcatttg ggcaggcatt caggcaagta ttccgcgctg a             531


<210> SEQ ID NO 35
<211> LENGTH: 176
<212> TYPE: PRT
<213> ORGANISM: Mycobacterium tuberculosis
<220> FEATURE:
<223> OTHER INFORMATION: RpfC

<400> SEQUENCE: 35

Val His Pro Leu Pro Ala Asp His Gly Arg Ser Arg Cys Asn Arg His
1               5                   10                  15

Pro Ile Ser Pro Leu Ser Leu Ile Gly Asn Ala Ser Ala Thr Ser Gly
            20                  25                  30

Asp Met Ser Ser Met Thr Arg Ile Ala Lys Pro Leu Ile Lys Ser Ala
        35                  40                  45

Met Ala Ala Gly Leu Val Thr Ala Ser Met Ser Leu Ser Thr Ala Val
    50                  55                  60

Ala His Ala Gly Pro Ser Pro Asn Trp Asp Ala Val Ala Gln Cys Glu
65                  70                  75                  80

Ser Gly Gly Asn Trp Ala Ala Asn Thr Gly Asn Gly Lys Tyr Gly Gly
                85                  90                  95

Leu Gln Phe Lys Pro Ala Thr Trp Ala Ala Phe Gly Gly Val Gly Asn
            100                 105                 110

Pro Ala Ala Ala Ser Arg Glu Gln Gln Ile Ala Val Ala Asn Arg Val
        115                 120                 125

Leu Ala Glu Gln Gly Leu Asp Ala Trp Pro Thr Cys Gly Ala Ala Ser
    130                 135                 140

Gly Leu Pro Ile Ala Leu Trp Ser Lys Pro Ala Gln Gly Ile Lys Gln
145                 150                 155                 160

Ile Ile Asn Glu Ile Ile Trp Ala Gly Ile Gln Ala Ser Ile Pro Arg
                165                 170                 175


<210> SEQ ID NO 36
<211> LENGTH: 465
<212> TYPE: DNA
<213> ORGANISM: Mycobacterium tuberculosis
<220> FEATURE:
<223> OTHER INFORMATION: RpfD

<400> SEQUENCE: 36

atgacaccgg gtttgcttac tactgcgggt gctggccgac cacgtgacag gtgcgccagg     60

atcgtatgca cggtgttcat cgaaaccgcc gttgtcgcga ccatgtttgt cgcgttgttg    120

ggtctgtcca ccatcagctc gaaagccgac gacatcgatt gggacgccat cgcgcaatgc    180

gaatccggcg gcaattgggc ggccaacacc ggtaacgggt tatacggtgg tctgcagatc    240

agccaggcga cgtgggattc caacggtggt gtcgggtcgc cggcggccgc gagtccccag    300

caacagatcg aggtcgcaga caacattatg aaaacccaag gcccgggtgc gtggccgaaa    360

tgtagttctt gtagtcaggg agacgcaccg ctgggctcgc tcacccacat cctgacgttc    420

ctcgcggccg agactggagg ttgttcgggg agcagggacg attga                    465
```

```
<210> SEQ ID NO 37
<211> LENGTH: 154
<212> TYPE: PRT
<213> ORGANISM: Mycobacterium tuberculosis
<220> FEATURE:
<223> OTHER INFORMATION: RpfD

<400> SEQUENCE: 37

Met Thr Pro Gly Leu Leu Thr Thr Ala Gly Ala Gly Arg Pro Arg Asp
1               5                   10                  15

Arg Cys Ala Arg Ile Val Cys Thr Val Phe Ile Glu Thr Ala Val Val
            20                  25                  30

Ala Thr Met Phe Val Ala Leu Leu Gly Leu Ser Thr Ile Ser Ser Lys
        35                  40                  45

Ala Asp Asp Ile Asp Trp Asp Ala Ile Ala Gln Cys Glu Ser Gly Gly
    50                  55                  60

Asn Trp Ala Ala Asn Thr Gly Asn Gly Leu Tyr Gly Gly Leu Gln Ile
65                  70                  75                  80

Ser Gln Ala Thr Trp Asp Ser Asn Gly Gly Val Gly Ser Pro Ala Ala
                85                  90                  95

Ala Ser Pro Gln Gln Gln Ile Glu Val Ala Asp Asn Ile Met Lys Thr
            100                 105                 110

Gln Gly Pro Gly Ala Trp Pro Lys Cys Ser Ser Cys Ser Gln Gly Asp
        115                 120                 125

Ala Pro Leu Gly Ser Leu Thr His Ile Leu Thr Phe Leu Ala Ala Glu
    130                 135                 140

Thr Gly Gly Cys Ser Gly Ser Arg Asp Asp
145                 150


<210> SEQ ID NO 38
<211> LENGTH: 2487
<212> TYPE: DNA
<213> ORGANISM: Mycobacterium tuberculosis
<220> FEATURE:
<223> OTHER INFORMATION: Rv1009-Rv3615c-Rv3136

<400> SEQUENCE: 38

atggcatgca aaacggtgac gttgaccgtc gacggaaccg cgatgcgggt gaccacgatg      60

aaatcgcggg tgatcgacat cgtcgaagag aacgggttct cagtcgacga ccgcgacgac     120

ctgtatcccg cggccggcgt gcaggtccat gacgccgaca ccatcgtgct gcggcgtagc     180

cgtccgctgc agatctcgct ggatggtcac gacgctaagc aggtgtggac gaccgcgtcg     240

acggtggacg aggcgctggc ccaactcgcg atgaccgaca cggcgccggc cgcggcttct     300

cgcgccagcc gcgtcccgct gtccgggatg gcgctaccgg tcgtcagcgc caagacggtg     360

cagctcaacg acggcgggtt ggtgcgcacg gtgcacttgc cggcccccaa tgtcgcgggg     420

ctgctgagtg cggccggcgt gccgctgttg caaagcgacc acgtggtgcc cgccgcgacg     480

gccccgatcg tcgaaggcat gcagatccag gtgacccgca atcggatcaa gaaggtcacc     540

gagcggctgc cgctgccgcc gaacgcgcgt cgtgtcgagg acccggagat gaacatgagc     600

cgggaggtcg tcgaagaccc gggggttccg gggacccagg atgtgacgtt cgcggtagct     660

gaggtcaacg gcgtcgagac cggccgtttg cccgtcgcca acgtcgtggt gaccccggcc     720

cacgaagccg tggtgcgggt gggcaccaag cccggtaccg aggtgccccc ggtgatcgac     780

ggaagcatct gggacgcgat cgccggctgt gaggccggtg gcaactgggc gatcaacacc     840

ggcaacgggt attacggtgg tgtgcagttt gaccagggca cctgggaggc caacggcggg     900
```

```
ctgcggtatg caccccgcgc tgacctcgcc acccgcgaag agcagatcgc cgttgccgag    960

gtgacccgac tgcgtcaagg ttggggcgcc tggccggtat gtgctgcacg agcgggtgcg   1020

cgcgaattca tgacggaaaa cttgaccgtc cagcccgagc gtctcggtgt actggcgtcg   1080

caccatgaca acgcggcggt cgatgcctcc tcgggcgtcg aagctgccgc tggcctaggc   1140

gaatctgtgg cgatcactca cggtccgtac tgctcacagt tcaacgacac gttaaatgtg   1200

tacttgactg cccacaatgc cctgggctcg tccttgcata cggccggtgt cgatctcgcc   1260

aaaagtcttc gaattgcggc gaagatatat agcgaggccg acgaagcgtg gcgcaaggct   1320

atcgacgggt tgtttaccaa gcttatggat ttcgcactgt taccaccgga agtcaactcc   1380

gcccggatgt acaccggccc tggggcagga tcgctgttgg ctgccgcggg cggctgggat   1440

tcgctggccg ccgagttggc caccacagcc gaggcatatg gatcggtgct gtccggactg   1500

gccgccttgc attggcgtgg accggcagcg gaatcgatgg cggtgacggc cgctccctat   1560

atcggttggc tgtacacgac cgccgaaaag acacagcaaa cagcgatcca agccagggcg   1620

gcagcgctgg ccttcgagca agcatacgca atgaccctgc cgccaccggt ggtagcggcc   1680

aaccggatac agctgctagc actgatcgcg acgaacttct tcggccagaa cactgcggcg   1740

atcgcggcca ccgaggcaca gtacgccgag atgtgggccc aggacgccgc cgcgatgtac   1800

ggttacgcca ccgcctcagc ggctgcggcc ctgctgacac cgttctcccc gccgcggcag   1860

accaccaacc cggccggcct gaccgctcag gccgccgcgg tcagccaggc caccgaccca   1920

ctgtcgctgc tgattgagac ggtgacccaa gcgctgcaag cgctgacgat tccgagcttc   1980

atccctgagg acttcacctt ccttgacgcc atattcgctg gatatgccac ggtaggtgtg   2040

acgcaggatg tcgagtcctt tgttgccggg accatcgggg ccgagagcaa cctaggcctt   2100

ttgaacgtcg gcgacgagaa tcccgcggag gtgacaccgg gcgactttgg gatcggcgag   2160

ttggtttccg cgaccagtcc cggcggtggg gtgtctgcgt cgggtgccgg cggtgcggcg   2220

agcgtcggca acacggtgct cgcgagtgtc ggccgggcaa actcgattgg gcaactatcg   2280

gtcccaccga gctgggccgc gccctcgacg cgccctgtct cggcattgtc gcccgccggc   2340

ctgaccacac tcccggggac cgacgtggcc gagcacggga tgccaggtgt accgggggtg   2400

ccagtggcag cagggcgagc ctccggcgtc ctacctcgat acggggttcg gctcacggtg   2460

atggcccacc cacccgcggc agggtaa                                       2487
```

<210> SEQ ID NO 39
<211> LENGTH: 828
<212> TYPE: PRT
<213> ORGANISM: Mycobacterium tuberculosis
<220> FEATURE:
<223> OTHER INFORMATION: Rv1009-Rv3615c-Rv3136

<400> SEQUENCE: 39

```
Met Ala Cys Lys Thr Val Thr Leu Thr Val Asp Gly Thr Ala Met Arg
1               5                   10                  15

Val Thr Thr Met Lys Ser Arg Val Ile Asp Ile Val Glu Glu Asn Gly
            20                  25                  30

Phe Ser Val Asp Asp Arg Asp Asp Leu Tyr Pro Ala Ala Gly Val Gln
        35                  40                  45

Val His Asp Ala Asp Thr Ile Val Leu Arg Arg Ser Arg Pro Leu Gln
    50                  55                  60

Ile Ser Leu Asp Gly His Asp Ala Lys Gln Val Trp Thr Thr Ala Ser
65                  70                  75                  80
```

-continued

```
Thr Val Asp Glu Ala Leu Ala Gln Leu Ala Met Thr Asp Thr Ala Pro
                85                  90                  95

Ala Ala Ala Ser Arg Ala Ser Arg Val Pro Leu Ser Gly Met Ala Leu
            100                 105                 110

Pro Val Val Ser Ala Lys Thr Val Gln Leu Asn Asp Gly Gly Leu Val
        115                 120                 125

Arg Thr Val His Leu Pro Ala Pro Asn Val Ala Gly Leu Leu Ser Ala
    130                 135                 140

Ala Gly Val Pro Leu Leu Gln Ser Asp His Val Val Pro Ala Ala Thr
145                 150                 155                 160

Ala Pro Ile Val Glu Gly Met Gln Ile Gln Val Thr Arg Asn Arg Ile
                165                 170                 175

Lys Lys Val Thr Glu Arg Leu Pro Leu Pro Pro Asn Ala Arg Arg Val
            180                 185                 190

Glu Asp Pro Glu Met Asn Met Ser Arg Glu Val Val Glu Asp Pro Gly
        195                 200                 205

Val Pro Gly Thr Gln Asp Val Thr Phe Ala Val Ala Glu Val Asn Gly
    210                 215                 220

Val Glu Thr Gly Arg Leu Pro Val Ala Asn Val Val Val Thr Pro Ala
225                 230                 235                 240

His Glu Ala Val Val Arg Val Gly Thr Lys Pro Gly Thr Glu Val Pro
                245                 250                 255

Pro Val Ile Asp Gly Ser Ile Trp Asp Ala Ile Ala Gly Cys Glu Ala
            260                 265                 270

Gly Gly Asn Trp Ala Ile Asn Thr Gly Asn Gly Tyr Tyr Gly Gly Val
        275                 280                 285

Gln Phe Asp Gln Gly Thr Trp Glu Ala Asn Gly Gly Leu Arg Tyr Ala
    290                 295                 300

Pro Arg Ala Asp Leu Ala Thr Arg Glu Glu Gln Ile Ala Val Ala Glu
305                 310                 315                 320

Val Thr Arg Leu Arg Gln Gly Trp Gly Ala Trp Pro Val Cys Ala Ala
                325                 330                 335

Arg Ala Gly Ala Arg Glu Phe Met Thr Glu Asn Leu Thr Val Gln Pro
            340                 345                 350

Glu Arg Leu Gly Val Leu Ala Ser His His Asp Asn Ala Ala Val Asp
        355                 360                 365

Ala Ser Ser Gly Val Glu Ala Ala Ala Gly Leu Gly Glu Ser Val Ala
    370                 375                 380

Ile Thr His Gly Pro Tyr Cys Ser Gln Phe Asn Asp Thr Leu Asn Val
385                 390                 395                 400

Tyr Leu Thr Ala His Asn Ala Leu Gly Ser Ser Leu His Thr Ala Gly
                405                 410                 415

Val Asp Leu Ala Lys Ser Leu Arg Ile Ala Ala Lys Ile Tyr Ser Glu
            420                 425                 430

Ala Asp Glu Ala Trp Arg Lys Ala Ile Asp Gly Leu Phe Thr Lys Leu
        435                 440                 445

Met Asp Phe Ala Leu Leu Pro Pro Glu Val Asn Ser Ala Arg Met Tyr
    450                 455                 460

Thr Gly Pro Gly Ala Gly Ser Leu Leu Ala Ala Ala Gly Gly Trp Asp
465                 470                 475                 480

Ser Leu Ala Ala Glu Leu Ala Thr Thr Ala Glu Ala Tyr Gly Ser Val
                485                 490                 495

Leu Ser Gly Leu Ala Ala Leu His Trp Arg Gly Pro Ala Ala Glu Ser
```

-continued

```
            500                 505                 510

Met Ala Val Thr Ala Ala Pro Tyr Ile Gly Trp Leu Tyr Thr Thr Ala
        515                 520                 525

Glu Lys Thr Gln Gln Thr Ala Ile Gln Ala Arg Ala Ala Ala Leu Ala
    530                 535                 540

Phe Glu Gln Ala Tyr Ala Met Thr Leu Pro Pro Pro Val Val Ala Ala
545                 550                 555                 560

Asn Arg Ile Gln Leu Leu Ala Leu Ile Ala Thr Asn Phe Phe Gly Gln
                565                 570                 575

Asn Thr Ala Ala Ile Ala Ala Thr Glu Ala Gln Tyr Ala Glu Met Trp
            580                 585                 590

Ala Gln Asp Ala Ala Ala Met Tyr Gly Tyr Ala Thr Ala Ser Ala Ala
        595                 600                 605

Ala Ala Leu Leu Thr Pro Phe Ser Pro Pro Arg Gln Thr Thr Asn Pro
    610                 615                 620

Ala Gly Leu Thr Ala Gln Ala Ala Ala Val Ser Gln Ala Thr Asp Pro
625                 630                 635                 640

Leu Ser Leu Leu Ile Glu Thr Val Thr Gln Ala Leu Gln Ala Leu Thr
                645                 650                 655

Ile Pro Ser Phe Ile Pro Glu Asp Phe Thr Phe Leu Asp Ala Ile Phe
            660                 665                 670

Ala Gly Tyr Ala Thr Val Gly Val Thr Gln Asp Val Glu Ser Phe Val
        675                 680                 685

Ala Gly Thr Ile Gly Ala Glu Ser Asn Leu Gly Leu Leu Asn Val Gly
    690                 695                 700

Asp Glu Asn Pro Ala Glu Val Thr Pro Gly Asp Phe Gly Ile Gly Glu
705                 710                 715                 720

Leu Val Ser Ala Thr Ser Pro Gly Gly Gly Val Ser Ala Ser Gly Ala
                725                 730                 735

Gly Gly Ala Ala Ser Val Gly Asn Thr Val Leu Ala Ser Val Gly Arg
            740                 745                 750

Ala Asn Ser Ile Gly Gln Leu Ser Val Pro Pro Ser Trp Ala Ala Pro
        755                 760                 765

Ser Thr Arg Pro Val Ser Ala Leu Ser Pro Ala Gly Leu Thr Thr Leu
    770                 775                 780

Pro Gly Thr Asp Val Ala Glu His Gly Met Pro Gly Val Pro Gly Val
785                 790                 795                 800

Pro Val Ala Ala Gly Arg Ala Ser Gly Val Leu Pro Arg Tyr Gly Val
                805                 810                 815

Arg Leu Thr Val Met Ala His Pro Pro Ala Ala Gly
            820                 825
```

<210> SEQ ID NO 40
<211> LENGTH: 2499
<212> TYPE: DNA
<213> ORGANISM: Mycobacterium tuberculosis
<220> FEATURE:
<223> OTHER INFORMATION: Rv1009-Rv2034-Rv3136

<400> SEQUENCE: 40

```
atggcatgca aaacggtgac gttgaccgtc gacggaaccg cgatgcgggt gaccacgatg      60

aaatcgcggg tgatcgacat cgtcgaagag aacgggttct cagtcgacga ccgcgacgac     120

ctgtatcccg cggccggcgt gcaggtccat gacgccgaca ccatcgtgct gcggcgtagc     180

cgtccgctgc agatctcgct ggatggtcac gacgctaagc aggtgtggac gaccgcgtcg     240
```

```
acggtggacg aggcgctggc ccaactcgcg atgaccgaca cggcgccggc cgcggcttct    300
cgcgccagcc gcgtcccgct gtccgggatg gcgctaccgg tcgtcagcgc caagacggtg    360
cagctcaacg acggcgggtt ggtgcgcacg gtgcacttgc cggcccccaa tgtcgcgggg    420
ctgctgagtg cggccggcgt gccgctgttg caaagcgacc acgtggtgcc cgccgcgacg    480
gccccgatcg tcgaaggcat gcagatccag gtgacccgca atcggatcaa gaaggtcacc    540
gagcggctgc cgctgccgcc gaacgcgcgt cgtgtcgagg acccggagat gaacatgagc    600
cgggaggtcg tcgaagaccc gggggttccg gggacccagg atgtgacgtt cgcggtagct    660
gaggtcaacg gcgtcgagac cggccgtttg cccgtcgcca acgtcgtggt gaccccggcc    720
cacgaagccg tggtgcgggt gggcaccaag cccggtaccg aggtgccccc ggtgatcgac    780
ggaagcatct gggacgcgat cgccggctgt gaggccggtg gcaactgggc gatcaacacc    840
ggcaacgggt attacggtgg tgtgcagttt gaccagggca cctgggaggc caacggcggg    900
ctgcggtatg caccccgcgc tgacctcgcc acccgcgaag agcagatcgc cgttgccgag    960
gtgacccgac tgcgtcaagg ttggggcgcc tggccggtat gtgctgcacg agcgggtgcg   1020
cgcgaattcg tgtccactta cagatcaccg gatcgcgctt ggcaggcgct ggcggacggc   1080
actcgccggg ccatcgtgga gcggctggcg cacggcccgc tggccgtcgg cgagttggcc   1140
cgcgacctgc ccgtcagccg acccgcggtg tcacagcacc tcaaagtgct caagaccgcc   1200
aggctggtgt gcgaccgccc cgcgggaaca cgccgcgtct accagctcga cccgacaggc   1260
cttgcggcat tgcgcaccga cctcgaccgg ttctggacac gcgccctgac tggctacgcg   1320
cagctcatcg actccgaagg agacgacaca aagcttatgg atttcgcact gttaccaccg   1380
gaagtcaact ccgcccggat gtacaccggc cctggggcag gatcgctgtt ggctgccgcg   1440
ggcggctggg attcgctggc cgccgagttg gccaccacag ccgaggcata tggatcggtg   1500
ctgtccggac tggccgcctt gcattggcgt ggaccggcag cggaatcgat ggcggtgacg   1560
gccgctccct atatcggttg gctgtacacg accgccgaaa agacacagca aacagcgatc   1620
caagccaggg cggcagcgct ggccttcgag caagcatacg caatgaccct gccgccaccg   1680
gtggtagcgg ccaaccggat acagctgcta gcactgatcg cgacgaactt cttcggccag   1740
aacactgcgg cgatcgcggc caccgaggca cagtacgccg agatgtgggc ccaggacgcc   1800
gccgcgatgt acggttacgc caccgcctca gcggctgcgg ccctgctgac accgttctcc   1860
ccgccgcggc agaccaccaa cccggccggc ctgaccgctc aggccgccgc ggtcagccag   1920
gccaccgacc cactgtcgct gctgattgag acggtgaccc aagcgctgca agcgctgacg   1980
attccgagct tcatccctga ggacttcacc ttccttgacg ccatattcgc tggatatgcc   2040
acggtaggtg tgacgcagga tgtcgagtcc tttgttgccg ggaccatcgg ggccgagagc   2100
aacctaggcc ttttgaacgt cggcgacgag aatcccgcgg aggtgacacc gggcgacttt   2160
gggatcggcg agttggtttc cgcgaccagt cccggcggtg gggtgtctgc gtcgggtgcc   2220
ggcggtgcgg cgagcgtcgg caacacggtg ctcgcgagtg tcggccgggc aaactcgatt   2280
gggcaactat cggtcccacc gagctgggcc gcgccctcga cgcgccctgt ctcggcattg   2340
tcgcccgccg gcctgaccac actcccgggg accgacgtgg ccgagcacgg gatgccaggt   2400
gtaccggggg tgccagtggc agcagggcga gcctccggcg tcctacctcg atacggggtt   2460
cggctcacgg tgatggccca cccacccgcg gcagggtaa                           2499
```

<210> SEQ ID NO 41

-continued

<211> LENGTH: 832
<212> TYPE: PRT
<213> ORGANISM: Mycobacterium tuberculosis
<220> FEATURE:
<223> OTHER INFORMATION: Rv1009-Rv2034-Rv3136

<400> SEQUENCE: 41

Met Ala Cys Lys Thr Val Thr Leu Thr Val Asp Gly Thr Ala Met Arg
1 5 10 15

Val Thr Thr Met Lys Ser Arg Val Ile Asp Ile Val Glu Glu Asn Gly
20 25 30

Phe Ser Val Asp Asp Arg Asp Asp Leu Tyr Pro Ala Ala Gly Val Gln
35 40 45

Val His Asp Ala Asp Thr Ile Val Leu Arg Arg Ser Arg Pro Leu Gln
50 55 60

Ile Ser Leu Asp Gly His Asp Ala Lys Gln Val Trp Thr Thr Ala Ser
65 70 75 80

Thr Val Asp Glu Ala Leu Ala Gln Leu Ala Met Thr Asp Thr Ala Pro
85 90 95

Ala Ala Ala Ser Arg Ala Ser Arg Val Pro Leu Ser Gly Met Ala Leu
100 105 110

Pro Val Val Ser Ala Lys Thr Val Gln Leu Asn Asp Gly Gly Leu Val
115 120 125

Arg Thr Val His Leu Pro Ala Pro Asn Val Ala Gly Leu Leu Ser Ala
130 135 140

Ala Gly Val Pro Leu Leu Gln Ser Asp His Val Val Pro Ala Ala Thr
145 150 155 160

Ala Pro Ile Val Glu Gly Met Gln Ile Gln Val Thr Arg Asn Arg Ile
165 170 175

Lys Lys Val Thr Glu Arg Leu Pro Leu Pro Pro Asn Ala Arg Arg Val
180 185 190

Glu Asp Pro Glu Met Asn Met Ser Arg Glu Val Val Glu Asp Pro Gly
195 200 205

Val Pro Gly Thr Gln Asp Val Thr Phe Ala Val Ala Glu Val Asn Gly
210 215 220

Val Glu Thr Gly Arg Leu Pro Val Ala Asn Val Val Val Thr Pro Ala
225 230 235 240

His Glu Ala Val Val Arg Val Gly Thr Lys Pro Gly Thr Glu Val Pro
245 250 255

Pro Val Ile Asp Gly Ser Ile Trp Asp Ala Ile Ala Gly Cys Glu Ala
260 265 270

Gly Gly Asn Trp Ala Ile Asn Thr Gly Asn Gly Tyr Tyr Gly Gly Val
275 280 285

Gln Phe Asp Gln Gly Thr Trp Glu Ala Asn Gly Gly Leu Arg Tyr Ala
290 295 300

Pro Arg Ala Asp Leu Ala Thr Arg Glu Glu Gln Ile Ala Val Ala Glu
305 310 315 320

Val Thr Arg Leu Arg Gln Gly Trp Gly Ala Trp Pro Val Cys Ala Ala
325 330 335

Arg Ala Gly Ala Arg Glu Phe Val Ser Thr Tyr Arg Ser Pro Asp Arg
340 345 350

Ala Trp Gln Ala Leu Ala Asp Gly Thr Arg Arg Ala Ile Val Glu Arg
355 360 365

Leu Ala His Gly Pro Leu Ala Val Gly Glu Leu Ala Arg Asp Leu Pro
370 375 380

-continued

```
Val Ser Arg Pro Ala Val Ser Gln His Leu Lys Val Leu Lys Thr Ala
385                 390                 395                 400

Arg Leu Val Cys Asp Arg Pro Ala Gly Thr Arg Arg Val Tyr Gln Leu
                405                 410                 415

Asp Pro Thr Gly Leu Ala Ala Leu Arg Thr Asp Leu Asp Arg Phe Trp
            420                 425                 430

Thr Arg Ala Leu Thr Gly Tyr Ala Gln Leu Ile Asp Ser Glu Gly Asp
        435                 440                 445

Asp Thr Lys Leu Met Asp Phe Ala Leu Leu Pro Pro Glu Val Asn Ser
    450                 455                 460

Ala Arg Met Tyr Thr Gly Pro Gly Ala Gly Ser Leu Leu Ala Ala Ala
465                 470                 475                 480

Gly Gly Trp Asp Ser Leu Ala Ala Glu Leu Ala Thr Thr Ala Glu Ala
                485                 490                 495

Tyr Gly Ser Val Leu Ser Gly Leu Ala Ala Leu His Trp Arg Gly Pro
            500                 505                 510

Ala Ala Glu Ser Met Ala Val Thr Ala Ala Pro Tyr Ile Gly Trp Leu
        515                 520                 525

Tyr Thr Thr Ala Glu Lys Thr Gln Gln Thr Ala Ile Gln Ala Arg Ala
    530                 535                 540

Ala Ala Leu Ala Phe Glu Gln Ala Tyr Ala Met Thr Leu Pro Pro Pro
545                 550                 555                 560

Val Val Ala Ala Asn Arg Ile Gln Leu Leu Ala Leu Ile Ala Thr Asn
                565                 570                 575

Phe Phe Gly Gln Asn Thr Ala Ala Ile Ala Ala Thr Glu Ala Gln Tyr
            580                 585                 590

Ala Glu Met Trp Ala Gln Asp Ala Ala Ala Met Tyr Gly Tyr Ala Thr
        595                 600                 605

Ala Ser Ala Ala Ala Ala Leu Leu Thr Pro Phe Ser Pro Pro Arg Gln
    610                 615                 620

Thr Thr Asn Pro Ala Gly Leu Thr Ala Gln Ala Ala Ala Val Ser Gln
625                 630                 635                 640

Ala Thr Asp Pro Leu Ser Leu Leu Ile Glu Thr Val Thr Gln Ala Leu
                645                 650                 655

Gln Ala Leu Thr Ile Pro Ser Phe Ile Pro Glu Asp Phe Thr Phe Leu
            660                 665                 670

Asp Ala Ile Phe Ala Gly Tyr Ala Thr Val Gly Val Thr Gln Asp Val
        675                 680                 685

Glu Ser Phe Val Ala Gly Thr Ile Gly Ala Glu Ser Asn Leu Gly Leu
    690                 695                 700

Leu Asn Val Gly Asp Glu Asn Pro Ala Glu Val Thr Pro Gly Asp Phe
705                 710                 715                 720

Gly Ile Gly Glu Leu Val Ser Ala Thr Ser Pro Gly Gly Gly Val Ser
                725                 730                 735

Ala Ser Gly Ala Gly Gly Ala Ala Ser Val Gly Asn Thr Val Leu Ala
            740                 745                 750

Ser Val Gly Arg Ala Asn Ser Ile Gly Gln Leu Ser Val Pro Pro Ser
        755                 760                 765

Trp Ala Ala Pro Ser Thr Arg Pro Val Ser Ala Leu Ser Pro Ala Gly
    770                 775                 780

Leu Thr Thr Leu Pro Gly Thr Asp Val Ala Glu His Gly Met Pro Gly
785                 790                 795                 800
```

-continued

```
Val Pro Gly Val Pro Val Ala Ala Gly Arg Ala Ser Gly Val Leu Pro
                805                 810                 815

Arg Tyr Gly Val Arg Leu Thr Val Met Ala His Pro Pro Ala Ala Gly
            820                 825                 830


<210> SEQ ID NO 42
<211> LENGTH: 2853
<212> TYPE: DNA
<213> ORGANISM: Mycobacterium tuberculosis
<220> FEATURE:
<223> OTHER INFORMATION: Rv1009-Rv2628-Rv3615c-Rv3136

<400> SEQUENCE: 42

atggcatgca aaacggtgac gttgaccgtc gacggaaccg cgatgcgggt gaccacgatg      60

aaatcgcggg tgatcgacat cgtcgaagag aacgggttct cagtcgacga ccgcgacgac     120

ctgtatcccg cggccggcgt gcaggtccat gacgccgaca ccatcgtgct gcggcgtagc     180

cgtccgctgc agatctcgct ggatggtcac gacgctaagc aggtgtggac gaccgcgtcg     240

acggtggacg aggcgctggc ccaactcgcg atgaccgaca cggcgccggc cgcggcttct     300

cgcgccagcc gcgtcccgct gtccgggatg gcgctaccgg tcgtcagcgc caagacggtg     360

cagctcaacg acggcgggtt ggtgcgcacg gtgcacttgc cggcccccaa tgtcgcgggg     420

ctgctgagtg cggccggcgt gccgctgttg caaagcgacc acgtggtgcc cgccgcgacg     480

gccccgatcg tcgaaggcat gcagatccag gtgacccgca atcggatcaa gaaggtcacc     540

gagcggctgc cgctgccgcc gaacgcgcgt cgtgtcgagg acccggagat gaacatgagc     600

cgggaggtcg tcgaagaccc gggggttccg gggacccagg atgtgacgtt cgcggtagct     660

gaggtcaacg gcgtcgagac cggccgtttg cccgtcgcca acgtcgtggt gaccccggcc     720

cacgaagccg tggtgcgggt gggcaccaag cccggtaccg aggtgccccc ggtgatcgac     780

ggaagcatct gggacgcgat cgccggctgt gaggccggtg gcaactgggc gatcaacacc     840

ggcaacgggt attacggtgg tgtgcagttt gaccagggca cctgggaggc caacggcggg     900

ctgcggtatg caccccgcgc tgacctcgcc acccgcgaag agcagatcgc cgttgccgag     960

gtgacccgac tgcgtcaagg ttggggcgcc tggccggtat gtgctgcacg agcgggtgcg    1020

cgcgaattca tgtccacgca acgaccgagg cactccggta ttcgggctgt tggcccctac    1080

gcatgggccg gccgatgtgg tcggatagc aggtgggggg tgcaccagga ggcgatgatg    1140

aatctagcga tatggcaccc gcgcaaggtg caatccgcca ccatctatca ggtgaccgat    1200

cgctcgcacg acgggcgcac agcacgggtg cctggtgacg agatcactag caccgtgtcc    1260

ggttggttgt cggagttggg cacccaaagc ccgttggccg atgagcttgc gcgtgcggtg    1320

cggatcggcg actggcccgc tgcgtacgca atcggtgagc acctgtccgt tgagattgcc    1380

gttgcggtcg agctcatgac ggaaaacttg accgtccagc ccgagcgtct cggtgtactg    1440

gcgtcgcacc atgacaacgc ggcggtcgat gcctcctcgg gcgtcgaagc tgccgctggc    1500

ctaggcgaat ctgtggcgat cactcacggt ccgtactgct cacagttcaa cgacacgtta    1560

aatgtgtact tgactgccca caatgccctg ggctcgtcct tgcatacggc cggtgtcgat    1620

ctcgccaaaa gtcttcgaat tgcggcgaag atatatagcg aggccgacga agcgtggcgc    1680

aaggctatcg acgggttgtt taccaagctt atggatttcg cactgttacc accggaagtc    1740

aactccgccc ggatgtacac cggccctggg gcaggatcgc tgttggctgc cgcgggcggc    1800

tgggattcgc tggccgccga gttggccacc acagccgagg catatggatc ggtgctgtcc    1860

ggactggccg ccttgcattg gcgtggaccg gcagcggaat cgatggcggt gacggccgct    1920
```

-continued ccctatatcg gttggctgta cacgaccgcc gaaaagacac agcaaacagc gatccaagcc 1980
agggcggcag cgctggcctt cgagcaagca tacgcaatga ccctgccgcc accggtggta 2040
gcggccaacc ggatacagct gctagcactg atcgcgacga acttcttcgg ccagaacact 2100
gcggcgatcg cggccaccga ggcacagtac gccgagatgt gggcccagga cgccgccgcg 2160
atgtacggtt acgccaccgc ctcagcggct gcggccctgc tgacaccgtt ctccccgccg 2220
cggcagacca ccaacccggc cggcctgacc gctcaggccg ccgcggtcag ccaggccacc 2280
gacccactgt cgctgctgat tgagacggtg acccaagcgc tgcaagcgct gacgattccg 2340
agcttcatcc ctgaggactt caccttcctt gacgccatat tcgctggata tgccacggta 2400
ggtgtgacgc aggatgtcga gtcctttgtt gccgggacca tcggggccga gagcaaccta 2460
ggccttttga acgtcggcga cgagaatccc gcggaggtga caccgggcga ctttgggatc 2520
ggcgagttgg tttccgcgac cagtcccggc ggtggggtgt ctgcgtcggg tgccggcggt 2580
gcggcgagcg tcggcaacac ggtgctcgcg agtgtcggcc gggcaaactc gattgggcaa 2640
ctatcggtcc caccgagctg ggccgcgccc tcgacgcgcc ctgtctcggc attgtcgccc 2700
gccggcctga ccacactccc ggggaccgac gtggccgagc acgggatgcc aggtgtaccg 2760
ggggtgccag tggcagcagg gcgagcctcc ggcgtcctac ctcgatacgg ggttcggctc 2820
acggtgatgg cccacccacc cgcggcaggg taa 2853

<210> SEQ ID NO 43
<211> LENGTH: 950
<212> TYPE: PRT
<213> ORGANISM: Mycobacterium tuberculosis
<220> FEATURE:
<223> OTHER INFORMATION: Rv1009-Rv2628-Rv3615c-Rv3136

<400> SEQUENCE: 43

Met Ala Cys Lys Thr Val Thr Leu Thr Val Asp Gly Thr Ala Met Arg
1               5                   10                  15

Val Thr Thr Met Lys Ser Arg Val Ile Asp Ile Val Glu Glu Asn Gly
            20                  25                  30

Phe Ser Val Asp Asp Arg Asp Asp Leu Tyr Pro Ala Ala Gly Val Gln
        35                  40                  45

Val His Asp Ala Asp Thr Ile Val Leu Arg Arg Ser Arg Pro Leu Gln
    50                  55                  60

Ile Ser Leu Asp Gly His Asp Ala Lys Gln Val Trp Thr Thr Ala Ser
65                  70                  75                  80

Thr Val Asp Glu Ala Leu Ala Gln Leu Ala Met Thr Asp Thr Ala Pro
                85                  90                  95

Ala Ala Ala Ser Arg Ala Ser Arg Val Pro Leu Ser Gly Met Ala Leu
            100                 105                 110

Pro Val Val Ser Ala Lys Thr Val Gln Leu Asn Asp Gly Gly Leu Val
        115                 120                 125

Arg Thr Val His Leu Pro Ala Pro Asn Val Ala Gly Leu Leu Ser Ala
    130                 135                 140

Ala Gly Val Pro Leu Leu Gln Ser Asp His Val Val Pro Ala Ala Thr
145                 150                 155                 160

Ala Pro Ile Val Glu Gly Met Gln Ile Gln Val Thr Arg Asn Arg Ile
                165                 170                 175

Lys Lys Val Thr Glu Arg Leu Pro Leu Pro Pro Asn Ala Arg Arg Val
            180                 185                 190

```
Glu Asp Pro Glu Met Asn Met Ser Arg Glu Val Val Glu Asp Pro Gly
        195                 200                 205

Val Pro Gly Thr Gln Asp Val Thr Phe Ala Val Ala Glu Val Asn Gly
    210                 215                 220

Val Glu Thr Gly Arg Leu Pro Val Ala Asn Val Val Val Thr Pro Ala
225                 230                 235                 240

His Glu Ala Val Val Arg Val Gly Thr Lys Pro Gly Thr Glu Val Pro
                245                 250                 255

Pro Val Ile Asp Gly Ser Ile Trp Asp Ala Ile Ala Gly Cys Glu Ala
            260                 265                 270

Gly Gly Asn Trp Ala Ile Asn Thr Gly Asn Gly Tyr Tyr Gly Gly Val
        275                 280                 285

Gln Phe Asp Gln Gly Thr Trp Glu Ala Asn Gly Gly Leu Arg Tyr Ala
    290                 295                 300

Pro Arg Ala Asp Leu Ala Thr Arg Glu Glu Gln Ile Ala Val Ala Glu
305                 310                 315                 320

Val Thr Arg Leu Arg Gln Gly Trp Gly Ala Trp Pro Val Cys Ala Ala
                325                 330                 335

Arg Ala Gly Ala Arg Glu Phe Met Ser Thr Gln Arg Pro Arg His Ser
            340                 345                 350

Gly Ile Arg Ala Val Gly Pro Tyr Ala Trp Ala Gly Arg Cys Gly Arg
        355                 360                 365

Ile Gly Arg Trp Gly Val His Gln Glu Ala Met Met Asn Leu Ala Ile
    370                 375                 380

Trp His Pro Arg Lys Val Gln Ser Ala Thr Ile Tyr Gln Val Thr Asp
385                 390                 395                 400

Arg Ser His Asp Gly Arg Thr Ala Arg Val Pro Gly Asp Glu Ile Thr
                405                 410                 415

Ser Thr Val Ser Gly Trp Leu Ser Glu Leu Gly Thr Gln Ser Pro Leu
            420                 425                 430

Ala Asp Glu Leu Ala Arg Ala Val Arg Ile Gly Asp Trp Pro Ala Ala
        435                 440                 445

Tyr Ala Ile Gly Glu His Leu Ser Val Glu Ile Ala Val Ala Val Glu
    450                 455                 460

Leu Met Thr Glu Asn Leu Thr Val Gln Pro Glu Arg Leu Gly Val Leu
465                 470                 475                 480

Ala Ser His His Asp Asn Ala Ala Val Asp Ala Ser Ser Gly Val Glu
                485                 490                 495

Ala Ala Ala Gly Leu Gly Glu Ser Val Ala Ile Thr His Gly Pro Tyr
            500                 505                 510

Cys Ser Gln Phe Asn Asp Thr Leu Asn Val Tyr Leu Thr Ala His Asn
        515                 520                 525

Ala Leu Gly Ser Ser Leu His Thr Ala Gly Val Asp Leu Ala Lys Ser
    530                 535                 540

Leu Arg Ile Ala Ala Lys Ile Tyr Ser Glu Ala Asp Glu Ala Trp Arg
545                 550                 555                 560

Lys Ala Ile Asp Gly Leu Phe Thr Lys Leu Met Asp Phe Ala Leu Leu
                565                 570                 575

Pro Pro Glu Val Asn Ser Ala Arg Met Tyr Thr Gly Pro Gly Ala Gly
            580                 585                 590

Ser Leu Leu Ala Ala Ala Gly Gly Trp Asp Ser Leu Ala Ala Glu Leu
        595                 600                 605

Ala Thr Thr Ala Glu Ala Tyr Gly Ser Val Leu Ser Gly Leu Ala Ala
```

```
    610                 615                 620

Leu His Trp Arg Gly Pro Ala Ala Glu Ser Met Ala Val Thr Ala Ala
625                 630                 635                 640

Pro Tyr Ile Gly Trp Leu Tyr Thr Thr Ala Glu Lys Thr Gln Gln Thr
                645                 650                 655

Ala Ile Gln Ala Arg Ala Ala Ala Leu Ala Phe Glu Gln Ala Tyr Ala
            660                 665                 670

Met Thr Leu Pro Pro Pro Val Val Ala Ala Asn Arg Ile Gln Leu Leu
        675                 680                 685

Ala Leu Ile Ala Thr Asn Phe Phe Gly Gln Asn Thr Ala Ala Ile Ala
    690                 695                 700

Ala Thr Glu Ala Gln Tyr Ala Glu Met Trp Ala Gln Asp Ala Ala Ala
705                 710                 715                 720

Met Tyr Gly Tyr Ala Thr Ala Ser Ala Ala Ala Ala Leu Leu Thr Pro
                725                 730                 735

Phe Ser Pro Pro Arg Gln Thr Thr Asn Pro Ala Gly Leu Thr Ala Gln
            740                 745                 750

Ala Ala Ala Val Ser Gln Ala Thr Asp Pro Leu Ser Leu Leu Ile Glu
        755                 760                 765

Thr Val Thr Gln Ala Leu Gln Ala Leu Thr Ile Pro Ser Phe Ile Pro
    770                 775                 780

Glu Asp Phe Thr Phe Leu Asp Ala Ile Phe Ala Gly Tyr Ala Thr Val
785                 790                 795                 800

Gly Val Thr Gln Asp Val Glu Ser Phe Val Ala Gly Thr Ile Gly Ala
                805                 810                 815

Glu Ser Asn Leu Gly Leu Leu Asn Val Gly Asp Glu Asn Pro Ala Glu
            820                 825                 830

Val Thr Pro Gly Asp Phe Gly Ile Gly Glu Leu Val Ser Ala Thr Ser
        835                 840                 845

Pro Gly Gly Gly Val Ser Ala Ser Gly Ala Gly Gly Ala Ala Ser Val
    850                 855                 860

Gly Asn Thr Val Leu Ala Ser Val Gly Arg Ala Asn Ser Ile Gly Gln
865                 870                 875                 880

Leu Ser Val Pro Pro Ser Trp Ala Ala Pro Ser Thr Arg Pro Val Ser
                885                 890                 895

Ala Leu Ser Pro Ala Gly Leu Thr Thr Leu Pro Gly Thr Asp Val Ala
            900                 905                 910

Glu His Gly Met Pro Gly Val Pro Gly Val Pro Val Ala Ala Gly Arg
        915                 920                 925

Ala Ser Gly Val Leu Pro Arg Tyr Gly Val Arg Leu Thr Val Met Ala
    930                 935                 940

His Pro Pro Ala Ala Gly
945                 950
```

<210> SEQ ID NO 44
<211> LENGTH: 3180
<212> TYPE: DNA
<213> ORGANISM: Mycobacterium tuberculosis
<220> FEATURE:
<223> OTHER INFORMATION: Rv1009-Rv2034-Rv2628-Rv3615c-Rv3136

<400> SEQUENCE: 44

```
atggcatgca aaacggtgac gttgaccgtc gacggaaccg cgatgcgggt gaccacgatg      60

aaatcgcggg tgatcgacat cgtcgaagag aacgggttct cagtcgacga ccgcgacgac     120
```

-continued

```
ctgtatcccg cggccggcgt gcaggtccat gacgccgaca ccatcgtgct gcggcgtagc    180
cgtccgctgc agatctcgct ggatggtcac gacgctaagc aggtgtggac gaccgcgtcg    240
acggtggacg aggcgctggc ccaactcgcg atgaccgaca cggcgccggc cgcggcttct    300
cgcgccagcc gcgtcccgct gtccgggatg gcgctaccgg tcgtcagcgc caagacggtg    360
cagctcaacg acggcgggtt ggtgcgcacg gtgcacttgc cggcccccaa tgtcgcgggg    420
ctgctgagtg cggccggcgt gccgctgttg caaagcgacc acgtggtgcc cgccgcgacg    480
gccccgatcg tcgaaggcat gcagatccag gtgacccgca atcggatcaa gaaggtcacc    540
gagcggctgc cgctgccgcc gaacgcgcgt cgtgtcgagg acccggagat gaacatgagc    600
cgggaggtcg tcgaagaccc gggggttccg gggacccagg atgtgacgtt cgcggtagct    660
gaggtcaacg gcgtcgagac cggccgtttg cccgtcgcca acgtcgtggt gaccccggcc    720
cacgaagccg tggtgcgggt gggcaccaag cccggtaccg aggtgccccc ggtgatcgac    780
ggaagcatct gggacgcgat cgccggctgt gaggccggtg gcaactgggc gatcaacacc    840
ggcaacgggt attacggtgg tgtgcagttt gaccagggca cctgggaggc caacggcggg    900
ctgcggtatg caccccgcgc tgacctcgcc acccgcgaag agcagatcgc cgttgccgag    960
gtgacccgac tgcgtcaagg ttggggcgcc tggccggtat gtgctgcacg agcgggtgcg   1020
cgcggatccg tgtccactta cagatcaccg gatcgcgctt ggcaggcgct ggcggacggc   1080
actcgccggg ccatcgtgga gcggctggcg cacggcccgc tggccgtcgg cgagttggcc   1140
cgcgacctgc ccgtcagccg acccgcggtg tcacagcacc tcaaagtgct caagaccgcc   1200
aggctggtgt gcgaccgccc cgcgggaaca cgccgcgtct accagctcga cccgacaggc   1260
cttgcggcat tgcgcaccga cctcgaccgg ttctggacac gcgccctgac tggctacgcg   1320
cagctcatcg actccgaagg agacgacaca gaattcatgt ccacgcaacg accgaggcac   1380
tccggtattc gggctgttgg cccctacgca tgggccggcc gatgtggtcg gataggcagg   1440
tggggggtgc accaggaggc gatgatgaat ctagcgatat ggcacccgcg caaggtgcaa   1500
tccgccacca tctatcaggt gaccgatcgc tcgcacgacg ggcgcacagc acgggtgcct   1560
ggtgacgaga tcactagcac cgtgtccggt tggttgtcgg agttgggcac ccaaagcccg   1620
ttggccgatg agcttgcgcg tgcggtgcgg atcggcgact ggcccgctgc gtacgcaatc   1680
ggtgagcacc tgtccgttga gattgccgtt gcggtcgagc tcatgacgga aaacttgacc   1740
gtccagcccg agcgtctcgg tgtactggcg tcgcaccatg acaacgcggc ggtcgatgcc   1800
tcctcgggcg tcgaagctgc cgctggccta ggcgaatctg tggcgatcac tcacggtccg   1860
tactgctcac agttcaacga cacgttaaat gtgtacttga ctgcccacaa tgccctgggc   1920
tcgtccttgc atacggccgg tgtcgatctc gccaaaagtc ttcgaattgc ggcgaagata   1980
tatagcgagg ccgacgaagc gtggcgcaag gctatcgacg ggttgtttac caagcttatg   2040
gatttcgcac tgttaccacc ggaagtcaac tccgcccgga tgtacaccgg ccctggggca   2100
ggatcgctgt tggctgccgc gggcggctgg gattcgctgg ccgccgagtt ggccaccaca   2160
gccgaggcat atggatcggt gctgtccgga ctggccgcct tgcattggcg tggaccggca   2220
gcggaatcga tggcggtgac ggccgctccc tatatcggtt ggctgtacac gaccgccgaa   2280
aagacacagc aaacagcgat ccaagccagg gcggcagcgc tggccttcga gcaagcatac   2340
gcaatgaccc tgccgccacc ggtggtagcg gccaaccgga tacagctgct agcactgatc   2400
gcgacgaact tcttcggcca gaacactgcg gcgatcgcgg ccaccgaggc acagtacgcc   2460
gagatgtggg cccaggacgc cgccgcgatg tacggttacg ccaccgcctc agcggctgcg   2520
```

```
gccctgctga caccgttctc cccgccgcgg cagaccacca acccggccgg cctgaccgct   2580

caggccgccg cggtcagcca ggccaccgac ccactgtcgc tgctgattga gacggtgacc   2640

caagcgctgc aagcgctgac gattccgagc ttcatccctg aggacttcac cttccttgac   2700

gccatattcg ctggatatgc cacggtaggt gtgacgcagg atgtcgagtc ctttgttgcc   2760

gggaccatcg gggccgagag caacctaggc cttttgaacg tcggcgacga gaatcccgcg   2820

gaggtgacac cgggcgactt tgggatcggc gagttggttt ccgcgaccag tcccggcggt   2880

ggggtgtctg cgtcgggtgc cggcggtgcg gcgagcgtcg gcaacacggt gctcgcgagt   2940

gtcggccggg caaactcgat tggcaacta tcggtcccac cgagctgggc cgcgccctcg   3000

acgcgccctg tctcggcatt gtcgcccgcc ggcctgacca cactcccggg gaccgacgtg   3060

gccgagcacg ggatgccagg tgtaccgggg gtgccagtgg cagcagggcg agcctccggc   3120

gtcctacctc gatacggggt tcggctcacg gtgatggccc acccacccgc ggcagggtaa   3180
```

<210> SEQ ID NO 45
<211> LENGTH: 1059
<212> TYPE: PRT
<213> ORGANISM: Mycobacterium tuberculosis
<220> FEATURE:
<223> OTHER INFORMATION: Rv1009-Rv2034-Rv2628-Rv3615c-Rv3136

<400> SEQUENCE: 45

```
Met Ala Cys Lys Thr Val Thr Leu Thr Val Asp Gly Thr Ala Met Arg
1               5                   10                  15

Val Thr Thr Met Lys Ser Arg Val Ile Asp Ile Val Glu Glu Asn Gly
            20                  25                  30

Phe Ser Val Asp Asp Arg Asp Asp Leu Tyr Pro Ala Ala Gly Val Gln
        35                  40                  45

Val His Asp Ala Asp Thr Ile Val Leu Arg Arg Ser Arg Pro Leu Gln
    50                  55                  60

Ile Ser Leu Asp Gly His Asp Ala Lys Gln Val Trp Thr Thr Ala Ser
65                  70                  75                  80

Thr Val Asp Glu Ala Leu Ala Gln Leu Ala Met Thr Asp Thr Ala Pro
                85                  90                  95

Ala Ala Ala Ser Arg Ala Ser Arg Val Pro Leu Ser Gly Met Ala Leu
            100                 105                 110

Pro Val Val Ser Ala Lys Thr Val Gln Leu Asn Asp Gly Gly Leu Val
        115                 120                 125

Arg Thr Val His Leu Pro Ala Pro Asn Val Ala Gly Leu Leu Ser Ala
    130                 135                 140

Ala Gly Val Pro Leu Leu Gln Ser Asp His Val Val Pro Ala Ala Thr
145                 150                 155                 160

Ala Pro Ile Val Glu Gly Met Gln Ile Gln Val Thr Arg Asn Arg Ile
                165                 170                 175

Lys Lys Val Thr Glu Arg Leu Pro Leu Pro Pro Asn Ala Arg Arg Val
            180                 185                 190

Glu Asp Pro Glu Met Asn Met Ser Arg Glu Val Val Glu Asp Pro Gly
        195                 200                 205

Val Pro Gly Thr Gln Asp Val Thr Phe Ala Val Ala Glu Val Asn Gly
    210                 215                 220

Val Glu Thr Gly Arg Leu Pro Val Ala Asn Val Val Val Thr Pro Ala
225                 230                 235                 240

His Glu Ala Val Val Arg Val Gly Thr Lys Pro Gly Thr Glu Val Pro
```

-continued

```
                245                 250                 255

Pro Val Ile Asp Gly Ser Ile Trp Asp Ala Ile Ala Gly Cys Glu Ala
            260                 265                 270

Gly Gly Asn Trp Ala Ile Asn Thr Gly Asn Gly Tyr Tyr Gly Gly Val
        275                 280                 285

Gln Phe Asp Gln Gly Thr Trp Glu Ala Asn Gly Gly Leu Arg Tyr Ala
    290                 295                 300

Pro Arg Ala Asp Leu Ala Thr Arg Glu Glu Gln Ile Ala Val Ala Glu
305                 310                 315                 320

Val Thr Arg Leu Arg Gln Gly Trp Gly Ala Trp Pro Val Cys Ala Ala
                325                 330                 335

Arg Ala Gly Ala Arg Gly Ser Val Ser Thr Tyr Arg Ser Pro Asp Arg
            340                 345                 350

Ala Trp Gln Ala Leu Ala Asp Gly Thr Arg Arg Ala Ile Val Glu Arg
        355                 360                 365

Leu Ala His Gly Pro Leu Ala Val Gly Glu Leu Ala Arg Asp Leu Pro
    370                 375                 380

Val Ser Arg Pro Ala Val Ser Gln His Leu Lys Val Leu Lys Thr Ala
385                 390                 395                 400

Arg Leu Val Cys Asp Arg Pro Ala Gly Thr Arg Arg Val Tyr Gln Leu
                405                 410                 415

Asp Pro Thr Gly Leu Ala Ala Leu Arg Thr Asp Leu Asp Arg Phe Trp
            420                 425                 430

Thr Arg Ala Leu Thr Gly Tyr Ala Gln Leu Ile Asp Ser Glu Gly Asp
        435                 440                 445

Asp Thr Glu Phe Met Ser Thr Gln Arg Pro Arg His Ser Gly Ile Arg
    450                 455                 460

Ala Val Gly Pro Tyr Ala Trp Ala Gly Arg Cys Gly Arg Ile Gly Arg
465                 470                 475                 480

Trp Gly Val His Gln Glu Ala Met Met Asn Leu Ala Ile Trp His Pro
                485                 490                 495

Arg Lys Val Gln Ser Ala Thr Ile Tyr Gln Val Thr Asp Arg Ser His
            500                 505                 510

Asp Gly Arg Thr Ala Arg Val Pro Gly Asp Glu Ile Thr Ser Thr Val
        515                 520                 525

Ser Gly Trp Leu Ser Glu Leu Gly Thr Gln Ser Pro Leu Ala Asp Glu
    530                 535                 540

Leu Ala Arg Ala Val Arg Ile Gly Asp Trp Pro Ala Ala Tyr Ala Ile
545                 550                 555                 560

Gly Glu His Leu Ser Val Glu Ile Ala Val Ala Val Glu Leu Met Thr
                565                 570                 575

Glu Asn Leu Thr Val Gln Pro Glu Arg Leu Gly Val Leu Ala Ser His
            580                 585                 590

His Asp Asn Ala Ala Val Asp Ala Ser Ser Gly Val Glu Ala Ala Ala
        595                 600                 605

Gly Leu Gly Glu Ser Val Ala Ile Thr His Gly Pro Tyr Cys Ser Gln
    610                 615                 620

Phe Asn Asp Thr Leu Asn Val Tyr Leu Thr Ala His Asn Ala Leu Gly
625                 630                 635                 640

Ser Ser Leu His Thr Ala Gly Val Asp Leu Ala Lys Ser Leu Arg Ile
                645                 650                 655

Ala Ala Lys Ile Tyr Ser Glu Ala Asp Glu Ala Trp Arg Lys Ala Ile
            660                 665                 670
```

```
Asp Gly Leu Phe Thr Lys Leu Met Asp Phe Ala Leu Leu Pro Pro Glu
        675                 680                 685

Val Asn Ser Ala Arg Met Tyr Thr Gly Pro Gly Ala Gly Ser Leu Leu
    690                 695                 700

Ala Ala Ala Gly Gly Trp Asp Ser Leu Ala Ala Glu Leu Ala Thr Thr
705                 710                 715                 720

Ala Glu Ala Tyr Gly Ser Val Leu Ser Gly Leu Ala Ala Leu His Trp
                725                 730                 735

Arg Gly Pro Ala Ala Glu Ser Met Ala Val Thr Ala Ala Pro Tyr Ile
            740                 745                 750

Gly Trp Leu Tyr Thr Thr Ala Glu Lys Thr Gln Gln Thr Ala Ile Gln
        755                 760                 765

Ala Arg Ala Ala Ala Leu Ala Phe Glu Gln Ala Tyr Ala Met Thr Leu
    770                 775                 780

Pro Pro Pro Val Val Ala Ala Asn Arg Ile Gln Leu Leu Ala Leu Ile
785                 790                 795                 800

Ala Thr Asn Phe Phe Gly Gln Asn Thr Ala Ala Ile Ala Ala Thr Glu
                805                 810                 815

Ala Gln Tyr Ala Glu Met Trp Ala Gln Asp Ala Ala Ala Met Tyr Gly
            820                 825                 830

Tyr Ala Thr Ala Ser Ala Ala Ala Ala Leu Leu Thr Pro Phe Ser Pro
        835                 840                 845

Pro Arg Gln Thr Thr Asn Pro Ala Gly Leu Thr Ala Gln Ala Ala Ala
    850                 855                 860

Val Ser Gln Ala Thr Asp Pro Leu Ser Leu Leu Ile Glu Thr Val Thr
865                 870                 875                 880

Gln Ala Leu Gln Ala Leu Thr Ile Pro Ser Phe Ile Pro Glu Asp Phe
                885                 890                 895

Thr Phe Leu Asp Ala Ile Phe Ala Gly Tyr Ala Thr Val Gly Val Thr
            900                 905                 910

Gln Asp Val Glu Ser Phe Val Ala Gly Thr Ile Gly Ala Glu Ser Asn
        915                 920                 925

Leu Gly Leu Leu Asn Val Gly Asp Glu Asn Pro Ala Glu Val Thr Pro
    930                 935                 940

Gly Asp Phe Gly Ile Gly Glu Leu Val Ser Ala Thr Ser Pro Gly Gly
945                 950                 955                 960

Gly Val Ser Ala Ser Gly Ala Gly Gly Ala Ala Ser Val Gly Asn Thr
                965                 970                 975

Val Leu Ala Ser Val Gly Arg Ala Asn Ser Ile Gly Gln Leu Ser Val
            980                 985                 990

Pro Pro Ser Trp Ala Ala Pro Ser  Thr Arg Pro Val Ser  Ala Leu Ser
        995                 1000                1005

Pro Ala  Gly Leu Thr Thr Leu  Pro Gly Thr Asp Val  Ala Glu His
    1010                 1015                 1020

Gly Met  Pro Gly Val Pro Gly  Val Pro Val Ala Ala  Gly Arg Ala
    1025                 1030                 1035

Ser Gly  Val Leu Pro Arg Tyr  Gly Val Arg Leu Thr  Val Met Ala
    1040                 1045                 1050

His Pro  Pro Ala Ala Gly
    1055
```

<210> SEQ ID NO 46
<211> LENGTH: 2499

<212> TYPE: DNA
<213> ORGANISM: Mycobacterium tuberculosis
<220> FEATURE:
<223> OTHER INFORMATION: Rv2034-Rv1009-Rv3136

<400> SEQUENCE: 46
atggtgtcca cttacagatc accggatcgc gcttggcagg cgctggcgga cggcactcgc 60
cgggccatcg tggagcggct ggcgcacggc ccgctggccg tcggcgagtt ggcccgcgac 120
ctgcccgtca gccgacccgc ggtgtcacag cacctcaaag tgctcaagac cgccaggctg 180
gtgtgcgacc gccccgcggg aacacgccgc gtctaccagc tcgacccgac aggccttgcg 240
gcattgcgca ccgacctcga ccggttctgg acacgcgccc tgactggcta cgcgcagctc 300
atcgactccg aaggagacga cacagaattc gcatgcaaaa cggtgacgtt gaccgtcgac 360
ggaaccgcga tgcgggtgac cacgatgaaa tcgcgggtga tcgacatcgt cgaagagaac 420
gggttctcag tcgacgaccg cgacgacctg tatcccgcgg ccggcgtgca ggtccatgac 480
gccgacacca tcgtgctgcg gcgtagccgt ccgctgcaga tctcgctgga tggtcacgac 540
gctaagcagg tgtggacgac cgcgtcgacg gtggacgagg cgctggccca actcgcgatg 600
accgacacgg cgccggccgc ggcttctcgc gccagccgcg tcccgctgtc cgggatggcg 660
ctaccggtcg tcagcgccaa gacggtgcag ctcaacgacg gcgggttggt gcgcacggtg 720
cacttgccgg cccccaatgt cgcggggctg ctgagtgcgg ccggcgtgcc gctgttgcaa 780
agcgaccacg tggtgccccgc cgcgacggcc ccgatcgtcg aaggcatgca gatccaggtg 840
acccgcaatc ggatcaagaa ggtcaccgag cggctgccgc tgccgccgaa cgcgcgtcgt 900
gtcgaggacc cggagatgaa catgagccgg gaggtcgtcg aagacccggg ggttccgggg 960
acccaggatg tgacgttcgc ggtagctgag gtcaacggcg tcgagaccgg ccgtttgccc 1020
gtcgccaacg tcgtggtgac ccggcccac gaagccgtgg tgcgggtggg caccaagccc 1080
ggtaccgagg tgcccccggt gatcgacgga agcatctggg acgcgatcgc cggctgtgag 1140
gccggtggca actgggcgat caacaccggc aacgggtatt acggtggtgt gcagtttgac 1200
cagggcacct gggaggccaa cggcgggctg cggtatgcac cccgcgctga cctcgccacc 1260
cgcgaagagc agatcgccgt tgccgaggtg acccgactgc gtcaaggttg ggcgcctgg 1320 ccggtatgtg ctgcacgagc gggtgcgcgc aagcttatgg atttcgcact gttaccaccg 1380
gaagtcaact ccgcccggat gtacaccggc cctggggcag gatcgctgtt ggctgccgcg 1440
ggcggctggg attcgctggc cgccgagttg gccaccacag ccgaggcata tggatcggtg 1500
ctgtccggac tggccgcctt gcattggcgt ggaccggcag cggaatcgat ggcggtgacg 1560
gccgctccct atatcggttg gctgtacacg accgccgaaa agacacagca aacagcgatc 1620
caagccaggg cggcagcgct ggccttcgag caagcatacg caatgaccct gccgccaccg 1680
gtggtagcgg ccaaccggat acagctgcta gcactgatcg cgacgaactt cttcggccag 1740
aacactgcgg cgatcgcggc caccgaggca cagtacgccg agatgtgggc ccaggacgcc 1800
gccgcgatgt acggttacgc caccgcctca gcggctgcgg ccctgctgac accgttctcc 1860
ccgccgcggc agaccaccaa cccggccggc ctgaccgctc aggccgccgc ggtcagccag 1920
gccaccgacc cactgtcgct gctgattgag acggtgaccc aagcgctgca agcgctgacg 1980
attccgagct tcatccctga ggacttcacc ttccttgacg ccatattcgc tggatatgcc 2040
acggtaggtg tgacgcagga tgtcgagtcc tttgttgccg ggaccatcgg ggccgagagc 2100
aacctaggcc ttttgaacgt cggcgacgag aatcccgcgg aggtgacacc gggcgacttt 2160

```
gggatcggcg agttggtttc cgcgaccagt cccggcggtg gggtgtctgc gtcgggtgcc   2220

ggcggtgcgg cgagcgtcgg caacacggtg ctcgcgagtg tcggccgggc aaactcgatt   2280

gggcaactat cggtcccacc gagctgggcc gcgccctcga cgcgccctgt ctcggcattg   2340

tcgcccgccg gcctgaccac actcccgggg accgacgtgg ccgagcacgg gatgccaggt   2400

gtaccggggg tgccagtggc agcagggcga gcctccggcg tcctacctcg atacggggtt   2460

cggctcacgg tgatggccca cccacccgcg gcagggtaa                          2499


<210> SEQ ID NO 47
<211> LENGTH: 832
<212> TYPE: PRT
<213> ORGANISM: Mycobacterium tuberculosis
<220> FEATURE:
<223> OTHER INFORMATION: Rv2034-Rv1009-Rv3136

<400> SEQUENCE: 47

Met Val Ser Thr Tyr Arg Ser Pro Asp Arg Ala Trp Gln Ala Leu Ala
1               5                   10                  15

Asp Gly Thr Arg Arg Ala Ile Val Glu Arg Leu Ala His Gly Pro Leu
            20                  25                  30

Ala Val Gly Glu Leu Ala Arg Asp Leu Pro Val Ser Arg Pro Ala Val
        35                  40                  45

Ser Gln His Leu Lys Val Leu Lys Thr Ala Arg Leu Val Cys Asp Arg
    50                  55                  60

Pro Ala Gly Thr Arg Arg Val Tyr Gln Leu Asp Pro Thr Gly Leu Ala
65                  70                  75                  80

Ala Leu Arg Thr Asp Leu Asp Arg Phe Trp Thr Arg Ala Leu Thr Gly
                85                  90                  95

Tyr Ala Gln Leu Ile Asp Ser Glu Gly Asp Asp Thr Glu Phe Ala Cys
            100                 105                 110

Lys Thr Val Thr Leu Thr Val Asp Gly Thr Ala Met Arg Val Thr Thr
        115                 120                 125

Met Lys Ser Arg Val Ile Asp Ile Val Glu Glu Asn Gly Phe Ser Val
    130                 135                 140

Asp Asp Arg Asp Asp Leu Tyr Pro Ala Ala Gly Val Gln Val His Asp
145                 150                 155                 160

Ala Asp Thr Ile Val Leu Arg Arg Ser Arg Pro Leu Gln Ile Ser Leu
                165                 170                 175

Asp Gly His Asp Ala Lys Gln Val Trp Thr Thr Ala Ser Thr Val Asp
            180                 185                 190

Glu Ala Leu Ala Gln Leu Ala Met Thr Asp Thr Ala Pro Ala Ala Ala
        195                 200                 205

Ser Arg Ala Ser Arg Val Pro Leu Ser Gly Met Ala Leu Pro Val Val
    210                 215                 220

Ser Ala Lys Thr Val Gln Leu Asn Asp Gly Gly Leu Val Arg Thr Val
225                 230                 235                 240

His Leu Pro Ala Pro Asn Val Ala Gly Leu Leu Ser Ala Ala Gly Val
                245                 250                 255

Pro Leu Leu Gln Ser Asp His Val Val Pro Ala Ala Thr Ala Pro Ile
            260                 265                 270

Val Glu Gly Met Gln Ile Gln Val Thr Arg Asn Arg Ile Lys Lys Val
        275                 280                 285

Thr Glu Arg Leu Pro Leu Pro Pro Asn Ala Arg Arg Val Glu Asp Pro
    290                 295                 300
```

-continued

```
Glu Met Asn Met Ser Arg Glu Val Val Glu Asp Pro Gly Val Pro Gly
305                 310                 315                 320

Thr Gln Asp Val Thr Phe Ala Val Ala Glu Val Asn Gly Val Glu Thr
                325                 330                 335

Gly Arg Leu Pro Val Ala Asn Val Val Val Thr Pro Ala His Glu Ala
            340                 345                 350

Val Val Arg Val Gly Thr Lys Pro Gly Thr Glu Val Pro Pro Val Ile
        355                 360                 365

Asp Gly Ser Ile Trp Asp Ala Ile Ala Gly Cys Glu Ala Gly Gly Asn
    370                 375                 380

Trp Ala Ile Asn Thr Gly Asn Gly Tyr Tyr Gly Gly Val Gln Phe Asp
385                 390                 395                 400

Gln Gly Thr Trp Glu Ala Asn Gly Gly Leu Arg Tyr Ala Pro Arg Ala
                405                 410                 415

Asp Leu Ala Thr Arg Glu Glu Gln Ile Ala Val Ala Glu Val Thr Arg
            420                 425                 430

Leu Arg Gln Gly Trp Gly Ala Trp Pro Val Cys Ala Ala Arg Ala Gly
        435                 440                 445

Ala Arg Lys Leu Met Asp Phe Ala Leu Leu Pro Pro Glu Val Asn Ser
    450                 455                 460

Ala Arg Met Tyr Thr Gly Pro Gly Ala Gly Ser Leu Leu Ala Ala Ala
465                 470                 475                 480

Gly Gly Trp Asp Ser Leu Ala Ala Glu Leu Ala Thr Thr Ala Glu Ala
                485                 490                 495

Tyr Gly Ser Val Leu Ser Gly Leu Ala Ala Leu His Trp Arg Gly Pro
            500                 505                 510

Ala Ala Glu Ser Met Ala Val Thr Ala Ala Pro Tyr Ile Gly Trp Leu
        515                 520                 525

Tyr Thr Thr Ala Glu Lys Thr Gln Gln Thr Ala Ile Gln Ala Arg Ala
    530                 535                 540

Ala Ala Leu Ala Phe Glu Gln Ala Tyr Ala Met Thr Leu Pro Pro Pro
545                 550                 555                 560

Val Val Ala Ala Asn Arg Ile Gln Leu Leu Ala Leu Ile Ala Thr Asn
                565                 570                 575

Phe Phe Gly Gln Asn Thr Ala Ala Ile Ala Ala Thr Glu Ala Gln Tyr
            580                 585                 590

Ala Glu Met Trp Ala Gln Asp Ala Ala Ala Met Tyr Gly Tyr Ala Thr
        595                 600                 605

Ala Ser Ala Ala Ala Ala Leu Leu Thr Pro Phe Ser Pro Pro Arg Gln
    610                 615                 620

Thr Thr Asn Pro Ala Gly Leu Thr Ala Gln Ala Ala Ala Val Ser Gln
625                 630                 635                 640

Ala Thr Asp Pro Leu Ser Leu Leu Ile Glu Thr Val Thr Gln Ala Leu
                645                 650                 655

Gln Ala Leu Thr Ile Pro Ser Phe Ile Pro Glu Asp Phe Thr Phe Leu
            660                 665                 670

Asp Ala Ile Phe Ala Gly Tyr Ala Thr Val Gly Val Thr Gln Asp Val
        675                 680                 685

Glu Ser Phe Val Ala Gly Thr Ile Gly Ala Glu Ser Asn Leu Gly Leu
    690                 695                 700

Leu Asn Val Gly Asp Glu Asn Pro Ala Glu Val Thr Pro Gly Asp Phe
705                 710                 715                 720

Gly Ile Gly Glu Leu Val Ser Ala Thr Ser Pro Gly Gly Gly Val Ser
```

```
                725                 730                 735

Ala Ser Gly Ala Gly Gly Ala Ala Ser Val Gly Asn Thr Val Leu Ala
            740                 745                 750

Ser Val Gly Arg Ala Asn Ser Ile Gly Gln Leu Ser Val Pro Pro Ser
        755                 760                 765

Trp Ala Ala Pro Ser Thr Arg Pro Val Ser Ala Leu Ser Pro Ala Gly
    770                 775                 780

Leu Thr Thr Leu Pro Gly Thr Asp Val Ala Glu His Gly Met Pro Gly
785                 790                 795                 800

Val Pro Gly Val Pro Val Ala Ala Gly Arg Ala Ser Gly Val Leu Pro
                805                 810                 815

Arg Tyr Gly Val Arg Leu Thr Val Met Ala His Pro Pro Ala Ala Gly
            820                 825                 830


<210> SEQ ID NO 48
<211> LENGTH: 2496
<212> TYPE: DNA
<213> ORGANISM: Mycobacterium tuberculosis
<220> FEATURE:
<223> OTHER INFORMATION: Rv3136-Rv2034-Rv1009

<400> SEQUENCE: 48

atggatttcg cactgttacc accggaagtc aactccgccc ggatgtacac cggccctggg     60

gcaggatcgc tgttggctgc cgcgggcggc tgggattcgc tggccgccga gttggccacc    120

acagccgagg catatggatc ggtgctgtcc ggactggccg ccttgcattg gcgtggaccg    180

gcagcggaat cgatggcggt gacggccgct ccctatatcg gttggctgta cacgaccgcc    240

gaaaagacac agcaaacagc gatccaagcc agggcggcag cgctggcctt cgagcaagca    300

tacgcaatga ccctgccgcc accggtggta gcggccaacc ggatacagct gctagcactg    360

atcgcgacga acttcttcgg ccagaacact gcggcgatcg cggccaccga ggcacagtac    420

gccgagatgt gggcccagga cgccgccgcg atgtacggtt acgccaccgc ctcagcggct    480

gcggccctgc tgacaccgtt ctccccgccg cggcagacca ccaacccggc cggcctgacc    540

gctcaggccg ccgcggtcag ccaggccacc gacccactgt cgctgctgat tgagacggtg    600

acccaagcgc tgcaagcgct gacgattccg agcttcatcc ctgaggactt caccttcctt    660

gacgccatat tcgctggata tgccacggta ggtgtgacgc aggatgtcga gtcctttgtt    720

gccgggacca tcggggccga gagcaaccta ggccttttga acgtcggcga cgagaatccc    780

gcggaggtga caccgggcga ctttgggatc ggcgagttgg tttccgcgac cagtcccggc    840

ggtggggtgt ctgcgtcggg tgccggcggt gcggcgagcg tcggcaacac ggtgctcgcg    900

agtgtcggcc gggcaaactc gattgggcaa ctatcggtcc caccgagctg ggccgcgccc    960

tcgacgcgcc ctgtctcggc attgtcgccc gccggcctga ccacactccc ggggaccgac   1020

gtggccgagc acgggatgcc aggtgtaccg ggggtgccag tggcagcagg gcgagcctcc   1080

ggcgtcctac ctcgatacgg ggttcggctc acggtgatgg cccacccacc cgcggcaggg   1140

gagctcgtgt ccacttacag atcaccggat cgcgcttggc aggcgctggc ggacggcact   1200

cgccgggcca tcgtggagcg gctggcgcac ggcccgctgg ccgtcggcga gttggcccgc   1260

gacctgcccg tcagccgacc cgcggtgtca cagcacctca aagtgctcaa gaccgccagg   1320

ctggtgtgcg accgccccgc gggaacacgc cgcgtctacc agctcgaccc gacaggcctt   1380

gcggcattgc gcaccgacct cgaccggttc tggacacgcg ccctgactgg ctacgcgcag   1440

ctcatcgact ccgaaggaga cgacacaaag cttgcatgca aaacggtgac gttgaccgtc   1500
```

gacggaaccg cgatgcgggt gaccacgatg aaatcgcggg tgatcgacat cgtcgaagag 1560
aacgggttct cagtcgacga ccgcgacgac ctgtatcccg cggccggcgt gcaggtccat 1620
gacgccgaca ccatcgtgct gcggcgtagc cgtccgctgc agatctcgct ggatggtcac 1680
gacgctaagc aggtgtggac gaccgcgtcg acggtggacg aggcgctggc ccaactcgcg 1740
atgaccgaca cggcgccggc cgcggcttct cgcgccagcc gcgtcccgct gtccgggatg 1800
gcgctaccgg tcgtcagcgc caagacggtg cagctcaacg acggcgggtt ggtgcgcacg 1860
gtgcacttgc cggcccccaa tgtcgcgggg ctgctgagtg cggccggcgt gccgctgttg 1920
caaagcgacc acgtggtgcc cgccgcgacg gccccgatcg tcgaaggcat gcagatccag 1980
gtgacccgca atcggatcaa gaaggtcacc gagcggctgc cgctgccgcc gaacgcgcgt 2040
cgtgtcgagg acccggagat gaacatgagc cgggaggtcg tcgaagaccc gggggttccg 2100
gggacccagg atgtgacgtt cgcggtagct gaggtcaacg gcgtcgagac cggccgtttg 2160
cccgtcgcca acgtcgtggt gaccccggcc cacgaagccg tggtgcgggt gggcaccaag 2220
cccggtaccg aggtgccccc ggtgatcgac ggaagcatct gggacgcgat cgccggctgt 2280
gaggccggtg gcaactgggc gatcaacacc ggcaacgggt attacggtgg tgtgcagttt 2340
gaccagggca cctgggaggc caacggcggg ctgcggtatg caccccgcgc tgacctcgcc 2400
acccgcgaag agcagatcgc cgttgccgag gtgacccgac tgcgtcaagg ttggggcgcc 2460
tggccggtat gtgctgcacg agcgggtgcg cgctga 2496

<210> SEQ ID NO 49
<211> LENGTH: 831
<212> TYPE: PRT
<213> ORGANISM: Mycobacterium tuberculosis
<220> FEATURE:
<223> OTHER INFORMATION: Rv3136-Rv2034-Rv1009

<400> SEQUENCE: 49

Met Asp Phe Ala Leu Leu Pro Pro Glu Val Asn Ser Ala Arg Met Tyr
1 5 10 15

Thr Gly Pro Gly Ala Gly Ser Leu Leu Ala Ala Ala Gly Gly Trp Asp
20 25 30

Ser Leu Ala Ala Glu Leu Ala Thr Thr Ala Glu Ala Tyr Gly Ser Val
35 40 45

Leu Ser Gly Leu Ala Ala Leu His Trp Arg Gly Pro Ala Ala Glu Ser
50 55 60

Met Ala Val Thr Ala Ala Pro Tyr Ile Gly Trp Leu Tyr Thr Thr Ala
65 70 75 80

Glu Lys Thr Gln Gln Thr Ala Ile Gln Ala Arg Ala Ala Ala Leu Ala
85 90 95

Phe Glu Gln Ala Tyr Ala Met Thr Leu Pro Pro Pro Val Val Ala Ala
100 105 110

Asn Arg Ile Gln Leu Leu Ala Leu Ile Ala Thr Asn Phe Phe Gly Gln
115 120 125

Asn Thr Ala Ala Ile Ala Ala Thr Glu Ala Gln Tyr Ala Glu Met Trp
130 135 140

Ala Gln Asp Ala Ala Ala Met Tyr Gly Tyr Ala Thr Ala Ser Ala Ala
145 150 155 160

Ala Ala Leu Leu Thr Pro Phe Ser Pro Pro Arg Gln Thr Thr Asn Pro
165 170 175

Ala Gly Leu Thr Ala Gln Ala Ala Ala Val Ser Gln Ala Thr Asp Pro

-continued

```
            180                 185                 190

Leu Ser Leu Leu Ile Glu Thr Val Thr Gln Ala Leu Gln Ala Leu Thr
        195                 200                 205

Ile Pro Ser Phe Ile Pro Glu Asp Phe Thr Phe Leu Asp Ala Ile Phe
    210                 215                 220

Ala Gly Tyr Ala Thr Val Gly Val Thr Gln Asp Val Glu Ser Phe Val
225                 230                 235                 240

Ala Gly Thr Ile Gly Ala Glu Ser Asn Leu Gly Leu Leu Asn Val Gly
                245                 250                 255

Asp Glu Asn Pro Ala Glu Val Thr Pro Gly Asp Phe Gly Ile Gly Glu
            260                 265                 270

Leu Val Ser Ala Thr Ser Pro Gly Gly Gly Val Ser Ala Ser Gly Ala
        275                 280                 285

Gly Gly Ala Ala Ser Val Gly Asn Thr Val Leu Ala Ser Val Gly Arg
    290                 295                 300

Ala Asn Ser Ile Gly Gln Leu Ser Val Pro Pro Ser Trp Ala Ala Pro
305                 310                 315                 320

Ser Thr Arg Pro Val Ser Ala Leu Ser Pro Ala Gly Leu Thr Thr Leu
                325                 330                 335

Pro Gly Thr Asp Val Ala Glu His Gly Met Pro Gly Val Pro Gly Val
            340                 345                 350

Pro Val Ala Ala Gly Arg Ala Ser Gly Val Leu Pro Arg Tyr Gly Val
        355                 360                 365

Arg Leu Thr Val Met Ala His Pro Pro Ala Ala Gly Glu Leu Val Ser
    370                 375                 380

Thr Tyr Arg Ser Pro Asp Arg Ala Trp Gln Ala Leu Ala Asp Gly Thr
385                 390                 395                 400

Arg Arg Ala Ile Val Glu Arg Leu Ala His Gly Pro Leu Ala Val Gly
                405                 410                 415

Glu Leu Ala Arg Asp Leu Pro Val Ser Arg Pro Ala Val Ser Gln His
            420                 425                 430

Leu Lys Val Leu Lys Thr Ala Arg Leu Val Cys Asp Arg Pro Ala Gly
        435                 440                 445

Thr Arg Arg Val Tyr Gln Leu Asp Pro Thr Gly Leu Ala Ala Leu Arg
    450                 455                 460

Thr Asp Leu Asp Arg Phe Trp Thr Arg Ala Leu Thr Gly Tyr Ala Gln
465                 470                 475                 480

Leu Ile Asp Ser Glu Gly Asp Asp Thr Lys Leu Ala Cys Lys Thr Val
                485                 490                 495

Thr Leu Thr Val Asp Gly Thr Ala Met Arg Val Thr Thr Met Lys Ser
            500                 505                 510

Arg Val Ile Asp Ile Val Glu Glu Asn Gly Phe Ser Val Asp Asp Arg
        515                 520                 525

Asp Asp Leu Tyr Pro Ala Ala Gly Val Gln Val His Asp Ala Asp Thr
    530                 535                 540

Ile Val Leu Arg Arg Ser Arg Pro Leu Gln Ile Ser Leu Asp Gly His
545                 550                 555                 560

Asp Ala Lys Gln Val Trp Thr Thr Ala Ser Thr Val Asp Glu Ala Leu
                565                 570                 575

Ala Gln Leu Ala Met Thr Asp Thr Ala Pro Ala Ala Ala Ser Arg Ala
            580                 585                 590

Ser Arg Val Pro Leu Ser Gly Met Ala Leu Pro Val Val Ser Ala Lys
        595                 600                 605
```

```
Thr Val Gln Leu Asn Asp Gly Gly Leu Val Arg Thr Val His Leu Pro
    610                 615                 620

Ala Pro Asn Val Ala Gly Leu Leu Ser Ala Ala Gly Val Pro Leu Leu
625                 630                 635                 640

Gln Ser Asp His Val Val Pro Ala Ala Thr Ala Pro Ile Val Glu Gly
                645                 650                 655

Met Gln Ile Gln Val Thr Arg Asn Arg Ile Lys Lys Val Thr Glu Arg
            660                 665                 670

Leu Pro Leu Pro Pro Asn Ala Arg Arg Val Glu Asp Pro Glu Met Asn
        675                 680                 685

Met Ser Arg Glu Val Val Glu Asp Pro Gly Val Pro Gly Thr Gln Asp
    690                 695                 700

Val Thr Phe Ala Val Ala Glu Val Asn Gly Val Glu Thr Gly Arg Leu
705                 710                 715                 720

Pro Val Ala Asn Val Val Val Thr Pro Ala His Glu Ala Val Val Arg
                725                 730                 735

Val Gly Thr Lys Pro Gly Thr Glu Val Pro Pro Val Ile Asp Gly Ser
            740                 745                 750

Ile Trp Asp Ala Ile Ala Gly Cys Glu Ala Gly Gly Asn Trp Ala Ile
        755                 760                 765

Asn Thr Gly Asn Gly Tyr Tyr Gly Gly Val Gln Phe Asp Gln Gly Thr
    770                 775                 780

Trp Glu Ala Asn Gly Gly Leu Arg Tyr Ala Pro Arg Ala Asp Leu Ala
785                 790                 795                 800

Thr Arg Glu Glu Gln Ile Ala Val Ala Glu Val Thr Arg Leu Arg Gln
                805                 810                 815

Gly Trp Gly Ala Trp Pro Val Cys Ala Ala Arg Ala Gly Ala Arg
            820                 825                 830


<210> SEQ ID NO 50
<211> LENGTH: 2034
<212> TYPE: DNA
<213> ORGANISM: Mycobacterium tuberculosis
<220> FEATURE:
<223> OTHER INFORMATION: Rv1009-Rv3615c-Rv2034-Rv2628

<400> SEQUENCE: 50

atggcatgca aaacggtgac gttgaccgtc gacggaaccg cgatgcgggt gaccacgatg     60

aaatcgcggg tgatcgacat cgtcgaagag aacgggttct cagtcgacga ccgcgacgac    120

ctgtatcccg cggccggcgt gcaggtccat gacgccgaca ccatcgtgct gcggcgtagc    180

cgtccgctgc agatctcgct ggatggtcac gacgctaagc aggtgtggac gaccgcgtcg    240

acggtggacg aggcgctggc ccaactcgcg atgaccgaca cggcgccggc cgcggcttct    300

cgcgccagcc gcgtcccgct gtccgggatg gcgctaccgg tcgtcagcgc caagacggtg    360

cagctcaacg acggcgggtt ggtgcgcacg gtgcacttgc cggcccccaa tgtcgcgggg    420

ctgctgagtg cggccggcgt gccgctgttg caaagcgacc acgtggtgcc cgccgcgacg    480

gccccgatcg tcgaaggcat gcagatccag gtgacccgca atcggatcaa gaaggtcacc    540

gagcggctgc cgctgccgcc gaacgcgcgt cgtgtcgagg acccggagat gaacatgagc    600

cgggaggtcg tcgaagaccc gggggttccg gggacccagg atgtgacgtt cgcggtagct    660

gaggtcaacg gcgtcgagac cggccgtttg cccgtcgcca acgtcgtggt gaccccggcc    720

cacgaagccg tggtgcgggt gggcaccaag cccggtaccg aggtgccccc ggtgatcgac    780
```

-continued ggaagcatct gggacgcgat cgccggctgt gaggccggtg gcaactgggc gatcaacacc 840
ggcaacgggt attacggtgg tgtgcagttt gaccagggca cctgggaggc caacggcggg 900
ctgcggtatg caccccgcgc tgacctcgcc acccgcgaag agcagatcgc cgttgccgag 960
gtgacccgac tgcgtcaagg ttggggcgcc tggccggtat gtgctgcacg agcgggtgcg 1020
cgcgaattca tgacggaaaa cttgaccgtc cagcccgagc gtctcggtgt actggcgtcg 1080
caccatgaca acgcggcggt cgatgcctcc tcgggcgtcg aagctgccgc tggcctaggc 1140
gaatctgtgg cgatcactca cggtccgtac tgctcacagt tcaacgacac gttaaatgtg 1200
tacttgactg cccacaatgc cctgggctcg tccttgcata cggccggtgt cgatctcgcc 1260
aaaagtcttc gaattgcggc gaagatatat agcgaggccg acgaagcgtg gcgcaaggct 1320
atcgacgggt tgtttaccga gctcgtgtcc acttacagat caccggatcg cgcttggcag 1380
gcgctggcgg acggcactcg ccgggccatc gtggagcggc tggcgcacgg cccgctggcc 1440
gtcggcgagt tggcccgcga cctgcccgtc agccgacccg cggtgtcaca gcacctcaaa 1500
gtgctcaaga ccgccaggct ggtgtgcgac cgccccgcgg gaacacgccg cgtctaccag 1560
ctcgacccga caggccttgc ggcattgcgc accgacctcg accggttctg gacacgcgcc 1620
ctgactggct acgcgcagct catcgactcc gaaggagacg acacaaagct tatgtccacg 1680
caacgaccga ggcactccgg tattcgggct gttggcccct acgcatgggc cggccgatgt 1740
ggtcggatag gcaggtgggg ggtgcaccag gaggcgatga tgaatctagc gatatggcac 1800
ccgcgcaagg tgcaatccgc caccatctat caggtgaccg atcgctcgca cgacgggcgc 1860
acagcacggg tgcctggtga cgagatcact agcaccgtgt ccggttggtt gtcggagttg 1920
ggcacccaaa gcccgttggc cgatgagctt gcgcgtgcgg tgcggatcgg cgactggccc 1980
gctgcgtacg caatcggtga gcacctgtcc gttgagattg ccgttgcggt ctaa 2034

<210> SEQ ID NO 51
<211> LENGTH: 677
<212> TYPE: PRT
<213> ORGANISM: Mycobacterium tuberculosis
<220> FEATURE:
<223> OTHER INFORMATION: Rv1009-Rv3615c-Rv2034-Rv2628

<400> SEQUENCE: 51

Met Ala Cys Lys Thr Val Thr Leu Thr Val Asp Gly Thr Ala Met Arg
1               5                   10                  15

Val Thr Thr Met Lys Ser Arg Val Ile Asp Ile Val Glu Glu Asn Gly
            20                  25                  30

Phe Ser Val Asp Asp Arg Asp Asp Leu Tyr Pro Ala Ala Gly Val Gln
        35                  40                  45

Val His Asp Ala Asp Thr Ile Val Leu Arg Arg Ser Arg Pro Leu Gln
    50                  55                  60

Ile Ser Leu Asp Gly His Asp Ala Lys Gln Val Trp Thr Thr Ala Ser
65                  70                  75                  80

Thr Val Asp Glu Ala Leu Ala Gln Leu Ala Met Thr Asp Thr Ala Pro
                85                  90                  95

Ala Ala Ala Ser Arg Ala Ser Arg Val Pro Leu Ser Gly Met Ala Leu
            100                 105                 110

Pro Val Val Ser Ala Lys Thr Val Gln Leu Asn Asp Gly Gly Leu Val
        115                 120                 125

Arg Thr Val His Leu Pro Ala Pro Asn Val Ala Gly Leu Leu Ser Ala
    130                 135                 140

-continued

```
Ala Gly Val Pro Leu Leu Gln Ser Asp His Val Val Pro Ala Ala Thr
145                 150                 155                 160

Ala Pro Ile Val Glu Gly Met Gln Ile Gln Val Thr Arg Asn Arg Ile
                165                 170                 175

Lys Lys Val Thr Glu Arg Leu Pro Leu Pro Pro Asn Ala Arg Arg Val
            180                 185                 190

Glu Asp Pro Glu Met Asn Met Ser Arg Glu Val Val Glu Asp Pro Gly
        195                 200                 205

Val Pro Gly Thr Gln Asp Val Thr Phe Ala Val Ala Glu Val Asn Gly
    210                 215                 220

Val Glu Thr Gly Arg Leu Pro Val Ala Asn Val Val Val Thr Pro Ala
225                 230                 235                 240

His Glu Ala Val Val Arg Val Gly Thr Lys Pro Gly Thr Glu Val Pro
                245                 250                 255

Pro Val Ile Asp Gly Ser Ile Trp Asp Ala Ile Ala Gly Cys Glu Ala
            260                 265                 270

Gly Gly Asn Trp Ala Ile Asn Thr Gly Asn Gly Tyr Tyr Gly Gly Val
        275                 280                 285

Gln Phe Asp Gln Gly Thr Trp Glu Ala Asn Gly Gly Leu Arg Tyr Ala
    290                 295                 300

Pro Arg Ala Asp Leu Ala Thr Arg Glu Glu Gln Ile Ala Val Ala Glu
305                 310                 315                 320

Val Thr Arg Leu Arg Gln Gly Trp Gly Ala Trp Pro Val Cys Ala Ala
                325                 330                 335

Arg Ala Gly Ala Arg Glu Phe Met Thr Glu Asn Leu Thr Val Gln Pro
            340                 345                 350

Glu Arg Leu Gly Val Leu Ala Ser His His Asp Asn Ala Ala Val Asp
        355                 360                 365

Ala Ser Ser Gly Val Glu Ala Ala Ala Gly Leu Gly Glu Ser Val Ala
    370                 375                 380

Ile Thr His Gly Pro Tyr Cys Ser Gln Phe Asn Asp Thr Leu Asn Val
385                 390                 395                 400

Tyr Leu Thr Ala His Asn Ala Leu Gly Ser Ser Leu His Thr Ala Gly
                405                 410                 415

Val Asp Leu Ala Lys Ser Leu Arg Ile Ala Ala Lys Ile Tyr Ser Glu
            420                 425                 430

Ala Asp Glu Ala Trp Arg Lys Ala Ile Asp Gly Leu Phe Thr Glu Leu
        435                 440                 445

Val Ser Thr Tyr Arg Ser Pro Asp Arg Ala Trp Gln Ala Leu Ala Asp
    450                 455                 460

Gly Thr Arg Arg Ala Ile Val Glu Arg Leu Ala His Gly Pro Leu Ala
465                 470                 475                 480

Val Gly Glu Leu Ala Arg Asp Leu Pro Val Ser Arg Pro Ala Val Ser
                485                 490                 495

Gln His Leu Lys Val Leu Lys Thr Ala Arg Leu Val Cys Asp Arg Pro
            500                 505                 510

Ala Gly Thr Arg Arg Val Tyr Gln Leu Asp Pro Thr Gly Leu Ala Ala
        515                 520                 525

Leu Arg Thr Asp Leu Asp Arg Phe Trp Thr Arg Ala Leu Thr Gly Tyr
    530                 535                 540

Ala Gln Leu Ile Asp Ser Glu Gly Asp Asp Thr Lys Leu Met Ser Thr
545                 550                 555                 560

Gln Arg Pro Arg His Ser Gly Ile Arg Ala Val Gly Pro Tyr Ala Trp
```

```
                565                 570                 575

Ala Gly Arg Cys Gly Arg Ile Gly Arg Trp Gly Val His Gln Glu Ala
            580                 585                 590

Met Met Asn Leu Ala Ile Trp His Pro Arg Lys Val Gln Ser Ala Thr
        595                 600                 605

Ile Tyr Gln Val Thr Asp Arg Ser His Asp Gly Arg Thr Ala Arg Val
    610                 615                 620

Pro Gly Asp Glu Ile Thr Ser Thr Val Ser Gly Trp Leu Ser Glu Leu
625                 630                 635                 640

Gly Thr Gln Ser Pro Leu Ala Asp Glu Leu Ala Arg Ala Val Arg Ile
                645                 650                 655

Gly Asp Trp Pro Ala Ala Tyr Ala Ile Gly Glu His Leu Ser Val Glu
            660                 665                 670

Ile Ala Val Ala Val
        675


<210> SEQ ID NO 52
<211> LENGTH: 2034
<212> TYPE: DNA
<213> ORGANISM: Mycobacterium tuberculosis
<220> FEATURE:
<223> OTHER INFORMATION: Rv3615c-Rv2034-Rv2628-Rv1009

<400> SEQUENCE: 52

atgacggaaa acttgaccgt ccagcccgag cgtctcggtg tactggcgtc gcaccatgac      60

aacgcggcgg tcgatgcctc ctcgggcgtc gaagctgccg ctggcctagg cgaatctgtg     120

gcgatcactc acggtccgta ctgctcacag ttcaacgaca cgttaaatgt gtacttgact     180

gcccacaatg ccctgggctc gtccttgcat acggccggtg tcgatctcgc caaaagtctt     240

cgaattgcgg cgaagatata tagcgaggcc gacgaagcgt ggcgcaaggc tatcgacggg     300

ttgtttaccg gatccgtgtc cacttacaga tcaccggatc gcgcttggca ggcgctggcg     360

gacggcactc gccgggccat cgtggagcgg ctggcgcacg gcccgctggc cgtcggcgag     420

ttggcccgcg acctgcccgt cagccgaccc gcggtgtcac agcacctcaa agtgctcaag     480

accgccaggc tggtgtgcga ccgccccgcg ggaacacgcc gcgtctacca gctcgacccg     540

acaggccttg cggcattgcg caccgacctc gaccggttct ggacacgcgc cctgactggc     600

tacgcgcagc tcatcgactc cgaaggagac gacacagaat tcatgtccac gcaacgaccg     660

aggcactccg gtattcgggc tgttggcccc tacgcatggg ccggccgatg tggtcggata     720

ggcaggtggg gggtgcacca ggaggcgatg atgaatctag cgatatggca cccgcgcaag     780

gtgcaatccg ccaccatcta tcaggtgacc gatcgctcgc acgacgggcg cacagcacgg     840

gtgcctggtg acgagatcac tagcaccgtg tccggttggt tgtcggagtt gggcacccaa     900

agcccgttgg ccgatgagct tgcgcgtgcg gtgcggatcg gcgactggcc cgctgcgtac     960

gcaatcggtg agcacctgtc cgttgagatt gccgttgcgg tcaagcttat ggcatgcaaa    1020

acggtgacgt tgaccgtcga cggaaccgcg atgcgggtga ccacgatgaa atcgcgggtg    1080

atcgacatcg tcgaagagaa cgggttctca gtcgacgacc gcgacgacct gtatcccgcg    1140

gccggcgtgc aggtccatga cgccgacacc atcgtgctgc ggcgtagccg tccgctgcag    1200

atctcgctgg atggtcacga cgctaagcag gtgtggacga ccgcgtcgac ggtggacgag    1260

gcgctggccc aactcgcgat gaccgacacg gcgccggccg cggcttctcg cgccagccgc    1320

gtcccgctgt ccgggatggc gctaccggtc gtcagcgcca agacggtgca gctcaacgac    1380
```

-continued ggcgggttgg tgcgcacggt gcacttgccg gcccccaatg tcgcggggct gctgagtgcg 1440
gccggcgtgc cgctgttgca aagcgaccac gtggtgcccg ccgcgacggc cccgatcgtc 1500
gaaggcatgc agatccaggt gacccgcaat cggatcaaga aggtcaccga gcggctgccg 1560
ctgccgccga acgcgcgtcg tgtcgaggac ccggagatga acatgagccg ggaggtcgtc 1620
gaagacccgg gggttccggg gacccaggat gtgacgttcg cggtagctga ggtcaacggc 1680
gtcgagaccg gccgtttgcc cgtcgccaac gtcgtggtga ccccggccca cgaagccgtg 1740
gtgcgggtgg gcaccaagcc cggtaccgag gtgcccccgg tgatcgacgg aagcatctgg 1800
gacgcgatcg ccggctgtga ggccggtggc aactgggcga tcaacaccgg caacgggtat 1860
tacggtggtg tgcagtttga ccagggcacc tgggaggcca acggcgggct gcggtatgca 1920
ccccgcgctg acctcgccac ccgcgaagag cagatcgccg ttgccgaggt gacccgactg 1980
cgtcaaggtt ggggcgcctg gccggtatgt gctgcacgag cgggtgcgcg ctga 2034

<210> SEQ ID NO 53
<211> LENGTH: 677
<212> TYPE: PRT
<213> ORGANISM: Mycobacterium tuberculosis
<220> FEATURE:
<223> OTHER INFORMATION: Rv3615c-Rv2034-Rv2628-Rv1009

<400> SEQUENCE: 53

Met Thr Glu Asn Leu Thr Val Gln Pro Glu Arg Leu Gly Val Leu Ala
1 5 10 15

Ser His His Asp Asn Ala Ala Val Asp Ala Ser Ser Gly Val Glu Ala
20 25 30

Ala Ala Gly Leu Gly Glu Ser Val Ala Ile Thr His Gly Pro Tyr Cys
35 40 45

Ser Gln Phe Asn Asp Thr Leu Asn Val Tyr Leu Thr Ala His Asn Ala
50 55 60

Leu Gly Ser Ser Leu His Thr Ala Gly Val Asp Leu Ala Lys Ser Leu
65 70 75 80

Arg Ile Ala Ala Lys Ile Tyr Ser Glu Ala Asp Glu Ala Trp Arg Lys
85 90 95

Ala Ile Asp Gly Leu Phe Thr Gly Ser Val Ser Thr Tyr Arg Ser Pro
100 105 110

Asp Arg Ala Trp Gln Ala Leu Ala Asp Gly Thr Arg Arg Ala Ile Val
115 120 125

Glu Arg Leu Ala His Gly Pro Leu Ala Val Gly Glu Leu Ala Arg Asp
130 135 140

Leu Pro Val Ser Arg Pro Ala Val Ser Gln His Leu Lys Val Leu Lys
145 150 155 160

Thr Ala Arg Leu Val Cys Asp Arg Pro Ala Gly Thr Arg Arg Val Tyr
165 170 175

Gln Leu Asp Pro Thr Gly Leu Ala Ala Leu Arg Thr Asp Leu Asp Arg
180 185 190

Phe Trp Thr Arg Ala Leu Thr Gly Tyr Ala Gln Leu Ile Asp Ser Glu
195 200 205

Gly Asp Asp Thr Glu Phe Met Ser Thr Gln Arg Pro Arg His Ser Gly
210 215 220

Ile Arg Ala Val Gly Pro Tyr Ala Trp Ala Gly Arg Cys Gly Arg Ile
225 230 235 240

Gly Arg Trp Gly Val His Gln Glu Ala Met Met Asn Leu Ala Ile Trp
245 250 255

-continued

```
His Pro Arg Lys Val Gln Ser Ala Thr Ile Tyr Gln Val Thr Asp Arg
            260                 265                 270

Ser His Asp Gly Arg Thr Ala Arg Val Pro Gly Asp Glu Ile Thr Ser
        275                 280                 285

Thr Val Ser Gly Trp Leu Ser Glu Leu Gly Thr Gln Ser Pro Leu Ala
    290                 295                 300

Asp Glu Leu Ala Arg Ala Val Arg Ile Gly Asp Trp Pro Ala Ala Tyr
305                 310                 315                 320

Ala Ile Gly Glu His Leu Ser Val Glu Ile Ala Val Ala Val Lys Leu
                325                 330                 335

Met Ala Cys Lys Thr Val Thr Leu Thr Val Asp Gly Thr Ala Met Arg
            340                 345                 350

Val Thr Thr Met Lys Ser Arg Val Ile Asp Ile Val Glu Glu Asn Gly
        355                 360                 365

Phe Ser Val Asp Asp Arg Asp Asp Leu Tyr Pro Ala Ala Gly Val Gln
    370                 375                 380

Val His Asp Ala Asp Thr Ile Val Leu Arg Arg Ser Arg Pro Leu Gln
385                 390                 395                 400

Ile Ser Leu Asp Gly His Asp Ala Lys Gln Val Trp Thr Thr Ala Ser
                405                 410                 415

Thr Val Asp Glu Ala Leu Ala Gln Leu Ala Met Thr Asp Thr Ala Pro
            420                 425                 430

Ala Ala Ala Ser Arg Ala Ser Arg Val Pro Leu Ser Gly Met Ala Leu
        435                 440                 445

Pro Val Val Ser Ala Lys Thr Val Gln Leu Asn Asp Gly Gly Leu Val
    450                 455                 460

Arg Thr Val His Leu Pro Ala Pro Asn Val Ala Gly Leu Leu Ser Ala
465                 470                 475                 480

Ala Gly Val Pro Leu Leu Gln Ser Asp His Val Val Pro Ala Ala Thr
                485                 490                 495

Ala Pro Ile Val Glu Gly Met Gln Ile Gln Val Thr Arg Asn Arg Ile
            500                 505                 510

Lys Lys Val Thr Glu Arg Leu Pro Leu Pro Pro Asn Ala Arg Arg Val
        515                 520                 525

Glu Asp Pro Glu Met Asn Met Ser Arg Glu Val Val Glu Asp Pro Gly
    530                 535                 540

Val Pro Gly Thr Gln Asp Val Thr Phe Ala Val Ala Glu Val Asn Gly
545                 550                 555                 560

Val Glu Thr Gly Arg Leu Pro Val Ala Asn Val Val Val Thr Pro Ala
                565                 570                 575

His Glu Ala Val Val Arg Val Gly Thr Lys Pro Gly Thr Glu Val Pro
            580                 585                 590

Pro Val Ile Asp Gly Ser Ile Trp Asp Ala Ile Ala Gly Cys Glu Ala
        595                 600                 605

Gly Gly Asn Trp Ala Ile Asn Thr Gly Asn Gly Tyr Tyr Gly Gly Val
    610                 615                 620

Gln Phe Asp Gln Gly Thr Trp Glu Ala Asn Gly Gly Leu Arg Tyr Ala
625                 630                 635                 640

Pro Arg Ala Asp Leu Ala Thr Arg Glu Glu Gln Ile Ala Val Ala Glu
                645                 650                 655

Val Thr Arg Leu Arg Gln Gly Trp Gly Ala Trp Pro Val Cys Ala Ala
            660                 665                 670
```

```
Arg Ala Gly Ala Arg
        675


<210> SEQ ID NO 54
<211> LENGTH: 2152
<212> TYPE: DNA
<213> ORGANISM: Mycobacterium tuberculosis
<220> FEATURE:
<223> OTHER INFORMATION: Rv2034-Rv3615c-Rv2628-Rv3136

<400> SEQUENCE: 54

atggtgtcca cttacagatc accggatcgc gcttggcagg cgctggcgga cggcactcgc     60

cgggccatcg tggagcggct ggcgcacggc ccgctggccg tcggcgagtt ggcccgcgac    120

ctgcccgtca gccgacccgc ggtgtcacag cacctcaaag tgctcaagac cgccaggctg    180

gtgtgcgacc gccccgcggg aacacgccgc gtctaccagc tcgacccgac aggccttgcg    240

gcattgcgca ccgacctcga ccggttctgg acacgcgccc tgactggcta cgcgcagctc    300

atcgactccg aaggagacga cacagaattc atgacggaaa acttgaccgt ccagcccgag    360

cgtctcggtg tactggcgtc gcaccatgac aacgcggcgg tcgatgcctc ctcgggcgtc    420

gaagctgccg ctggcctagg cgaatctgtg gcgatcactc acggtccgta ctgctcacag    480

ttcaacgaca cgttaaatgt gtacttgact gcccacaatg ccctgggctc gtccttgcat    540

acggccggtg tcgatctcgc caaaagtctt cgaattgcgg cgaagatata tagcgaggcc    600

gacgaagcgt ggcgcaaggc tatcgacggg ttgtttaccg agctcatgtc cacgcaacga    660

ccgaggcact ccggtattcg ggctgttggc cctacgcat gggccggccg atgtggtcgg    720

ataggcaggt ggggggtgca ccaggaggcg atgatgaatc tagcgatggc acccgcgcaa    780

ggtgcaatcc gccaccatct atcaggtgac cgatcgctcg cacgacgggc gcacagcacg    840

ggtgcctggt gacgagatca ctagcaccgt gtccggttgg ttgtcggagt tgggcaccca    900

aagcccgttg gccgatgagc ttgcgcgtgc ggtgcggatc ggcgactggc ccgctgcgta    960

cgcaatcggt gagcacctgt ccgttgagat tgccgttgcg gtcaagctta tggatttcgc   1020

actgttacca ccggaagtca actccgcccg gatgtacacc ggccctgggg caggatcgct   1080

gttggctgcc gcgggcggct gggattcgct ggccgccgag ttggccacca cagccgaggc   1140

atatggatcg gtgctgtccg gactggccgc cttgcattgg cgtggaccgg cagcggaatc   1200

gatggcggtg acggccgctc cctatatcgg ttggctgtac acgaccgccg aaaagacaca   1260

gcaaacagcg atccaagcca gggcggcagc gctggccttc gagcaagcat acgcaatgac   1320

cctgccgcca ccggtggtag cggccaaccg gatacagctg ctagcactga tcgcgacgaa   1380

cttcttcggc cagaacactg cggcgatcgc ggccaccgag gcacagtacg ccgagatgtg   1440

ggcccaggac gccgccgcga tgtacggtta cgccaccgcc tcagcggctg cggccctgct   1500

gacaccgttc tccccgccgc ggcagaccac caacccggcc ggcctgaccg ctcaggccgc   1560

cgcggtcagc caggccaccg acccactgtc gctgctgatt gagacggtga cccaagcgct   1620

gcaagcgctg acgattccga gcttcatccc tgaggacttc accttccttg acgccatatt   1680

cgctggatat gccacggtag gtgtgacgca ggatgtcgag tcctttgttg ccgggaccat   1740

cggggccgag agcaacctag gcctttgaa cgtcggcgac gagaatcccg cggaggtgac   1800

accgggcgac tttgggatcg gcgagttggt ttccgcgacc agtcccggcg gtggggtgtc   1860

tgcgtcgggt gccggcggtg cggcgagcgt cggcaacacg gtgctcgcga gtgtcggccg   1920

ggcaaactcg attgggcaac tatcggtccc accgagctgg gccgcgccct cgacgcgccc   1980
```

-continued

```
tgtctcggca ttgtcgcccg ccggcctgac cacactcccg gggaccgacg tggccgagca   2040

cgggatgcca ggtgtaccgg gggtgccagt ggcagcaggg cgagcctccg gcgtcctacc   2100

tcgatacggg gttcggctca cggtgatggc ccacccaccc gcggcagggt ag           2152


<210> SEQ ID NO 55
<211> LENGTH: 717
<212> TYPE: PRT
<213> ORGANISM: Mycobacterium tuberculosis
<220> FEATURE:
<223> OTHER INFORMATION: Rv2034-Rv3615c-Rv2628-Rv3136

<400> SEQUENCE: 55

Met Val Ser Thr Tyr Arg Ser Pro Asp Arg Ala Trp Gln Ala Leu Ala
1               5                   10                  15

Asp Gly Thr Arg Arg Ala Ile Val Glu Arg Leu Ala His Gly Pro Leu
            20                  25                  30

Ala Val Gly Glu Leu Ala Arg Asp Leu Pro Val Ser Arg Pro Ala Val
        35                  40                  45

Ser Gln His Leu Lys Val Leu Lys Thr Ala Arg Leu Val Cys Asp Arg
    50                  55                  60

Pro Ala Gly Thr Arg Arg Val Tyr Gln Leu Asp Pro Thr Gly Leu Ala
65                  70                  75                  80

Ala Leu Arg Thr Asp Leu Asp Arg Phe Trp Thr Arg Ala Leu Thr Gly
                85                  90                  95

Tyr Ala Gln Leu Ile Asp Ser Glu Gly Asp Asp Thr Glu Phe Met Thr
            100                 105                 110

Glu Asn Leu Thr Val Gln Pro Glu Arg Leu Gly Val Leu Ala Ser His
        115                 120                 125

His Asp Asn Ala Ala Val Asp Ala Ser Ser Gly Val Glu Ala Ala Ala
    130                 135                 140

Gly Leu Gly Glu Ser Val Ala Ile Thr His Gly Pro Tyr Cys Ser Gln
145                 150                 155                 160

Phe Asn Asp Thr Leu Asn Val Tyr Leu Thr Ala His Asn Ala Leu Gly
                165                 170                 175

Ser Ser Leu His Thr Ala Gly Val Asp Leu Ala Lys Ser Leu Arg Ile
            180                 185                 190

Ala Ala Lys Ile Tyr Ser Glu Ala Asp Glu Ala Trp Arg Lys Ala Ile
        195                 200                 205

Asp Gly Leu Phe Thr Glu Leu Met Ser Thr Gln Arg Pro Arg His Ser
    210                 215                 220

Gly Ile Arg Ala Val Gly Pro Tyr Ala Trp Ala Gly Arg Cys Gly Arg
225                 230                 235                 240

Ile Gly Arg Trp Gly Val His Gln Glu Ala Met Met Asn Leu Ala Ile
                245                 250                 255

Trp His Pro Arg Lys Val Gln Ser Ala Thr Ile Tyr Gln Val Thr Asp
            260                 265                 270

Arg Ser His Asp Gly Arg Thr Ala Arg Val Pro Gly Asp Glu Ile Thr
        275                 280                 285

Ser Thr Val Ser Gly Trp Leu Ser Glu Leu Gly Thr Gln Ser Pro Leu
    290                 295                 300

Ala Asp Glu Leu Ala Arg Ala Val Arg Ile Gly Asp Trp Pro Ala Ala
305                 310                 315                 320

Tyr Ala Ile Gly Glu His Leu Ser Val Glu Ile Ala Val Ala Val Lys
                325                 330                 335
```

```
Leu Met Asp Phe Ala Leu Leu Pro Pro Glu Val Asn Ser Ala Arg Met
            340                 345                 350

Tyr Thr Gly Pro Gly Ala Gly Ser Leu Leu Ala Ala Ala Gly Gly Trp
        355                 360                 365

Asp Ser Leu Ala Ala Glu Leu Ala Thr Thr Ala Glu Ala Tyr Gly Ser
    370                 375                 380

Val Leu Ser Gly Leu Ala Ala Leu His Trp Arg Gly Pro Ala Ala Glu
385                 390                 395                 400

Ser Met Ala Val Thr Ala Ala Pro Tyr Ile Gly Trp Leu Tyr Thr Thr
                405                 410                 415

Ala Glu Lys Thr Gln Gln Thr Ala Ile Gln Ala Arg Ala Ala Ala Leu
            420                 425                 430

Ala Phe Glu Gln Ala Tyr Ala Met Thr Leu Pro Pro Pro Val Val Ala
        435                 440                 445

Ala Asn Arg Ile Gln Leu Leu Ala Leu Ile Ala Thr Asn Phe Phe Gly
    450                 455                 460

Gln Asn Thr Ala Ala Ile Ala Ala Thr Glu Ala Gln Tyr Ala Glu Met
465                 470                 475                 480

Trp Ala Gln Asp Ala Ala Ala Met Tyr Gly Tyr Ala Thr Ala Ser Ala
                485                 490                 495

Ala Ala Ala Leu Leu Thr Pro Phe Ser Pro Pro Arg Gln Thr Thr Asn
            500                 505                 510

Pro Ala Gly Leu Thr Ala Gln Ala Ala Ala Val Ser Gln Ala Thr Asp
        515                 520                 525

Pro Leu Ser Leu Leu Ile Glu Thr Val Thr Gln Ala Leu Gln Ala Leu
    530                 535                 540

Thr Ile Pro Ser Phe Ile Pro Glu Asp Phe Thr Phe Leu Asp Ala Ile
545                 550                 555                 560

Phe Ala Gly Tyr Ala Thr Val Gly Val Thr Gln Asp Val Glu Ser Phe
                565                 570                 575

Val Ala Gly Thr Ile Gly Ala Glu Ser Asn Leu Gly Leu Leu Asn Val
            580                 585                 590

Gly Asp Glu Asn Pro Ala Glu Val Thr Pro Gly Asp Phe Gly Ile Gly
        595                 600                 605

Glu Leu Val Ser Ala Thr Ser Pro Gly Gly Gly Val Ser Ala Ser Gly
    610                 615                 620

Ala Gly Gly Ala Ala Ser Val Gly Asn Thr Val Leu Ala Ser Val Gly
625                 630                 635                 640

Arg Ala Asn Ser Ile Gly Gln Leu Ser Val Pro Pro Ser Trp Ala Ala
                645                 650                 655

Pro Ser Thr Arg Pro Val Ser Ala Leu Ser Pro Ala Gly Leu Thr Thr
            660                 665                 670

Leu Pro Gly Thr Asp Val Ala Glu His Gly Met Pro Gly Val Pro Gly
        675                 680                 685

Val Pro Val Ala Ala Gly Arg Ala Ser Gly Val Leu Pro Arg Tyr Gly
    690                 695                 700

Val Arg Leu Thr Val Met Ala His Pro Pro Ala Ala Gly
705                 710                 715
```

<210> SEQ ID NO 56
<211> LENGTH: 2152
<212> TYPE: DNA
<213> ORGANISM: Mycobacterium tuberculosis
<220> FEATURE:
<223> OTHER INFORMATION: Rv3136-Rv2628-Rv3615c-Rv2034

<400> SEQUENCE: 56
atggatttcg cactgttacc accggaagtc aactccgccc ggatgtacac cggccctggg 60
gcaggatcgc tgttggctgc cgcgggcggc tgggattcgc tggccgccga gttggccacc 120
acagccgagg catatggatc ggtgctgtcc ggactggccg ccttgcattg gcgtggaccg 180
gcagcggaat cgatggcggt gacggccgct ccctatatcg gttggctgta cacgaccgcc 240
gaaaagacac agcaaacagc gatccaagcc agggcggcag cgctggcctt cgagcaagca 300
tacgcaatga ccctgccgcc accggtggta gcggccaacc ggatacagct gctagcactg 360
atcgcgacga acttcttcgg ccagaacact gcggcgatcg cggccaccga ggcacagtac 420
gccgagatgt gggcccagga cgccgccgcg atgtacggtt acgccaccgc ctcagcggct 480
gcggccctgc tgacaccgtt ctccccgccg cggcagacca ccaacccggc cggcctgacc 540
gctcaggccg ccgcggtcag ccaggccacc gacccactgt cgctgctgat tgagacggtg 600
acccaagcgc tgcaagcgct gacgattccg agcttcatcc ctgaggactt caccttcctt 660
gacgccatat tcgctggata tgccacggta ggtgtgacgc aggatgtcga gtcctttgtt 720
gccgggacca tcggggccga gagcaaccta ggccttttga acgtcggcga cgagaatccc 780
gcggaggtga caccgggcga ctttgggatc ggcgagttgg tttccgcgac cagtcccggc 840
ggtggggtgt ctgcgtcggg tgccggcggt gcggcgagcg tcggcaacac ggtgctcgcg 900
agtgtcggcc gggcaaactc gattgggcaa ctatcggtcc caccgagctg ggccgcgccc 960
tcgacgcgcc ctgtctcggc attgtcgccc gccggcctga ccacactccc ggggaccgac 1020
gtggccgagc acgggatgcc aggtgtaccg ggggtgccag tggcagcagg gcgagcctcc 1080
ggcgtcctac ctcgatacgg ggttcggctc acggtgatgg cccacccacc cgcggcaggg 1140
gaattcatgt ccacgcaacg accgaggcac tccggtattc gggctgttgg cccctacgca 1200
tgggccggcc gatgtggtcg gataggcagg tggggggtgc accaggaggc gatgatgaat 1260
ctagcgatat ggcacccgcg caaggtgcaa tccgccacca tctatcaggt gaccgatcgc 1320
tcgcaccggg cgcacagcac gggtgcctgg tgacgagatc actagcaccg tgtccggttg 1380
gttgtcggag ttgggcaccc aaagcccgtt ggccgatgag cttgcgcgtg cggtgcggat 1440
cggcgactgg cccgctgcgt acgcaatcgg tgagcacctg tccgttgaga ttgccgttgc 1500
ggtcgagctc atgacggaaa acttgaccgt ccagcccgag cgtctcggtg tactggcgtc 1560
gcaccatgac aacgcggcgg tcgatgcctc ctcgggcgtc gaagctgccg ctggcctagg 1620
cgaatctgtg gcgatcactc acggtccgta ctgctcacag ttcaacgaca cgttaaatgt 1680
gtacttgact gcccacaatg ccctgggctc gtccttgcat acggccggtg tcgatctcgc 1740
caaaagtctt cgaattgcgg cgaagatata tagcgaggcc gacgaagcgt ggcgcaaggc 1800
tatcgacggg ttgtttacca agcttatggt gtccacttac agatcaccgg atcgcgcttg 1860
gcaggcgctg gcggacggca ctcgccgggc catcgtggag cggctggcgc acggcccgct 1920
ggccgtcggc gagttggccc gcgacctgcc cgtcagccga cccgcggtgt cacagcacct 1980
caaagtgctc aagaccgcca ggctggtgtg cgaccgcccc gcgggaacac gccgcgtcta 2040
ccagctcgac ccgacaggcc ttgcggcatt gcgcaccgac ctcgaccggt tctggacacg 2100
cgccctgact ggctacgcgc agctcatcga ctccgaagga gacgacacat ag 2152

<210> SEQ ID NO 57
<211> LENGTH: 717
<212> TYPE: PRT

-continued

<213> ORGANISM: Mycobacterium tuberculosis
<220> FEATURE:
<223> OTHER INFORMATION: Rv3136-Rv2628-Rv3615c-Rv2034

<400> SEQUENCE: 57

```
Met Asp Phe Ala Leu Leu Pro Pro Glu Val Asn Ser Ala Arg Met Tyr
1               5                   10                  15

Thr Gly Pro Gly Ala Gly Ser Leu Leu Ala Ala Ala Gly Gly Trp Asp
            20                  25                  30

Ser Leu Ala Ala Glu Leu Ala Thr Thr Ala Glu Ala Tyr Gly Ser Val
        35                  40                  45

Leu Ser Gly Leu Ala Ala Leu His Trp Arg Gly Pro Ala Ala Glu Ser
    50                  55                  60

Met Ala Val Thr Ala Ala Pro Tyr Ile Gly Trp Leu Tyr Thr Thr Ala
65                  70                  75                  80

Glu Lys Thr Gln Gln Thr Ala Ile Gln Ala Arg Ala Ala Ala Leu Ala
                85                  90                  95

Phe Glu Gln Ala Tyr Ala Met Thr Leu Pro Pro Pro Val Val Ala Ala
            100                 105                 110

Asn Arg Ile Gln Leu Leu Ala Leu Ile Ala Thr Asn Phe Phe Gly Gln
        115                 120                 125

Asn Thr Ala Ala Ile Ala Ala Thr Glu Ala Gln Tyr Ala Glu Met Trp
    130                 135                 140

Ala Gln Asp Ala Ala Ala Met Tyr Gly Tyr Ala Thr Ala Ser Ala Ala
145                 150                 155                 160

Ala Ala Leu Leu Thr Pro Phe Ser Pro Pro Arg Gln Thr Thr Asn Pro
                165                 170                 175

Ala Gly Leu Thr Ala Gln Ala Ala Ala Val Ser Gln Ala Thr Asp Pro
            180                 185                 190

Leu Ser Leu Leu Ile Glu Thr Val Thr Gln Ala Leu Gln Ala Leu Thr
        195                 200                 205

Ile Pro Ser Phe Ile Pro Glu Asp Phe Thr Phe Leu Asp Ala Ile Phe
    210                 215                 220

Ala Gly Tyr Ala Thr Val Gly Val Thr Gln Asp Val Glu Ser Phe Val
225                 230                 235                 240

Ala Gly Thr Ile Gly Ala Glu Ser Asn Leu Gly Leu Leu Asn Val Gly
                245                 250                 255

Asp Glu Asn Pro Ala Glu Val Thr Pro Gly Asp Phe Gly Ile Gly Glu
            260                 265                 270

Leu Val Ser Ala Thr Ser Pro Gly Gly Gly Val Ser Ala Ser Gly Ala
        275                 280                 285

Gly Gly Ala Ala Ser Val Gly Asn Thr Val Leu Ala Ser Val Gly Arg
    290                 295                 300

Ala Asn Ser Ile Gly Gln Leu Ser Val Pro Pro Ser Trp Ala Ala Pro
305                 310                 315                 320

Ser Thr Arg Pro Val Ser Ala Leu Ser Pro Ala Gly Leu Thr Thr Leu
                325                 330                 335

Pro Gly Thr Asp Val Ala Glu His Gly Met Pro Gly Val Pro Gly Val
            340                 345                 350

Pro Val Ala Ala Gly Arg Ala Ser Gly Val Leu Pro Arg Tyr Gly Val
        355                 360                 365

Arg Leu Thr Val Met Ala His Pro Pro Ala Ala Gly Glu Phe Met Ser
    370                 375                 380

Thr Gln Arg Pro Arg His Ser Gly Ile Arg Ala Val Gly Pro Tyr Ala
```

-continued

```
385                 390                 395                 400

Trp Ala Gly Arg Cys Gly Arg Ile Gly Arg Trp Gly Val His Gln Glu
                405                 410                 415

Ala Met Met Asn Leu Ala Ile Trp His Pro Arg Lys Val Gln Ser Ala
            420                 425                 430

Thr Ile Tyr Gln Val Thr Asp Arg Ser His Asp Gly Arg Thr Ala Arg
        435                 440                 445

Val Pro Gly Asp Glu Ile Thr Ser Thr Val Ser Gly Trp Leu Ser Glu
    450                 455                 460

Leu Gly Thr Gln Ser Pro Leu Ala Asp Glu Leu Ala Arg Ala Val Arg
465                 470                 475                 480

Ile Gly Asp Trp Pro Ala Ala Tyr Ala Ile Gly Glu His Leu Ser Val
                485                 490                 495

Glu Ile Ala Val Ala Val Glu Leu Met Thr Glu Asn Leu Thr Val Gln
            500                 505                 510

Pro Glu Arg Leu Gly Val Leu Ala Ser His His Asp Asn Ala Ala Val
        515                 520                 525

Asp Ala Ser Ser Gly Val Glu Ala Ala Ala Gly Leu Gly Glu Ser Val
    530                 535                 540

Ala Ile Thr His Gly Pro Tyr Cys Ser Gln Phe Asn Asp Thr Leu Asn
545                 550                 555                 560

Val Tyr Leu Thr Ala His Asn Ala Leu Gly Ser Ser Leu His Thr Ala
                565                 570                 575

Gly Val Asp Leu Ala Lys Ser Leu Arg Ile Ala Ala Lys Ile Tyr Ser
            580                 585                 590

Glu Ala Asp Glu Ala Trp Arg Lys Ala Ile Asp Gly Leu Phe Thr Lys
        595                 600                 605

Leu Met Val Ser Thr Tyr Arg Ser Pro Asp Arg Ala Trp Gln Ala Leu
    610                 615                 620

Ala Asp Gly Thr Arg Arg Ala Ile Val Glu Arg Leu Ala His Gly Pro
625                 630                 635                 640

Leu Ala Val Gly Glu Leu Ala Arg Asp Leu Pro Val Ser Arg Pro Ala
                645                 650                 655

Val Ser Gln His Leu Lys Val Leu Lys Thr Ala Arg Leu Val Cys Asp
            660                 665                 670

Arg Pro Ala Gly Thr Arg Arg Val Tyr Gln Leu Asp Pro Thr Gly Leu
        675                 680                 685

Ala Ala Leu Arg Thr Asp Leu Asp Arg Phe Trp Thr Arg Ala Leu Thr
    690                 695                 700

Gly Tyr Ala Gln Leu Ile Asp Ser Glu Gly Asp Asp Thr
705                 710                 715
```

<210> SEQ ID NO 58
<211> LENGTH: 2580
<212> TYPE: DNA
<213> ORGANISM: Mycobacterium tuberculosis
<220> FEATURE:
<223> OTHER INFORMATION: Rv1009-Rv3136Nt-Rv2628-Rv2034-Rv3615c

<400> SEQUENCE: 58

```
atggcatgca aaacggtgac gttgaccgtc gacggaaccg cgatgcgggt gaccacgatg      60

aaatcgcggg tgatcgacat cgtcgaagag aacgggttct cagtcgacga ccgcgacgac     120

ctgtatcccg cggccggcgt gcaggtccat gacgccgaca ccatcgtgct gcggcgtagc     180

cgtccgctgc agatctcgct ggatggtcac gacgctaagc aggtgtggac gaccgcgtcg     240
```

-continued

```
acggtggacg aggcgctggc ccaactcgcg atgaccgaca cggcgccggc cgcggcttct    300
cgcgccagcc gcgtcccgct gtccgggatg gcgctaccgg tcgtcagcgc caagacggtg    360
cagctcaacg acggcgggtt ggtgcgcacg gtgcacttgc cggcccccaa tgtcgcgggg    420
ctgctgagtg cggccggcgt gccgctgttg caaagcgacc acgtggtgcc cgccgcgacg    480
gccccgatcg tcgaaggcat gcagatccag gtgacccgca atcggatcaa gaaggtcacc    540
gagcggctgc cgctgccgcc gaacgcgcgt cgtgtcgagg acccggagat gaacatgagc    600
cgggaggtcg tcgaagaccc gggggttccg gggacccagg atgtgacgtt cgcggtagct    660
gaggtcaacg gcgtcgagac cggccgtttg cccgtcgcca acgtcgtggt gaccccggcc    720
cacgaagccg tggtgcgggt gggcaccaag cccggtaccg aggtgccccc ggtgatcgac    780
ggaagcatct gggacgcgat cgccggctgt gaggccggtg gcaactgggc gatcaacacc    840
ggcaacgggt attacggtgg tgtgcagttt gaccagggca cctgggaggc caacggcggg    900
ctgcggtatg caccccgcgc tgacctcgcc acccgcgaag agcagatcgc cgttgccgag    960
gtgacccgac tgcgtcaagg ttggggcgcc tggccggtat gtgctgcacg agcgggtgcg   1020
cgcggattca tggatttcgc actgttacca ccggaagtca actccgcccg gatgtacacc   1080
ggccctgggg caggatcgct gttggctgcc gcgggcggct gggattcgct ggccgccgag   1140
ttggccacca cagccgaggc atatggatcg gtgctgtccg gactggccgc cttgcattgg   1200
cgtggaccgg cagcggaatc gatggcggtg acggccgctc cctatatcgg ttggctgtac   1260
acgaccgccg aaaagacaca gcaaacagcg atccaagcca gggcggcagc gctggccttc   1320
gagcaagcat acgcaatgac cctgccgcca ccggtggtag cggccaaccg gatacagctg   1380
ctagcactga tcgcgacgaa cttcttcggc cagaacactg cggcgatcgc ggccaccgag   1440
gcacagtacg ccgagatgtg ggcccaggac gccgccgcga tgtacggtta cgccaccgcc   1500
tcagcggctg cggccctgct gacaccgttc tccccgccgc ggcagaccac caacccggcc   1560
ggcctgaccg aattcatgtc cacgcaacga ccgaggcact ccggtattcg ggctgttggc   1620
ccctacgcat gggccggccg atgtggtcgg ataggcaggt ggggggtgca ccaggaggcg   1680
atgatgaatc tagcgatatg gcacccgcgc aaggtgcaat ccgccaccat ctatcaggtg   1740
accgatcgct cgcacgacgg gcgcacagca cgggtgcctg gtgacgagat cactagcacc   1800
gtgtccggtt ggttgtcgga gttgggcacc caaagcccgt tggccgatga gcttgcgcgt   1860
gcggtgcgga tcggcgactg gcccgctgcg tacgcaatcg gtgagcacct gtccgttgag   1920
attgccgttg cggtcgagct cgtgtccact tacagatcac cggatcgcgc ttggcaggcg   1980
ctggcggacg gcactcgccg ggccatcgtg gagcggctgg cgcacggccc gctggccgtc   2040
ggcgagttgg cccgcgacct gcccgtcagc cgacccgcgg tgtcacagca cctcaaagtg   2100
ctcaagaccg ccaggctggt gtgcgaccgc cccgcgggaa cacgccgcgt ctaccagctc   2160
gacccgacag gccttgcggc attgcgcacc gacctcgacc ggttctggac acgcgccctg   2220
actggctacg cgcagctcat cgactccgaa ggagacgaca caaagcttat gacggaaaac   2280
ttgaccgtcc agcccgagcg tctcggtgta ctggcgtcgc accatgacaa cgcggcggtc   2340
gatgcctcct cgggcgtcga agctgccgct ggcctaggcg aatctgtggc gatcactcac   2400
ggtccgtact gctcacagtt caacgacacg ttaaatgtgt acttgactgc ccacaatgcc   2460
ctgggctcgt ccttgcatac ggccggtgtc gatctcgcca aaagtcttcg aattgcggcg   2520
aagatatata gcgaggccga cgaagcgtgg cgcaaggcta tcgacgggtt gtttacctga   2580
```

<210> SEQ ID NO 59
<211> LENGTH: 859
<212> TYPE: PRT
<213> ORGANISM: Mycobacterium tuberculosis
<220> FEATURE:
<223> OTHER INFORMATION: Rv1009-Rv3136Nt-Rv2628-Rv2034-Rv3615c

<400> SEQUENCE: 59

Met Ala Cys Lys Thr Val Thr Leu Thr Val Asp Gly Thr Ala Met Arg
1 5 10 15

Val Thr Thr Met Lys Ser Arg Val Ile Asp Ile Val Glu Glu Asn Gly
20 25 30

Phe Ser Val Asp Asp Arg Asp Asp Leu Tyr Pro Ala Ala Gly Val Gln
35 40 45

Val His Asp Ala Asp Thr Ile Val Leu Arg Arg Ser Arg Pro Leu Gln
50 55 60

Ile Ser Leu Asp Gly His Asp Ala Lys Gln Val Trp Thr Thr Ala Ser
65 70 75 80

Thr Val Asp Glu Ala Leu Ala Gln Leu Ala Met Thr Asp Thr Ala Pro
85 90 95

Ala Ala Ala Ser Arg Ala Ser Arg Val Pro Leu Ser Gly Met Ala Leu
100 105 110

Pro Val Val Ser Ala Lys Thr Val Gln Leu Asn Asp Gly Gly Leu Val
115 120 125

Arg Thr Val His Leu Pro Ala Pro Asn Val Ala Gly Leu Leu Ser Ala
130 135 140

Ala Gly Val Pro Leu Leu Gln Ser Asp His Val Val Pro Ala Ala Thr
145 150 155 160

Ala Pro Ile Val Glu Gly Met Gln Ile Gln Val Thr Arg Asn Arg Ile
165 170 175

Lys Lys Val Thr Glu Arg Leu Pro Leu Pro Pro Asn Ala Arg Arg Val
180 185 190

Glu Asp Pro Glu Met Asn Met Ser Arg Glu Val Val Glu Asp Pro Gly
195 200 205

Val Pro Gly Thr Gln Asp Val Thr Phe Ala Val Ala Glu Val Asn Gly
210 215 220

Val Glu Thr Gly Arg Leu Pro Val Ala Asn Val Val Val Thr Pro Ala
225 230 235 240

His Glu Ala Val Val Arg Val Gly Thr Lys Pro Gly Thr Glu Val Pro
245 250 255

Pro Val Ile Asp Gly Ser Ile Trp Asp Ala Ile Ala Gly Cys Glu Ala
260 265 270

Gly Gly Asn Trp Ala Ile Asn Thr Gly Asn Gly Tyr Tyr Gly Gly Val
275 280 285

Gln Phe Asp Gln Gly Thr Trp Glu Ala Asn Gly Gly Leu Arg Tyr Ala
290 295 300

Pro Arg Ala Asp Leu Ala Thr Arg Glu Glu Gln Ile Ala Val Ala Glu
305 310 315 320

Val Thr Arg Leu Arg Gln Gly Trp Gly Ala Trp Pro Val Cys Ala Ala
325 330 335

Arg Ala Gly Ala Arg Gly Phe Met Asp Phe Ala Leu Leu Pro Pro Glu
340 345 350

Val Asn Ser Ala Arg Met Tyr Thr Gly Pro Gly Ala Gly Ser Leu Leu
355 360 365

-continued

```
Ala Ala Ala Gly Gly Trp Asp Ser Leu Ala Ala Glu Leu Ala Thr Thr
    370                 375                 380

Ala Glu Ala Tyr Gly Ser Val Leu Ser Gly Leu Ala Ala Leu His Trp
385                 390                 395                 400

Arg Gly Pro Ala Ala Glu Ser Met Ala Val Thr Ala Ala Pro Tyr Ile
                405                 410                 415

Gly Trp Leu Tyr Thr Thr Ala Glu Lys Thr Gln Gln Thr Ala Ile Gln
            420                 425                 430

Ala Arg Ala Ala Ala Leu Ala Phe Glu Gln Ala Tyr Ala Met Thr Leu
        435                 440                 445

Pro Pro Pro Val Val Ala Ala Asn Arg Ile Gln Leu Leu Ala Leu Ile
    450                 455                 460

Ala Thr Asn Phe Phe Gly Gln Asn Thr Ala Ala Ile Ala Ala Thr Glu
465                 470                 475                 480

Ala Gln Tyr Ala Glu Met Trp Ala Gln Asp Ala Ala Ala Met Tyr Gly
                485                 490                 495

Tyr Ala Thr Ala Ser Ala Ala Ala Ala Leu Leu Thr Pro Phe Ser Pro
            500                 505                 510

Pro Arg Gln Thr Thr Asn Pro Ala Gly Leu Thr Glu Phe Met Ser Thr
        515                 520                 525

Gln Arg Pro Arg His Ser Gly Ile Arg Ala Val Gly Pro Tyr Ala Trp
    530                 535                 540

Ala Gly Arg Cys Gly Arg Ile Gly Arg Trp Gly Val His Gln Glu Ala
545                 550                 555                 560

Met Met Asn Leu Ala Ile Trp His Pro Arg Lys Val Gln Ser Ala Thr
                565                 570                 575

Ile Tyr Gln Val Thr Asp Arg Ser His Asp Gly Arg Thr Ala Arg Val
            580                 585                 590

Pro Gly Asp Glu Ile Thr Ser Thr Val Ser Gly Trp Leu Ser Glu Leu
        595                 600                 605

Gly Thr Gln Ser Pro Leu Ala Asp Glu Leu Ala Arg Ala Val Arg Ile
    610                 615                 620

Gly Asp Trp Pro Ala Ala Tyr Ala Ile Gly Glu His Leu Ser Val Glu
625                 630                 635                 640

Ile Ala Val Ala Val Glu Leu Val Ser Thr Tyr Arg Ser Pro Asp Arg
                645                 650                 655

Ala Trp Gln Ala Leu Ala Asp Gly Thr Arg Arg Ala Ile Val Glu Arg
            660                 665                 670

Leu Ala His Gly Pro Leu Ala Val Gly Glu Leu Ala Arg Asp Leu Pro
        675                 680                 685

Val Ser Arg Pro Ala Val Ser Gln His Leu Lys Val Leu Lys Thr Ala
    690                 695                 700

Arg Leu Val Cys Asp Arg Pro Ala Gly Thr Arg Arg Val Tyr Gln Leu
705                 710                 715                 720

Asp Pro Thr Gly Leu Ala Ala Leu Arg Thr Asp Leu Asp Arg Phe Trp
                725                 730                 735

Thr Arg Ala Leu Thr Gly Tyr Ala Gln Leu Ile Asp Ser Glu Gly Asp
            740                 745                 750

Asp Thr Lys Leu Met Thr Glu Asn Leu Thr Val Gln Pro Glu Arg Leu
        755                 760                 765

Gly Val Leu Ala Ser His His Asp Asn Ala Ala Val Asp Ala Ser Ser
    770                 775                 780

Gly Val Glu Ala Ala Ala Gly Leu Gly Glu Ser Val Ala Ile Thr His
```

-continued

```
785                 790                 795                 800

Gly Pro Tyr Cys Ser Gln Phe Asn Asp Thr Leu Asn Val Tyr Leu Thr
                805                 810                 815

Ala His Asn Ala Leu Gly Ser Ser Leu His Thr Ala Gly Val Asp Leu
            820                 825                 830

Ala Lys Ser Leu Arg Ile Ala Ala Lys Ile Tyr Ser Glu Ala Asp Glu
        835                 840                 845

Ala Trp Arg Lys Ala Ile Asp Gly Leu Phe Thr
    850                 855
```

<210> SEQ ID NO 60
<211> LENGTH: 2580
<212> TYPE: DNA
<213> ORGANISM: Mycobacterium tuberculosis
<220> FEATURE:
<223> OTHER INFORMATION: Rv2034-Rv3615c-Rv3136Nt-Rv2628-Rv1009

<400> SEQUENCE: 60

```
atggtgtcca cttacagatc accggatcgc gcttggcagg cgctggcgga cggcactcgc     60
cgggccatcg tggagcggct ggcgcacggc ccgctggccg tcggcgagtt ggcccgcgac    120
ctgcccgtca gccgacccgc ggtgtcacag cacctcaaag tgctcaagac cgccaggctg    180
gtgtgcgacc gccccgcggg aacacgccgc gtctaccagc tcgacccgac aggccttgcg    240
gcattgcgca ccgacctcga ccggttctgg acacgcgccc tgactggcta cgcgcagctc    300
atcgactccg aaggagacga cacaggatcc atgacggaaa acttgaccgt ccagcccgag    360
cgtctcggtg tactggcgtc gcaccatgac aacgcggcgg tcgatgcctc ctcgggcgtc    420
gaagctgccg ctggcctagg cgaatctgtg gcgatcactc acggtccgta ctgctcacag    480
ttcaacgaca cgttaaatgt gtacttgact gcccacaatg ccctgggctc gtccttgcat    540
acggccggtg tcgatctcgc caaaagtctt cgaattgcgg cgaagatata tagcgaggcc    600
gacgaagcgt ggcgcaaggc tatcgacggg ttgtttaccg aattcatgga tttcgcactg    660
ttaccaccgg aagtcaactc cgcccggatg tacaccggcc ctggggcagg atcgctgttg    720
gctgccgcgg gcggctggga ttcgctggcc gccgagttgg ccaccacagc cgaggcatat    780
ggatcggtgc tgtccggact ggccgccttg cattggcgtg gaccggcagc ggaatcgatg    840
gcggtgacgg ccgctcccta tatcggttgg ctgtacacga ccgccgaaaa gacacagcaa    900
acagcgatcc aagccagggc ggcagcgctg gccttcgagc aagcatacgc aatgaccctg    960
ccgccaccgg tggtagcggc caaccggata cagctgctag cactgatcgc gacgaacttc   1020
ttcggccaga acactgcggc gatcgcggcc accgaggcac agtacgccga gatgtgggcc   1080
caggacgccg ccgcgatgta cggttacgcc accgcctcag cggctgcggc cctgctgaca   1140
ccgttctccc cgccgcggca gaccaccaac ccggccggcc tgaccgagct catgtccacg   1200
caacgaccga ggcactccgg tattcgggct gttggcccct acgcatgggc cggccgatgt   1260
ggtcggatag gcaggtgggg ggtgcaccag gaggcgatga tgaatctagc gatatggcac   1320
ccgcgcaagg tgcaatccgc caccatctat caggtgaccg atcgctcgca cgacgggcgc   1380
acagcacggg tgcctggtga cgagatcact agcaccgtgt ccggttggtt gtcggagttg   1440
ggcacccaaa gcccgttggc cgatgagctt gcgcgtgcgg tgcggatcgg cgactggccc   1500
gctgcgtacg caatcggtga gcacctgtcc gttgagattg ccgttgcggt caagcttgca   1560
tgcaaaacgg tgacgttgac cgtcgacgga accgcgatgc gggtgaccac gatgaaatcg   1620
cgggtgatcg acatcgtcga agagaacggg ttctcagtcg acgaccgcga cgacctgtat   1680
```

```
cccgcggccg gcgtgcaggt ccatgacgcc gacaccatcg tgctgcggcg tagccgtccg   1740

ctgcagatct cgctggatgg tcacgacgct aagcaggtgt ggacgaccgc gtcgacggtg   1800

gacgaggcgc tggcccaact cgcgatgacc gacacggcgc cggccgcggc ttctcgcgcc   1860

agccgcgtcc cgctgtccgg gatggcgcta ccggtcgtca gcgccaagac ggtgcagctc   1920

aacgacggcg ggttggtgcg cacggtgcac ttgccggccc ccaatgtcgc ggggctgctg   1980

agtgcggccg gcgtgccgct gttgcaaagc gaccacgtgg tgcccgccgc gacggccccg   2040

atcgtcgaag gcatgcagat ccaggtgacc cgcaatcgga tcaagaaggt caccgagcgg   2100

ctgccgctgc cgccgaacgc gcgtcgtgtc gaggacccgg agatgaacat gagccgggag   2160

gtcgtcgaag acccgggggt tccggggacc caggatgtga cgttcgcggt agctgaggtc   2220

aacggcgtcg agaccggccg tttgcccgtc gccaacgtcg tggtgacccc ggcccacgaa   2280

gccgtggtgc gggtgggcac caagcccggt accgaggtgc cccccggtgat cgacggaagc   2340

atctgggacg cgatcgccgg ctgtgaggcc ggtggcaact gggcgatcaa caccggcaac   2400

gggtattacg gtggtgtgca gtttgaccag ggcacctggg aggccaacgg cgggctgcgg   2460

tatgcacccc gcgctgacct cgccacccgc gaagagcaga tcgccgttgc cgaggtgacc   2520

cgactgcgtc aaggttgggg cgcctggccg gtatgtgctg cacgagcggg tgcgcgctga   2580
```

<210> SEQ ID NO 61
<211> LENGTH: 859
<212> TYPE: PRT
<213> ORGANISM: Mycobacterium tuberculosis
<220> FEATURE:
<223> OTHER INFORMATION: Rv2034-Rv3615c-Rv3136Nt-Rv2628-Rv1009

<400> SEQUENCE: 61

```
Met Val Ser Thr Tyr Arg Ser Pro Asp Arg Ala Trp Gln Ala Leu Ala
1               5                   10                  15

Asp Gly Thr Arg Arg Ala Ile Val Glu Arg Leu Ala His Gly Pro Leu
            20                  25                  30

Ala Val Gly Glu Leu Ala Arg Asp Leu Pro Val Ser Arg Pro Ala Val
        35                  40                  45

Ser Gln His Leu Lys Val Leu Lys Thr Ala Arg Leu Val Cys Asp Arg
    50                  55                  60

Pro Ala Gly Thr Arg Arg Val Tyr Gln Leu Asp Pro Thr Gly Leu Ala
65                  70                  75                  80

Ala Leu Arg Thr Asp Leu Asp Arg Phe Trp Thr Arg Ala Leu Thr Gly
                85                  90                  95

Tyr Ala Gln Leu Ile Asp Ser Glu Gly Asp Asp Thr Gly Ser Met Thr
            100                 105                 110

Glu Asn Leu Thr Val Gln Pro Glu Arg Leu Gly Val Leu Ala Ser His
        115                 120                 125

His Asp Asn Ala Ala Val Asp Ala Ser Ser Gly Val Glu Ala Ala Ala
    130                 135                 140

Gly Leu Gly Glu Ser Val Ala Ile Thr His Gly Pro Tyr Cys Ser Gln
145                 150                 155                 160

Phe Asn Asp Thr Leu Asn Val Tyr Leu Thr Ala His Asn Ala Leu Gly
                165                 170                 175

Ser Ser Leu His Thr Ala Gly Val Asp Leu Ala Lys Ser Leu Arg Ile
            180                 185                 190

Ala Ala Lys Ile Tyr Ser Glu Ala Asp Glu Ala Trp Arg Lys Ala Ile
        195                 200                 205
```

-continued

```
Asp Gly Leu Phe Thr Glu Phe Met Asp Phe Ala Leu Leu Pro Pro Glu
    210                 215                 220

Val Asn Ser Ala Arg Met Tyr Thr Gly Pro Gly Ala Gly Ser Leu Leu
225                 230                 235                 240

Ala Ala Ala Gly Gly Trp Asp Ser Leu Ala Ala Glu Leu Ala Thr Thr
                245                 250                 255

Ala Glu Ala Tyr Gly Ser Val Leu Ser Gly Leu Ala Ala Leu His Trp
            260                 265                 270

Arg Gly Pro Ala Ala Glu Ser Met Ala Val Thr Ala Ala Pro Tyr Ile
        275                 280                 285

Gly Trp Leu Tyr Thr Thr Ala Glu Lys Thr Gln Gln Thr Ala Ile Gln
    290                 295                 300

Ala Arg Ala Ala Ala Leu Ala Phe Glu Gln Ala Tyr Ala Met Thr Leu
305                 310                 315                 320

Pro Pro Pro Val Val Ala Ala Asn Arg Ile Gln Leu Leu Ala Leu Ile
                325                 330                 335

Ala Thr Asn Phe Phe Gly Gln Asn Thr Ala Ala Ile Ala Ala Thr Glu
            340                 345                 350

Ala Gln Tyr Ala Glu Met Trp Ala Gln Asp Ala Ala Ala Met Tyr Gly
        355                 360                 365

Tyr Ala Thr Ala Ser Ala Ala Ala Ala Leu Leu Thr Pro Phe Ser Pro
    370                 375                 380

Pro Arg Gln Thr Thr Asn Pro Ala Gly Leu Thr Glu Leu Met Ser Thr
385                 390                 395                 400

Gln Arg Pro Arg His Ser Gly Ile Arg Ala Val Gly Pro Tyr Ala Trp
                405                 410                 415

Ala Gly Arg Cys Gly Arg Ile Gly Arg Trp Gly Val His Gln Glu Ala
            420                 425                 430

Met Met Asn Leu Ala Ile Trp His Pro Arg Lys Val Gln Ser Ala Thr
        435                 440                 445

Ile Tyr Gln Val Thr Asp Arg Ser His Asp Gly Arg Thr Ala Arg Val
    450                 455                 460

Pro Gly Asp Glu Ile Thr Ser Thr Val Ser Gly Trp Leu Ser Glu Leu
465                 470                 475                 480

Gly Thr Gln Ser Pro Leu Ala Asp Glu Leu Ala Arg Ala Val Arg Ile
                485                 490                 495

Gly Asp Trp Pro Ala Ala Tyr Ala Ile Gly Glu His Leu Ser Val Glu
            500                 505                 510

Ile Ala Val Ala Val Lys Leu Ala Cys Lys Thr Val Thr Leu Thr Val
        515                 520                 525

Asp Gly Thr Ala Met Arg Val Thr Thr Met Lys Ser Arg Val Ile Asp
    530                 535                 540

Ile Val Glu Glu Asn Gly Phe Ser Val Asp Asp Arg Asp Asp Leu Tyr
545                 550                 555                 560

Pro Ala Ala Gly Val Gln Val His Asp Ala Asp Thr Ile Val Leu Arg
                565                 570                 575

Arg Ser Arg Pro Leu Gln Ile Ser Leu Asp Gly His Asp Ala Lys Gln
            580                 585                 590

Val Trp Thr Thr Ala Ser Thr Val Asp Glu Ala Leu Ala Gln Leu Ala
        595                 600                 605

Met Thr Asp Thr Ala Pro Ala Ala Ala Ser Arg Ala Ser Arg Val Pro
    610                 615                 620
```

```
Leu Ser Gly Met Ala Leu Pro Val Val Ser Ala Lys Thr Val Gln Leu
625                 630                 635                 640

Asn Asp Gly Gly Leu Val Arg Thr Val His Leu Pro Ala Pro Asn Val
                645                 650                 655

Ala Gly Leu Leu Ser Ala Ala Gly Val Pro Leu Leu Gln Ser Asp His
            660                 665                 670

Val Val Pro Ala Ala Thr Ala Pro Ile Val Glu Gly Met Gln Ile Gln
        675                 680                 685

Val Thr Arg Asn Arg Ile Lys Lys Val Thr Glu Arg Leu Pro Leu Pro
    690                 695                 700

Pro Asn Ala Arg Arg Val Glu Asp Pro Glu Met Asn Met Ser Arg Glu
705                 710                 715                 720

Val Val Glu Asp Pro Gly Val Pro Gly Thr Gln Asp Val Thr Phe Ala
                725                 730                 735

Val Ala Glu Val Asn Gly Val Glu Thr Gly Arg Leu Pro Val Ala Asn
            740                 745                 750

Val Val Val Thr Pro Ala His Glu Ala Val Val Arg Val Gly Thr Lys
        755                 760                 765

Pro Gly Thr Glu Val Pro Pro Val Ile Asp Gly Ser Ile Trp Asp Ala
    770                 775                 780

Ile Ala Gly Cys Glu Ala Gly Gly Asn Trp Ala Ile Asn Thr Gly Asn
785                 790                 795                 800

Gly Tyr Tyr Gly Gly Val Gln Phe Asp Gln Gly Thr Trp Glu Ala Asn
                805                 810                 815

Gly Gly Leu Arg Tyr Ala Pro Arg Ala Asp Leu Ala Thr Arg Glu Glu
            820                 825                 830

Gln Ile Ala Val Ala Glu Val Thr Arg Leu Arg Gln Gly Trp Gly Ala
        835                 840                 845

Trp Pro Val Cys Ala Ala Arg Ala Gly Ala Arg
    850                 855
```

<210> SEQ ID NO 62
<211> LENGTH: 2580
<212> TYPE: DNA
<213> ORGANISM: Mycobacterium tuberculosis
<220> FEATURE:
<223> OTHER INFORMATION: Rv3615c-Rv2628-Rv1009-Rv3136Nt-Rv2034

<400> SEQUENCE: 62

```
atgacggaaa acttgaccgt ccagcccgag cgtctcggtg tactggcgtc gcaccatgac      60

aacgcggcgg tcgatgcctc ctcgggcgtc gaagctgccg ctggcctagg cgaatctgtg     120

gcgatcactc acggtccgta ctgctcacag ttcaacgaca cgttaaatgt gtacttgact     180

gcccacaatg ccctgggctc gtccttgcat acggccggtg tcgatctcgc caaaagtctt     240

cgaattgcgg cgaagatata tagcgaggcc gacgaagcgt ggcgcaaggc tatcgacggg     300

ttgtttaccg gattcatgtc cacgcaacga ccgaggcact ccggtattcg ggctgttggc     360

ccctacgcat gggccggccg atgtggtcgg ataggcaggt ggggggtgca ccaggaggcg     420

atgatgaatc tagcgatatg gcacccgcgc aaggtgcaat ccgccaccat ctatcaggtg     480

accgatcgct cgcacgacgg gcgcacagca cgggtgcctg gtgacgagat cactagcacc     540

gtgtccggtt ggttgtcgga gttgggcacc caaagcccgt tggccgatga gcttgcgcgt     600

gcggtgcgga tcggcgactg gcccgctgcg tacgcaatcg gtgagcacct gtccgttgag     660

attgccgttg cggtcgaatt cgcatgcaaa acggtgacgt tgaccgtcga cggaaccgcg     720
```

-continued

```
atgcgggtga ccacgatgaa atcgcgggtg atcgacatcg tcgaagagaa cgggttctca    780
gtcgacgacc gcgacgacct gtatcccgcg gccggcgtgc aggtccatga cgccgacacc    840
atcgtgctgc ggcgtagccg tccgctgcag atctcgctgg atggtcacga cgctaagcag    900
gtgtggacga ccgcgtcgac ggtggacgag gcgctggccc aactcgcgat gaccgacacg    960
gcgccggccg cggcttctcg cgccagccgc gtcccgctgt ccgggatggc gctaccggtc   1020
gtcagcgcca agacggtgca gctcaacgac ggcgggttgg tgcgcacggt gcacttgccg   1080
gcccccaatg tcgcggggct gctgagtgcg gccggcgtgc cgctgttgca aagcgaccac   1140
gtggtgcccg ccgcgacggc cccgatcgtc gaaggcatgc agatccaggt gacccgcaat   1200
cggatcaaga aggtcaccga gcggctgccg ctgccgccga acgcgcgtcg tgtcgaggac   1260
ccggagatga acatgagccg ggaggtcgtc gaagacccgg gggttccggg gacccaggat   1320
gtgacgttcg cggtagctga ggtcaacggc gtcgagaccg gccgtttgcc cgtcgccaac   1380
gtcgtggtga ccccggccca cgaagccgtg gtgcgggtgg gcaccaagcc cggtaccgag   1440
gtgcccccgg tgatcgacgg aagcatctgg gacgcgatcg ccggctgtga ggccggtggc   1500
aactgggcga tcaacaccgg caacgggtat tacggtggtg tgcagtttga ccagggcacc   1560
tgggaggcca acggcgggct gcggtatgca ccccgcgctg acctcgccac ccgcgaagag   1620
cagatcgccg ttgccgaggt gacccgactg cgtcaaggtt ggggcgcctg gccggtatgt   1680
gctgcacgag cgggtgcgcg cgagctcatg gatttcgcac tgttaccacc ggaagtcaac   1740
tccgcccgga tgtacaccgg ccctggggca ggatcgctgt tggctgccgc gggcggctgg   1800
gattcgctgg ccgccgagtt ggccaccaca gccgaggcat atggatcggt gctgtccgga   1860
ctggccgcct tgcattggcg tggaccggca gcggaatcga tggcggtgac ggccgctccc   1920
tatatcggtt ggctgtacac gaccgccgaa aagacacagc aaacagcgat ccaagccagg   1980
gcggcagcgc tggccttcga gcaagcatac gcaatgaccc tgccgccacc ggtggtagcg   2040
gccaaccgga tacagctgct agcactgatc gcgacgaact tcttcggcca gaacactgcg   2100
gcgatcgcgg ccaccgaggc acagtacgcc gagatgtggg cccaggacgc cgccgcgatg   2160
tacggttacg ccaccgcctc agcggctgcg gccctgctga caccgttctc cccgccgcgg   2220
cagaccacca acccggccgg cctgaccaag cttatggtgt ccacttacag atcaccggat   2280
cgcgcttggc aggcgctggc ggacggcact cgccgggcca tcgtggagcg gctggcgcac   2340
ggcccgctgg ccgtcggcga gttggcccgc gacctgcccg tcagccgacc cgcggtgtca   2400
cagcacctca aagtgctcaa gaccgccagg ctggtgtgcg accgccccgc gggaacacgc   2460
cgcgtctacc agctcgaccc gacaggcctt gcggcattgc gcaccgacct cgaccggttc   2520
tggacacgcg ccctgactgg ctacgcgcag ctcatcgact ccgaaggaga cgacacataa   2580
```

<210> SEQ ID NO 63
<211> LENGTH: 859
<212> TYPE: PRT
<213> ORGANISM: Mycobacterium tuberculosis
<220> FEATURE:
<223> OTHER INFORMATION: Rv3615c-Rv2628-Rv1009-Rv3136Nt-Rv2034

<400> SEQUENCE: 63

```
Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
            20                  25                  30

Ala Ala Gly Leu Gly Glu Ser Val Ala Ile Thr His Gly Pro Tyr Cys
```

-continued

```
        35                  40                  45

Ser Gln Phe Asn Asp Thr Leu Asn Val Tyr Leu Thr Ala His Asn Ala
    50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr Gly Phe Met Ser Thr Gln Arg Pro Arg
            100                 105                 110

His Ser Gly Ile Arg Ala Val Gly Pro Tyr Ala Trp Ala Gly Arg Cys
        115                 120                 125

Gly Arg Ile Gly Arg Trp Gly Val His Gln Glu Ala Met Met Asn Leu
    130                 135                 140

Ala Ile Trp His Pro Arg Lys Val Gln Ser Ala Thr Ile Tyr Gln Val
145                 150                 155                 160

Thr Asp Arg Ser His Asp Gly Arg Thr Ala Arg Val Pro Gly Asp Glu
                165                 170                 175

Ile Thr Ser Thr Val Ser Gly Trp Leu Ser Glu Leu Gly Thr Gln Ser
            180                 185                 190

Pro Leu Ala Asp Glu Leu Ala Arg Ala Val Arg Ile Gly Asp Trp Pro
        195                 200                 205

Ala Ala Tyr Ala Ile Gly Glu His Leu Ser Val Glu Ile Ala Val Ala
    210                 215                 220

Val Glu Phe Ala Cys Lys Thr Val Thr Leu Thr Val Asp Gly Thr Ala
225                 230                 235                 240

Met Arg Val Thr Thr Met Lys Ser Arg Val Ile Asp Ile Val Glu Glu
                245                 250                 255

Asn Gly Phe Ser Val Asp Asp Arg Asp Asp Leu Tyr Pro Ala Ala Gly
            260                 265                 270

Val Gln Val His Asp Ala Asp Thr Ile Val Leu Arg Arg Ser Arg Pro
        275                 280                 285

Leu Gln Ile Ser Leu Asp Gly His Asp Ala Lys Gln Val Trp Thr Thr
    290                 295                 300

Ala Ser Thr Val Asp Glu Ala Leu Ala Gln Leu Ala Met Thr Asp Thr
305                 310                 315                 320

Ala Pro Ala Ala Ala Ser Arg Ala Ser Arg Val Pro Leu Ser Gly Met
                325                 330                 335

Ala Leu Pro Val Val Ser Ala Lys Thr Val Gln Leu Asn Asp Gly Gly
            340                 345                 350

Leu Val Arg Thr Val His Leu Pro Ala Pro Asn Val Ala Gly Leu Leu
        355                 360                 365

Ser Ala Ala Gly Val Pro Leu Leu Gln Ser Asp His Val Val Pro Ala
    370                 375                 380

Ala Thr Ala Pro Ile Val Glu Gly Met Gln Ile Gln Val Thr Arg Asn
385                 390                 395                 400

Arg Ile Lys Lys Val Thr Glu Arg Leu Pro Leu Pro Pro Asn Ala Arg
                405                 410                 415

Arg Val Glu Asp Pro Glu Met Asn Met Ser Arg Glu Val Val Glu Asp
            420                 425                 430

Pro Gly Val Pro Gly Thr Gln Asp Val Thr Phe Ala Val Ala Glu Val
        435                 440                 445

Asn Gly Val Glu Thr Gly Arg Leu Pro Val Ala Asn Val Val Val Thr
    450                 455                 460
```

-continued

```
Pro Ala His Glu Ala Val Val Arg Val Gly Thr Lys Pro Gly Thr Glu
465                 470                 475                 480

Val Pro Pro Val Ile Asp Gly Ser Ile Trp Asp Ala Ile Ala Gly Cys
                485                 490                 495

Glu Ala Gly Gly Asn Trp Ala Ile Asn Thr Gly Asn Gly Tyr Tyr Gly
            500                 505                 510

Gly Val Gln Phe Asp Gln Gly Thr Trp Glu Ala Asn Gly Gly Leu Arg
        515                 520                 525

Tyr Ala Pro Arg Ala Asp Leu Ala Thr Arg Glu Glu Gln Ile Ala Val
    530                 535                 540

Ala Glu Val Thr Arg Leu Arg Gln Gly Trp Gly Ala Trp Pro Val Cys
545                 550                 555                 560

Ala Ala Arg Ala Gly Ala Arg Glu Leu Met Asp Phe Ala Leu Leu Pro
                565                 570                 575

Pro Glu Val Asn Ser Ala Arg Met Tyr Thr Gly Pro Gly Ala Gly Ser
            580                 585                 590

Leu Leu Ala Ala Ala Gly Gly Trp Asp Ser Leu Ala Ala Glu Leu Ala
        595                 600                 605

Thr Thr Ala Glu Ala Tyr Gly Ser Val Leu Ser Gly Leu Ala Ala Leu
    610                 615                 620

His Trp Arg Gly Pro Ala Ala Glu Ser Met Ala Val Thr Ala Ala Pro
625                 630                 635                 640

Tyr Ile Gly Trp Leu Tyr Thr Thr Ala Glu Lys Thr Gln Gln Thr Ala
                645                 650                 655

Ile Gln Ala Arg Ala Ala Ala Leu Ala Phe Glu Gln Ala Tyr Ala Met
            660                 665                 670

Thr Leu Pro Pro Pro Val Val Ala Ala Asn Arg Ile Gln Leu Leu Ala
        675                 680                 685

Leu Ile Ala Thr Asn Phe Phe Gly Gln Asn Thr Ala Ala Ile Ala Ala
    690                 695                 700

Thr Glu Ala Gln Tyr Ala Glu Met Trp Ala Gln Asp Ala Ala Ala Met
705                 710                 715                 720

Tyr Gly Tyr Ala Thr Ala Ser Ala Ala Ala Ala Leu Leu Thr Pro Phe
                725                 730                 735

Ser Pro Pro Arg Gln Thr Thr Asn Pro Ala Gly Leu Thr Lys Leu Met
            740                 745                 750

Val Ser Thr Tyr Arg Ser Pro Asp Arg Ala Trp Gln Ala Leu Ala Asp
        755                 760                 765

Gly Thr Arg Arg Ala Ile Val Glu Arg Leu Ala His Gly Pro Leu Ala
    770                 775                 780

Val Gly Glu Leu Ala Arg Asp Leu Pro Val Ser Arg Pro Ala Val Ser
785                 790                 795                 800

Gln His Leu Lys Val Leu Lys Thr Ala Arg Leu Val Cys Asp Arg Pro
                805                 810                 815

Ala Gly Thr Arg Arg Val Tyr Gln Leu Asp Pro Thr Gly Leu Ala Ala
            820                 825                 830

Leu Arg Thr Asp Leu Asp Arg Phe Trp Thr Arg Ala Leu Thr Gly Tyr
        835                 840                 845

Ala Gln Leu Ile Asp Ser Glu Gly Asp Asp Thr
    850                 855
```

<210> SEQ ID NO 64
<211> LENGTH: 2049

<212> TYPE: DNA
<213> ORGANISM: Mycobacterium tuberculosis
<220> FEATURE:
<223> OTHER INFORMATION: Ag85A-Ag85B-Rv3407

<400> SEQUENCE: 64
atggcatttt cccggccggg cttgccggtg gagtacctgc aggtgccgtc gccgtcgatg 60
ggccgtgaca tcaaggtcca attccaaagt ggtggtgcca actcgcccgc cctgtacctg 120
ctcgacggcc tgcgcgcgca ggacgacttc agcggctggg acatcaacac cccggcgttc 180
gagtggtacg accagtcggg cctgtcggtg gtcatgccgg tgggtggcca gtcaagcttc 240
tactccgact ggtaccagcc cgcctgcggc aaggccggtt gccagactta caagtgggag 300
accttcctga ccagcgagct gccggggtgg ctgcaggcca acaggcacgt caagcccacc 360
ggaagcgccg tcgtcggtct ttcgatggct gcttcttcgg cgctgacgct ggcgatctat 420
cacccccagc agttcgtcta cgcgggagcg atgtcgggcc tgttggaccc ctcccaggcg 480
atgggtccca ccctgatcgg cctggcgatg ggtgacgctg gcggctacaa ggcctccgac 540
atgtggggcc cgaaggagga cccggcgtgg cagcgcaacg acccgctgtt gaacgtcggg 600
aagctgatcg ccaacaacac ccgcgtctgg gtgtactgcg gcaacggcaa gccgtcggat 660
ctgggtggca acaacctgcc ggccaagttc ctcgagggct tcgtgcggac cagcaacatc 720
aagttccaag acgcctacaa cgccggtggc ggccacaacg gcgtgttcga cttcccggac 780
agcggtacgc acagctggga gtactggggc gcgcagctca acgctatgaa gcccgacctg 840
caacgggcac tgggtgccac gcccaacacc gggcccgcgc cccagggcgc catgttctcc 900
cggccggggc tgccggtcga gtacctgcag gtgccgtcgc cgtcgatggg ccgcgacatc 960
aaggttcagt tccagagcgg tgggaacaac tcacctgcgg tttatctgct cgacggcctg 1020
cgcgcccaag acgactacaa cggctgggat atcaacaccc cggcgttcga gtggtactac 1080
cagtcgggac tgtcgatagt catgccggtc ggcgggcagt ccagcttcta cagcgactgg 1140
tacagcccgg cctgcggtaa ggctggctgc cagacttaca agtgggaaac cttcctgacc 1200
agcgagctgc cgcaatggtt gtccgccaac agggccgtga agcccaccgg cagcgctgca 1260
atcggcttgt cgatggccgg ctcgtcggca atgatcttgg ccgcctacca cccccagcag 1320
ttcatctacg ccggctcgct gtcggccctg ctggacccct ctcaggggat ggggcctagc 1380
ctgatcggcc tcgcgatggg tgacgccggc ggttacaagg ccgcagacat gtggggtccc 1440
tcgagtgacc cggcatggga gcgcaacgac cctacgcagc agatccccaa gctggtcgca 1500
aacaacaccc ggctatgggt ttattgcggg aacggcaccc cgaacgagtt gggcggtgcc 1560
aacatacccg ccgagttctt ggagaacttc gttcgtagca gcaacctgaa gttccaggat 1620
gcgtacaacg ccgcgggcgg gcacaacgcc gtgttcaact tcccgcccaa cggcacgcac 1680
agctgggagt actggggcgc tcagctcaac gccatgaagg gtgacctgca gagttcgtta 1740
ggcgccggca tgcgtgctac cgttgggctt gtggaggcaa tcggaatccg agaactaaga 1800
cagcacgcat cgcgatacct cgcccgggtt gaagccggcg aggaacttgg cgtcaccaac 1860
aaaggaagac ttgtggcccg actcatcccg gtgcaggccg cggagcgttc tcgcgaagcc 1920
ctgattgaat caggtgtcct gattccggct cgtcgtccac aaaaccttct cgacgtcacc 1980
gccgaaccgg cgcgcggccg caagcgcacc ctgtccgatg ttctcaacga aatgcgcgac 2040
gagcagtga 2049

<210> SEQ ID NO 65

<211> LENGTH: 683
<212> TYPE: PRT
<213> ORGANISM: Mycobacterium tuberculosis
<220> FEATURE:
<223> OTHER INFORMATION: Ag85A-Ag85B-Rv3407

<400> SEQUENCE: 65

Met Ala Phe Ser Arg Pro Gly Leu Pro Val Glu Tyr Leu Gln Val Pro
1 5 10 15

Ser Pro Ser Met Gly Arg Asp Ile Lys Val Gln Phe Gln Ser Gly Gly
20 25 30

Ala Asn Ser Pro Ala Leu Tyr Leu Leu Asp Gly Leu Arg Ala Gln Asp
35 40 45

Asp Phe Ser Gly Trp Asp Ile Asn Thr Pro Ala Phe Glu Trp Tyr Asp
50 55 60

Gln Ser Gly Leu Ser Val Val Met Pro Val Gly Gly Gln Ser Ser Phe
65 70 75 80

Tyr Ser Asp Trp Tyr Gln Pro Ala Cys Gly Lys Ala Gly Cys Gln Thr
85 90 95

Tyr Lys Trp Glu Thr Phe Leu Thr Ser Glu Leu Pro Gly Trp Leu Gln
100 105 110

Ala Asn Arg His Val Lys Pro Thr Gly Ser Ala Val Val Gly Leu Ser
115 120 125

Met Ala Ala Ser Ser Ala Leu Thr Leu Ala Ile Tyr His Pro Gln Gln
130 135 140

Phe Val Tyr Ala Gly Ala Met Ser Gly Leu Leu Asp Pro Ser Gln Ala
145 150 155 160

Met Gly Pro Thr Leu Ile Gly Leu Ala Met Gly Asp Ala Gly Gly Tyr
165 170 175

Lys Ala Ser Asp Met Trp Gly Pro Lys Glu Asp Pro Ala Trp Gln Arg
180 185 190

Asn Asp Pro Leu Leu Asn Val Gly Lys Leu Ile Ala Asn Asn Thr Arg
195 200 205

Val Trp Val Tyr Cys Gly Asn Gly Lys Pro Ser Asp Leu Gly Gly Asn
210 215 220

Asn Leu Pro Ala Lys Phe Leu Glu Gly Phe Val Arg Thr Ser Asn Ile
225 230 235 240

Lys Phe Gln Asp Ala Tyr Asn Ala Gly Gly Gly His Asn Gly Val Phe
245 250 255

Asp Phe Pro Asp Ser Gly Thr His Ser Trp Glu Tyr Trp Gly Ala Gln
260 265 270

Leu Asn Ala Met Lys Pro Asp Leu Gln Arg Ala Leu Gly Ala Thr Pro
275 280 285

Asn Thr Gly Pro Ala Pro Gln Gly Ala Phe Ser Arg Pro Gly Leu Pro
290 295 300

Val Glu Tyr Leu Gln Val Pro Ser Pro Ser Met Gly Arg Asp Ile Lys
305 310 315 320

Val Gln Phe Gln Ser Gly Gly Asn Asn Ser Pro Ala Val Tyr Leu Leu
325 330 335

Asp Gly Leu Arg Ala Gln Asp Asp Tyr Asn Gly Trp Asp Ile Asn Thr
340 345 350

Pro Ala Phe Glu Trp Tyr Tyr Gln Ser Gly Leu Ser Ile Val Met Pro
355 360 365

Val Gly Gly Gln Ser Ser Phe Tyr Ser Asp Trp Tyr Ser Pro Ala Cys
370 375 380

```
Gly Lys Ala Gly Cys Gln Thr Tyr Lys Trp Glu Thr Phe Leu Thr Ser
385                 390                 395                 400

Glu Leu Pro Gln Trp Leu Ser Ala Asn Arg Ala Val Lys Pro Thr Gly
                405                 410                 415

Ser Ala Ala Ile Gly Leu Ser Met Ala Gly Ser Ser Ala Met Ile Leu
            420                 425                 430

Ala Ala Tyr His Pro Gln Gln Phe Ile Tyr Ala Gly Ser Leu Ser Ala
        435                 440                 445

Leu Leu Asp Pro Ser Gln Gly Met Gly Pro Ser Leu Ile Gly Leu Ala
    450                 455                 460

Met Gly Asp Ala Gly Gly Tyr Lys Ala Ala Asp Met Trp Gly Pro Ser
465                 470                 475                 480

Ser Asp Pro Ala Trp Glu Arg Asn Asp Pro Thr Gln Gln Ile Pro Lys
                485                 490                 495

Leu Val Ala Asn Asn Thr Arg Leu Trp Val Tyr Cys Gly Asn Gly Thr
            500                 505                 510

Pro Asn Glu Leu Gly Gly Ala Asn Ile Pro Ala Glu Phe Leu Glu Asn
        515                 520                 525

Phe Val Arg Ser Ser Asn Leu Lys Phe Gln Asp Ala Tyr Asn Ala Ala
    530                 535                 540

Gly Gly His Asn Ala Val Phe Asn Phe Pro Pro Asn Gly Thr His Ser
545                 550                 555                 560

Trp Glu Tyr Trp Gly Ala Gln Leu Asn Ala Met Lys Gly Asp Leu Gln
                565                 570                 575

Ser Ser Leu Gly Ala Gly Ala Ala Ala Arg Ala Thr Val Gly Leu Val
            580                 585                 590

Glu Ala Ile Gly Ile Arg Glu Leu Arg Gln His Ala Ser Arg Tyr Leu
        595                 600                 605

Ala Arg Val Glu Ala Gly Glu Glu Leu Gly Val Thr Asn Lys Gly Arg
    610                 615                 620

Leu Val Ala Arg Leu Ile Pro Val Gln Ala Ala Glu Arg Ser Arg Glu
625                 630                 635                 640

Ala Leu Ile Glu Ser Gly Val Leu Ile Pro Ala Arg Arg Pro Gln Asn
                645                 650                 655

Leu Leu Asp Val Thr Ala Glu Pro Ala Arg Gly Arg Lys Arg Thr Leu
            660                 665                 670

Ser Asp Val Leu Asn Glu Met Arg Asp Glu Gln
        675                 680
```

<210> SEQ ID NO 66
<211> LENGTH: 1062
<212> TYPE: DNA
<213> ORGANISM: Mycobacterium tuberculosis
<220> FEATURE:
<223> OTHER INFORMATION: Rv1733-Rv2626c

<400> SEQUENCE: 66

```
atgaccaccg cacgcgacat catgaacgca ggtgtgacct gtgttggcga acacgagacg      60

ctaaccgctg ccgctcaata catgcgtgag cacgacatcg gcgcgttgcc gatctgcggg     120

gacgacgacc ggctgcacgg catgctcacc gaccgcgaca ttgtgatcaa aggcctggct     180

gcgggcctag acccgaatac cgccacggct ggcgagttgg cccgggacag catctactac     240

gtcgatgcga acgcaagcat ccaggagatg ctcaacgtca tggaagaaca tcaggtccgc     300

cgtgttccgg tcatctcaga gcaccgcttg gtcggaatcg tcaccgaagc cgacatcgcc     360
```

```
cgacacctgc ccgagcacgc cattgtgcag ttcgtcaagg caatctgctc gcccatggcc    420

ctcgccagca tgatcgccac aacccgcgat cgtgaaggag ccaccatgat cacgtttagg    480

ctgcgcttgc cgtgccggac gatactgcgg gtgttcagcc gcaatccgct ggtgcgtggg    540

acggatcgac tcgaggcggt cgtcatgctg ctggccgtca cggtctcgct gctgactatc    600

ccgttcgccg ccgcggccgg caccgcagtc caggattccc gcagccacgt ctatgcccac    660

caggcccaga cccgccatcc cgcaaccgcg accgtgatcg atcacgaggg ggtgatcgac    720

agcaacacga ccgccacgtc agcgccgccg cgcacgaaga tcaccgtgcc tgcccgatgg    780

gtcgtgaacg gaatagaacg cagcggtgag gtcaacgcga agccgggaac caaatccggt    840

gaccgcgtcg gcatttgggt cgacagtgcc ggtcagctgg tcgatgaacc agctccgccg    900

gcccgtgcca ttgcggatgc ggccctggcc gccttgggac tctggttgag cgtcgccgcg    960

gttgcgggcg ccctgctggc gctcactcgg gcgattctga tccgcgttcg caacgccagt   1020

tggcaacacg acatcgacag cctgttctgc acgcagcggt ga                      1062
```

<210> SEQ ID NO 67
<211> LENGTH: 353
<212> TYPE: PRT
<213> ORGANISM: Mycobacterium tuberculosis
<220> FEATURE:
<223> OTHER INFORMATION: Rv1733-Rv2626c

<400> SEQUENCE: 67

```
Met Thr Thr Ala Arg Asp Ile Met Asn Ala Gly Val Thr Cys Val Gly
1               5                   10                  15

Glu His Glu Thr Leu Thr Ala Ala Ala Gln Tyr Met Arg Glu His Asp
            20                  25                  30

Ile Gly Ala Leu Pro Ile Cys Gly Asp Asp Asp Arg Leu His Gly Met
        35                  40                  45

Leu Thr Asp Arg Asp Ile Val Ile Lys Gly Leu Ala Ala Gly Leu Asp
    50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
            100                 105                 110

Ile Val Thr Glu Ala Asp Ile Ala Arg His Leu Pro Glu His Ala Ile
        115                 120                 125

Val Gln Phe Val Lys Ala Ile Cys Ser Pro Met Ala Leu Ala Ser Met
    130                 135                 140

Ile Ala Thr Thr Arg Asp Arg Glu Gly Ala Thr Met Ile Thr Phe Arg
145                 150                 155                 160

Leu Arg Leu Pro Cys Arg Thr Ile Leu Arg Val Phe Ser Arg Asn Pro
                165                 170                 175

Leu Val Arg Gly Thr Asp Arg Leu Glu Ala Val Val Met Leu Leu Ala
            180                 185                 190

Val Thr Val Ser Leu Leu Thr Ile Pro Phe Ala Ala Ala Ala Gly Thr
        195                 200                 205

Ala Val Gln Asp Ser Arg Ser His Val Tyr Ala His Gln Ala Gln Thr
    210                 215                 220

Arg His Pro Ala Thr Ala Thr Val Ile Asp His Glu Gly Val Ile Asp
225                 230                 235                 240
```

```
Ser Asn Thr Thr Ala Thr Ser Ala Pro Pro Arg Thr Lys Ile Thr Val
                245                 250                 255

Pro Ala Arg Trp Val Val Asn Gly Ile Glu Arg Ser Gly Glu Val Asn
            260                 265                 270

Ala Lys Pro Gly Thr Lys Ser Gly Asp Arg Val Gly Ile Trp Val Asp
        275                 280                 285

Ser Ala Gly Gln Leu Val Asp Glu Pro Ala Pro Pro Ala Arg Ala Ile
    290                 295                 300

Ala Asp Ala Ala Leu Ala Ala Leu Gly Leu Trp Leu Ser Val Ala Ala
305                 310                 315                 320

Val Ala Gly Ala Leu Leu Ala Leu Thr Arg Ala Ile Leu Ile Arg Val
                325                 330                 335

Arg Asn Ala Ser Trp Gln His Asp Ile Asp Ser Leu Phe Cys Thr Gln
            340                 345                 350

Arg


<210> SEQ ID NO 68
<211> LENGTH: 2217
<212> TYPE: DNA
<213> ORGANISM: Mycobacterium tuberculosis
<220> FEATURE:
<223> OTHER INFORMATION: RpfA-RpfC-RpfD

<400> SEQUENCE: 68

atggcgtcag ggaggcatcg gaaaccaact acaagcaatg tatctgttgc caagattgct      60

ttcaccggcg cagttcttgg aggtggcgga attgccatgg ctgcccaggc aacagccgct     120

acagatggag agtgggatca ggtggctcga tgtgagtctg gtggcaactg gtctatcaac     180

actgggaacg ggtatcttgg cggcttgcaa tttactcaga gcacttgggc tgcccacgga     240

gggggtgaat ttgctcctag cgcgcagctg gcctcccgcg agcagcagat cgctgtggga     300

gagagggtgt tggccacaca gggaagaggt gcctggcctg tctgtggccg cggactcagt     360

aatgctaccc ctagggaggt gctgcccgcc tcagccgcta tggacgctcc actggatgct     420

gccgccgtga atggcgagcc agctccgctg gcacccccac ctgcagaccc cgctccccca     480

gtcgagctgg cggcaaacga cctgcccgca cctctcggag aaccacttcc tgcagcgcct     540

gccgatccag ctccacctgc tgatttggct ccccccgctc ccgccgatgt agcccctccg     600

gtcgagttgg ctgtgaatga cctgccggca cctctgggcg agcccctccc agccgctccg     660

gccgaccctg cccctcctgc tgatctggca ccacccgctc ctgccgacct cgccccaccc     720

gccccagcag acctggctcc accagcgcct gcggatcttg ccccgcctgt tgagctggct     780

gtcaacgatc ttcctgcgcc tcttggagag cccctgcccg ctgctccagc cgaactcgca     840

ccaccggcag atctggctcc cgcctctgcc gatcttgcac ctcccgcacc ggcggacttg     900

gcacctccag caccagcaga actggctccc cctgcgccgg ctgacctggc ccctccagca     960

gccgttaatg agcaaaccgc accaggggac cagccggcta cggcaccagg tggaccggtg    1020

gggctggcca ccgacctgga gctgcctgag ccggatcccc aaccagctga tgctccccca    1080

cctggcgacg taactgaggc cccagctgaa acgccccagg tcagtaacat cgcttacaca    1140

aagaaactgt ggcaggcaat tagggctcag gacgtgtgtg ggaacgacgc cctggacagc    1200

ttggcccaac cgtacgtgat cggtatgcac cccctccccg ctgatcatgg tcgcagtcgc    1260

tgtaaccgcc accccatttc acctctcagc cttattggga atgcgtctgc tacaagtggc    1320

gacatgtcta gtatgacaag gattgctaag cccctcatca aaagtgcgat ggctgccggt    1380
```

```
ctggtaacag catccatgag cttgtccacc gcagtggctc acgctgggcc ttccccgaac   1440

tgggatgccg tcgcccagtg cgagtcaggc ggcaattggg ccgcaaatac cggtaacggt   1500

aagtatggag gactgcagtt taaacctgca acttgggccg cctttggagg agtgggtaat   1560

cctgcagctg cttctagaga acagcagatt gccgtggcta accgcgttct cgcggagcag   1620

ggtctggacg cctggccgac ctgtggcgcc gcatcaggtt tgccgatcgc gttgtggtca   1680

aagcccgccc agggaatcaa gcagattatc aatgagatca tctgggccgg aatacaggca   1740

agcatcccta gaatgactcc tggcttctg acaaccgctg gcgctgggag gcccagggat   1800

aggtgcgccc ggatcgtttg taccgtattc atagagaccg ccgtggtcgc gacaatgttc   1860

gtggctctct tgggcttgag caccattagc tctaaggccg atgatataga ttgggatgct   1920

attgctcaat gcgaatccgg tgggaactgg gccgctaata ccggaaatgg gctctacggc   1980

ggactgcaga tcagccaggc tacatgggat agcaacggag gagtcgggtc ccctgccgct   2040

gcatccccgc aacagcaaat cgaggtggcc gataacatca tgaaaaccca gggacccgga   2100

gcctggccca aatgtagctc atgtagccaa ggagatgcgc ccctcggttc actgacgcac   2160

atcctcacct tcctcgccgc ggaaaccgga gggtgctctg gcagccggga cgactga      2217
```

```
<210> SEQ ID NO 69
<211> LENGTH: 737
<212> TYPE: PRT
<213> ORGANISM: Mycobacterium tuberculosis
<220> FEATURE:
<223> OTHER INFORMATION: RpfA-RpfC-RpfD

<400> SEQUENCE: 69

Met Ser Gly Arg His Arg Lys Pro Thr Thr Ser Asn Val Ser Val Ala
1               5                   10                  15

Lys Ile Ala Phe Thr Gly Ala Val Leu Gly Gly Gly Gly Ile Ala Met
            20                  25                  30

Ala Ala Gln Ala Thr Ala Ala Thr Asp Gly Glu Trp Asp Gln Val Ala
        35                  40                  45

Arg Cys Glu Ser Gly Gly Asn Trp Ser Ile Asn Thr Gly Asn Gly Tyr
    50                  55                  60

Leu Gly Gly Leu Gln Phe Thr Gln Ser Thr Trp Ala Ala His Gly Gly
65                  70                  75                  80

Gly Glu Phe Ala Pro Ser Ala Gln Leu Ala Ser Arg Glu Gln Gln Ile
                85                  90                  95

Ala Val Gly Glu Arg Val Leu Ala Thr Gln Gly Arg Gly Ala Trp Pro
            100                 105                 110

Val Cys Gly Arg Gly Leu Ser Asn Ala Thr Pro Arg Glu Val Leu Pro
        115                 120                 125

Ala Ser Ala Ala Met Asp Ala Pro Leu Asp Ala Ala Ala Val Asn Gly
    130                 135                 140

Glu Pro Ala Pro Leu Ala Pro Pro Pro Ala Asp Pro Ala Pro Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Pro Ala Asp Leu Ala Pro Pro Ala
            180                 185                 190

Pro Ala Asp Val Ala Pro Pro Val Glu Leu Ala Val Asn Asp Leu Pro
        195                 200                 205

Ala Pro Leu Gly Glu Pro Leu Pro Ala Ala Pro Ala Asp Pro Ala Pro
```

```
    210                 215                 220

Pro Ala Asp Leu Ala Pro Pro Ala Pro Ala Asp Leu Ala Pro Pro Ala
225                 230                 235                 240

Pro Ala Asp Leu Ala Pro Pro Ala Pro Ala Asp Leu Ala Pro Pro Val
                245                 250                 255

Glu Leu Ala Val Asn Asp Leu Pro Ala Pro Leu Gly Glu Pro Leu Pro
            260                 265                 270

Ala Ala Pro Ala Glu Leu Ala Pro Pro Ala Asp Leu Ala Pro Ala Ser
        275                 280                 285

Ala Asp Leu Ala Pro Pro Ala Pro Ala Asp Leu Ala Pro Pro Ala Pro
    290                 295                 300

Ala Glu Leu Ala Pro Pro Ala Pro Ala Asp Leu Ala Pro Pro Ala Ala
305                 310                 315                 320

Val Asn Glu Gln Thr Ala Pro Gly Asp Gln Pro Ala Thr Ala Pro Gly
                325                 330                 335

Gly Pro Val Gly Leu Ala Thr Asp Leu Glu Leu Pro Glu Pro Asp Pro
            340                 345                 350

Gln Pro Ala Asp Ala Pro Pro Pro Gly Asp Val Thr Glu Ala Pro Ala
        355                 360                 365

Glu Thr Pro Gln Val Ser Asn Ile Ala Tyr Thr Lys Lys Leu Trp Gln
    370                 375                 380

Ala Ile Arg Ala Gln Asp Val Cys Gly Asn Asp Ala Leu Asp Ser Leu
385                 390                 395                 400

Ala Gln Pro Tyr Val Ile Gly Val His Pro Leu Pro Ala Asp His Gly
                405                 410                 415

Arg Ser Arg Cys Asn Arg His Pro Ile Ser Pro Leu Ser Leu Ile Gly
            420                 425                 430

Asn Ala Ser Ala Thr Ser Gly Asp Met Ser Ser Met Thr Arg Ile Ala
        435                 440                 445

Lys Pro Leu Ile Lys Ser Ala Met Ala Ala Gly Leu Val Thr Ala Ser
    450                 455                 460

Met Ser Leu Ser Thr Ala Val Ala His Ala Gly Pro Ser Pro Asn Trp
465                 470                 475                 480

Asp Ala Val Ala Gln Cys Glu Ser Gly Gly Asn Trp Ala Ala Asn Thr
                485                 490                 495

Gly Asn Gly Lys Tyr Gly Gly Leu Gln Phe Lys Pro Ala Thr Trp Ala
            500                 505                 510

Ala Phe Gly Gly Val Gly Asn Pro Ala Ala Ala Ser Arg Glu Gln Gln
        515                 520                 525

Ile Ala Val Ala Asn Arg Val Leu Ala Glu Gln Gly Leu Asp Ala Trp
    530                 535                 540

Pro Thr Cys Gly Ala Ala Ser Gly Leu Pro Ile Ala Leu Trp Ser Lys
545                 550                 555                 560

Pro Ala Gln Gly Ile Lys Gln Ile Ile Asn Glu Ile Ile Trp Ala Gly
                565                 570                 575

Ile Gln Ala Ser Ile Pro Arg Met Thr Pro Gly Leu Leu Thr Thr Ala
            580                 585                 590

Gly Ala Gly Arg Pro Arg Asp Arg Cys Ala Arg Ile Val Cys Thr Val
        595                 600                 605

Phe Ile Glu Thr Ala Val Val Ala Thr Met Phe Val Ala Leu Leu Gly
    610                 615                 620

Leu Ser Thr Ile Ser Ser Lys Ala Asp Asp Ile Asp Trp Asp Ala Ile
625                 630                 635                 640
```

```
Ala Gln Cys Glu Ser Gly Gly Asn Trp Ala Ala Asn Thr Gly Asn Gly
                645                 650                 655

Leu Tyr Gly Gly Leu Gln Ile Ser Gln Ala Thr Trp Asp Ser Asn Gly
            660                 665                 670

Gly Val Gly Ser Pro Ala Ala Ala Ser Pro Gln Gln Gln Ile Glu Val
        675                 680                 685

Ala Asp Asn Ile Met Lys Thr Gln Gly Pro Gly Ala Trp Pro Lys Cys
    690                 695                 700

Ser Ser Cys Ser Gln Gly Asp Ala Pro Leu Gly Ser Leu Thr His Ile
705                 710                 715                 720

Leu Thr Phe Leu Ala Ala Glu Thr Gly Gly Cys Ser Gly Ser Arg Asp
                725                 730                 735

Asp
```

<210> SEQ ID NO 70
<211> LENGTH: 2580
<212> TYPE: DNA
<213> ORGANISM: Mycobacterium tuberculosis
<220> FEATURE:
<223> OTHER INFORMATION: Rv1009-Rv2628-Rv3136Nt-Rv2034-Rv3615c

<400> SEQUENCE: 70

```
atggcatgca aaacggtgac gttgaccgtc gacggaaccg cgatgcgggt gaccacgatg     60
aaatcgcggg tgatcgacat cgtcgaagag aacgggttct cagtcgacga ccgcgacgac    120
ctgtatcccg cggccggcgt gcaggtccat gacgccgaca ccatcgtgct gcggcgtagc    180
cgtccgctgc agatctcgct ggatggtcac gacgctaagc aggtgtggac gaccgcgtcg    240
acggtggacg aggcgctggc ccaactcgcg atgaccgaca cggcgccggc cgcggcttct    300
cgcgccagcc gcgtcccgct gtccgggatg gcgctaccgg tcgtcagcgc caagacggtg    360
cagctcaacg acggcgggtt ggtgcgcacg gtgcacttgc cggcccccaa tgtcgcgggg    420
ctgctgagtg cggccggcgt gccgctgttg caaagcgacc acgtggtgcc cgccgcgacg    480
gccccgatcg tcgaaggcat gcagatccag gtgacccgca atcggatcaa gaaggtcacc    540
gagcggctgc cgctgccgcc gaacgcgcgt cgtgtcgagg acccggagat gaacatgagc    600
cgggaggtcg tcgaagaccc gggggttccg gggacccagg atgtgacgtt cgcggtagct    660
gaggtcaacg gcgtcgagac cggccgtttg cccgtcgcca acgtcgtggt gaccccggcc    720
cacgaagccg tggtgcgggt gggcaccaag cccggtaccg aggtgccccc ggtgatcgac    780
ggaagcatct gggacgcgat cgccggctgt gaggccggtg gcaactgggc gatcaacacc    840
ggcaacgggt attacggtgg tgtgcagttt gaccagggca cctgggaggc caacggcggg    900
ctgcggtatg caccccgcgc tgacctcgcc acccgcgaag agcagatcgc cgttgccgag    960
gtgacccgac tgcgtcaagg ttggggcgcc tggccggtat gtgctgcacg agcgggtgcg   1020
cgcggatcca tgtccacgca acgaccgagg cactccggta ttcgggctgt tggcccctac   1080
gcatgggccg gccgatgtgg tcggataggc aggtgggggg tgcaccagga ggcgatgatg   1140
aatctagcga tatggcaccc gcgcaaggtg caatccgcca ccatctatca ggtgaccgat   1200
cgctcgcacg acgggcgcac agcacgggtg cctggtgacg agatcactag caccgtgtcc   1260
ggttggttgt cggagttggg cacccaaagc ccgttggccg atgagcttgc gcgtgcggtg   1320
cggatcggcg actggcccgc tgcgtacgca atcggtgagc acctgtccgt tgagattgcc   1380
gttgcggtcg aattcatgga tttcgcactg ttaccaccgg aagtcaactc cgcccggatg   1440
```

-continued

```
tacaccggcc ctggggcagg atcgctgttg gctgccgcgg gcggctggga ttcgctggcc   1500

gccgagttgg ccaccacagc cgaggcatat ggatcggtgc tgtccggact ggccgccttg   1560

cattggcgtg gaccggcagc ggaatcgatg gcggtgacgg ccgctcccta tatcggttgg   1620

ctgtacacga ccgccgaaaa gacacagcaa acagcgatcc aagccagggc ggcagcgctg   1680

gccttcgagc aagcatacgc aatgaccctg ccgccaccgg tggtagcggc caaccggata   1740

cagctgctag cactgatcgc gacgaacttc ttcggccaga acactgcggc gatcgcggcc   1800

accgaggcac agtacgccga gatgtgggcc caggacgccg ccgcgatgta cggttacgcc   1860

accgcctcag cggctgcggc cctgctgaca ccgttctccc cgccgcggca gaccaccaac   1920

ccggccggcc tgaccgagct cgtgtccact tacagatcac cggatcgcgc ttggcaggcg   1980

ctggcggacg gcactcgccg ggccatcgtg gagcggctgg cgcacggccc gctggccgtc   2040

ggcgagttgg cccgcgacct gcccgtcagc cgacccgcgg tgtcacagca cctcaaagtg   2100

ctcaagaccg ccaggctggt gtgcgaccgc cccgcgggaa cacgccgcgt ctaccagctc   2160

gacccgacag gccttgcggc attgcgcacc gacctcgacc ggttctggac acgcgccctg   2220

actggctacg cgcagctcat cgactccgaa ggagacgaca caaagcttat gacggaaaac   2280

ttgaccgtcc agcccgagcg tctcggtgta ctggcgtcgc accatgacaa cgcggcggtc   2340

gatgcctcct cgggcgtcga agctgccgct ggcctaggcg aatctgtggc gatcactcac   2400

ggtccgtact gctcacagtt caacgacacg ttaaatgtgt acttgactgc ccacaatgcc   2460

ctgggctcgt ccttgcatac ggccggtgtc gatctcgcca aaagtcttcg aattgcggcg   2520

aagatatata gcgaggccga cgaagcgtgg cgcaaggcta tcgacgggtt gtttacctga   2580
```

```
<210> SEQ ID NO 71
<211> LENGTH: 859
<212> TYPE: PRT
<213> ORGANISM: Mycobacterium tuberculosis
<220> FEATURE:
<223> OTHER INFORMATION: Rv1009-Rv2628-Rv3136Nt-Rv2034-Rv3615c

<400> SEQUENCE: 71

Met Ala Cys Lys Thr Val Thr Leu Thr Val Asp Gly Thr Ala Met Arg
1               5                   10                  15

Val Thr Thr Met Lys Ser Arg Val Ile Asp Ile Val Glu Glu Asn Gly
            20                  25                  30

Phe Ser Val Asp Asp Arg Asp Asp Leu Tyr Pro Ala Ala Gly Val Gln
        35                  40                  45

Val His Asp Ala Asp Thr Ile Val Leu Arg Arg Ser Arg Pro Leu Gln
    50                  55                  60

Ile Ser Leu Asp Gly His Asp Ala Lys Gln Val Trp Thr Thr Ala Ser
65                  70                  75                  80

Thr Val Asp Glu Ala Leu Ala Gln Leu Ala Met Thr Asp Thr Ala Pro
                85                  90                  95

Ala Ala Ala Ser Arg Ala Ser Arg Val Pro Leu Ser Gly Met Ala Leu
            100                 105                 110

Pro Val Val Ser Ala Lys Thr Val Gln Leu Asn Asp Gly Gly Leu Val
        115                 120                 125

Arg Thr Val His Leu Pro Ala Pro Asn Val Ala Gly Leu Leu Ser Ala
    130                 135                 140

Ala Gly Val Pro Leu Leu Gln Ser Asp His Val Val Pro Ala Ala Thr
145                 150                 155                 160

Ala Pro Ile Val Glu Gly Met Gln Ile Gln Val Thr Arg Asn Arg Ile
```

-continued

```
                165                 170                 175

Lys Lys Val Thr Glu Arg Leu Pro Leu Pro Pro Asn Ala Arg Arg Val
            180                 185                 190

Glu Asp Pro Glu Met Asn Met Ser Arg Glu Val Val Glu Asp Pro Gly
        195                 200                 205

Val Pro Gly Thr Gln Asp Val Thr Phe Ala Val Ala Glu Val Asn Gly
    210                 215                 220

Val Glu Thr Gly Arg Leu Pro Val Ala Asn Val Val Val Thr Pro Ala
225                 230                 235                 240

His Glu Ala Val Val Arg Val Gly Thr Lys Pro Gly Thr Glu Val Pro
                245                 250                 255

Pro Val Ile Asp Gly Ser Ile Trp Asp Ala Ile Ala Gly Cys Glu Ala
            260                 265                 270

Gly Gly Asn Trp Ala Ile Asn Thr Gly Asn Gly Tyr Tyr Gly Gly Val
        275                 280                 285

Gln Phe Asp Gln Gly Thr Trp Glu Ala Asn Gly Gly Leu Arg Tyr Ala
    290                 295                 300

Pro Arg Ala Asp Leu Ala Thr Arg Glu Glu Gln Ile Ala Val Ala Glu
305                 310                 315                 320

Val Thr Arg Leu Arg Gln Gly Trp Gly Ala Trp Pro Val Cys Ala Ala
                325                 330                 335

Arg Ala Gly Ala Arg Gly Ser Met Ser Thr Gln Arg Pro Arg His Ser
            340                 345                 350

Gly Ile Arg Ala Val Gly Pro Tyr Ala Trp Ala Gly Arg Cys Gly Arg
        355                 360                 365

Ile Gly Arg Trp Gly Val His Gln Glu Ala Met Met Asn Leu Ala Ile
    370                 375                 380

Trp His Pro Arg Lys Val Gln Ser Ala Thr Ile Tyr Gln Val Thr Asp
385                 390                 395                 400

Arg Ser His Asp Gly Arg Thr Ala Arg Val Pro Gly Asp Glu Ile Thr
                405                 410                 415

Ser Thr Val Ser Gly Trp Leu Ser Glu Leu Gly Thr Gln Ser Pro Leu
            420                 425                 430

Ala Asp Glu Leu Ala Arg Ala Val Arg Ile Gly Asp Trp Pro Ala Ala
        435                 440                 445

Tyr Ala Ile Gly Glu His Leu Ser Val Glu Ile Ala Val Ala Val Glu
    450                 455                 460

Phe Met Asp Phe Ala Leu Leu Pro Pro Glu Val Asn Ser Ala Arg Met
465                 470                 475                 480

Tyr Thr Gly Pro Gly Ala Gly Ser Leu Leu Ala Ala Ala Gly Gly Trp
                485                 490                 495

Asp Ser Leu Ala Ala Glu Leu Ala Thr Thr Ala Glu Ala Tyr Gly Ser
            500                 505                 510

Val Leu Ser Gly Leu Ala Ala Leu His Trp Arg Gly Pro Ala Ala Glu
        515                 520                 525

Ser Met Ala Val Thr Ala Ala Pro Tyr Ile Gly Trp Leu Tyr Thr Thr
    530                 535                 540

Ala Glu Lys Thr Gln Gln Thr Ala Ile Gln Ala Arg Ala Ala Ala Leu
545                 550                 555                 560

Ala Phe Glu Gln Ala Tyr Ala Met Thr Leu Pro Pro Pro Val Val Ala
                565                 570                 575

Ala Asn Arg Ile Gln Leu Leu Ala Leu Ile Ala Thr Asn Phe Phe Gly
            580                 585                 590
```

-continued

```
Gln Asn Thr Ala Ala Ile Ala Ala Thr Glu Ala Gln Tyr Ala Glu Met
        595                 600                 605

Trp Ala Gln Asp Ala Ala Ala Met Tyr Gly Tyr Ala Thr Ala Ser Ala
    610                 615                 620

Ala Ala Ala Leu Leu Thr Pro Phe Ser Pro Pro Arg Gln Thr Thr Asn
625                 630                 635                 640

Pro Ala Gly Leu Thr Glu Leu Val Ser Thr Tyr Arg Ser Pro Asp Arg
                645                 650                 655

Ala Trp Gln Ala Leu Ala Asp Gly Thr Arg Arg Ala Ile Val Glu Arg
            660                 665                 670

Leu Ala His Gly Pro Leu Ala Val Gly Glu Leu Ala Arg Asp Leu Pro
        675                 680                 685

Val Ser Arg Pro Ala Val Ser Gln His Leu Lys Val Leu Lys Thr Ala
    690                 695                 700

Arg Leu Val Cys Asp Arg Pro Ala Gly Thr Arg Arg Val Tyr Gln Leu
705                 710                 715                 720

Asp Pro Thr Gly Leu Ala Ala Leu Arg Thr Asp Leu Asp Arg Phe Trp
                725                 730                 735

Thr Arg Ala Leu Thr Gly Tyr Ala Gln Leu Ile Asp Ser Glu Gly Asp
            740                 745                 750

Asp Thr Lys Leu Met Thr Glu Asn Leu Thr Val Gln Pro Glu Arg Leu
        755                 760                 765

Gly Val Leu Ala Ser His His Asp Asn Ala Ala Val Asp Ala Ser Ser
    770                 775                 780

Gly Val Glu Ala Ala Ala Gly Leu Gly Glu Ser Val Ala Ile Thr His
785                 790                 795                 800

Gly Pro Tyr Cys Ser Gln Phe Asn Asp Thr Leu Asn Val Tyr Leu Thr
                805                 810                 815

Ala His Asn Ala Leu Gly Ser Ser Leu His Thr Ala Gly Val Asp Leu
            820                 825                 830

Ala Lys Ser Leu Arg Ile Ala Ala Lys Ile Tyr Ser Glu Ala Asp Glu
        835                 840                 845

Ala Trp Arg Lys Ala Ile Asp Gly Leu Phe Thr
    850                 855
```

<210> SEQ ID NO 72
<211> LENGTH: 2580
<212> TYPE: DNA
<213> ORGANISM: Mycobacterium tuberculosis
<220> FEATURE:
<223> OTHER INFORMATION: Rv2628-Rv3136Nt-Rv1009-Rv2034-Rv3615c

<400> SEQUENCE: 72

```
atgtccacgc aacgaccgag gcactccggt attcgggctg ttggccccta cgcatgggcc      60

ggccgatgtg gtcggatagg caggtggggg gtgcaccagg aggcgatgat gaatctagcg     120

atatggcacc cgcgcaaggt gcaatccgcc accatctatc aggtgaccga tcgctcgcac     180

gacgggcgca cagcacgggt gcctggtgac gagatcacta gcaccgtgtc cggttggttg     240

tcggagttgg gcacccaaag cccgttggcc gatgagcttg cgcgtgcggt gcggatcggc     300

gactggcccg ctgcgtacgc aatcggtgag cacctgtccg ttgagattgc cgttgcggtc     360

ggattcatgg atttcgcact gttaccaccg gaagtcaact ccgcccggat gtacaccggc     420

cctggggcag gatcgctgtt ggctgccgcg ggcggctggg attcgctggc cgccgagttg     480

gccaccacag ccgaggcata tggatcggtg ctgtccggac tggccgcctt gcattggcgt     540
```

-continued

```
ggaccggcag cggaatcgat ggcggtgacg gccgctccct atatcggttg gctgtacacg    600
accgccgaaa agacacagca aacagcgatc caagccaggg cggcagcgct ggccttcgag    660
caagcatacg caatgaccct gccgccaccg gtggtagcgg ccaaccggat acagctgcta    720
gcactgatcg cgacgaactt cttcggccag aacactgcgg cgatcgcggc caccgaggca    780
cagtacgccg agatgtgggc ccaggacgcc gccgcgatgt acggttacgc caccgcctca    840
gcggctgcgg ccctgctgac accgttctcc ccgccgcggc agaccaccaa cccggccggc    900
ctgaccgaat tcatggcatg caaaacggtg acgttgaccg tcgacggaac cgcgatgcgg    960
gtgaccacga tgaaatcgcg ggtgatcgac atcgtcgaag agaacgggtt ctcagtcgac   1020
gaccgcgacg acctgtatcc cgcggccggc gtgcaggtcc atgacgccga caccatcgtg   1080
ctgcggcgta gccgtccgct gcagatctcg ctggatggtc acgacgctaa gcaggtgtgg   1140
acgaccgcgt cgacggtgga cgaggcgctg gcccaactcg cgatgaccga cacggcgccg   1200
gccgcggctt ctcgcgccag ccgcgtcccg ctgtccggga tggcgctacc ggtcgtcagc   1260
gccaagacgg tgcagctcaa cgacggcggg ttggtgcgca cggtgcactt gccggccccc   1320
aatgtcgcgg ggctgctgag tgcggccggc gtgccgctgt tgcaaagcga ccacgtggtg   1380
cccgccgcga cggccccgat cgtcgaaggc atgcagatcc aggtgacccg caatcggatc   1440
aagaaggtca ccgagcggct gccgctgccg ccgaacgcgc gtcgtgtcga ggacccggag   1500
atgaacatga gccgggaggt cgtcgaagac ccgggggttc cggggaccca ggatgtgacg   1560
ttcgcggtag ctgaggtcaa cggcgtcgag accggccgtt tgcccgtcgc caacgtcgtg   1620
gtgaccccgg cccacgaagc cgtggtgcgg gtgggcacca agcccggtac cgaggtgccc   1680
ccggtgatcg acggaagcat ctgggacgcg atcgccggct gtgaggccgg tggcaactgg   1740
gcgatcaaca ccggcaacgg gtattacggt ggtgtgcagt ttgaccaggg cacctgggag   1800
gccaacggcg ggctgcggta tgcaccccgc gctgacctcg ccacccgcga agagcagatc   1860
gccgttgccg aggtgacccg actgcgtcaa ggttggggcg cctggccggt atgtgctgca   1920
cgagcgggtg cgcgcgagct cgtgtccact tacagatcac cggatcgcgc ttggcaggcg   1980
ctggcggacg gcactcgccg ggccatcgtg gagcggctgg cgcacggccc gctggccgtc   2040
ggcgagttgg cccgcgacct gcccgtcagc cgacccgcgg tgtcacagca cctcaaagtg   2100
ctcaagaccg ccaggctggt gtgcgaccgc cccgcgggaa cacgccgcgt ctaccagctc   2160
gacccgacag gccttgcggc attgcgcacc gacctcgacc ggttctggac acgcgccctg   2220
actggctacg cgcagctcat cgactccgaa ggagacgaca caaagcttat gacggaaaac   2280
ttgaccgtcc agcccgagcg tctcggtgta ctggcgtcgc accatgacaa cgcggcggtc   2340
gatgcctcct cgggcgtcga agctgccgct ggcctaggcg aatctgtggc gatcactcac   2400
ggtccgtact gctcacagtt caacgacacg ttaaatgtgt acttgactgc ccacaatgcc   2460
ctgggctcgt ccttgcatac ggccggtgtc gatctcgcca aaagtcttcg aattgcggcg   2520
aagatatata gcgaggccga cgaagcgtgg cgcaaggcta tcgacgggtt gtttacctga   2580
```

<210> SEQ ID NO 73
<211> LENGTH: 859
<212> TYPE: PRT
<213> ORGANISM: Mycobacterium tuberculosis
<220> FEATURE:
<223> OTHER INFORMATION: Rv2628-Rv3136Nt-Rv1009-Rv2034-Rv3615c

<400> SEQUENCE: 73

-continued

```
Met Ser Thr Gln Arg Pro Arg His Ser Gly Ile Arg Ala Val Gly Pro
1               5                   10                  15

Tyr Ala Trp Ala Gly Arg Cys Gly Arg Ile Gly Arg Trp Gly Val His
            20                  25                  30

Gln Glu Ala Met Met Asn Leu Ala Ile Trp His Pro Arg Lys Val Gln
        35                  40                  45

Ser Ala Thr Ile Tyr Gln Val Thr Asp Arg Ser His Asp Gly Arg Thr
    50                  55                  60

Ala Arg Val Pro Gly Asp Glu Ile Thr Ser Thr Val Ser Gly Trp Leu
65                  70                  75                  80

Ser Glu Leu Gly Thr Gln Ser Pro Leu Ala Asp Glu Leu Ala Arg Ala
                85                  90                  95

Val Arg Ile Gly Asp Trp Pro Ala Ala Tyr Ala Ile Gly Glu His Leu
            100                 105                 110

Ser Val Glu Ile Ala Val Ala Val Gly Phe Met Asp Phe Ala Leu Leu
        115                 120                 125

Pro Pro Glu Val Asn Ser Ala Arg Met Tyr Thr Gly Pro Gly Ala Gly
    130                 135                 140

Ser Leu Leu Ala Ala Ala Gly Gly Trp Asp Ser Leu Ala Ala Glu Leu
145                 150                 155                 160

Ala Thr Thr Ala Glu Ala Tyr Gly Ser Val Leu Ser Gly Leu Ala Ala
                165                 170                 175

Leu His Trp Arg Gly Pro Ala Ala Glu Ser Met Ala Val Thr Ala Ala
            180                 185                 190

Pro Tyr Ile Gly Trp Leu Tyr Thr Thr Ala Glu Lys Thr Gln Gln Thr
        195                 200                 205

Ala Ile Gln Ala Arg Ala Ala Ala Leu Ala Phe Glu Gln Ala Tyr Ala
    210                 215                 220

Met Thr Leu Pro Pro Pro Val Val Ala Ala Asn Arg Ile Gln Leu Leu
225                 230                 235                 240

Ala Leu Ile Ala Thr Asn Phe Phe Gly Gln Asn Thr Ala Ala Ile Ala
                245                 250                 255

Ala Thr Glu Ala Gln Tyr Ala Glu Met Trp Ala Gln Asp Ala Ala Ala
            260                 265                 270

Met Tyr Gly Tyr Ala Thr Ala Ser Ala Ala Ala Ala Leu Leu Thr Pro
        275                 280                 285

Phe Ser Pro Pro Arg Gln Thr Thr Asn Pro Ala Gly Leu Thr Glu Phe
    290                 295                 300

Met Ala Cys Lys Thr Val Thr Leu Thr Val Asp Gly Thr Ala Met Arg
305                 310                 315                 320

Val Thr Thr Met Lys Ser Arg Val Ile Asp Ile Val Glu Glu Asn Gly
                325                 330                 335

Phe Ser Val Asp Asp Arg Asp Asp Leu Tyr Pro Ala Ala Gly Val Gln
            340                 345                 350

Val His Asp Ala Asp Thr Ile Val Leu Arg Arg Ser Arg Pro Leu Gln
        355                 360                 365

Ile Ser Leu Asp Gly His Asp Ala Lys Gln Val Trp Thr Thr Ala Ser
    370                 375                 380

Thr Val Asp Glu Ala Leu Ala Gln Leu Ala Met Thr Asp Thr Ala Pro
385                 390                 395                 400

Ala Ala Ala Ser Arg Ala Ser Arg Val Pro Leu Ser Gly Met Ala Leu
                405                 410                 415

Pro Val Val Ser Ala Lys Thr Val Gln Leu Asn Asp Gly Gly Leu Val
```

```
            420                 425                 430

Arg Thr Val His Leu Pro Ala Pro Asn Val Ala Gly Leu Leu Ser Ala
        435                 440                 445

Ala Gly Val Pro Leu Leu Gln Ser Asp His Val Val Pro Ala Ala Thr
    450                 455                 460

Ala Pro Ile Val Glu Gly Met Gln Ile Gln Val Thr Arg Asn Arg Ile
465                 470                 475                 480

Lys Lys Val Thr Glu Arg Leu Pro Leu Pro Pro Asn Ala Arg Arg Val
                485                 490                 495

Glu Asp Pro Glu Met Asn Met Ser Arg Glu Val Val Glu Asp Pro Gly
            500                 505                 510

Val Pro Gly Thr Gln Asp Val Thr Phe Ala Val Ala Glu Val Asn Gly
        515                 520                 525

Val Glu Thr Gly Arg Leu Pro Val Ala Asn Val Val Val Thr Pro Ala
    530                 535                 540

His Glu Ala Val Val Arg Val Gly Thr Lys Pro Gly Thr Glu Val Pro
545                 550                 555                 560

Pro Val Ile Asp Gly Ser Ile Trp Asp Ala Ile Ala Gly Cys Glu Ala
                565                 570                 575

Gly Gly Asn Trp Ala Ile Asn Thr Gly Asn Gly Tyr Tyr Gly Gly Val
            580                 585                 590

Gln Phe Asp Gln Gly Thr Trp Glu Ala Asn Gly Gly Leu Arg Tyr Ala
        595                 600                 605

Pro Arg Ala Asp Leu Ala Thr Arg Glu Glu Gln Ile Ala Val Ala Glu
    610                 615                 620

Val Thr Arg Leu Arg Gln Gly Trp Gly Ala Trp Pro Val Cys Ala Ala
625                 630                 635                 640

Arg Ala Gly Ala Arg Glu Leu Val Ser Thr Tyr Arg Ser Pro Asp Arg
                645                 650                 655

Ala Trp Gln Ala Leu Ala Asp Gly Thr Arg Arg Ala Ile Val Glu Arg
            660                 665                 670

Leu Ala His Gly Pro Leu Ala Val Gly Glu Leu Ala Arg Asp Leu Pro
        675                 680                 685

Val Ser Arg Pro Ala Val Ser Gln His Leu Lys Val Leu Lys Thr Ala
    690                 695                 700

Arg Leu Val Cys Asp Arg Pro Ala Gly Thr Arg Arg Val Tyr Gln Leu
705                 710                 715                 720

Asp Pro Thr Gly Leu Ala Ala Leu Arg Thr Asp Leu Asp Arg Phe Trp
                725                 730                 735

Thr Arg Ala Leu Thr Gly Tyr Ala Gln Leu Ile Asp Ser Glu Gly Asp
            740                 745                 750

Asp Thr Lys Leu Met Thr Glu Asn Leu Thr Val Gln Pro Glu Arg Leu
        755                 760                 765

Gly Val Leu Ala Ser His His Asp Asn Ala Ala Val Asp Ala Ser Ser
    770                 775                 780

Gly Val Glu Ala Ala Ala Gly Leu Gly Glu Ser Val Ala Ile Thr His
785                 790                 795                 800

Gly Pro Tyr Cys Ser Gln Phe Asn Asp Thr Leu Asn Val Tyr Leu Thr
                805                 810                 815

Ala His Asn Ala Leu Gly Ser Ser Leu His Thr Ala Gly Val Asp Leu
            820                 825                 830

Ala Lys Ser Leu Arg Ile Ala Ala Lys Ile Tyr Ser Glu Ala Asp Glu
        835                 840                 845
```

Ala Trp Arg Lys Ala Ile Asp Gly Leu Phe Thr
850 855

<210> SEQ ID NO 74
<211> LENGTH: 2580
<212> TYPE: DNA
<213> ORGANISM: Mycobacterium tuberculosis
<220> FEATURE:
<223> OTHER INFORMATION: Rv2628-Rv3136Nt-Rv2034-Rv3615c-Rv1009

<400> SEQUENCE: 74
atgtccacgc aacgaccgag gcactccggt attcgggctg ttggccccta cgcatgggcc 60
ggccgatgtg gtcggatagg caggtggggg gtgcaccagg aggcgatgat gaatctagcg 120
atatggcacc cgcgcaaggt gcaatccgcc accatctatc aggtgaccga tcgctcgcac 180
gacgggcgca cagcacgggt gcctggtgac gagatcacta gcaccgtgtc cggttggttg 240
tcggagttgg gcacccaaag cccgttggcc gatgagcttg cgcgtgcggt gcggatcggc 300
gactggcccg ctgcgtacgc aatcggtgag cacctgtccg ttgagattgc cgttgcggtc 360
ggattcatgg atttcgcact gttaccaccg gaagtcaact ccgcccggat gtacaccggc 420
cctggggcag gatcgctgtt ggctgccgcg ggcggctggg attcgctggc cgccgagttg 480
gccaccacag ccgaggcata tggatcggtg ctgtccggac tggccgcctt gcattggcgt 540
ggaccggcag cggaatcgat ggcggtgacg gccgctccct atatcggttg gctgtacacg 600
accgccgaaa agacacagca aacagcgatc caagccaggg cggcagcgct ggccttcgag 660
caagcatacg caatgaccct gccgccaccg gtggtagcgg ccaaccggat acagctgcta 720
gcactgatcg cgacgaactt cttcggccag aacactgcgg cgatcgcggc caccgaggca 780
cagtacgccg agatgtgggc ccaggacgcc gccgcgatgt acggttacgc caccgcctca 840
gcggctgcgg ccctgctgac accgttctcc ccgccgcggc agaccaccaa cccggccggc 900
ctgaccgaat tcgtgtccac ttacagatca ccggatcgcg cttggcaggc gctggcggac 960
ggcactcgcc gggccatcgt ggagcggctg gcgcacggcc cgctggccgt cggcgagttg 1020
gcccgcgacc tgcccgtcag ccgacccgcg gtgtcacagc acctcaaagt gctcaagacc 1080
gccaggctgg tgtgcgaccg ccccgcggga acacgccgcg tctaccagct cgacccgaca 1140
ggccttgcgg cattgcgcac cgacctcgac cggttctgga cacgcgccct gactggctac 1200
gcgcagctca tcgactccga aggagacgac acagagctca tgacggaaaa cttgaccgtc 1260
cagcccgagc gtctcggtgt actggcgtcg caccatgaca acgcggcggt cgatgcctcc 1320
tcgggcgtcg aagctgccgc tggcctaggc gaatctgtgg cgatcactca cggtccgtac 1380
tgctcacagt tcaacgacac gttaaatgtg tacttgactg cccacaatgc cctgggctcg 1440
tccttgcata cggccggtgt cgatctcgcc aaaagtcttc gaattgcggc gaagatatat 1500
agcgaggccg acgaagcgtg gcgcaaggct atcgacgggt tgtttaccaa gcttatggca 1560
tgcaaaacgg tgacgttgac cgtcgacgga accgcgatgc gggtgaccac gatgaaatcg 1620
cgggtgatcg acatcgtcga agagaacggg ttctcagtcg acgaccgcga cgacctgtat 1680
cccgcggccg gcgtgcaggt ccatgacgcc gacaccatcg tgctgcggcg tagccgtccg 1740
ctgcagatct cgctggatgg tcacgacgct aagcaggtgt ggacgaccgc gtcgacggtg 1800
gacgaggcgc tggcccaact cgcgatgacc gacacggcgc cggccgcggc ttctcgcgcc 1860
agccgcgtcc cgctgtccgg gatggcgcta ccggtcgtca gcgccaagac ggtgcagctc 1920
aacgacggcg ggttggtgcg cacggtgcac ttgccggccc ccaatgtcgc ggggctgctg 1980

```
agtgcggccg gcgtgccgct gttgcaaagc gaccacgtgg tgcccgccgc gacggccccg   2040

atcgtcgaag gcatgcagat ccaggtgacc cgcaatcgga tcaagaaggt caccgagcgg   2100

ctgccgctgc cgccgaacgc gcgtcgtgtc gaggacccgg agatgaacat gagccgggag   2160

gtcgtcgaag acccgggggt tccggggacc caggatgtga cgttcgcggt agctgaggtc   2220

aacggcgtcg agaccggccg tttgcccgtc gccaacgtcg tggtgacccc ggcccacgaa   2280

gccgtggtgc gggtgggcac caagcccggt accgaggtgc ccccggtgat cgacggaagc   2340

atctgggacg cgatcgccgg ctgtgaggcc ggtggcaact gggcgatcaa caccggcaac   2400

gggtattacg gtggtgtgca gtttgaccag ggcacctggg aggccaacgg cgggctgcgg   2460

tatgcacccc gcgctgacct cgccacccgc gaagagcaga tcgccgttgc cgaggtgacc   2520

cgactgcgtc aaggttgggg cgcctggccg gtatgtgctg cacgagcggg tgcgcgctga   2580
```

<210> SEQ ID NO 75
<211> LENGTH: 859
<212> TYPE: PRT
<213> ORGANISM: Mycobacterium tuberculosis
<220> FEATURE:
<223> OTHER INFORMATION: Rv2628-Rv3136Nt-Rv2034-Rv3615c-Rv1009

<400> SEQUENCE: 75

```
Met Ser Thr Gln Arg Pro Arg His Ser Gly Ile Arg Ala Val Gly Pro
1               5                   10                  15

Tyr Ala Trp Ala Gly Arg Cys Gly Arg Ile Gly Arg Trp Gly Val His
            20                  25                  30

Gln Glu Ala Met Met Asn Leu Ala Ile Trp His Pro Arg Lys Val Gln
        35                  40                  45

Ser Ala Thr Ile Tyr Gln Val Thr Asp Arg Ser His Asp Gly Arg Thr
    50                  55                  60

Ala Arg Val Pro Gly Asp Glu Ile Thr Ser Thr Val Ser Gly Trp Leu
65                  70                  75                  80

Ser Glu Leu Gly Thr Gln Ser Pro Leu Ala Asp Glu Leu Ala Arg Ala
                85                  90                  95

Val Arg Ile Gly Asp Trp Pro Ala Ala Tyr Ala Ile Gly Glu His Leu
            100                 105                 110

Ser Val Glu Ile Ala Val Ala Val Gly Phe Met Asp Phe Ala Leu Leu
        115                 120                 125

Pro Pro Glu Val Asn Ser Ala Arg Met Tyr Thr Gly Pro Gly Ala Gly
    130                 135                 140

Ser Leu Leu Ala Ala Ala Gly Gly Trp Asp Ser Leu Ala Ala Glu Leu
145                 150                 155                 160

Ala Thr Thr Ala Glu Ala Tyr Gly Ser Val Leu Ser Gly Leu Ala Ala
                165                 170                 175

Leu His Trp Arg Gly Pro Ala Ala Glu Ser Met Ala Val Thr Ala Ala
            180                 185                 190

Pro Tyr Ile Gly Trp Leu Tyr Thr Thr Ala Glu Lys Thr Gln Gln Thr
        195                 200                 205

Ala Ile Gln Ala Arg Ala Ala Ala Leu Ala Phe Glu Gln Ala Tyr Ala
    210                 215                 220

Met Thr Leu Pro Pro Pro Val Val Ala Ala Asn Arg Ile Gln Leu Leu
225                 230                 235                 240

Ala Leu Ile Ala Thr Asn Phe Phe Gly Gln Asn Thr Ala Ala Ile Ala
                245                 250                 255
```

-continued

```
Ala Thr Glu Ala Gln Tyr Ala Glu Met Trp Ala Gln Asp Ala Ala Ala
            260                 265                 270

Met Tyr Gly Tyr Ala Thr Ala Ser Ala Ala Ala Ala Leu Leu Thr Pro
        275                 280                 285

Phe Ser Pro Pro Arg Gln Thr Thr Asn Pro Ala Gly Leu Thr Glu Phe
    290                 295                 300

Val Ser Thr Tyr Arg Ser Pro Asp Arg Ala Trp Gln Ala Leu Ala Asp
305                 310                 315                 320

Gly Thr Arg Arg Ala Ile Val Glu Arg Leu Ala His Gly Pro Leu Ala
                325                 330                 335

Val Gly Glu Leu Ala Arg Asp Leu Pro Val Ser Arg Pro Ala Val Ser
            340                 345                 350

Gln His Leu Lys Val Leu Lys Thr Ala Arg Leu Val Cys Asp Arg Pro
        355                 360                 365

Ala Gly Thr Arg Arg Val Tyr Gln Leu Asp Pro Thr Gly Leu Ala Ala
    370                 375                 380

Leu Arg Thr Asp Leu Asp Arg Phe Trp Thr Arg Ala Leu Thr Gly Tyr
385                 390                 395                 400

Ala Gln Leu Ile Asp Ser Glu Gly Asp Asp Thr Glu Leu Met Thr Glu
                405                 410                 415

Asn Leu Thr Val Gln Pro Glu Arg Leu Gly Val Leu Ala Ser His His
            420                 425                 430

Asp Asn Ala Ala Val Asp Ala Ser Ser Gly Val Glu Ala Ala Ala Gly
        435                 440                 445

Leu Gly Glu Ser Val Ala Ile Thr His Gly Pro Tyr Cys Ser Gln Phe
    450                 455                 460

Asn Asp Thr Leu Asn Val Tyr Leu Thr Ala His Asn Ala Leu Gly Ser
465                 470                 475                 480

Ser Leu His Thr Ala Gly Val Asp Leu Ala Lys Ser Leu Arg Ile Ala
                485                 490                 495

Ala Lys Ile Tyr Ser Glu Ala Asp Glu Ala Trp Arg Lys Ala Ile Asp
            500                 505                 510

Gly Leu Phe Thr Lys Leu Met Ala Cys Lys Thr Val Thr Leu Thr Val
        515                 520                 525

Asp Gly Thr Ala Met Arg Val Thr Thr Met Lys Ser Arg Val Ile Asp
    530                 535                 540

Ile Val Glu Glu Asn Gly Phe Ser Val Asp Asp Arg Asp Asp Leu Tyr
545                 550                 555                 560

Pro Ala Ala Gly Val Gln Val His Asp Ala Asp Thr Ile Val Leu Arg
                565                 570                 575

Arg Ser Arg Pro Leu Gln Ile Ser Leu Asp Gly His Asp Ala Lys Gln
            580                 585                 590

Val Trp Thr Thr Ala Ser Thr Val Asp Glu Ala Leu Ala Gln Leu Ala
        595                 600                 605

Met Thr Asp Thr Ala Pro Ala Ala Ala Ser Arg Ala Ser Arg Val Pro
    610                 615                 620

Leu Ser Gly Met Ala Leu Pro Val Val Ser Ala Lys Thr Val Gln Leu
625                 630                 635                 640

Asn Asp Gly Gly Leu Val Arg Thr Val His Leu Pro Ala Pro Asn Val
                645                 650                 655

Ala Gly Leu Leu Ser Ala Ala Gly Val Pro Leu Leu Gln Ser Asp His
            660                 665                 670

Val Val Pro Ala Ala Thr Ala Pro Ile Val Glu Gly Met Gln Ile Gln
```

-continued

```
        675                 680                 685

Val Thr Arg Asn Arg Ile Lys Lys Val Thr Glu Arg Leu Pro Leu Pro
    690                 695                 700

Pro Asn Ala Arg Arg Val Glu Asp Pro Glu Met Asn Met Ser Arg Glu
705                 710                 715                 720

Val Val Glu Asp Pro Gly Val Pro Gly Thr Gln Asp Val Thr Phe Ala
                725                 730                 735

Val Ala Glu Val Asn Gly Val Glu Thr Gly Arg Leu Pro Val Ala Asn
            740                 745                 750

Val Val Val Thr Pro Ala His Glu Ala Val Val Arg Val Gly Thr Lys
        755                 760                 765

Pro Gly Thr Glu Val Pro Pro Val Ile Asp Gly Ser Ile Trp Asp Ala
    770                 775                 780

Ile Ala Gly Cys Glu Ala Gly Gly Asn Trp Ala Ile Asn Thr Gly Asn
785                 790                 795                 800

Gly Tyr Tyr Gly Gly Val Gln Phe Asp Gln Gly Thr Trp Glu Ala Asn
                805                 810                 815

Gly Gly Leu Arg Tyr Ala Pro Arg Ala Asp Leu Ala Thr Arg Glu Glu
            820                 825                 830

Gln Ile Ala Val Ala Glu Val Thr Arg Leu Arg Gln Gly Trp Gly Ala
        835                 840                 845

Trp Pro Val Cys Ala Ala Arg Ala Gly Ala Arg
    850                 855
```

TUBERCULOSIS COMPOSITIONS AND METHODS OF TREATING OR PREVENTING TUBERCULOSIS

CROSS-REFERENCE TO RELATED APPLICATIONS

This application claims priority to U.S. provisional application Ser. No. 62/350,837 filed Jun. 16, 2016, which is incorporated herein by reference in its entirety.

FIELD

The present disclosure is directed, in part, to fusion proteins comprising *Mycobacterium tuberculosis* (Mtb) antigens, nucleic acid molecules encoding the same, vectors comprising nucleic acid molecules, compositions comprising the same, and methods of eliciting an immune response against tuberculosis.

BACKGROUND

Tuberculosis (TB) is a global health problem resulting in 8 million new cases and 2 million deaths each year. The emergence of multi-drug and totally-drug resistant strains of TB only makes this problem more severe. The life cycle of Mtb has 3 stages. In the acute phase following initial infection the bacteria replicate in the host and virulence factors are expressed, leading to the generation of an immune response by the host. As the immune response begins to control the infection, the Mtb enters a latent, asymptomatic state in which the bacteria become non-replicating and are encased in granulomas. The bacterium can persist in this latent state in infected individuals for many years, making diagnosis and treatment of disease difficult. In some cases, the bacteria are reactivated and begin replicating again, leading back to the disease state. Reactivation can occur for numerous reasons, including immune suppression caused by diseases such as HIV, treatments such as chemotherapy, or the weakening of the immune system due to aging. An estimated 2 billion people are latently infected with Mtb worldwide, and reactivation of latent Mtb accounts for most new cases of active TB disease. Reactivation is associated with inflammation, necrosis and cavitation of the lung, a process that results in draining of the lesions into the bronchus. Aerosols generated when individuals with bronchial lesions cough causes dissemination of the Mtb organism to uninfected, susceptible persons, and the transmission cycle is thus maintained.

The only currently available vaccine against TB, *Mycobacterium bovis* (Bacille Calmette-Guérin) (BCG), was first introduced in 1921. BCG has been widely utilized and while studies show that for some purposes BCG is effective (e.g. against disseminated TB), it is known to be ineffective with respect to preventing the development, persistence and reactivation of latent TB. There is an ongoing need to develop improved, more effective vaccines against TB. In particular, there is a need to develop vaccines that provide protection against the development, maintenance and/or reactivation of latent tuberculosis infection. With the availability of the entire genomic sequence of Mtb, and the tools for bioinformatic and experimental analysis of Mtb antigens, many new potential Mtb vaccine candidates have been identified in recent years. These include antigens that are involved in acute infection, maintenance of latency, or reactivation of Mtb. There are a range of delivery strategies in clinical development that are comprised of combinations of these and other antigens that have been tested in animal models and are currently or will soon be in clinical trials.

While vaccines are often effective to immunize individuals prophylactically or therapeutically against pathogen infection or human diseases, there is a need for improved vaccines. There is also a need for compositions and methods that produce an enhanced immune response. Likewise, while some immunotherapeutics are useful to modulate immune response in a patient, there remains a need for improved immunotherapeutic compositions and methods.

SUMMARY

This disclosure describes antigen cassettes (and specified variants) that can be used to create tuberculosis vaccines comprising specified *Mycobacterium tuberculosis* (Mtb) antigens. The disclosure also describes the strategic combination of antigens which are incorporated into a variety of delivery platforms in such a way as to provide pathways to a matrix of matched combinations of antigen delivery to obtain an optimized immune response. The subject matter described herein can be used as a prophylactic or therapeutic TB vaccine. The initial selection of antigens for inclusion into a usable cassette was based on a number of parameters including, for example, a thorough review of the literature, expression data, responses by human T cells, inclusion of human immunogenic regions, mouse protection studies, and conservation in sequence across most strains of TB with full genome sequences. Specific antigens were then probed to be sure they were able to be expressed in a variety of systems (BCG, protein, viral vectors, nucleic acids), that they were immunogenic, and they could be made as fusions in proteins or other vectors to simplify downstream manufacturing concerns. All of the selected antigens were then shown to be immunogenic in mice, either when used alone, or in a variety of combinations, to arrive at the present application.

The constructs described herein have been integrated into a specified range of delivery platforms that include the following classes (but not exhaustive) of representative delivery platforms: 1) viral vector delivery systems, 2) recombinant BCG, 3) recombinant purified protein fusions, 4) DNA plasmid vector systems, and 5) RNA vector systems. These delivery platforms can be used either in a single platform alone or in combinations as matched antigen prime-boost approaches. In addition, the use of these antigens in a single rBCG vector system, which is envisioned to be used as an antigen matched prime for a boost with any of the modalities above, including protein, viral vectors, nucleic acids, or others.

The present disclosure provides fusion proteins that comprise at least two or three *Mycobacterium tuberculosis* (Mtb) antigens.

The present disclosure also provides nucleic acid molecules encoding fusion proteins that comprise at least two or three *Mycobacterium tuberculosis* (Mtb) antigens.

The present disclosure also provides: compositions comprising the fusion proteins and a pharmaceutically acceptable carrier; vectors encoding the fusion proteins; compositions comprising the vectors and a pharmaceutically acceptable carrier; cells comprising the vectors; compositions comprising the cells and a pharmaceutically acceptable carrier.

The present disclosure also provides compositions that comprise at least two or three *Mycobacterium tuberculosis* (Mtb) antigens, and a pharmaceutically acceptable carrier.

The present disclosure also provides compositions that comprise at least two or three *Mycobacterium tuberculosis*

(Mtb) antigens, wherein the composition comprises at least one nucleic acid molecule encoding at least one of the Mtb antigens, and a pharmaceutically acceptable carrier.

The present disclosure also provides methods of eliciting an immune response against *Mycobacterium tuberculosis* in a mammal comprising administering to the mammal an immunologically sufficient amount of one or more fusion proteins comprising at least two or three *Mycobacterium tuberculosis* (Mtb) antigens.

The present disclosure also provides methods of eliciting an immune response against *Mycobacterium tuberculosis* in a mammal comprising administering to the mammal an immunologically sufficient amount of a composition comprising at least two or three *Mycobacterium tuberculosis* (Mtb) antigens, and a pharmaceutically acceptable carrier.

The present disclosure also provides methods of eliciting an immune response against *Mycobacterium tuberculosis* in a mammal comprising administering to the mammal an immunologically sufficient amount of a composition comprising at least two or three *Mycobacterium tuberculosis* (Mtb) antigens, and a pharmaceutically acceptable carrier, wherein the composition comprises at least one nucleic acid molecule encoding at least one of the Mtb antigens.

The present disclosure also provides fusion proteins for use in the preparation of a medicament for treating or preventing a *Mycobacterium tuberculosis* infection, wherein the fusion protein comprises at least two or three *Mycobacterium tuberculosis* (Mtb) antigens.

The present disclosure also provides fusion proteins for use in treating or preventing a *Mycobacterium tuberculosis* infection, wherein the fusion protein comprises at least two or three *Mycobacterium tuberculosis* (Mtb) antigens.

The present disclosure also provides uses of a fusion protein in the preparation of a medicament for treating or preventing a *Mycobacterium tuberculosis* infection, wherein the fusion protein comprises at least two or three *Mycobacterium tuberculosis* (Mtb) antigens.

The present disclosure also provides uses of a fusion protein in treating or preventing a *Mycobacterium tuberculosis* infection, wherein the fusion protein comprises at least two or three *Mycobacterium tuberculosis* (Mtb) antigens.

The present disclosure also provides compositions for use in the preparation of a medicament for treating or preventing a *Mycobacterium tuberculosis* infection, wherein the composition comprises at least two or three *Mycobacterium tuberculosis* (Mtb) antigens, and a pharmaceutically acceptable carrier.

The present disclosure also provides composition for use in treating or preventing a *Mycobacterium tuberculosis* infection, wherein the composition comprises at least two or three *Mycobacterium tuberculosis* (Mtb) antigens, and a pharmaceutically acceptable carrier.

The present disclosure also provides uses of a composition in the preparation of a medicament for treating or preventing a *Mycobacterium tuberculosis* infection, wherein the composition comprises at least two or three *Mycobacterium tuberculosis* (Mtb) antigens, and a pharmaceutically acceptable carrier.

The present disclosure also provides uses of a composition in treating or preventing a *Mycobacterium tuberculosis* infection, wherein the composition comprises at least two or three *Mycobacterium tuberculosis* (Mtb) antigens, and a pharmaceutically acceptable carrier.

The present disclosure also provides compositions for use in the preparation of a medicament for treating or preventing a *Mycobacterium tuberculosis* infection, wherein the composition comprises at least two or three *Mycobacterium tuberculosis* (Mtb) antigens, and a pharmaceutically acceptable carrier; wherein the composition comprises at least one nucleic acid molecule encoding at least one of the Mtb antigens.

The present disclosure also provides compositions for use in treating or preventing a *Mycobacterium tuberculosis* infection, wherein the composition comprises at least two or three *Mycobacterium tuberculosis* (Mtb) antigens, and a pharmaceutically acceptable carrier, wherein the composition comprises at least one nucleic acid molecule encoding at least one of the Mtb antigens.

The present disclosure also provides uses of a composition in the preparation of a medicament for treating or preventing a *Mycobacterium tuberculosis* infection, wherein the composition comprises at least two or three *Mycobacterium tuberculosis* (Mtb) antigens, and a pharmaceutically acceptable carrier, wherein the composition comprises at least one nucleic acid molecule encoding at least one of the Mtb antigens.

The present disclosure also provides uses of a composition in treating or preventing a *Mycobacterium tuberculosis* infection, wherein the composition comprises at least two or three *Mycobacterium tuberculosis* (Mtb) antigens, and a pharmaceutically acceptable carrier, wherein the composition comprises at least one nucleic acid molecule encoding at least one of the Mtb antigens.

The present disclosure also provides fusion proteins, compositions, cells, vectors, methods, and uses, as described herein, substantially as described with reference to the accompanying examples and/or figures.

DESCRIPTION OF EMBODIMENTS

Figure 1:
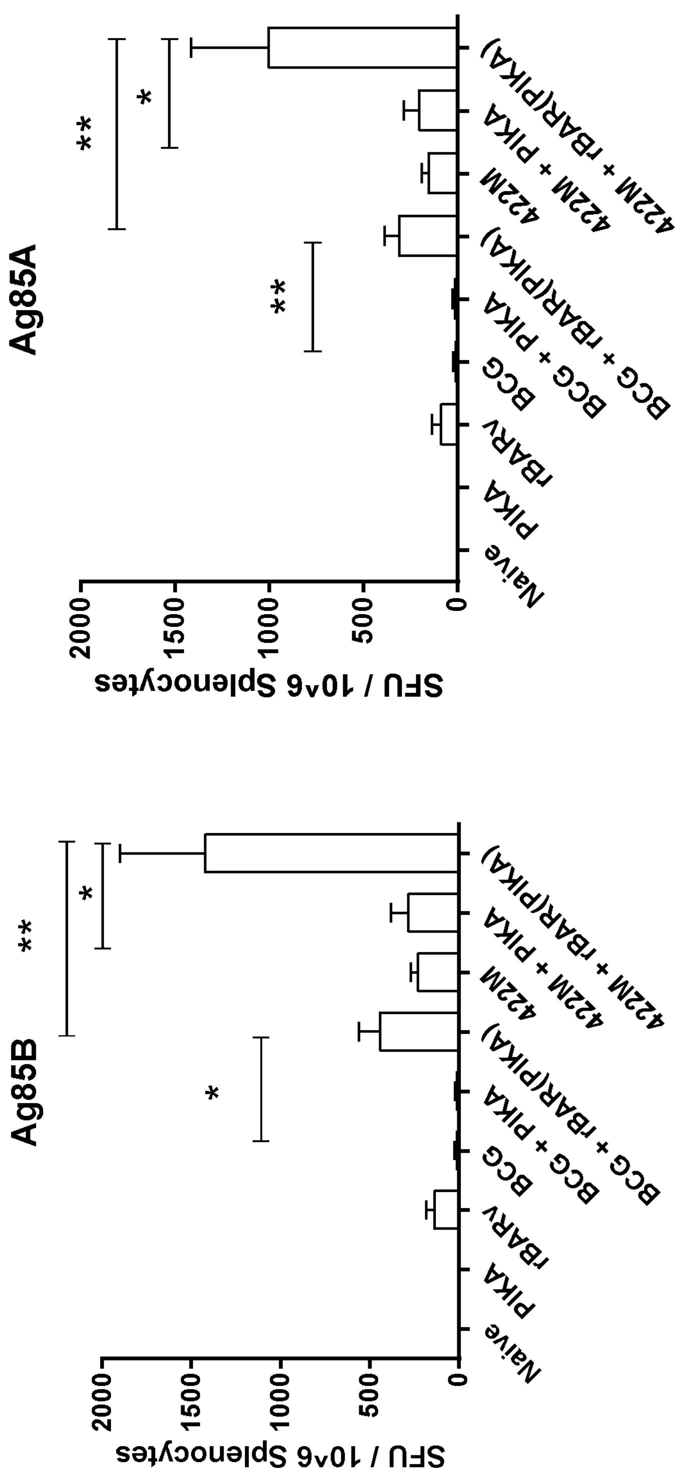
FIG. 1 shows mouse immunogenicity data for a recombinant protein form of the Ag85B, Ag85A, Rv3407 construct and a recombinant BCG encoding the same.

The terminology used herein is for the purpose of describing particular embodiments only and is not intended to be limiting.

As used herein, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, "adjuvant" means any molecule added to any composition described herein to enhance the immunogenicity of the Mtb antigens.

As used herein, "coding sequence" or "encoding nucleic acid" means the nucleic acids (RNA or DNA molecule) that comprise a nucleotide sequence which encodes an Mtb antigen. The coding sequence can further include initiation and termination signals operably linked to regulatory elements including a promoter and polyadenylation signal capable of directing expression in the cells of an individual or mammal to which the nucleic acid is administered.

As used herein, "consensus" or "consensus sequence" means a polypeptide sequence based on analysis of an alignment of multiple subtypes of a particular Mtb antigen. Nucleic acid sequences that encode a consensus polypeptide sequence can be prepared. Vaccines comprising Mtb antigens that comprise consensus sequences and/or nucleic acid molecules that encode such antigens can be used to induce broad immunity against multiple subtypes or serotypes of a particular antigen.

As used herein, "electroporation" means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, "fragment" with respect to nucleic acid sequences, means a nucleic acid sequence or a portion thereof, that encodes a portion of an Mtb antigen capable of eliciting an immune response in a mammal that cross reacts with a full length wild type Mtb antigen. The fragments can be DNA fragments selected from at least one of the various nucleotide sequences that encode protein fragments set forth below.

As used herein, "fragment" or "immunogenic fragment" with respect to polypeptide sequences, means a portion of an MTB antigen capable of eliciting an immune response in a mammal that cross reacts with a full length wild type strain Mtb antigen. Fragments of consensus or wild type Mtb antigens can comprise at least 10%, at least 20%, at least 30%, at least 40%, at least 50%, at least 60%, at least 70%, at least 80%, at least 90% or at least 95% of a consensus or wild type Mtb antigen. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a consensus or wild type protein.

As used herein, "genetic construct" refers to the DNA or RNA molecules that comprise a nucleotide sequence which encodes an Mtb antigen. The coding sequence includes initiation and termination signals operably linked to regulatory elements including a promoter and polyadenylation signal capable of directing expression in the cells of the individual to whom the nucleic acid molecule is administered.

As used herein, "expressible form" refers to gene constructs that contain the necessary regulatory elements operable linked to a coding sequence that encodes an Mtb antigen such that when present in the cell of the individual, the coding sequence will be expressed.

As used herein, "homology" refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous" refers to a probe that can hybridize to a strand of the double-stranded nucleic acid sequence under conditions of low stringency. When used in reference to a single-stranded nucleic acid sequence, the term "substantially homologous" refers to a probe that can hybridize to (i.e., is the complement of) the single-stranded nucleic acid template sequence under conditions of low stringency.

As used herein, "identical" or "identity" in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) residues can be considered equivalent. Identity can be performed manually or by using a computer sequence algorithm such as BLAST or BLAST 2.0.

As used herein, "immune response" means the activation of a host's immune system, e.g., that of a mammal, in response to the introduction of an Mtb antigen. The immune response can be in the form of a cellular or humoral response, or both.

As used herein, "Mtb antigen" means an antigen from *Mycobacterium tuberculosis*, which may be an isolated antigen, or an antigen that forms part of a fusion protein with other antigen(s).

As used herein, "nucleic acid" or "oligonucleotide" or "polynucleotide" means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

As used herein, "operably linked" means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

As used herein, “promoter” means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

As used herein, “signal peptide” and “leader sequence”, used interchangeably, refer to an amino acid sequence that can be linked at the amino terminus of an Mtb antigenic protein set forth herein. Signal peptides/leader sequences typically direct localization of a protein. Signal peptides/leader sequences used herein can facilitate secretion of the protein from the cell in which it is produced or anchor it in the membrane. Signal peptides/leader sequences are often cleaved from the remainder of the protein, often referred to as the mature protein, upon secretion from the cell. Signal peptides/leader sequences are linked at the N terminus of the protein.

As used herein, “stringent hybridization conditions” means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5 to 10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01 to 1.0 M sodium ion concentration (or other salts) at pH 7.0 to 8.3 and the temperature is at least about 30° C. for short probes (e.g., about 10 to 50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

As used herein, “substantially complementary” means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used herein, “substantially identical” means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used herein, “variant” with respect to a nucleic acid means: i) a portion or fragment of a referenced nucleotide sequence; ii) the complement of a referenced nucleotide sequence or portion thereof; iii) a nucleic acid that is substantially identical to a referenced nucleic acid or the complement thereof; or iv) a nucleic acid that hybridizes under stringent conditions to the referenced nucleic acid, complement thereof, or a sequences substantially identical thereto.

As used herein, “variant” with respect to a peptide or polypeptide means that it differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. Amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, “vector” means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector.

The present disclosure provides fusion proteins comprising at least two *Mycobacterium tuberculosis* (Mtb) antigens. In some embodiments, the fusion protein comprises at least three *Mycobacterium tuberculosis* (Mtb) antigens. In some embodiments, the fusion protein comprises at least four *Mycobacterium tuberculosis* (Mtb) antigens. In some embodiments, the fusion protein comprises at least five *Mycobacterium tuberculosis* (Mtb) antigens.

In some embodiments, the nucleic acid molecule encoding any particular Mtb antigen can be a mycobacterial sequence, a bacterial codon optimized sequence (such as an *E. coli* optimized sequence), or a mammalian optimized sequence (such as a human optimized sequence). The *E. coli* optimized sequences can be used, for example, to produce fusion proteins. The human optimized sequences can be used in, for example, viral vectors. Methods of codon optimization (whether for bacterial or mammalian) are well known to the skilled artisan.

In some embodiments, the Mtb antigen is Rv1009 (also known as RpfB), Rv3136 (also known as PPE51), Rv3615c (also known as EspC), Rv2628, Rv2034, Rv3136 terminus, Ag85A, Ag85B (also known as Rv1886c), Rv3407, Rv1733, Rv2626c, RpfA, RpfC, or RpfD.

A nucleotide sequence encoding Rv1009 (including the signal sequence) is shown in Table 1 as SEQ ID NO:1, and an amino acid sequence of Rv1009 (including the signal sequence) is shown in Table 1 as SEQ ID NO:2. A nucleotide sequence encoding Rv1009 (without the signal sequence) is shown in Table 1 as SEQ ID NO:3, and an amino acid sequence of Rv1009 (without the signal sequence) is shown in Table 1 as SEQ ID NO:4.

A nucleotide sequence encoding Rv3136 is shown in Table 1 as SEQ ID NO:5 (mycobacterial sequence; not codon optimized), SEQ ID NO:6 (*E. coli* optimized), and as SEQ ID NO:7 (human optimized), and an amino acid sequence of Rv3136 is shown in Table 1 as SEQ ID NO:8.

A nucleotide sequence encoding Rv3615c is shown in Table 1 as SEQ ID NO:9 (mycobacterial sequence; not codon optimized) and as SEQ ID NO:10 (human optimized), and an amino acid sequence of Rv3615c is shown in Table 1 as SEQ ID NO:11.

A nucleotide sequence encoding Rv2628 is shown in Table 1 as SEQ ID NO:12 (mycobacterial sequence; not codon optimized) and as SEQ ID NO:13 (human optimized), and an amino acid sequence of Rv2628 is shown in Table 1 as SEQ ID NO:14.

A nucleotide sequence encoding Rv2034 is shown in Table 1 as SEQ ID NO:15, and an amino acid sequence of Rv2034 is shown in Table 1 as SEQ ID NO:16.

A nucleotide sequence encoding Rv3136 N-terminus (Rv3136Nt) is shown in Table 1 as SEQ ID NO:17, and an amino acid sequence of Rv3136 N-terminus (Rv3136Nt) is shown in Table 1 as SEQ ID NO:18.

A nucleotide sequence encoding Ag85A is shown in Table 1 as SEQ ID NO:19, and an amino acid sequence of Ag85A is shown in Table 1 as SEQ ID NO:20.

A nucleotide sequence encoding Ag85B is shown in Table 1 as SEQ ID NO:21 (mycobacterial sequence; not codon optimized), SEQ ID NO:22 (*E. coli* optimized), and SEQ ID NO:23 (human optimized), and an amino acid sequence of Ag85B is shown in Table 1 as SEQ ID NO:24 (mycobacterial sequence) and SEQ ID NO:25 (*E. coli* and human optimized).

A nucleotide sequence encoding Rv3407 is shown in Table 1 as SEQ ID NO:26, and an amino acid sequence of Rv3407 is shown in Table 1 as SEQ ID NO:27.

A nucleotide sequence encoding Rv1733 is shown in Table 1 as SEQ ID NO:28, and an amino acid sequence of Rv1733 is shown in Table 1 as SEQ ID NO:29.

A nucleotide sequence encoding Rv2626c is shown in Table 1 as SEQ ID NO:30, and an amino acid sequence of Rv2626c is shown in Table 1 as SEQ ID NO:31.

A nucleotide sequence encoding RpfA is shown in Table 1 as SEQ ID NO:32, and an amino acid sequence of RpfA is shown in Table 1 as SEQ ID NO:33.

A nucleotide sequence encoding RpfC is shown in Table 1 as SEQ ID NO:34, and an amino acid sequence of RpfC is shown in Table 1 as SEQ ID NO:35.

A nucleotide sequence encoding RpfD is shown in Table 1 as SEQ ID NO:36, and an amino acid sequence of RpfD is shown in Table 1 as SEQ ID NO:37.

The amino acid and nucleotide sequences shown in Table 1 are derived from H37Rv.

TABLE 1

| Construct | nucleotide sequence<br>amino acid sequence |
|---|---|
| Rv1009 | atgttgcgcctggtagtcggtgcgctgctgctggtgttggcgttcgccggtggctat<br>gcggtcgccgcatgcaaaacggtgacgttgaccgtcgacggaaccgcgatgcgggtg<br>accacgatgaaatcgcgggtgatcgacatcgtcgaagagaacgggttctcagtcgac<br>gaccgcgacgacctgtatcccgcggccggcgtgcaggtccatgacgccgacaccatc<br>gtgctgcggcgtagccgtccgctgcagatctcgctggatggtcacgacgctaagcag<br>gtgtggacgaccgcgtcgacggtggacgaggcgctggcccaactcgcgatgaccgac<br>acggcgccggccgcggcttctcgcgccagccgcgtcccgctgtccgggatggcgcta<br>ccggtcgtcagcgccaagacggtgcagctcaacgacggcgggttggtgcgcacggtg<br>cacttgccggcccccaatgtcgcggggctgctgagtgcggccggcgtgccgctgttg<br>caaagcgaccacgtggtgcccgccgcgacggccccgatcgtcgaaggcatgcagatc<br>caggtgacccgcaatcggatcaagaaggtcaccgagcggctgccgctgccgccgaac<br>gcgcgtcgtgtcgaggacccggagatgaacatgagccgggaggtcgtcgaagacccg<br>gggggttccggggacccaggatgtgacgttcgcggtagctgaggtcaacggcgtcgag<br>accggccgtttgcccgtcgccaacgtcgtggtgaccccggcccacgaagccgtggtg<br>cgggtgggcaccaagcccggtaccgaggtgcccccggtgatcgacggaagcatctgg<br>gacgcgatcgccggctgtgaggccggtggcaactgggcgatcaacaccggcaacggg<br>tattacggtggtgtgcagtttgaccagggcacctgggaggccaacggcgggctgcgg<br>tatgcaccccgcgctgacctcgccacccgcgaagagcagatcgccgttgccgaggtg<br>acccgactgcgtcaaggttggggcgcctggccggtatgtgctgcacgagcgggtgcg<br>cgctga<br>(SEQ ID NO: 1)<br>MLRLVVGALLLVLAFAGGYAVAACKTVTLTVDGTAMRVTTMKSRVIDIVEENGFSVD<br>DRDDLYPAAGVQVHDADTIVLRRSRPLQISLDGHDAKQVWTTASTVDEALAQLAMTD<br>TAPAAASRASRVPLSGMALPVVSAKTVQLNDGGLVRTVHLPAPNVAGLLSAAGVPLL<br>QSDHVVPAATAPIVEGMQIQVTRNRIKKVTERLPLPPNARRVEDPEMNMSREVVEDP<br>GVPGTQDVTFAVAEVNGVETGRLPVANVVVTPAHEAVVRVGTKPGTEVPPVIDGSIW<br>DAIAGCEAGGNWAINTGNGYYGGVQFDQGTWEANGGLRYAPRADLATREEQIAVAEV<br>TRLRQGWGAWPVCAARAGAR<br>(SEQ ID NO: 2) |
| Rv1009<br>No signal<br>sequence | gcatgcaaaacggtgacgttgaccgtcgacggaaccgcgatgcgggtgaccacgatg<br>aaatcgcgggtgatcgacatcgtcgaagagaacgggttctcagtcgacgaccgcgac<br>gacctgtatcccgcggccggcgtgcaggtccatgacgccgacaccatcgtgctgcgg<br>cgtagccgtccgctgcagatctcgctggatggtcacgacgctaagcaggtgtggacg<br>accgcgtcgacggtggacgaggcgctggcccaactcgcgatgaccgacacggcgccg<br>gccgcggcttctcgcgccagccgcgtcccgctgtccgggatggcgctaccggtcgtc<br>agcgccaagacggtgcagctcaacgacggcgggttggtgcgcacggtgcacttgccg<br>gcccccaatgtcgcggggctgctgagtgcggccggcgtgccgctgttgcaaagcgac<br>cacgtggtgcccgccgcgacggccccgatcgtcgaaggcatgcagatccaggtgacc |

TABLE 1-continued

| Construct | nucleotide sequence<br>amino acid sequence |
|---|---|
| | cgcaatcggatcaagaaggtcaccgagcggctgccgctgccgccgaacgcgcgtcgt<br>gtcgaggacccggagatgaacatgagccgggaggtcgtcgaagacccgggggttccg<br>gggacccaggatgtgacgttcgcggtagctgaggtcaacggcgtcgagaccggccgt<br>ttgcccgtcgccaacgtcgtggtgaccccggcccacgaagccgtggtgcgggtgggc<br>accaagcccggtaccgaggtgcccccggtgatcgacggaagcatctgggacgcgatc<br>gccggctgtgaggccggtggcaactgggcgatcaacaccggcaacgggtattacggt<br>ggtgtgcagtttgaccagggcacctgggaggccaacggcgggctgcggtatgcaccc<br>cgcgctgacctcgccacccgcgaagagcagatcgccgttgccgaggtgacccgactg<br>cgtcaaggttggggcgcctggccggtatgtgctgcacgagcgggtgcgcgctga<br>(SEQ ID NO: 3)<br>ACKTVTLTVDGTAMRVTTMKSRVIDIVEENGFSVDDRDDLYPAAGVQVHDADTIVLR<br>RSRPLQISLDGHDAKQVWTTASTVDEALAQLAMTDTAPAAASRASRVPLSGMALPVV<br>SAKTVQLNDGGLVRTVHLPAPNVAGLLSAAGVPLLQSDHVVPAATAPIVEGMQIQVT<br>RNRIKKVTERLPLPPNARRVEDPEMNMSREVVEDPGVPGTQDVTFAVAEVNGVETGR<br>LPVANVVVTPAHEAVVRVGTKPGTEVPPVIDGSIWDAIAGCEAGGNWAINTGNGYYG<br>GVQFDQGTWEANGGLRYAPRADLATREEQIAVAEVTRLRQGWGAWPVCAARAGAR<br>(SEQ ID NO: 4) |
| Rv3136 | atggatttcgcactgttaccaccggaagtcaactccgcccggatgtacaccggccct<br>ggggcaggatcgctgttggctgccgcgggcggctgggattcgctggccgccgagttg<br>gccaccacagccgaggcatatggatcggtgctgtccggactggccgccttgcattgg<br>cgtggaccggcagcggaatcgatggcggtgacggccgctccctatatcggttggctg<br>tacacgaccgccgaaaagacacagcaaacagcgatccaagccagggcggcagcgctg<br>gccttcgagcaagcatacgcaatgaccctgccgccaccggtggtagcggccaaccgg<br>atacagctgctagcactgatcgcgacgaacttcttcggccagaacactgcggcgatc<br>gcggccaccgaggcacagtacgccgagatgtgggcccaggacgccgccgcgatgtac<br>ggttacgccaccgcctcagcggctgcggccctgctgacaccgttctccccgccgcgg<br>cagaccaccaacccggccggcctgaccgctcaggccgccgcggtcagccaggccacc<br>gacccactgtcgctgctgattgagacggtgacccaagcgctgcaagcgctgacgatt<br>ccgagcttcatccctgaggacttcaccttccttgacgccatattcgctggatatgcc<br>acggtaggtgtgacgcaggatgtcgagtcctttgttgccgggaccatcggggccgag<br>agcaacctaggccttttgaacgtcggcgacgagaatcccgcggaggtgacaccgggc<br>gactttgggatcggcgagttggtttccgcgaccagtcccggcggtggggtgtctgcg<br>tcgggtgccggcggtgcggcgagcgtcggcaacacggtgctcgcgagtgtcggccgg<br>gcaaactcgattgggcaactatcggtcccaccgagctgggccgcgccctcgacgcgc<br>cctgtctcggcattgtcgcccgccggcctgaccacactcccggggaccgacgtggcc<br>gagcacgggatgccaggtgtaccgggggtgccagtggcagcagggcgagcctccggc<br>gtcctacctcgatacggggttcggctcacggtgatggcccacccacccgcggcaggg<br>taa<br>(SEQ ID NO: 5)<br>atggattttgcgctgctgccgccggaagtgaacagcgcgcgcatgtataccggcccg<br>ggcgcgggcagcctgctggcggcggcgggcggctgggatagcctggcggcggaactg<br>gcgaccaccgcggaagcgtatggcagcgtgctgagcggcctggcggcgctgcattgg<br>cgcggcccggcggcggaaagcatggcggtgaccgcggcgccgtatattggctggctg<br>tataccaccgcggaaaaaacccagcagaccgcgattcaggcgcgcgcggcggcgctg<br>gcgtttgaacaggcgtatgcgatgaccctgccgccgccggtggtggcggcgaaccgc<br>attcagctgctggcgctgattgcgaccaactttttggccagaacaccgcggcgatt<br>gcggcgaccgaagcgcagtatgcggaaatgtgggcgcaggatgcggcggcgatgtat<br>ggctatgcgaccgcgagcgcggcggcggcgctgctgaccccgtttagcccgccgcgc<br>cagaccaccaacccggcgggcctgaccgcgcaggcggcggcggtgagccaggcgacc<br>gatccgctgagcctgctgattgaaaccgtgacccaggcgctgcaggcgctgaccatt<br>ccgagctttattccggaagattttacctttctggatgcgatttttgcgggctatgcg<br>accgtgggcgtgacccaggatgtggaaagctttgtggcgggcaccattggcgcggaa<br>agcaacctgggcctgctgaacgtgggcgatgaaaacccggcggaagtgaccccgggc<br>gattttggcattggcgaactggtgagcgcgaccagcccgggcggcggcgtgagcgcg<br>agcggcgcgggcggcgcggcgagcgtgggcaacaccgtgctggcgagcgtgggccgc<br>gcgaacagcattggccagctgagcgtgccgccgagctgggcggcgccgagcacccgc<br>ccggtgagcgcgctgagcccggcgggcctgaccaccctgccgggcaccgatgtggcg<br>gaacatggcatgccgggcgtgccgggcgtgccggtggcggcgggccgcgcgagcggc<br>gtgctgccgcgctatggcgtgcgcctgaccgtgatggcgcatccgccggcggcgggc<br>gaattt<br>(SEQ ID NO: 6)<br>atggatttcgctctgctcccccccgaggtgaatagcgctaggatgtacacaggaccc<br>ggagctggaagcctcctggctgctgctggaggatgggactccctggctgccgagctc<br>gctacaaccgctgaggcttacggaagcgtgctctccggcctggctgctctccattgg<br>agaggccctgctgccgagtccatggctgtcacagccgctccctacattggatggctg<br>tacaccaccgccgagaagacccagcaaaccgctattcaggccagagctgccgccctg<br>gccttcgaacaggcctacgctatgacactccccccccctgtcgtggctgccaatagg<br>atccagctcctggccctcatcgccaccaacttcttcggccaaaacaccgctgccatc<br>gctgccaccgaagcccagtacgccgaaatgtgggcccaggatgccgctgctatgtac<br>ggctatgccacagctagcgctgccgctgctctgctcacacccttcagcccccccagg<br>caaacaaccaaccctgccggactgacagcccaagctgctgccgtcagccaagctacc<br>gacccccctgagcctcctgatcgaaaccgtgacacaggccctgcaggccctgaccatt<br>cccagctttatccccgaggacttcacctttctggacgctatcttcgctggctacgcc<br>accgtgggcgtgacacaagacgtcgagtccttcgtcgccggcacaatcggagccgag<br>tccaacctcggactcctcaacgtcggcgacgaaaatcccgccgaagtgacacctgga<br>gacttcggcattggagaactcgtcagcgccacatcccctggcggaggagtgagcgct |

TABLE 1-continued

| Construct | nucleotide sequence<br>amino acid sequence |
|---|---|
| | tccggagctggaggagctgcttccgtgggcaataccgtgctggccagcgtgggaagg<br>gccaactccattggccagctcagcgtcccccttcctgggctgccccttccacaagg<br>cctgtgtccgctctcagccctgctggactgaccacactccctggcacagacgtggct<br>gagcatggcatgcccggagtgcctggagtccctgtggctgctggcagagcttccgga<br>gtcctccctaggtatggcgtgaggctgacagtgatggctcatcccccgctgccgga<br>taa<br>(SEQ ID NO: 7)<br>MDFALLPPEVNSARMYTGPGAGSLLAAAGGWDSLAAELATTAEAYGSVLSGLAALHW<br>RGPAAESMAVTAAPYIGWLYTTAEKTQQTAIQARAAALAFEQAYAMTLPPPVVAANR<br>IQLLALIATNFFGQNTAAIAATEAQYAEMWAQDAAAMYGYATASAAAALLTPFSPPR<br>QTTNPAGLTAQAAAVSQATDPLSLLIETVTQALQALTIPSFIPEDFTFLDAIFAGYA<br>TVGVTQDVESFVAGTIGAESNLGLLNVGDENPAEVTPGDFGIGELVSATSPGGGVSA<br>SGAGGAASVGNTVLASVGRANSIGQLSVPPSWAAPSTRPVSALSPAGLTTLPGTDVA<br>EHGMPGVPGVPVAAGRASGVLPRYGVRLTVMAHPPAAG<br>(SEQ ID NO: 8) |
| Rv3615c | atgacggaaaacttgaccgtccagcccgagcgtctcggtgtactggcgtcgcaccat<br>gacaacgcggcggtcgatgcctcctcgggcgtcgaagctgccgctggcctaggcgaa<br>tctgtggcgatcactcacggtccgtactgctcacagttcaacgacacgttaaatgtg<br>tacttgactgcccacaatgccctgggctcgtccttgcatacggccggtgtcgatctc<br>gccaaaagtcttcgaattgcggcgaagatatatagcgaggccgacgaagcgtggcgc<br>aaggctatcgacgggttgtttacctga<br>(SEQ ID NO: 9)<br>atgaccgagaacctgaccgtgcagcctgagaggctgggagtgctggccagccaccac<br>gacaacgctgccgtggacgcttccagcggagtggaggctgctgctggactgggagag<br>agcgtggccatcacccacggaccctactgcagccagttcaacgacaccctgaacgtg<br>tacctgacagcccacaacgccctgggaagcagcctgcatacagccggcgtggacctg<br>gctaagtccctgaggatcgccgccaagatctacagcgaggccgacgaggcctggagg<br>aaagccatcgacggcctgttcacctaa<br>(SEQ ID NO: 10)<br>MTENLTVQPERLGVLASHHDNAAVDASSGVEAAAGLGESVAITHGPYCSQFNDTLNV<br>YLTAHNALGSSLHTAGVDLAKSLRIAAKIYSEADEAWRKAIDGLFT<br>(SEQ ID NO: 11) |
| Rv2628 | atgtccacgcaacgaccgaggcactccggtattcgggctgttggcccctacgcatgg<br>gccggccgatgtggtcggataggcaggtgggggtgcaccaggaggcgatgatgaat<br>ctagcgatatggcacccgcgcaaggtgcaatccgccaccatctatcaggtgaccgat<br>cgctcgcacgacgggcgcacagcacgggtgcctggtgacgagatcactagcaccgtg<br>tccggttggttgtcggagttgggcacccaaagcccgttggccgatgagcttgcgcgt<br>gcggtgcggatcggcgactggcccgctgcgtacgcaatcggtgagcacctgtccgtt<br>gagattgccgttgcggtctaa<br>(SEQ ID NO: 12)<br>atgagcacccagagacccaggcacagcggcattagggccgtgggaccttatgcttgg<br>gccggcagatgcggaaggatcggcagatggggcgtgcaccaagaggccatgatgaac<br>ctggccatctggcaccccaggaaggtgcagagcgccaccatctaccaggtgaccgac<br>aggagccatgacggaaggaccgccagagtgcccggcgatgagatcaccagcaccgtg<br>agcggctggctgagcgaactgggcacccaatccccccctggctgatgaactggccagg<br>gctgtgaggatcggcgattggcctgccgcctatgccatcggcgagcatctgagcgtg<br>gagatcgccgtggccgtgtaa<br>(SEQ ID NO: 13)<br>MSTQRPRHSGIRAVGPYAWAGRCGRIGRWGVHQEAMMNLAIWHPRKVQSATIYQVTD<br>RSHDGRTARVPGDEITSTVSGWLSELGTQSPLADELARAVRIGDWPAAYAIGEHLSV<br>EIAVAV<br>(SEQ ID NO: 14) |
| Rv2034 | gtgtccacttacagatcaccggatcgcgcttggcaggcgctggcggacggcactcgc<br>cgggccatcgtggagcggctggcgcacggcccgctggccgtcggcgagttggcccgc<br>gacctgcccgtcagccgacccgcggtgtcacagcacctcaaagtgctcaagaccgcc<br>aggctggtgtgcgaccgccccgcgggaacacgccgcgtctaccagctcgacccgaca<br>ggccttgcggcattgcgcaccgacctcgaccggttctggacacgcgccctgactggc<br>tacgcgcagctcatcgactccgaaggagacgacacatga<br>(SEQ ID NO: 15)<br>VSTYRSPDRAWQALADGTRRAIVERLAHGPLAVGELARDLPVSRPAVSQHLKVLKTA<br>RLVCDRPAGTRRVYQLDPTGLAALRTDLDRFWTRALTGYAQLIDSEGDDT<br>(SEQ ID NO: 16) |
| Rv3136<br>N-terminus<br>(Rv3136Nt) | atggatttcgcactgttaccaccggaagtcaactccgcccggatgtacaccggccct<br>ggggcaggatcgctgttggctgccgcgggcggctgggattcgctggccgccgagttg<br>gccaccacagccgaggcatatggatcggtgctgtccggactggccgccttgcattgg<br>cgtggaccggcagcggaatcgatggcggtgacggccgctccctatatcggttggctg<br>tacacgaccgccgaaaagacacagcaaacagcgatccaagccagggcggcagcgctg<br>gccttcgagcaagcatacgcaatgaccctgccgccaccggtggtagcggccaaccgg<br>atacagctgctagcactgatcgcgacgaacttcttcggccagaacactgcggcgatc<br>gcggccaccgaggcacagtacgccgagatgtgggcccaggacgccgccgcgatgtac<br>ggttacgccaccgcctcagcggctgcggccctgctgacaccgttctccccgccgcgg<br>cagaccaccaacccggccggcctgacc<br>(SEQ ID NO: 17) |

TABLE 1-continued

| Construct | nucleotide sequence<br>amino acid sequence |
|---|---|
| | MDFALLPPEVNSARMYTGPGAGSLLAAAGGWDSLAAELATTAEAYGSVLSGLAALHW<br>RGPAAESMAVTAAPYIGWLYTTAEKTQQTAIQARAAALAFEQAYAMTLPPPVVAANR<br>IQLLALIATNFFGQNTAAIAATEAQYAEMWAQDAAAMYGYATASAAAALLTPFSPPR<br>QTTNPAGLT<br>(SEQ ID NO: 18) |
| Ag85A | atgcagcttgttgacagggttcgtggcgccgtcacgggtatgtcgcgtcgactcgtg<br>gtcggggccgtcggcgcggccctagtgtcgggtctggtcggcgccgtcggtggcacg<br>gcgaccgcgggggcattttcccggccgggcttgccggtggagtacctgcaggtgccg<br>tcgccgtcgatgggccgtgacatcaaggtccaattccaaagtggtggtgccaactcg<br>cccgccctgtacctgctcgacggcctgcgcgcgcaggacgacttcagcggctgggac<br>atcaacaccccggcgttcgagtggtacgaccagtcgggcctgtcggtggtcatgccg<br>gtgggtggccagtcaagcttctactccgactggtaccagcccgcctgcggcaaggcc<br>ggttgccagacttacaagtgggagaccttcctgaccagcgagctgccggggtggctg<br>caggccaacaggcacgtcaagcccaccggaagcgccgtcgtcggtctttcgatggct<br>gcttcttcggcgtgacgctggcgatctatcacccccagcagttcgtctacgcgggag<br>cgatgtcgggcctgttggacccctcccaggcgatgggtcccaccctgatcggcctgg<br>cgatgggtgacgctggcggctacaaggcctccgacatgtggggcccgaaggaggacc<br>cggcgtggcagcgcaacgacccgctgttgaacgtcgggaagctgatcgccaacaaca<br>cccgcgtctgggtgtactgcggcaacggcaagccgtcggatctgggtggcaacaacc<br>tgccggccaagttcctcgagggcttcgtgcggaccagcaacatcaagttccaagacg<br>cctacaacgccggtggcggccacaacggcgtgttcgacttcccggacagcggtacgc<br>acagctgggagtactggggcgcgcagctcaacgctatgaagcccgacctgcaacggg<br>cactgggtgccacgcccaacaccgggcccgcgccccagggcgcctag<br>(SEQ ID NO: 19)<br>MQLVDRVRGAVTGMSRRLVVGAVGAALVSGLVGAVGGTATAGAFSRPGLPVEYLQVP<br>SPSMGRDIKVQFQSGGANSPALYLLDGLRAQDDFSGWDINTPAFEWYDQSGLSVVMP<br>VGGQSSFYSDWYQPACGKAGCQTYKWETFLTSELPGWLQANRHVKPTGSAVVGLSMA<br>ASSALTLAIYHPQQFVYAGAMSGLLDPSQAMGPTLIGLAMGDAGGYKASDMWGPKED<br>PAWQRNDPLLNVGKLIANNTRVWVYCGNGKPSDLGGNNLPAKFLEGFVRTSNIKFQD<br>AYNAGGGHNGVFDFPDSGTHSWEYWGAQLNAMKPDLQRALGATPNTGPAPQGA<br>(SEQ ID NO: 20) |
| Ag85B | atgacagacgtgagccgaaagattcgagcttggggacgccgattgatgatcggcacg<br>gcagcggctgtagtccttccgggcctggtggggcttgccgcggagcggcaaccgcgg<br>gcgcgttctcccggccggggctgccggtcgagtacctgcaggtgccgtcgccgtcga<br>tgggccgcgacatcaaggttcagttccagagcggtgggaacaactcacctgcggttt<br>atctgctcgacggcctgcgcgcccaagacgactacaacggctgggatatcaacaccc<br>cggcgttcgagtggtactaccagtcgggactgtcgatagtcatgccggtcggcgggc<br>agtccagcttctacagcgactggtacagcccggcctgcggtaaggctggctgccaga<br>cttacaagtgggaaaccttcctgaccagcgagctgccgcaatggttgtccgccaaca<br>gggccgtgaagcccaccggcagcgctgcaatcggcttgtcgatggccggctcgtcgg<br>caatgatcttggccgcctaccacccccagcagttcatctacgccggctcgctgtcgg<br>ccctgctggacccctctcaggggatggggcctagcctgatcggcctcgcgatgggtg<br>acgccggcggttacaaggccgcagacatgtggggtccctcgagtgacccggcatggg<br>agcgcaacgaccctacgcagcagatccccaagctggtcgcaaacaacacccggctat<br>gggtttattgcgggaacggcaccccgaacgagttgggcggtgccaacatacccgccg<br>agttcttggagaacttcgttcgtagcagcaacctgaagttccaggatgcgtacaacg<br>ccgcgggcgggcacaacgccgtgttcaacttcccgcccaacggcacgcacagctggg<br>agtactggggcgctcagctcaacgccatgaagggtgacctgcagagttcgttaggcg<br>ccggctga<br>(SEQ ID NO: 21)<br>atgtttagccgtcctggcctgccagttgaatacctgcaagttccgagcccgtccatg<br>ggtcgtgacattaaggtgcagttccagagcggcggtaacaatagcccggctgtgtac<br>ctgctggacggtctgcgtgcgcaggatgattacaacggctgggacatcaataccccg<br>gcatttgcatttgagtggtattaccagtcgggtctgagcattgtgatgccggttggc<br>ggtcaaagcagcttctatagcgattggtacagcccggcatgcggcaaggctggttgc<br>caaacctacaagtgggaaactttcttgaccagcgagctgccgcaatggttgagcgcc<br>aaccgtgcggtcaaaccgaccggtagcgctgctattggcctgtccatggccggcagc<br>agcgcgatgatcttggcggcataccatccgcagcagtttatctacgccggtagcctg<br>agcgcattgctggacccgagccaaggcatgggtccgagcctgattggtctggcaatg<br>ggtgacgcaggtggttacaaagcggccgatatgtggggcccatctagcgacccggca<br>tgggagcgtaatgacccgacccagcaaattccgaaactggtggcgaataacacgcgc<br>ctgtgggtctactgtggcaatggtacgccgaacgagctgggtggcgcgaatatccct<br>gcggagtttctggaaaactttgttcgcagcagcaacctgaaattccaggacgcgtat<br>aacgcagccggtggtcacaatgcggttttcaatttcccgccaaatggcactcatagc<br>tgggagtactggggtgcgcagttgaacgcaatgaaaggcgatctgcaatcctctctg<br>ggtgcgggc<br>(SEQ ID NO: 22)<br>atgttctccaggcccggcctgcctgtcgagtatctgcaggtcccctcccccctccatg<br>ggcagagacatcaaggtgcagttccaatccggaggcaacaacagccccgccgtgtat<br>ctcctcgacggcctgagggctcaggacgactacaacggctgggacatcaacaccccc<br>gccttcgagtggtactaccagtccggactgagcatcgtcatgcccgtgggcggccag<br>agctccttctacagcgactggtatagccctgcctgcggcaaagccggatgccagacc<br>tacaagtgggagacctttctgaccagcgaactgccccagtggctgtccgccaatagg<br>gccgtcaaacctaccggctccgctgccatcggactcagcatggccggaagctccgct<br>atgatcctggccgcctaccacccccagcaatttatctacgctggcagcctgtccgct |

TABLE 1-continued

| Construct | nucleotide sequence<br>amino acid sequence |
|---|---|
| | ctgctggatcctagccaaggcatgggccctagcctcattggcctggccatgggcgat<br>gctggcggctataaggccgccgatatgtggggccctagctccgatcctgcctgggag<br>aggaatgaccccacccagcagatccccaagctggtggccaacaacacaaggctctgg<br>gtgtactgcggcaatggcacccccaacgaactgggcggagccaacattcccgccgag<br>ttcctggagaacttcgtcaggagcagcaacctgaagttccaggacgcctacaatgcc<br>gccggaggccacaacgctgtgttcaacttccctcccaacggcacccacagctgggag<br>tattggggcgctcagctgaacgccatgaaaggcgacctccagagctccctgggagct<br>gga<br>(SEQ ID NO: 23)<br>MTDVSRKIRAWGRRLMIGTAAAVVLPGLVGLAGGAATAGAFSRPGLPVEYLQVPSPS<br>MGRDIKVQFQSGGNNSPAVYLLDGLRAQDDYNGWDINTPAFEWYYQSGLSIVMPVGG<br>QSSFYSDWYSPACGKAGCQTYKWETFLTSELPQWLSANRAVKPTGSAAIGLSMAGSS<br>AMILAAYHPQQFIYAGSLSALLDPSQGMGPSLIGLAMGDAGGYKAADMWGPSSDPAW<br>ERNDPTQQIPKLVANNTRLWVYCGNGTPNELGGANIPAEFLENFVRSSNLKFQDAYN<br>AAGGHNAVFNFPPNGTHSWEYWGAQLNAMKGDLQSSLGAG<br>(SEQ ID NO: 24)<br>MFSRPGLPVEYLQVPSPSMGRDIKVQFQSGGNNSPAVYLLDGLRAQDDYNGWDINTP<br>AFEWYYQSGLSIVMPVGGQSSFYSDWYSPACGKAGCQTYKWETFLTSELPQWLSANR<br>AVKPTGSAAIGLSMAGSSAMILAAYHPQQFIYAGSLSALLDPSQGMGPSLIGLAMGD<br>AGGYKAADMWGPSSDPAWERNDPTQQIPKLVANNTRLWVYCGNGTPNELGGANIPAE<br>FLENFVRSSNLKFQDAYNAAGGHNAVFNFPPNGTHSWEYWGAQLNAMKGDLQSSLGA<br>G<br>(SEQ ID NO: 25) |
| Rv3407 | atgcgtgctaccgttgggcttgtggaggcaatcggaatccgagaactaagacagcac<br>gcatcgcgatacctcgcccgggttgaagccggcgaggaacttggcgtcaccaacaaa<br>ggaagacttgtggcccgactcatcccggtgcaggccgcggagcgttctcgcgaagcc<br>ctgattgaatcaggtgtcctgattccggctcgtcgtccacaaaaccttctcgacgtc<br>accgccgaaccggcgcgcggccgcaagcgcaccctgtccgatgttctcaacgaaatg<br>cgcgacgagcagtga<br>(SEQ ID NO: 26)<br>MRATVGLVEAIGIRELRQHASRYLARVEAGEELGVTNKGRLVARLIPVQAAERSREA<br>LIESGVLIPARRPQNLLDVTAEPARGRKRTLSDVLNEMRDEQ<br>(SEQ ID NO: 27) |
| Rv1733 | atgatcgccacaacccgcgatcgtgaaggagccaccatgatcacgtttaggctgcgc<br>ttgccgtgccggacgatactgcgggtgttcagccgcaatccgctggtgcgtgggacg<br>gatcgactcgaggcggtcgtcatgctgctggccgtcacggtctcgctgctgactatc<br>ccgttcgccgccgcggccggcaccgcagtccaggattcccgcagccacgtctatgcc<br>caccaggcccagacccgccatcccgcaaccgcgaccgtgatcgatcacgagggggtg<br>atcgacagcaacacgaccgccacgtcagcgccgccgcgcacgaagatcaccgtgcct<br>gcccgatgggtcgtgaacggaatagaacgcagcggtgaggtcaacgcgaagccggga<br>accaaatccggtgaccgcgtcggcatttgggtcgacagtgccggtcagctggtcgat<br>gaaccagctccgccggcccgtgccattgcggatgcggccctggccgccttgggactc<br>tggttgagcgtcgccgcggttgcgggcgccctgctggcgctcactcgggcgattctg<br>atccgcgttcgcaacgccagttggcaacacgacatcgacagcctgttctgcacgcag<br>cggtga<br>(SEQ ID NO: 28)<br>MIATTRDREGATMITFRLRLPCRTILRVFSRNPLVRGTDRLEAVVMLLAVTVSLLTI<br>PFAAAAGTAVQDSRSHVYAHQAQTRHPATATVIDHEGVIDSNTTATSAPPRTKITVP<br>ARWVVNGIERSGEVNAKPGTKSGDRVGIWVDSAGQLVDEPAPPARAIADAALAALGL<br>WLSVAAVAGALLALTRAILIRVRNASWQHDIDSLFCTQR<br>(SEQ ID NO: 29) |
| Rv2626c | atgaccaccgcacgcgacatcatgaacgcaggtgtgacctgtgttggcgaacacgag<br>acgctaaccgctgccgctcaatacatgcgtgagcacgacatcggcgcgttgccgatc<br>tgcggggacgacgaccggctgcacggcatgctcaccgaccgcgacattgtgatcaaa<br>ggcctggctgcgggcctagacccgaataccgccacggctggcgagttggcccgggac<br>agcatctactacgtcgatgcgaacgcaagcatccaggagatgctcaacgtcatggaa<br>gaacatcaggtccgccgtgttccggtcatctcagagcaccgcttggtcggaatcgtc<br>accgaagccgacatcgcccgacacctgcccgagcacgccattgtgcagttcgtcaag<br>gcaatctgctcgcccatggccctcgccagctag<br>(SEQ ID NO: 30)<br>MTTARDIMNAGVTCVGEHETLTAAAQYMREHDIGALPICGDDDRLHGMLTDRDIVIK<br>GLAAGLDPNTATAGELARDSIYYVDANASIQEMLNVMEEHQVRRVPVISEHRLVGIV<br>TEADIARHLPEHAIVQFVKAICSPMALAS<br>(SEQ ID NO: 31) |
| RpfA | atgagtggacgccaccgtaagcccaccacatccaacgtcagcgtcgccaagatcgcc<br>tttaccggcgcagtactcggtggcggcggcatcgccatggccgctcaggcgaccgcg<br>gccaccgacggggaatgggatcaggtggcccgctgcgagtcgggcggcaactggtcg<br>atcaacaccggcaacggttacctcggtggcttgcagttcactcaaagcacctgggcc<br>gcacatggtggcggcgagttcgccccgtcggctcagctggccagccgggagcagcag<br>attgccgtcggtgagcgggtgctggccacccagggtcgcggcgcctggccggtgtgc<br>ggccgcgggttatcgaacgcaacaccccgcgaagtgcttcccgcttcggcagcgatg<br>gacgctccgttggacgcggccgcggtcaacggcgaaccagcaccgctggccccgccg<br>cccgccgacccggcgccacccgtggaacttgccgctaacgacctgcccgcaccgctg |

TABLE 1-continued

| Construct | nucleotide sequence<br>amino acid sequence |
|---|---|
| | ggtgaacccctcccggcagctcccgccgacccggcaccacccgccgacctggcacca<br>cccgcgcccgccgacgtcgcgccacccgtggaacttgccgtaaacgacctgcccgca<br>ccgctgggtgaacccctcccggcagctcccgccgacccggcaccacccgccgacctg<br>gcaccacccgcgcccgccgacctggcgccacccgcgcccgccgacctggcgccaccc<br>gcgcccgccgacctggcaccacccgtggaacttgccgtaaacgacctgcccgcgccg<br>ctgggtgaacccctcccggcagctcccgccgaactggcgccacccgccgatctggca<br>cccgcgtccgccgacctggcgccacccgcgcccgccgacctggcgccacccgcgccc<br>gccgaactggcgccacccgcgcccgccgacctggcaccacccgctgcggtgaacgag<br>caaaccgcgccgggcgatcagcccgccacagctccaggcggcccggttggccttgcc<br>accgatttggaactccccgagcccgacccccaaccagctgacgcaccgccgcccggc<br>gacgtcaccgaggcgcccgccgaaacgccccaagtctcgaacatcgcctatacgaag<br>aagctgtggcaggcgattcgggcccaggacgtctgcggcaacgatgcgctggactcg<br>ctcgcacagccgtacgtcatcggctga<br>(SEQ ID NO: 32)<br>MSGRHRKPTTSNVSVAKIAFTGAVLGGGGIAMAAQATAATDGEWDQVARCESGGNWS<br>INTGNGYLGGLQFTQSTWAAHGGGEFAPSAQLASREQQIAVGERVLATQGRGAWPVC<br>GRGLSNATPREVLPASAAMDAPLDAAAVNGEPAPLAPPPADPAPPVELAANDLPAPL<br>GEPLPAAPADPAPPADLAPPAPADVAPPVELAVNDLPAPLGEPLPAAPADPAPPADL<br>APPAPADLAPPAPADLAPPAPADLAPPVELAVNDLPAPLGEPLPAAPAELAPPADLA<br>PASADLAPPAPADLAPPAPAELAPPAPADLAPPAAVNEQTAPGDQPATAPGGPVGLA<br>TDLELPEPDPQPADAPPPGDVTEAPAETPQVSNIAYTKKLWQAIRAQDVCGNDALDS<br>LAQPYVIG<br>(SEQ ID NO: 33) |
| RpfC | gtgcatcctttgccggccgaccacggccggtcgcggtgcaatagacacccgatctca<br>ccactctctctaatcggtaacgcttcggccacttccggcgatatgtcgagcatgaca<br>agaatcgccaagccgctcatcaagtccgccatggccgcaggactcgtcacggcatcc<br>atgtcgctctccaccgccgttgcccacgccggtcccagcccgaactgggacgccgtc<br>gcgcagtgcgaatccgggggcaactgggcggccaacaccggaaacggcaaatacggc<br>ggactgcagttcaagccggccacctgggccgcattcggcggtgtcggcaacccagca<br>gctgcctctcgggaacaacaaatcgcagttgccaatcgggttctcgccgaacaggga<br>ttggacgcgtggccgacgtgcggcgccgcctctggccttccgatcgcactgtggtcg<br>aaacccgcgcagggcatcaagcaaatcatcaacgagatcatttgggcaggcattcag<br>gcaagtattccgcgctga<br>(SEQ ID NO: 34)<br>VHPLPADHGRSRCNRHPISPLSLIGNASATSGDMSSMTRIAKPLIKSAMAAGLVTAS<br>MSLSTAVAHAGPSPNWDAVAQCESGGNWAANTGNGKYGGLQFKPATWAAFGGVGNPA<br>AASREQQIAVANRVLAEQGLDAWPTCGAASGLPIALWSKPAQGIKQIINEIIWAGIQ<br>ASIPR<br>(SEQ ID NO: 35) |
| RpfD | atgacaccgggtttgcttactactgcgggtgctggccgaccacgtgacaggtgcgcc<br>aggatcgtatgcacggtgttcatcgaaaccgccgttgtcgcgaccatgtttgtcgcg<br>ttgttgggtctgtccaccatcagctcgaaagccgacgacatcgattgggacgccatc<br>gcgcaatgcgaatccggcggcaattgggcggccaacaccggtaacgggttatacggt<br>ggtctgcagatcagccaggcgacgtgggattccaacggtggtgtcgggtcgccggcg<br>gccgcgagtccccagcaacagatcgaggtcgcagacaacattatgaaaacccaaggc<br>ccgggtgcgtggccgaaatgtagttcttgtagtcagggagacgcaccgctgggctcg<br>ctcacccacatcctgacgttcctcgcggccgagactggaggttgttcggggagcagg<br>gacgattga<br>(SEQ ID NO: 36)<br>MTPGLLTTAGAGRPRDRCARIVCTVFIETAVVATMFVALLGLSTISSKADDIDWDAI<br>AQCESGGNWAANTGNGLYGGLQISQATWDSNGGVGSPAAASPQQQIEVADNIMKTQG<br>PGAWPKCSSCSQGDAPLGSLTHILTFLAAETGGCSGSRDD<br>(SEQ ID NO: 37) |

In some embodiments, the fusion protein comprises at least two *Mycobacterium tuberculosis* (Mtb) antigens. In some embodiments, the fusion protein comprises at least three *Mycobacterium tuberculosis* (Mtb) antigens. In some embodiments, the fusion protein comprises at least four *Mycobacterium tuberculosis* (Mtb) antigens. In some embodiments, the fusion protein comprises at least five Mtb antigens. In some embodiments, the fusion protein comprises at least six Mtb antigens. In some embodiments, the fusion protein comprises from at least two to at least six Mtb antigens. In some embodiments, the fusion protein comprises from at least three to at least six Mtb antigens. In some embodiments, the fusion protein comprises from at least three to at least five Mtb antigens. In some embodiments, the fusion protein comprises at least three or at least four Mtb antigens. In some embodiments, the fusion protein comprises from at least four to at least six Mtb antigens. In some embodiments, the fusion protein comprises at least four or at least five Mtb antigens.

In some embodiments, the fusion protein comprises Rv1009, Rv3615c, and Rv3136 Mtb antigens. In some embodiments, the fusion protein comprises Rv1009, Rv2034, and Rv3136 Mtb antigens. In some embodiments, the fusion protein comprises Rv1009, Rv2628, Rv3615c, and Rv3136 Mtb antigens. In some embodiments, the fusion protein comprises Rv1009, Rv3615c, Rv2034, and Rv2628 Mtb antigens. In some embodiments, the fusion protein comprises Rv2034, Rv3615c, Rv2628, and Rv3136 Mtb antigens. In some embodiments, the fusion protein comprises Rv1009, Rv2034, Rv2628, Rv3615c, and Rv3136 Mtb antigens. In some embodiments, the fusion protein comprises Rv1009, Rv3136Nt, Rv2628, Rv2034, and Rv3615c Mtb antigens. In some embodiments, the fusion protein comprises Ag85A, Ag85B, and Rv3407 Mtb antigens. In some embodiments, the fusion protein comprises Rv1733 and Rv2626c Mtb antigens. In some embodiments, the fusion protein comprises RfpA, RpfC, and Rpm Mtb antigens.

In any of the embodiments of fusion proteins set forth herein, the individual Mtb antigens can be present in any order. For example, for a fusion protein comprising Rv3615c, Rv2034, Rv2628, and Rv1009 Mtb antigens, the first (or N-terminal) antigen may be Rv3615c, Rv2034, Rv2628, or Rv1009; the second antigen may be Rv3615c, Rv2034, Rv2628, or Rv1009 (whichever one is not the first Mtb antigen); the third antigen may be Rv3615c, Rv2034, Rv2628, or Rv1009 (whichever one is not the first or second Mtb antigen); and the fourth (or C-terminal) antigen may be Rv3615c, Rv2034, Rv2628, or Rv1009 (whichever one is not the first, second, or third Mtb antigen). Likewise for every fusion protein disclosed herein.

Individual Mtb antigens may be linked together in a C-terminus to N-terminus or N-terminus to C-terminus manner without any linker. Alternately, a linker may be present between any two Mtb antigens within any of the fusion proteins disclosed herein. In some embodiments, the linker is a segment of DNA or RNA optionally containing one or more restrictions sites, wherein the linker is inserted between nucleic acid molecules encoding two Mtb antigens of any of the fusion proteins disclosed herein.

In some embodiments, the fusion protein comprises Rv1009-Rv3615c-Rv3136 (Construct A; see Table 2). The nucleotide sequence is SEQ ID NO:38 (inserted EcoRI and HindIII restriction sites are bolded), and the corresponding amino acid sequence is SEQ ID NO:39.

In some embodiments, the fusion protein comprises Rv1009-Rv2034-Rv3136 (Construct B; see Table 2). The nucleotide sequence is SEQ ID NO:40 (inserted SacI and HindIII restriction sites are bolded), and the corresponding amino acid sequence is SEQ ID NO:41.

In some embodiments, the fusion protein comprises Rv1009-Rv2628-Rv3615c-Rv3136 (Construct C; see Table 2). The nucleotide sequence is SEQ ID NO:42 (inserted EcoRI, SacI, and HindIII restriction sites are bolded), and the corresponding amino acid sequence is SEQ ID NO:43.

In some embodiments, the fusion protein comprises Rv1009-Rv2034-Rv2628-Rv3615c-Rv3136 (Construct D; see Table 2). The nucleotide sequence is SEQ ID NO:44 (inserted BamHI, EcoRI, SacI, and HindIII restriction sites are bolded), and the corresponding amino acid sequence is SEQ ID NO:45.

In some embodiments, the fusion protein comprises Rv2034-Rv1009-Rv3136 (Construct E; see Table 2). The nucleotide sequence is SEQ ID NO:46 (inserted EcoRI and HindIII restriction sites are bolded), and the corresponding amino acid sequence is SEQ ID NO:47.

In some embodiments, the fusion protein comprises Rv3136-Rv2034-Rv1009 (Construct F; see Table 2). The nucleotide sequence is SEQ ID NO:48 (inserted SacI and HindIII restriction sites are bolded), and the corresponding amino acid sequence is SEQ ID NO:49.

In some embodiments, the fusion protein comprises Rv1009-Rv3615c-Rv2034-Rv2628 (Construct G; see Table 2). The nucleotide sequence is SEQ ID NO:50 (inserted EcoRI, SacI and HindIII restriction sites are bolded), and the corresponding amino acid sequence is SEQ ID NO:51.

In some embodiments, the fusion protein comprises Rv3615c-Rv2034-Rv2628-Rv1009 (Construct H; see Table 2). The nucleotide sequence is SEQ ID NO:52 (inserted BamHI, EcoRI, and HindIII restriction sites are bolded), and the corresponding amino acid sequence is SEQ ID NO:53.

In some embodiments, the fusion protein comprises Rv2034-Rv3615c-Rv2628-Rv3136 (Construct I; see Table 2). The nucleotide sequence is SEQ ID NO:54 (inserted EcoRI, SacI, and HindIII restriction sites are bolded), and the corresponding amino acid sequence is SEQ ID NO:55.

In some embodiments, the fusion protein comprises Rv3136-Rv2628-Rv3615c-Rv2034 (Construct J; see Table 2). The nucleotide sequence is SEQ ID NO:56 (inserted EcoRI, SacI, and HindIII restriction sites are bolded), and the corresponding amino acid sequence is SEQ ID NO:57.

In some embodiments, the fusion protein comprises Rv1009-Rv3136Nt-Rv2628-Rv2034-Rv3615c (Construct K; see Table 2). The nucleotide sequence is SEQ ID NO:58 (inserted BamHI, EcoRI, SacI, and HindIII restriction sites are bolded), and the corresponding amino acid sequence is SEQ ID NO:59.

In some embodiments, the fusion protein comprises Rv2034-Rv3615c-Rv3136Nt-Rv2628-Rv1009 (Construct L; see Table 2). The nucleotide sequence is SEQ ID NO:60 (inserted BamHI, EcoRI, SacI, and HindIII restriction sites are bolded), and the corresponding amino acid sequence is SEQ ID NO:61.

In some embodiments, the fusion protein comprises Rv3615c-Rv2628-Rv1009-Rv3136Nt-Rv2034 (Construct M; see Table 2). The nucleotide sequence is SEQ ID NO:62 (inserted BamHI, EcoRI, SacI, and HindIII restriction sites are bolded), and the corresponding amino acid sequence is SEQ ID NO:63.

In some embodiments, the fusion protein comprises Ag85A-Ag85B-Rv3407 (Construct N; see Table 2). The nucleotide sequence is SEQ ID NO:64, and the corresponding amino acid sequence is SEQ ID NO:65.

In some embodiments, the fusion protein comprises Rv1733-Rv2626c (Construct 0; see Table 2). The nucleotide sequence is SEQ ID NO:66, and the corresponding amino acid sequence is SEQ ID NO:67.

In some embodiments, the fusion protein comprises RpfA-RpfC-RpfD (Construct P; see Table 2). The nucleotide sequence is SEQ ID NO:68, and the corresponding amino acid sequence is SEQ ID NO:69.

In some embodiments, the fusion protein comprises Rv1009-Rv2628-Rv3136Nt-Rv2034-Rv3615c (Construct Q; see Table 2). The nucleotide sequence is SEQ ID NO:70 (inserted BamHI, EcoRI, SacI, and HindIII restriction sites are bolded), and the corresponding amino acid sequence is SEQ ID NO:71.

In some embodiments, the fusion protein comprises Rv2628-Rv3136Nt-Rv1009-Rv2034-Rv3615c (Construct R; see Table 2). The nucleotide sequence is SEQ ID NO:72 (inserted BamHI, EcoRI, SacI, and HindIII restriction sites are bolded), and the corresponding amino acid sequence is SEQ ID NO:73.

In some embodiments, the fusion protein comprises Rv2628-Rv3136Nt-Rv2034-Rv3615c-Rv1009 (Construct S; see Table 2). The nucleotide sequence is SEQ ID NO:74 (inserted BamHI, EcoRI, SacI, and HindIII restriction sites are bolded), and the corresponding amino acid sequence is SEQ ID NO:75.

TABLE 2

| Construct | nucleotide sequence<br>amino acid sequence |
|---|---|
| A | atggcatgcaaaacggtgacgttgaccgtcgacggaaccgcgatgcgggtgaccacgatgaaatcgcgggt<br>gatcgacatcgtcgaagagaacgggttctcagtcgacgaccgcgacgacctgtatcccgcggccggcgtgc<br>aggtccatgacgccgacaccatcgtgctgcggcgtagccgtccgctgcagatctcgctggatggtcacgac<br>gctaagcaggtgtggacgaccgcgtcgacggtggacgaggcgctggcccaactcgcgatgaccgacacggc<br>gccggccgcggcttctcgcgccagccgcgtcccgctgtccgggatggcgctaccggtcgtcagcgccaaga<br>cggtgcagctcaacgacggcgggttggtgcgcacggtgcacttgccggcccccaatgtcgcggggctgatg<br>agtgcggccggcgtgccgctgttgcaaagcgaccacgtggtgcccgccgcgacggccccgatcgtcgaagg<br>catgcagatccaggtgacccgcaatcggatcaagaaggtcaccgagcggctgccgctgccgccgaacgcgc<br>gtcgtgtcgaggacccggagatgaacatgagccgggaggtcgtcgaagacccgggggttccggggacccag<br>gatgtgacgttcgcggtagctgaggtcaacggcgtcgagaccggccgtttgcccgtcgccaacgtcgtggt<br>gaccccggcccacgaagccgtggtgcgggtgggcaccaagcccggtaccgaggtgcccccggtgatcgacg<br>gaagcatctgggacgcgatcgccggctgtgaggccggtggcaactgggcgatcaacaccggcaacgggtat<br>tacggtggtgtgcagtttgaccagggcacctgggaggccaacggcgggctgcggtatgcaccccgcgctga<br>cctcgccacccgcgaagagcagatcgccgttgccgaggtgacccgactcgtcaaggttggggcgcctggcc<br>ggtatgtgctgcacgagcgggtgcgcgc**gaattc**atgacggaaaacttgaccgtccagcccgagcgtctcg<br>gtgtactggcgtcgcaccatgacaacgcggcggtcgatgcctcctcgggcgtcgaagctgccgctggccta<br>ggcgaatctgtggcgatcactcacggtccgtactgctcacagttcaacgacacgttaaatgtgtacttgac<br>tgcccacaatgccctgggctcgtccttgcatacggccggtgtcgatctcgccaaaagtcttcgaattgcgg<br>cgaagatatatagcgaggccgacgaagcgtggcgcaaggctatcgacgggttgtttacc**aagctt**atggat<br>ttcgcactgttaccaccggaagtcaactccgcccggatgtacaccggccctggggcaggatcgctgttggc<br>tgccgcgggcggctgggattcgctggccgccgagttggccaccacagccgaggcatatggatcggtgctgt<br>ccggactggccgccttgcattggcgtggaccggcagcggaatcgatggcggtgacggccgctccctatatc<br>ggttggctgtacacgaccgccgaaaagacacagcaaacagcgatccaagccagggcggcagcgctggcctt<br>cgagcaagcatacgcaatgaccctgccgccaccggtggtagcggccaaccggatacagctgctagcactga<br>tcgcgacgaacttcttcggccagaacactgcggcgatcgcggccaccgaggcacagtacgccgagatgtgg<br>gcccaggacgccgccgcgatgtacggttacgccaccgcctcagcggctgcggccctgctgacaccgttctc<br>cccgccgcggcagaccaccaacccggccggcctgaccgctcaggccgccgcggtcagccaggccaccgacc<br>cactgtcgctgctgattgagacggtgacccaagcgctgcaagcgctgacgattccgagcttcatccctgag<br>gacttcaccttccttgacgccatattcgctggatatgccacggtaggtgtgacgcaggatgtcgagtcctt<br>tgttgccgggaccatcggggccgagagcaacctaggccttttgaacgtcggcgacgagaatcccgcggagg<br>tgacaccgggcgactttgggatcggcgagttggtttccgcgaccagtcccggcggtggggtgtctgcgtcg<br>ggtgccggcggtgcggcgagcgtcggcaacacggtgctcgcgagtgtcggccgggcaaactcgattgggca<br>actatcggtcccaccgagctgggccgcgccctcgacgcgccctgtctcggcattgtcgcccgccggcctga<br>ccacactcccggggaccgacgtggccgagcacgggatgccaggtgtaccgggggtgccagtggcagcaggg<br>cgagcctccggcgtcctacctcgatacggggttcggctcacggtgatggcccacccacccgcggcagggta<br>a<br>(SEQ ID NO: 38)<br>MACKTVTLTVDGTAMRVTTMKSRVIDIVEENGFSVDDRDDLYPAAGVQVHDADTIVLRRSRPLQISLDGHD<br>AKQVWTTASTVDEALAQLAMTDTAPAAASRASRVPLSGMALPVVSAKTVQLNDGGLVRTVHLPAPNVAGLL<br>SAAGVPLLQSDHVVPAATAPIVEGMQIQVTRNRIKKVTERLPLPPNARRVEDPEMNMSREVVEDPGVPGTQ<br>DVTFAVAEVNGVETGRLPVANVVVTPAHEAVVRVGTKPGTEVPPVIDGSIWDAIAGCEAGGNWAINTGNGY<br>YGGVQFDQGTWEANGGLRYAPRADLATREEQIAVAEVTRLRQGWGAWPVCAARAGAREFMTENLTVQPERL<br>GVLASHHDNAAVDASSGVEAAAGLGESVAITHGPYCSQFNDTLNVYLTAHNALGSSLHTAGVDLAKSLRIA<br>AKIYSEADEAWRKAIDGLFTKLMDFALLPPEVNSARMYTGPGAGSLLAAAGGWDSLAAELATTAEAYGSVL<br>SGLAALHWRGPAAESMAVTAAPYIGWLYTTAEKTQQTAIQARAAALAFEQAYAMTLPPPVVAANRIQLLAL<br>IATNFFGQNTAAIAATEAQYAEMWAQDAAAMYGYATASAAAALLTPFSPPRQTTNPAGLTAQAAAVSQATD<br>PLSLLIETVTQALQALTIPSFIPEDFTFLDAIFAGYATVGVTQDVESFVAGTIGAESNLGLLNVGDENPAE<br>VTPGDFGIGELVSATSPGGGVSASGAGGAASVGNTVLASVGRANSIGQLSVPPSWAAPSTRPVSALSPAGL<br>TTLPGTDVAEHGMPGVPGVPVAAGRASGVLPRYGVRLTVMAHPPAAG<br>(SEQ ID NO: 39) |
| B | atggcatgcaaaacggtgacgttgaccgtcgacggaaccgcgatgcgggtgaccacgatgaaatcgcgggt<br>gatcgacatcgtcgaagagaacgggttctcagtcgacgaccgcgacgacctgtatcccgcggccggcgtgc<br>aggtccatgacgccgacaccatcgtgctgcggcgtagccgtccgctgcagatctcgctggatggtcacgac<br>gctaagcaggtgtggacgaccgcgtcgacggtggacgaggcgctggcccaactcgcgatgaccgacacggc<br>gccggccgcggcttctcgcgccagccgcgtcccgctgtccgggatggcgctaccggtcgtcagcgccaaga<br>cggtgcagctcaacgacggcgggttggtgcgcacggtgcacttgccggcccccaatgtcgcggggctgctg<br>agtgcggccggcgtgccgctgttgcaaagcgaccacgtggtgcccgccgcgacggccccgatcgtcgaagg<br>catgcagatccaggtgacccgcaatcggatcaagaaggtcaccgagcggctgccgctgccgccgaacgcgc<br>gtcgtgtcgaggacccggagatgaacatgagccgggaggtcgtcgaagacccgggggttccggggacccag<br>gatgtgacgttcgcggtagctgaggtcaacggcgtcgagaccggccgtttgcccgtcgccaacgtcgtggt<br>gaccccggcccacgaagccgtggtgcgggtgggcaccaagcccggtaccgaggtgcccccggtgatcgacg<br>gaagcatctgggacgcgatcgccggctgtgaggccggtggcaactgggcgatcaacaccggcaacgggtat<br>tacggtggtgtgcagtttgaccagggcacctgggaggccaacggcgggctgcggtatgcaccccgcgctga<br>cctcgccacccgcgaagagcagatcgccgttgccgaggtgacccgactgcgtcaaggttggggcgcctggc<br>cggtatgtgctgcacgagcgggtgcgcgc**gaattc**gtgtccacttacagatcaccggatcgcgcttggcag<br>gcgctggcggacggcactcgccgggccatcgtggagcggctggcgcacggcccgctggccgtcggcgagtt<br>ggcccgcgacctgcccgtcagccgacccgcggtgtcacagcacctcaaagtgctcaagaccgccaggctgg<br>tgtgcgaccgccccgcgggaacacgccgcgtctaccagctcgacccgacaggccttgcggcattgcgcacc<br>gacctcgaccggttctggacacgcgccctgactggctacgcgcagctcatcgactccgaaggagacgacac<br>a**aagctt**atggatttcgcactgttaccaccggaagtcaactccgcccggatgtacaccggccctggggcag<br>gatcgctgttggctgccgcgggcggctgggattcgctggccgccgagttggccaccacagccgaggcatat<br>ggatcggtgctgtccggactggccgccttgcattggcgtggaccggcagcggaatcgatggcggtgacggc<br>cgctccctatatcggttggctgtacacgaccgccgaaaagacacagcaaacagcgatccaagccagggcgg<br>cagcgctggccttcgagcaagcatacgcaatgaccctgccgccaccggtggtagcggccaaccggatacag<br>ctgctagcactgatcgcgacgaacttcttcggccagaacactgcggcgatcgcggccaccgaggcacagta<br>cgccgagatgtgggcccaggacgccgccgcgatgtacggttacgccaccgcctcagcggctgcggccctgc |

TABLE 2-continued

| Construct | nucleotide sequence<br>amino acid sequence |
|---|---|
| | tgacaccgttctccccgccgcggcagaccaccaacccggccggcctgaccgctcaggccgccgcggtcagc<br>caggccaccgacccactgtcgctgctgattgagacggtgacccaagcgctgcaagcgctgacgattccgag<br>cttcatccctgaggacttcaccttccttgacgccatattcgctggatatgccacggtaggtgtgacgcagg<br>atgtcgagtcctttgttgccgggaccatcggggccgagagcaacctaggccttttgaacgtcggcgacgag<br>aatcccgcggaggtgacaccgggcgactttgggatcggcgagttggtttccgcgaccagtcccggcggtgg<br>ggtgtctgcgtcgggtgccggcggtgcggcgagcgtcggcaacacggtgctcgcgagtgtcggccgggcaa<br>actcgattgggcaactatcggtcccaccgagctgggccgcgccctcgacgcgccctgtctcggcattgtcg<br>cccgccggcctgaccacactcccggggaccgacgtggccgagcacgggatgccaggtgtaccgggggtgcc<br>agtggcagcagggcgagcctccggcgtcctacctcgatacggggttcggctcacggtgatggcccacccac<br>ccgcggcagggtaa<br>(SEQ ID NO: 40)<br>MACKTVTLTVDGTAMRVTTMKSRVIDIVEENGFSVDDRDDLYPAAGVQVHDADTIVLRRSRPLQISLDGHD<br>AKQVWTTASTVDEALAQLAMTDTAPAAASRASRVPLSGMALPVVSAKTVQLNDGGLVRTVHLPAPNVAGLL<br>SAAGVPLLQSDHVVPAATAPIVEGMQIQVTRNRIKKVTERLPLPPNARRVEDPEMNMSREVVEDPGVPGTQ<br>DVTFAVAEVNGVETGRLPVANVVVTPAHEAVVRVGTKPGTEVPPVIDGSIWDAIAGCEAGGNWAINTGNGY<br>YGGVQFDQGTWEANGGLRYAPRADLATREEQIAVAEVTRLRQGWGAWPVCAARAGAREFVSTYRSPDRAWQ<br>ALADGTRRAIVERLAHGPLAVGELARDLPVSRPAVSQHLKVLKTARLVCDRPAGTRRVYQLDPTGLAALRT<br>DLDRFWTRALTGYAQLIDSEGDDTKLMDFALLPPEVNSARMYTGPGAGSLLAAAGGWDSLAAELATTAEAY<br>GSVLSGLAALHWRGPAAESMAVTAAPYIGWLYTTAEKTQQTAIQARAAALAFEQAYAMTLPPPVVAANRIQ<br>LLALIATNFFGQNTAAIAATEAQYAEMWAQDAAAMYGYATASAAAALLTPFSPPRQTTNPAGLTAQAAAVS<br>QATDPLSLLIETVTQALQALTIPSFIPEDFTFLDAIFAGYATVGVTQDVESFVAGTIGAESNLGLLNVGDE<br>NPAEVTPGDFGIGELVSATSPGGGVSASGAGGAASVGNTVLASVGRANSIGQLSVPPSWAAPSTRPVSALS<br>PAGLTTLPGTDVAEHGMPGVPGVPVAAGRASGVLPRYGVRLTVMAHPPAAG<br>(SEQ ID NO: 41) |
| C | atggcatgcaaaacggtgacgttgaccgtcgacggaaccgcgatgcgggtgaccacgatgaaatcgcgggt<br>gatcgacatcgtcgaagagaacgggttctcagtcgacgaccgcgacgacctgtatcccgcggccggcgtgc<br>aggtccatgacgccgacaccatcgtgctgcggcgtagccgtccgctgcagatctcgctggatggtcacgac<br>gctaagcaggtgtggacgaccgcgtcgacggtggacgaggcgctggcccaactcgcgatgaccgacacggc<br>gccggccgcgcggcttctcgcgccagccgcgtcccgctgtccgggatggcgctaccggtcgtcagcgccaaga<br>cggtgcagctcaacgacggcgggttggtgcgcacggtgcacttgccggcccccaatgtcgcggggctgctg<br>agtgcggccggcgtgccgctgttgcaaagcgaccacgtggtgcccgccgcgacggccccgatcgtcgaagg<br>catgcagatccaggtgacccgcaatcggatcaagaaggtcaccgagcggctgccgctgccgccgaacgcgc<br>gtcgtgtcgaggacccggagatgaacatgagccgggaggtcgtcgaagacccgggggttccggggacccag<br>gatgtgacgttcgcggtagctgaggtcaacggcgtcgagaccggccgtttgcccgtcgccaacgtcgtggt<br>gaccccggcccacgaagccgtggtgcgggtgggcaccaagccgggtaccgaggtgcccccggtgatcgacg<br>gaagcatctgggacgcgatcgccggctgtgaggccggtggcaactgggcgatcaacaccggcaacgggtat<br>tacggtggtgtgcagtttgaccagggcacctgggaggccaacggcgggctgcggtatgcaccccgcgctga<br>cctcgccacccgcgaagagcagatcgccgttgccgaggtgacccgactgcgtcaaggttggggcgcctggc<br>cggtatgtgctgcacgagcgggtgcgcgc**gaattc**atgtccacgcaacgaccgaggcactccggtattcgg<br>gctgttggccccctacgcatgggccggccgatgtggtcggatggcaggtggggggtgcaccaggaggcgat<br>gatgaatctagcgatatggcacccgcgcaaggtgcaatccgccaccatctatcaggtgaccgatcgctcgc<br>acgacgggcgcacagcacgggtgcctggtgacgagatcactagcaccgtgtccggttggttgtcggagttg<br>ggcacccaaagcccgttggccgatgagcttgcgcgtgcggtgcggatcggcgactggcccgctgcgtacgc<br>aatcggtgagcacctgtccgttgagattgccgttgcggtc**gagctc**atgacggaaaacttgaccgtccagc<br>ccgagcgtctcggtgtactggcgtcgcaccatgacaacgcggcggtcgatgcctcctcgggcgtcgaagct<br>gccgctggcctaggcgaatctgtggcgatcactcacggtccgtactgctcacagttcaacgacacgttaaa<br>tgtgtacttgactgcccacaatgccctgggctcgtccttgcatacggccggtgtcgatctcgccaaaagtc<br>ttcgaattgcggcgaagatatatagcgaggccgacgaagcgtggcgcaaggctatcgacgggttgtttacc<br>**aagctt**atggatttcgcactgttaccaccggaagtcaactccgcccggatgtacaccggccctggggcagg<br>atcgctgttggctgccgcgggcggctgggattcgctggccgccgagttggccaccacagccgaggcatatg<br>gatcggtgctgtccggactggccgccttgcattggcgtggaccggcagcggaatcgatggcggtgacggcc<br>gctccctatatcggttggctgtacacgaccgccgaaaagacacagcaaacagcgatccaagccagggcggc<br>agcgctggccttcgagcaagcatacgcaatgaccctgccgccaccggtggtagcggccaaccggatacagc<br>tgctagcactgatcgcgacgaacttcttcggccagaacactgcggcgatcgcggccaccgaggcacagtac<br>gccgagatgtgggcccaggacgccgccgcgatgtacggttacgccaccgcctcagcggctgcggccctgct<br>gacaccgttctccccgccgcggcagaccaccaacccggccggcctgaccgctcaggccgccgcggtcagcc<br>aggccaccgacccactgtcgctgctgattgagacggtgacccaagcgctgcaagcgctgacgattccgagc<br>ttcatccctgaggacttcaccttccttgacgccatattcgctggatatgccacggtaggtgtgacgcagga<br>tgtcgagtcctttgttgccgggaccatcggggccgagagcaacctaggccttttgaacgtcggcgacgaga<br>atcccgcggaggtgacaccgggcgactttgggatcggcgagttggtttccgcgaccagtcccggcggtggg<br>gtgtctgcgtcgggtgccggcggtgcggcgagcgtcggcaacacggtgctcgcgagtgtcggccgggcaaa<br>ctcgattgggcaactatcggtcccaccgagctgggccgcgccctcgacgcgccctgtctcggcattgtcgc<br>ccgccggcctgaccacactcccggggaccgacgtggccgagcacgggatgccaggtgtaccgggggtgcca<br>gtggcagcagggcgagcctccggcgtcctacctcgatacggggttcggctcacggtgatggcccacccacc<br>cgcggcagggtaa<br>(SEQ ID NO: 42)<br>MACKTVTLTVDGTAMRVTTMKSRVIDIVEENGFSVDDRDDLYPAAGVQVHDADTIVLRRSRPLQISLDGHD<br>AKQVWTTASTVDEALAQLAMTDTAPAAASRASRVPLSGMALPVVSAKTVQLNDGGLVRTVHLPAPNVAGLL<br>SAAGVPLLQSDHVVPAATAPIVEGMQIQVTRNRIKKVTERLPLPPNARRVEDPEMNMSREVVEDPGVPGTQ<br>DVTFAVAEVNGVETGRLPVANVVVTPAHEAVVRVGTKPGTEVPPVIDGSIWDAIAGCEAGGNWAINTGNGY<br>YGGVQFDQGTWEANGGLRYAPRADLATREEQIAVAEVTRLRQGWGAWPVCAARAGAREFMSTQRPRHSGIR<br>AVGPYAWAGRCGRIGRWGVHQEAMMNLAIWHPRKVQSATIYQVTDRSHDGRTARVPGDEITSTVSGWLSEL<br>GTQSPLADELARAVRIGDWPAAYAIGEHLSVEIAVAVELMTENLTVQPERLGVLASHHDNAAVDASSGVEA<br>AAGLGESVAITHGPYCSQFNDTLNVYLTAHNALGSSLHTAGVDLAKSLRIAAKIYSEADEAWRKAIDGLFT<br>KLMDFALLPPEVNSARMYTGPGAGSLLAAAGGWDSLAAELATTAEAYGSVLSGLAALHWRGPAAESMAVTA<br>APYIGWLYTTAEKTQQTAIQARAAALAFEQAYAMTLPPPVVAANRIQLLALIATNFFGQNTAAIAATEAQY |

TABLE 2-continued

| Construct | nucleotide sequence<br>amino acid sequence |
|---|---|
| | AEMWAQDAAAMYGYATASAAAALLTPFSPPRQTTNPAGLTAQAAAVSQATDPLSLLIETVTQALQALTIPS<br>FIPEDFTFLDAIFAGYATVGVTQDVESFVAGTIGAESNLGLLNVGDENPAEVTPGDFGIGELVSATSPGGG<br>VSASGAGGAASVGNTVLASVGRANSIGQLSVPPSWAAPSTRPVSALSPAGLTTLPGTDVAEHGMPGVPGVP<br>VAAGRASGVLPRYGVRLTVMAHPPAAG<br>(SEQ ID NO: 43) |
| D | atggcatgcaaaacggtgacgttgaccgtcgacggaaccgcgatgcgggtgaccacgatgaaatcgcgggt<br>gatcgacatcgtcgaagagaacgggttctcagtcgacgaccgcgacgacctgtatcccgcggccggcgtgc<br>aggtccatgacgccgacaccatcgtgctgcggcgtagccgtccgctgcagatctcgctggatggtcacgac<br>gctaagcaggtgtggacgaccgcgtcgacggtggacgaggcgctggcccaactcgcgatgaccgacacggc<br>gccggccgcggcttctcgcgccagccgcgtcccgctgtccgggatggcgctaccggtcgtcagcgcaagac<br>ggtgcagctcaacgacggcgggttggtgcgcacggtgcacttgccggcccccaatgtcgcggggctgctga<br>gtgcggccggcgtgccgctgttgcaaagcgaccacgtggtgcccgccgcgacggccccgatcgtcgaaggc<br>atgcagatccaggtgacccgcaatcggatcaagaaggtcaccgagcggctgccgctgccgccgaacgcgcg<br>tcgtgtcgaggacccggagatgaacatgagccgggaggtcgtcgaagacccggggttccggggacccagg<br>atgtgacgttcgcggtagctgaggtcaacggcgtcgagaccggccgtttgcccgtcgccaacgtcgtggtg<br>accccggcccacgaagccgtggtgcgggtgggcaccaagcccggtaccgaggtgcccccggtgatcgacgg<br>aagcatctgggacgcgatcgccggctgtgaggccggtggcaactgggcgatcaacaccggcaacgggtatt<br>acggtggtgtgcagtttgaccagggcacctgggaggccaacggcgggctgcggtatgcaccccgcgctgac<br>ctcgccacccgcgaagagcagatcgccgttgccgaggtgacccgactgcgtcaaggttggggcgcctggcc<br>ggtatgtgctgcacgagcgggtgcgcgc**ggatcc**gtgtccacttacagatcaccggatcgcgcttggcagg<br>cgctggcggacggcactcgccgggccatcgtggagcggctggcgcacggcccgctggccgtcggcgagttg<br>gcccgcgacctgcccgtcagccgacccgcggtgtcacagcacctcaaagtgctcaagaccgccaggctggt<br>gtgcgaccgccccgcgggaacacgccgcgtctaccagctcgacccgacaggccttgcggcattgcgcaccg<br>acctcgaccggttctggacacgcgccctgactggctacgcgcagctcatcgactccgaaggagacgacaca<br>**gaattc**atgtccacgcaacgaccgaggcactccggtattcgggctgttggccccctacgcatgggccggccg<br>atgtggtcggataggcaggtgggggtgcaccaggaggcgatgatgaatctagcgatatggcacccgcgca<br>aggtgcaatccgccaccatctatcaggtgaccgatcgctcgcacgacgggcgcacagcacgggtgcctggt<br>gacgagatcactagcaccgtgtccggttggttgtcggagttgggcacccaaagcccgttggccgatgagct<br>tgcgcgtgcggtgcggatcggcgactggcccgctgcgtacgcaatcggtgagcacctgtccgttgagattg<br>ccgttgcggtc**gagctc**atgacggaaaacttgaccgtccagcccgagcgtctcggtgtactggcgtcgcac<br>catgacaacgcggcggtcgatgcctcctcgggcgtcgaagctgccgctggcctaggcgaatctgtggcgat<br>cactcacggtccgtactgctcacagttcaacgacacgttaaatgtgtacttgactgcccacaatgccctgg<br>gctcgtccttgcatacggccggtgtcgatctcgccaaaagtcttcgaattgcggcgaagatatatagcgag<br>gccgacgaagcgtggcgcaaggctatcgacgggttgtttacc**aagctt**atggatttcgcactgttaccacc<br>ggaagtcaactccgcccggatgtacaccggccctggggcaggatcgctgttggctgccgcgggcggctggg<br>attcgctggccgccgagttggccaccacagccgaggcatatggatcggtgctgtccggactggccgccttg<br>cattggcgtggaccggcagcggaatcgatggcggtgacggccgctccctatatcggttggctgtacacgac<br>cgccgaaaagacacagcaaacagcgatccaagccagggcggcagcgctggccttcgagcaagcatacgcaa<br>tgaccctgccgccaccggtggtagcggccaaccggatacagctgctagcactgatcgcgacgaacttcttc<br>ggccagaacactgcggcgatcgcggccaccgaggcacagtacgccgagatgtgggcccaggacgccgccgc<br>gatgtacggttacgccaccgcctcagcggctgcggccctgctgacaccgttctccccgccgcggcagacca<br>ccaacccggccggcctgaccgctcaggccgccgcggtcagccaggccaccgacccactgtcgctgctgatt<br>gagacggtgacccaagcgctgcaagcgctgacgattccgagcttcatccctgaggacttcaccttccttga<br>cgccatattcgctggatatgccacggtaggtgtgacgcaggatgtcgagtcctttgttgccgggaccatcg<br>gggccgagagcaacctaggccttttgaacgtcggcgacgagaatcccgcggaggtgacaccgggcgacttt<br>gggatcggcgagttggtttccgcgaccagtcccggcggtggggtgtctgcgtcgggtgccggcggtgcggc<br>gagcgtcggcaacacggtgctcgcgagtgtcggccgggcaaactcgattgggcaactatcggtcccaccga<br>gctgggccgcgccctcgacgcgccctgtctcggcattgtcgcccgccggcctgaccacactcccggggacc<br>gacgtggccgagcacgggatgccaggtgtaccgggggtgccagtggcagcagggcgagcctccggcgtcct<br>acctcgatacggggttcggctcacggtgatggcccacccacccgcggcagggtaa<br>(SEQ ID NO: 44)<br>MACKTVTLTVDGTAMRVTTMKSRVIDIVEENGFSVDDRDDLYPAAGVQVHDADTIVLRRSRPLQISLDGHD<br>AKQVWTTASTVDEALAQLAMTDTAPAAASRASRVPLSGMALPVVSAKTVQLNDGGLVRTVHLPAPNVAGLL<br>SAAGVPLLQSDHVVPAATAPIVEGMQIQVTRNRIKKVTERLPLPPNARRVEDPEMNMSREVVEDPGVPGTQ<br>DVTFAVAEVNGVETGRLPVANVVVTPAHEAVVRVGTKPGTEVPPVIDGSIWDAIAGCEAGGNWAINTGNGY<br>YGGVQFDQGTWEANGGLRYAPRADLATREEQIAVAEVTRLRQGWGAWPVCAARAGARGSVSTYRSPDRAWQ<br>ALADGTRRAIVERLAHGPLAVGELARDLPVSRPAVSQHLKVLKTARLVCDRPAGTRRVYQLDPTGLAALRT<br>DLDRFWTRALTGYAQLIDSEGDDTEFMSTQRPRHSGIRAVGPYAWAGRCGRIGRWGVHQEAMMNLAIWHPR<br>KVQSATIYQVTDRSHDGRTARVPGDEITSTVSGWLSELGTQSPLADELARAVRIGDWPAAYAIGEHLSVEI<br>AVAVELMTENLTVQPERLGVLASHHDNAAVDASSGVEAAAGLGESVAITHGPYCSQFNDTLNVYLTAHNAL<br>GSSLHTAGVDLAKSLRIAAKIYSEADEAWRKAIDGLFTKLMDFALLPPEVNSARMYTGPGAGSLLAAAGGW<br>DSLAAELATTAEAYGSVLSGLAALHWRGPAAESMAVTAAPYIGWLYTTAEKTQQTAIQARAAALAFEQAYA<br>MTLPPPVVAANRIQLLALIATNFFGQNTAAIAATEAQYAEMWAQDAAAMYGYATASAAAALLTPFSPPRQT<br>TNPAGLTAQAAAVSQATDPLSLLIETVTQALQALTIPSFIPEDFTFLDAIFAGYATVGVTQDVESFVAGTI<br>GAESNLGLLNVGDENPAEVTPGDFGIGELVSATSPGGGVSASGAGGAASVGNTVLASVGRANSIGQLSVPP<br>SWAAPSTRPVSALSPAGLTTLPGTDVAEHGMPGVPGVPVAAGRASGVLPRYGVRLTVMAHPPAAG<br>(SEQ ID NO: 45) |
| E | atggtgtccacttacagatcaccggatcgcgcttggcaggcgctggcggacggcactcgccgggccatcgt<br>ggagcggctggcgcacggcccgctggccgtcggcgagttggcccgcgacctgcccgtcagccgacccgcgg<br>tgtcacagcacctcaaagtgctcaagaccgccaggctggtgtgcgaccgccccgcgggaacacgccgcgtc<br>taccagctcgacccgacaggccttgcggcattgcgcaccgacctcgaccggttctggacacgcgccctgac<br>tggctacgcgcagctcatcgactccgaaggagacgacaca**gaattc**gcatgcaaaacggtgacgttgaccg<br>tcgacggaaccgcgatgcgggtgaccacgatgaaatcgcgggtgatcgacatcgtcgaagagaacgggttc<br>tcagtcgacgaccgcgacgacctgtatcccgcggccggcgtgcaggtccatgacgccgacaccatcgtgct<br>gcggcgtagccgtccgctgcagatctcgctggatggtcacgacgctaagcaggtgtggacgaccgcgtcga |

TABLE 2-continued

| Construct | nucleotide sequence<br>amino acid sequence |
|---|---|
| | cggtggacgaggcgctggcccaactcgcgatgaccgacacggcgccggccgcggcttctcgcgccagccgc<br>gtcccgctgtccgggatggcgctaccggtcgtcagcgccaagacggtgcagctcaacgacggcgggttggt<br>gcgcacggtgcacttgccggcccccaatgtcgcggggctgctgagtgcggccggcgtgccgctgttgcaaa<br>gcgaccacgtggtgcccgccgcgacggccccgatcgtcgaaggcatgcagatccaggtgacccgcaatcgg<br>atcaagaaggtcaccgagcggctgccgctgccgccgaacgcgcgtcgtgtcgaggacccggagatgaacat<br>gagccgggaggtcgtcgaagacccggggggttccggggacccaggatgtgacgttcgcggtagctgaggtca<br>acggcgtcgagaccggccgtttgcccgtcgccaacgtcgtggtgaccccggcccacgaagccgtggtgcgg<br>gtgggcaccaagcccggtaccgaggtgccccccggtgatcgacggaagcatctgggacgcgatcgccggctg<br>tgaggccggtggcaactgggcgatcaacaccggcaacgggtattacggtggtgtgcagtttgaccagggca<br>cctgggaggccaacggcgggctgcggtatgcaccccgcgctgacctcgccacccgcgaagagcagatcgcc<br>gttgccgaggtgacccgactgcgtcaaggttggggcgcctggccggtatgtgctgcacgagcgggtgcgcg<br>c**aagctt**atggatttcgcactgttaccaccggaagtcaatccgcccggatgtacaccggccctggggcagg<br>atcgctgttggctgccgcgggcggctgggattcgctggccgccgagttggccaccacagccgaggctatgg<br>atcggtgctgtccggactggccgccttgcattggcgtggaccggcagcggaatcgatggcggtgacggccg<br>ctccctatatcggttggctgtacacgaccgccgaaaagacacagcaaacagcgatccaagccagggcggca<br>gcgctggccttcgagcaagcatacgcaatgaccctgccgccaccggtggtagcggccaaccggatacagct<br>gctagcactgatcgcgacgaacttcttcggccagaacactgcggcgatcgcggccaccgagaggcacagta<br>cgccgagatgtgggcccaggacgccgccgcgatgtacggttacgccaccgcctcagcggctgcggccctgc<br>tgacaccgttctccccgccgcggcagaccaccaacccggccggcctgaccgctcaggccgccgcggtcagc<br>caggccaccgacccactgtcgctgctgattgagacggtgacccaagcgctgcaagcgctgacgattccgag<br>cttcatccctgaggacttcaccttccttgacgccatattcgctggatatgccacggtaggtgtgacgcagg<br>atgtcgagtcctttgttgccgggaccatcggggccgagagcaacctaggccttttgaacgtcggcgacgag<br>aatcccgcggaggtgacaccgggcgactttgggatcggcgagttggtttccgcgaccagtcccggcggtgg<br>ggtgtctgcgtcgggtgccggcggtgcggcgagcgtcggcaacacggtgctcgcgagtgtcggccgggcaa<br>actcgattgggcaactatcggtcccaccgagctgggccgcgccctcgacgcgccctgtctcggcattgtcg<br>cccgccggcctgaccacactcccggggaccgacgtggccgagcacgggatgccaggtgtaccgggggtgcc<br>agtggcagcagggcgagcctccggcgtcctacctcgatacggggttcggctcacggtgatggcccacccac<br>ccgcggcagggtaa<br>(SEQ ID NO: 46)<br>MVSTYRSPDRAWQALADGTRRAIVERLAHGPLAVGELARDLPVSRPAVSQHLKVLKTARLVCDRPAGTRRV<br>YQLDPTGLAALRTDLDRFWTRALTGYAQLIDSEGDDTEFACKTVTLTVDGTAMRVTTMKSRVIDIVEENGF<br>SVDDRDDLYPAAGVQVHDADTIVLRRSRPLQISLDGHDAKQVWTTASTVDEALAQLAMTDTAPAAASRASR<br>VPLSGMALPVVSAKTVQLNDGGLVRTVHLPAPNVAGLLSAAGVPLLQSDHVVPAATAPIVEGMQIQVTRNR<br>IKKVTERLPLPPNARRVEDPEMNMSREVVEDPGVPGTQDVTFAVAEVNGVETGRLPVANVVVTPAHEAVVR<br>VGTKPGTEVPPVIDGSIWDAIAGCEAGGNWAINTGNGYYGGVQFDQGTWEANGGLRYAPRADLATREEQIA<br>VAEVTRLRQGWGAWPVCAARAGARKLMDFALLPPEVNSARMYTGPGAGSLLAAAGGWDSLAAELATTAEAY<br>GSVLSGLAALHWRGPAAESMAVTAAPYIGWLYTTAEKTQQTAIQARAAALAFEQAYAMTLPPPVVAANRIQ<br>LLALIATNFFGQNTAAIAATEAQYAEMWAQDAAAMYGYATASAAAALLTPFSPPRQTTNPAGLTAQAAAVS<br>QATDPLSLLIETVTQALQALTIPSFIPEDFTFLDAIFAGYATVGVTQDVESFVAGTIGAESNLGLLNVGDE<br>NPAEVTPGDFGIGELVSATSPGGGVSASGAGGAASVGNTVLASVGRANSIGQLSVPPSWAAPSTRPVSALS<br>PAGLTTLPGTDVAEHGMPGVPGVPVAAGRASGVLPRYGVRLTVMAHPPAAG<br>(SEQ ID NO: 47) |
| F | atggatttcgcactgttaccaccggaagtcaactccgcccggatgtacaccggccctggggcaggatcgct<br>gttggctgccgcgggcggctgggattcgctggccgccgagttggccaccacagccgaggcatatggatcgg<br>tgctgtccggactggccgccttgcattggcgtggaccggcagcggaatcgatggcggtgacggccgctccc<br>tatatcggttggctgtacacgaccgccgaaaagacacagcaaacagcgatccaagccagggcggcagcgct<br>ggccttcgagcaagcatacgcaatgaccctgccgccaccggtggtagcggccaaccggatacagctgctag<br>cactgatcgcgacgaacttcttcggccagaacactgcggcgatcgcggccaccgaggcacagtacgccgag<br>atgtgggcccaggacgccgccgcgatgtacggttacgccaccgcctcagcggctgcggccctgctgacacc<br>gttctccccgccgcggcagaccaccaacccggccggcctgaccgctcaggccgccgcggtcagccaggcca<br>ccgacccactgtcgctgctgattgagacggtgacccaagcgctgcaagcgctgacgattccgagcttcatc<br>cctgaggacttcaccttccttgacgccatattcgctggatatgccacggtaggtgtgacgcaggatgtcga<br>gtcctttgttgccgggaccatcggggccgagagcaacctaggccttttgaacgtcggcgacgagaatcccg<br>cggaggtgacaccgggcgactttgggatcggcgagttggtttccgcgaccagtcccggcggtggggtgtct<br>gcgtcgggtgccggcggtgcggcgagcgtcggcaacacggtgctcgcgagtgtcggccgggcaaactcgat<br>tgggcaactatcggtcccaccgagctgggccgcgccctcgacgcgccctgtctcggcattgtcgcccgccg<br>gcctgaccacactcccggggaccgacgtggccgagcacgggatgccaggtgtaccgggggtgccagtggca<br>gcagggcgagcctccggcgtcctacctcgatacggggttcggctcacggtgatggcccacccacccgcggc<br>aggg**gagctc**gtgtccacttacagatcaccggatcgcgcttggcaggcgctggcggacggcactcgccggg<br>ccatcgtggagcggctggcgcacggcccgctggccgtcggcgagttggcccgcgacctgcccgtcagccga<br>cccgcggtgtcacagcacctcaaagtgctcaagaccgccaggctggtgtgcgaccgccccgcgggaacacg<br>ccgcgtctaccagctcgacccgacaggccttgcggcattgcgcaccgacctcgaccggttctggacacgcg<br>ccctgactggctacgcgcagctcatcgactccgaaggagacgacaca**aagctt**gcatgcaaaacggtgacg<br>ttgaccgtcgacggaaccgcgatgcgggtgaccacgatgaaatcgcgggtgatcgacatcgtcgaagagaa<br>cgggttctcagtcgacgaccgcgacgacctgtatcccgcggccggcgtgcaggtccatgacgccgacacca<br>tcgtgctgcggcgtagccgtccgctgcagatctcgctggatggtcacgacgctaagcaggtgtggacgacc<br>gcgtcgacggtggacgaggcgctggcccaactcgcgatgaccgacacggcgccggccgcggcttctcgcgc<br>cagccgcgtcccgctgtccgggatggcgctaccggtcgtcagcgccaagacggtgcagctcaacgacggcg<br>ggttggtgcgcacggtgcacttgccggcccccaatgtcgcggggctgctgagtgcggccggcgtgccgctg<br>ttgcaaagcgaccacgtggtgcccgccgcgacggccccgatcgtcgaaggcatgcagatccaggtgacccg<br>caatcggatcaagaaggtcaccgagcggctgccgctgccgccgaacgcgcgtcgtgtcgaggacccggaga<br>tgaacatgagccgggaggtcgtcgaagacccggggggttccggggacccaggatgtgacgttcgcggtagct<br>gaggtcaacggcgtcgagaccggccgtttgcccgtcgccaacgtcgtggtgaccccggcccacgaagccgt<br>ggtgcgggtgggcaccaagcccggtaccgaggtgccccccggtgatcgacggaagcatctgggacgcgatcg<br>ccggctgtgaggccggtggcaactgggcgatcaacaccggcaacgggtattacggtggtgtgcagtttgac<br>cagggcacctgggaggccaacggcgggctgcggtatgcaccccgcgctgacctcgccacccgcgaagagca |

TABLE 2-continued

| Construct | nucleotide sequence<br>amino acid sequence |
|---|---|
| | gatcgccgttgccgaggtgacccgactgcgtcaaggttggggcgcctggccggtatgtgctgcacgagcgg<br>gtgcgcgctga<br>(SEQ ID NO: 48)<br>MDFALLPPEVNSARMYTGPGAGSLLAAAGGWDSLAAELATTAEAYGSVLSGLAALHWRGPAAESMAVTAAP<br>YIGWLYTTAEKTQQTAIQARAAALAFEQAYAMTLPPPVVAANRIQLLALIATNFFGQNTAAIAATEAQYAE<br>MWAQDAAAMYGYATASAAAALLTPFSPPRQTTNPAGLTAQAAAVSQATDPLSLLIETVTQALQALTIPSFI<br>PEDFTFLDAIFAGYATVGVTQDVESFVAGTIGAESNLGLLNVGDENPAEVTPGDFGIGELVSATSPGGGVS<br>ASGAGGAASVGNTVLASVGRANSIGQLSVPPSWAAPSTRPVSALSPAGLTTLPGTDVAEHGMPGVPGVPVA<br>AGRASGVLPRYGVRLTVMAHPPAAGELVSTYRSPDRAWQALADGTRRAIVERLAHGPLAVGELARDLPVSR<br>PAVSQHLKVLKTARLVCDRPAGTRRVYQLDPTGLAALRTDLDRFWTRALTGYAQLIDSEGDDTKLACKTVT<br>LTVDGTAMRVTTMKSRVIDIVEENGFSVDDRDDLYPAAGVQVHDADTIVLRRSRPLQISLDGHDAKQVWTT<br>ASTVDEALAQLAMTDTAPAAASRASRVPLSGMALPVVSAKTVQLNDGGLVRTVHLPAPNVAGLLSAAGVPL<br>LQSDHVVPAATAPIVEGMQIQVTRNRIKKVTERLPLPPNARRVEDPEMNMSREVVEDPGVPGTQDVTFAVA<br>EVNGVETGRLPVANVVVTPAHEAVVRVGTKPGTEVPPVIDGSIWDAIAGCEAGGNWAINTGNGYYGGVQFD<br>QGTWEANGGLRYAPRADLATREEQIAVAEVTRLRQGWGAWPVCAARAGAR<br>(SEQ ID NO: 49) |
| G | atggcatgcaaaacggtgacgttgaccgtcgacggaaccgcgatcgggtgaccacgatgaaatcgcgggtg<br>atcgacatcgtcgaagagaacgggttctcagtcgacgaccgcgacgacctgtatcccgcggccggcgtgca<br>ggtccatgacgccgacaccatcgtgctgcggcgtagccgtccgctgcagatctcgctggatggtcacgacg<br>ctaagcaggtgtggacgaccgcgtcgacggtggacgaggcgctggcccaactcgcgatgaccgacacggcg<br>ccggccgcggcttctcgcgccagccgcgtcccgctgtccgggatggcgctaccggtcgtcagcgccaagac<br>ggtgcagctcaacgacggcgggttggtgcgcacggtgcacttgccggcccccaatgtcgcggggctgctga<br>gtgcggccggcgtgccgctgttgcaaagcgaccacgtggtgcccgccgcgacggccccgatcgtcgaaggc<br>atgcagatccaggtgacccgcaatcggatcaagaaggtcaccgagcggctgccgctgccgccgaacgcgcg<br>tcgtgtcgaggacccggagatgaacatgagccgggaggtcgtcgaagacccggggggttccggggacccagg<br>atgtgacgttcgcggtagctgaggtcaacggcgtcgagaccggccgtttgcccgtcgccaacgtcgtggtg<br>accccggcccacgaagccgtggtgcgggtgggcaccaagcccggtaccgaggtgcccccggtgatcgacgg<br>aagcatctgggacgcgatcgccggctgtgaggccggtggcaactgggcgatcaacaccggcaacgggtatt<br>acggtggtgtgcagtttgaccagggcacctgggaggccaacggcgggctgcggtatgcaccccgcgctgac<br>ctcgccacccgcgaagagcagatcgccgttgccgaggtgacccgactgcgtcaaggttggggcgcctggcc<br>ggtatgtgctgcacgagcgggtgcgcgc**gaattc**atgacggaaaacttgaccgtccagcccgagcgtctcg<br>gtgtactggcgtcgcaccatgacaacgcggcggtcgatgcctcctcgggcgtcgaagctgccgctggccta<br>ggcgaatctgtggcgatcactcacggtccgtactgctcacagttcaacgacacgttaaatgtgtacttgac<br>tgcccacaatgccctgggctcgtccttgcatacggccggtgtcgatctcgccaaaagtcttcgaattgcgg<br>cgaagatatatagcgaggccgacgaagcgtggcgcaaggctatcgacgggttgtttacc**gagctc**gtgtcc<br>acttacagatcaccggatcgcgcttggcaggcgctggcggacggcactcgccgggccatcgtggagcggct<br>ggcgcacggcccgctggccgtcggcgagttggcccgcgacctgcccgtcagccgacccgcggtgtcacagc<br>acctcaaagtgctcaagaccgccaggctggtgtgcgaccgccccgcgggaacacgccgcgtctaccagctc<br>gacccgacaggccttgcggcattgcgcaccgacctcgaccggttctggacacgcgccctgactggctacgc<br>gcagctcatcgactccgaaggagacgacaca**aagctt**atgtccacgcaacgaccgaggcactccggtattc<br>gggctgttggcccctacgcatgggccggccgatgtggtcggataggcaggtgggggggtgcaccaggaggcg<br>atgatgaatctagcgatatggcacccgcgcaaggtgcaatccgccaccatctatcaggtgaccgatcgctc<br>gcacgacgggcgcacagcacgggtgcctggtgacgagatcactagcaccgtgtccggttggttgtcggagt<br>tgggcacccaaagcccgttggccgatgagcttgcgcgtgcggtgcggatcggcgactggcccgctgcgtac<br>gcaatcggtgagcacctgtccgttgagattgccgttgcggtctaa<br>(SEQ ID NO: 50)<br>MACKTVTLTVDGTAMRVTTMKSRVIDIVEENGFSVDDRDDLYPAAGVQVHDADTIVLRRSRPLQISLDGHD<br>AKQVWTTASTVDEALAQLAMTDTAPAAASRASRVPLSGMALPVVSAKTVQLNDGGLVRTVHLPAPNVAGLL<br>SAAGVPLLQSDHVVPAATAPIVEGMQIQVTRNRIKKVTERLPLPPNARRVEDPEMNMSREVVEDPGVPGTQ<br>DVTFAVAEVNGVETGRLPVANVVVTPAHEAVVRVGTKPGTEVPPVIDGSIWDAIAGCEAGGNWAINTGNGY<br>YGGVQFDQGTWEANGGLRYAPRADLATREEQIAVAEVTRLRQGWGAWPVCAARAGAREFMTENLTVQPERL<br>GVLASHHDNAAVDASSGVEAAAGLGESVAITHGPYCSQFNDTLNVYLTAHNALGSSLHTAGVDLAKSLRIA<br>AKIYSEADEAWRKAIDGLFTELVSTYRSPDRAWQALADGTRRAIVERLAHGPLAVGELARDLPVSRPAVSQ<br>HLKVLKTARLVCDRPAGTRRVYQLDPTGLAALRTDLDRFWTRALTGYAQLIDSEGDDTKLMSTQRPRHSGI<br>RAVGPYAWAGRCGRIGRWGVHQEAMMNLAIWHPRKVQSATIYQVTDRSHDGRTARVPGDEITSTVSGWLSE<br>LGTQSPLADELARAVRIGDWPAAYAIGEHLSVEIAVAV<br>(SEQ ID NO: 51) |
| H | atgacggaaaacttgaccgtccagcccgagcgtctcggtgtactggcgtcgcaccatgacaacgcggcggt<br>cgatgcctcctcgggcgtcgaagctgccgctggcctaggcgaatctgtggcgatcactcacggtccgtact<br>gctcacagttcaacgacacgttaaatgtgtacttgactgcccacaatgccctgggctcgtccttgcatacg<br>gccggtgtcgatctcgccaaaagtcttcgaattgcggcgaagatatatagcgaggccgacgaagcgtggcg<br>caaggctatcgacgggttgtttacc**ggatcc**gtgtccacttacagatcaccggatcgcgcttggcaggcgc<br>tggcggacggcactcgccgggccatcgtggagcggctggcgcacggcccgctggccgtcggcgagttggcc<br>cgcgacctgcccgtcagccgacccgcggtgtcacagcacctcaaagtgctcaagaccgccaggctggtgtg<br>cgaccgccccgcgggaacacgccgcgtctaccagctcgacccgacaggccttgcggcattgcgcaccgacc<br>tcgaccggttctggacacgcgccctgactggctacgcgcagctcatcgactccgaaggagacgacaca**gga**<br>**ttc**atgtccacgcaacgaccgaggcactccggtattcgggctgttggcccctacgcatgggccggccgatg<br>tggtcggataggcaggtgggggggtgcaccaggaggcgatgatgaatctagcgatatggcacccgcgcaagg<br>tgcaatccgccaccatctatcaggtgaccgatcgctcgcacgacgggcgcacagcacgggtgcctggtgac<br>gagatcactagcaccgtgtccggttggttgtcggagttgggcacccaaagcccgttggccgatgagcttgc<br>gcgtgcggtgcggatcggcgactggcccgctgcgtacgcaatcggtgagcacctgtccgttgagattgccg<br>ttgcggtc**aagctt**atggcatgcaaaacggtgacgttgaccgtcgacggaaccgcgatgcgggtgaccacg<br>atgaaatcgcgggtgatcgacatcgtcgaagagaacgggttctcagtcgacgaccgcgacgacctgtatcc<br>cgcggccggcgtgcaggtccatgacgccgacaccatcgtgctgcggcgtagccgtccgctgcagatctcgc<br>tggatggtcacgacgctaagcaggtgtggacgaccgcgtcgacggtggacgaggcgctggcccaactcgcg |

TABLE 2-continued

| Construct | nucleotide sequence<br>amino acid sequence |
|---|---|
| | atgaccgacacggcgccggccgcggcttctcgcgccagccgcgtcccgctgtccgggatggcgctaccggt<br>cgtcagcgccaagacggtgcagctcaacgacggcgggttggtgcgcacggtgcacttgccggcccccaatg<br>tcgcggggctgctgagtgcggccggcgtgccgctgttgcaaagcgaccacgtggtgcccgccgcgacggcc<br>ccgatcgtcgaaggcatgcagatccaggtgacccgcaatcggatcaagaaggtcaccgagcggctgccgct<br>gccgccgaacgcgcgtcgtgtcgaggacccggagatgaacatgagccgggaggtcgtcgaagacccggggg<br>ttccggggacccaggatgtgacgttcgcggtagctgaggtcaacggcgtcgagaccggccgtttgcccgtc<br>gccaacgtcgtggtgaccccggcccacgaagccgtggtgcgggtgggcaccaagcccggtaccgaggtgcc<br>cccggtgatcgacggaagcatctgggacgcgatcgccggctgtgaggccggtggcaactgggcgatcaaca<br>ccggcaacgggtattacggtggtgtgcagtttgaccagggcacctgggaggccaacggcgggctgcggtat<br>gcaccccgcgctgacctcgccacccgcgaagagcagatcgccgttgccgaggtgacccgactgcgtcaagg<br>ttggggcgcctggccggtatgtgctgcacgagcgggtgcgcgctga<br>(SEQ ID NO: 52)<br>MTENLTVQPERLGVLASHHDNAAVDASSGVEAAAGLGESVAITHGPYCSQFNDTLNVYLTAHNALGSSLHT<br>AGVDLAKSLRIAAKIYSEADEAWRKAIDGLFTGSVSTYRSPDRAWQALADGTRRAIVERLAHGPLAVGELA<br>RDLPVSRPAVSQHLKVLKTARLVCDRPAGTRRVYQLDPTGLAALRTDLDRFWTRALTGYAQLIDSEGDDTE<br>FMSTQRPRHSGIRAVGPYAWAGRCGRIGRWGVHQEAMMNLAIWHPRKVQSATIYQVTDRSHDGRTARVPGD<br>EITSTVSGWLSELGTQSPLADELARAVRIGDWPAAYAIGEHLSVEIAVAVKLMACKTVTLTVDGTAMRVTT<br>MKSRVIDIVEENGFSVDDRDDLYPAAGVQVHDADTIVLRRSRPLQISLDGHDAKQVWTTASTVDEALAQLA<br>MTDTAPAAASRASRVPLSGMALPVVSAKTVQLNDGGLVRTVHLPAPNVAGLLSAAGVPLLQSDHVVPAATA<br>PIVEGMQIQVTRNRIKKVTERLPLPPNARRVEDPEMNMSREVVEDPGVPGTQDVTFAVAEVNGVETGRLPV<br>ANVVVTPAHEAVVRVGTKPGTEVPPVIDGSIWDAIAGCEAGGNWAINTGNGYYGGVQFDQGTWEANGGLRY<br>APRADLATREEQIAVAEVTRLRQGWGAWPVCAARAGAR<br>(SEQ ID NO: 53) |
| I | atggtgtccacttacagatcaccggatcgcgcttggcaggcgctggcggacggcactcgccgggccatcgt<br>ggagcggctggcgcacggcccgctggccgtcggcgagttggcccgcgacctgcccgtcagccgacccgcgg<br>tgtcacagcacctcaaagtgctcaagaccgccaggctggtgtgcgaccgccccgcgggaacacgccgcgtc<br>taccagctcgacccgacaggccttgcggcattgcgcaccgacctcgaccggttctggacacgcgccctgac<br>tggctacgcgcagctcatcgactccgaaggagacgacaca**gaattc**atgacggaaaacttgaccgtccagc<br>ccgagcgtctcggtgtactggcgtcgcaccatgacaacgcggcggtcgatgcctcctcgggcgtcgaagct<br>gccgctggcctaggcgaatctgtggcgatcactcacggtccgtactgctcacagttcaacgacacgttaaa<br>tgtgtacttgactgcccacaatgccctgggctcgtccttgcatacggccggtgtcgatctcgccaaaagtc<br>ttcgaattgcggcgaagatatatagcgaggccgacgaagcgtggcgcaaggctatcgacgggttgtttacc<br>**gagctc**atgtccacgcaacgaccgaggcactccggtattcgggctgttggcccctacgcatgggccggccg<br>atgtggtcggataggcaggtggggggtgcaccaggaggcgatgatgaatctagcgatggcacccgcgcaag<br>gtgcaatccgccaccatctatcaggtgaccgatcgctcgcacgacgggcgcacagcacgggtgcctggtga<br>cgagatcactagcaccgtgtccggttggttgtcggagttgggcacccaaagcccgttggccgatgagcttg<br>cgcgtgcggtgcggatcggcgactggcccgctgcgtacgcaatcggtgagcacctgtccgttgagattgcc<br>gttgcggtc**aagctt**atggatttcgcactgttaccaccggaagtcaactccgcccggatgtacaccggccc<br>tggggcaggatcgctgttggctgccgcgggcggctgggattcgctggccgccgagttggccaccacagccg<br>aggcatatggatcggtgctgtccggactggccgccttgcattggcgtggaccggcagcggaatcgatggcg<br>gtgacggccgctccctatatcggttggctgtacacgaccgccgaaaagacacagcaaacagcgatccaagc<br>cagggcggcagcgctggccttcgagcaagcatacgcaatgaccctgccgccaccggtggtagcggccaacc<br>ggatacagctgctagcactgatcgcgacgaacttcttcggccagaacactgcggcgatcgcggccaccgag<br>gcacagtacgccgagatgtgggcccaggacgccgccgcgatgtacggttacgccaccgcctcagcggctgc<br>ggccctgctgacaccgttctccccgccgcggcagaccaccaacccggccggcctgaccgctcaggccgccg<br>cggtcagccaggccaccgacccactgtcgctgctgattgagacggtgacccaagcgctgcaagcgctgacg<br>attccgagcttcatccctgaggacttcaccttccttgacgccatattcgctggatatgccacggtaggtgt<br>gacgcaggatgtcgagtcctttgttgccgggaccatcggggccgagagcaacctaggcctttgaacgtcgg<br>cgacgagaatcccgcggaggtgacaccgggcgactttgggatcggcgagttggtttccgcgaccagtcccg<br>gcggtggggtgtctgcgtcgggtgccggcggtgcggcgagcgtcggcaacacggtgctcgcgagtgtcggc<br>cgggcaaactcgattgggcaactatcggtcccaccgagctgggccgcgccctcgacgcgccctgtctcggc<br>attgtcgcccgccggcctgaccacactcccggggaccgacgtggccgagcacgggatgccaggtgtaccgg<br>gggtgccagtggcagcagggcgagcctccggcgtcctacctcgatacggggttcggctcacggtgatggcc<br>cacccacccgcggcagggtag<br>(SEQ ID NO: 54)<br>MVSTYRSPDRAWQALADGTRRAIVERLAHGPLAVGELARDLPVSRPAVSQHLKVLKTARLVCDRPAGTRRV<br>YQLDPTGLAALRTDLDRFWTRALTGYAQLIDSEGDDTEFMTENLTVQPERLGVLASHHDNAAVDASSGVEA<br>AAGLGESVAITHGPYCSQFNDTLNVYLTAHNALGSSLHTAGVDLAKSLRIAAKIYSEADEAWRKAIDGLFT<br>ELMSTQRPRHSGIRAVGPYAWAGRCGRIGRWGVHQEAMMNLAIWHPRKVQSATIYQVTDRSHDGRTARVPG<br>DEITSTVSGWLSELGTQSPLADELARAVRIGDWPAAYAIGEHLSVEIAVAVKLMDFALLPPEVNSARMYTG<br>PGAGSLLAAAGGWDSLAAELATTAEAYGSVLSGLAALHWRGPAAESMAVTAAPYIGWLYTTAEKTQQTAIQ<br>ARAAALAFEQAYAMTLPPPVVAANRIQLLALIATNFFGQNTAAIAATEAQYAEMWAQDAAAMYGYATASAA<br>AALLTPFSPPRQTTNPAGLTAQAAAVSQATDPLSLLIETVTQALQALTIPSFIPEDFTFLDAIFAGYATVG<br>VTQDVESFVAGTIGAESNLGLLNVGDENPAEVTPGDFGIGELVSATSPGGGVSASGAGGAASVGNTVLASV<br>GRANSIGQLSVPPSWAAPSTRPVSALSPAGLTTLPGTDVAEHGMPGVPGVPVAAGRASGVLPRYGVRLTVM<br>AHPPAAG<br>(SEQ ID NO: 55) |
| J | atggatttcgcactgttaccaccggaagtcaactccgcccggatgtacaccggccctggggcaggatcgct<br>gttggctgccgcgggcggctgggattcgctggccgccgagttggccaccacagccgaggcatatggatcgg<br>tgctgtccggactggccgccttgcattggcgtggaccggcagcggaatcgatggcggtgacggccgctccc<br>tatatcggttggctgtacacgaccgccgaaaagacacagcaaacagcgatccaagccagggcggcagcgct<br>ggccttcgagcaagcatacgcaatgaccctgccgccaccggtggtagcggccaaccggatacagctgctag<br>cactgatcgcgacgaacttcttcggccagaacactgcggcgatcgcggccaccgaggcacagtacgccgag<br>atgtgggcccaggacgccgccgcgatgtacggttacgccaccgcctcagcggctgcggccctgctgacacc<br>gttctccccgccgcggcagaccaccaacccggccggcctgaccgctcaggccgccgcggtcagccaggcca |

TABLE 2-continued

| Construct | nucleotide sequence<br>amino acid sequence |
|---|---|
| | ccgacccactgtcgctgctgattgagacggtgacccaagcgctgcaagcgctgacgattccgagcttcatc<br>cctgaggacttcaccttccttgacgccatattcgctggatatgccacggtaggtgtgacgcaggatgtcga<br>gtcctttgttgccgggaccatcggggccgagagcaacctaggccttttgaacgtcggcgacgagaatcccg<br>cggaggtgacaccgggcgactttgggatcggcgagttggtttccgcgaccagtcccggcggtggggtgtct<br>gcgtcgggtgccggcggtgcggcgagcgtcggcaacacggtgctcgcgagtgtcggccgggcaaactcgat<br>tgggcaactatcggtcccaccgagctgggccgcgccctcgacgcgccctgtctcggcattgtcgcccgccg<br>gcctgaccacactcccggggaccgacgtggccgagcacgggatgccaggtgtaccgggggtgccagtggca<br>gcagggcgagcctccggcgtcctacctcgatacggggttcggctcacggtgatggcccacccacccgcggc<br>aggg**gaattc**atgtccacgcaacgaccgaggcactccggtattcgggctgttggcccctacgcatgggccg<br>gccgatgtggtcggataggcaggtgggggtgcaccaggaggcgatgatgaatctagcgatatggcacccg<br>cgcaaggtgcaatccgccaccatctatcaggtgaccgatcgctcgcaccgggcgcacagcacgggtgcctg<br>gtgacgagatcactagcaccgtgtccggttggttgtcggagttgggcacccaaagcccgttggccgatgag<br>cttgcgcgtgcggtgcggatcggcgactggcccgctgcgtacgcaatcggtgagcacctgtccgttgagat<br>tgccgttgcggtc**gagctc**atgacggaaaacttgaccgtccagcccgagcgtctcggtgtactggcgtcgc<br>accatgacaacgcggcggtcgatgcctcctcgggcgtcgaagctgccgctggcctaggcgaatctgtggcg<br>atcactcacggtccgtactgctcacagttcaacgacacgttaaatgtgtacttgactgcccacaatgccct<br>gggctcgtccttgcatacggccggtgtcgatctcgccaaaagtcttcgaattgcggcgaagatatatagcg<br>aggccgacgaagcgtggcgcaaggctatcgacgggttgtttacc**aagctt**atggtgtccacttacagatca<br>ccggatcgcgcttggcaggcgctggcggacggcactcgccgggccatcgtggagcggctggcgcacggccc<br>gctggccgtcggcgagttggcccgcgacctgcccgtcagccgacccgcggtgtcacagcacctcaaagtgc<br>tcaagaccgccaggctggtgtgcgaccgccccgcgggaacacgccgcgtctaccagctcgacccgacaggc<br>cttgcggcattgcgcaccgacctcgaccggttctggacacgcgccctgactggctacgcgcagctcatcga<br>ctccgaaggagacgacacatag<br>(SEQ ID NO: 56)<br>MDFALLPPEVNSARMYTGPGAGSLLAAAGGWDSLAAELATTAEAYGSVLSGLAALHWRGPAAESMAVTAAP<br>YIGWLYTTAEKTQQTAIQARAAALAFEQAYAMTLPPPVVAANRIQLLALIATNFFGQNTAAIAATEAQYAE<br>MWAQDAAAMYGYATASAAAALLTPFSPPRQTTNPAGLTAQAAAVSQATDPLSLLIETVTQALQALTIPSFI<br>PEDFTFLDAIFAGYATVGVTQDVESFVAGTIGAESNLGLLNVGDENPAEVTPGDFGIGELVSATSPGGGVS<br>ASGAGGAASVGNTVLASVGRANSIGQLSVPPSWAAPSTRPVSALSPAGLTTLPGTDVAEHGMPGVPGVPVA<br>AGRASGVLPRYGVRLTVMAHPPAAGEFMSTQRPRHSGIRAVGPYAWAGRCGRIGRWGVHQEAMMNLAIWHP<br>RKVQSATIYQVTDRSHDGRTARVPGDEITSTVSGWLSELGTQSPLADELARAVRIGDWPAAYAIGEHLSVE<br>IAVAVELMTENLTVQPERLGVLASHHDNAAVDASSGVEAAAGLGESVAITHGPYCSQFNDTLNVYLTAHNA<br>LGSSLHTAGVDLAKSLRIAAKIYSEADEAWRKAIDGLFTKLMVSTYRSPDRAWQALADGTRRAIVERLAHG<br>PLAVGELARDLPVSRPAVSQHLKVLKTARLVCDRPAGTRRVYQLDPTGLAALRTDLDRFWTRALTGYAQLI<br>DSEGDDT<br>(SEQ ID NO: 57) |
| K | atggcatgcaaaacggtgacgttgaccgtcgacggaaccgcgatgcgggtgaccacgatgaaatcgcgggt<br>gatcgacatcgtcgaagagaacgggttctcagtcgacgaccgcgacgacctgtatcccgcggccggcgtgc<br>aggtccatgacgccgacaccatcgtgctgcggcgtagccgtccgctgcagatctcgctggatggtcacgac<br>gctaagcaggtgtggacgaccgcgtcgacggtggacgaggcgctggcccaactcgcgatgaccgacacggc<br>gccggccgcggcttctcgcgccagccgcgtcccgctgtccgggatggcgctaccggtcgtcagcgccaaga<br>cggtgcagctcaacgacggcgggttggtgcgcacggtgcacttgccggcccccaatgtcgcggggctgctg<br>agtgcggccggcgtgccgctgttgcaaagcgaccacgtggtgcccgccgcgacggccccgatcgtcgaagg<br>catgcagatccaggtgacccgcaatcggatcaagaaggtcaccgagcggctgccgctgccgccgaacgcgc<br>gtcgtgtcgaggacccggagatgaacatgagccgggaggtcgtcgaagacccggggggttccggggacccag<br>gatgtgacgttcgcggtagctgaggtcaacggcgtcgagaccggccgtttgcccgtcgccaacgtcgtggt<br>gaccccggcccacgaagccgtggtgcgggtgggcaccaagcccggtaccgaggtgcccccggtgatcgacg<br>gaagcatctgggacgcgatcgccggctgtgaggccggtggcaactgggcgatcaacaccggcaacgggtat<br>tacggtggtgtgcagtttgaccagggcacctgggaggccaacggcgggctgcggtatgcaccccgcgctga<br>cctcgccacccgcgaagagcagatcgccgttgccgaggtgacccgactgcgtcaaggttggggcgcctggc<br>cggtatgtgctgcacgagcgggtgcgcgc**ggattc**atggatttcgcactgttaccaccggaagtcaactcc<br>gcccggatgtacaccggccctggggcaggatcgctgttggctgccgcgggcggctgggattcgctggccgc<br>cgagttggccaccacagccgaggcatatggatcggtgctgtccggactggccgccttgcattggcgtggac<br>cggcagcggaatcgatggcggtgacggccgctccctatatcggttggctgtacacgaccgccgaaaagaca<br>cagcaaacagcgatccaagccagggcggcagcgctggccttcgagcaagcatacgcaatgaccctgccgcc<br>accggtggtagcggccaaccggatacagctgctagcactgatcgcgacgaacttcttcggccagaacactg<br>cggcgatcgcggccaccgaggcacagtacgccgagatgtgggcccaggacgccgccgcgatgtacggttac<br>gccaccgcctcagcggctgcggccctgctgacaccgttctccccgccgcggcagaccaccaacccggccgg<br>cctgacc**gaattc**atgtccacgcaacgaccgaggcactccggtattcgggctgttggcccctacgcatggg<br>ccggccgatgtggtcggataggcaggtgggggtgcaccaggaggcgatgatgaatctagcgatatggcac<br>ccgcgcaaggtgcaatccgccaccatctatcaggtgaccgatcgctcgcacgacgggcgcacagcacgggt<br>gcctggtgacgagatcactagcaccgtgtccggttggttgtcggagttgggcacccaaagcccgttggccg<br>atgagcttgcgcgtgcggtgcggatcggcgactggcccgctgcgtacgcaatcggtgagcacctgtccgtt<br>gagattgccgttgcggtc**gagctc**gtgtccacttacagatcaccggatcgcgcttggcaggcgctggcgga<br>cggcactcgccgggccatcgtggagcggctggcgcacggcccgctggccgtcggcgagttggcccgcgacc<br>tgcccgtcagccgacccgcggtgtcacagcacctcaaagtgctcaagaccgccaggctggtgtgcgaccgc<br>cccgcgggaacacgccgcgtctaccagctcgacccgacaggccttgcggcattgcgcaccgacctcgaccg<br>gttctggacacgcgccctgactggctacgcgcagctcatcgactccgaaggagacgacaca**aagctt**atga<br>cggaaaacttgaccgtccagcccgagcgtctcggtgtactggcgtcgcaccatgacaacgcggcggtcgat<br>gcctcctcgggcgtcgaagctgccgctggcctaggcgaatctgtggcgatcactcacggtccgtactgctc<br>acagttcaacgacacgttaaatgtgtacttgactgcccacaatgccctgggctcgtccttgcatacggccg<br>gtgtcgatctcgccaaaagtcttcgaattgcggcgaagatatatagcgaggccgacgaagcgtggcgcaag<br>gctatcgacgggttgtttacctga<br>(SEQ ID NO: 58)<br>MACKTVTLTVDGTAMRVTTMKSRVIDIVEENGFSVDDRDDLYPAAGVQVHDADTIVLRRSRPLQISLDGHD<br>AKQVWTTASTVDEALAQLAMTDTAPAAASRASRVPLSGMALPVVSAKTVQLNDGGLVRTVHLPAPNVAGLL |

TABLE 2-continued

| Construct | nucleotide sequence<br>amino acid sequence |
|---|---|
| | SAAGVPLLQSDHVVPAATAPIVEGMQIQVTRNRIKKVTERLPLPPNARRVEDPEMNMSREVVEDPGVPGTQ<br>DVTFAVAEVNGVETGRLPVANVVVTPAHEAVVRVGTKPGTEVPPVIDGSIWDAIAGCEAGGNWAINTGNGY<br>YGGVQFDQGTWEANGGLRYAPRADLATREEQIAVAEVTRLRQGWGAWPVCAARAGARGFMDFALLPPEVNS<br>ARMYTGPGAGSLLAAAGGWDSLAAELATTAEAYGSVLSGLAALHWRGPAAESMAVTAAPYIGWLYTTAEKT<br>QQTAIQARAAALAFEQAYAMTLPPPVVAANRIQLLALIATNFFGQNTAAIAATEAQYAEMWAQDAAAMYGY<br>ATASAAAALLTPFSPPRQTTNPAGLTEFMSTQRPRHSGIRAVGPYAWAGRCGRIGRWGVHQEAMMNLAIWH<br>PRKVQSATIYQVTDRSHDGRTARVPGDEITSTVSGWLSELGTQSPLADELARAVRIGDWPAAYAIGEHLSV<br>EIAVAVELVSTYRSPDRAWQALADGTRRAIVERLAHGPLAVGELARDLPVSRPAVSQHLKVLKTARLVCDR<br>PAGTRRVYQLDPTGLAALRTDLDRFWTRALTGYAQLIDSEGDDTKLMTENLTVQPERLGVLASHHDNAAVD<br>ASSGVEAAAGLGESVAITHGPYCSQFNDTLNVYLTAHNALGSSLHTAGVDLAKSLRIAAKIYSEADEAWRK<br>AIDGLFT<br>(SEQ ID NO: 59) |
| L | atggtgtccacttacagatcaccggatcgcgcttggcaggcgctggcggacggcactcgccgggccatcgt<br>ggagcggctggcgcacggcccgctggccgtcggcgagttggcccgcgacctgcccgtcagccgacccgcgg<br>tgtcacagcacctcaaagtgctcaagaccgccaggctggtgtgcgaccgccccgcgggaacacgccgcgtc<br>taccagctcgacccgacaggccttgcggcattgcgcaccgacctcgaccggttctggacacgcgccctgac<br>tggctacgcgcagctcatcgactccgaaggagacgacaca**ggatcc**atgacggaaaacttgaccgtccagc<br>ccgagcgtctcggtgtactggcgtcgcaccatgacaacgcggcggtcgatgcctcctcgggcgtcgaagct<br>gccgctggcctaggcgaatctgtggcgatcactcacggtccgtactgctcacagttcaacgacacgttaaa<br>tgtgtacttgactgcccaccatgccctgggctcgtccttgcatacggccggtgtcgatctcgccaaaagtc<br>ttcgaattgcggcgaagatatatagcgaggccgacgaagcgtggcgcaaggctatcgacgggttgtttacc<br>**gaattc**atggatttcgcactgttaccaccggaagtcaactccgcccggatgtacaccggccctggggcagg<br>atcgctgttggctgccgcgggcggctgggattcgctggccgccgagttggccaccacagccgaggcatatg<br>gatcggtgctgtccggactggccgccttgcattggcgtggaccggcagcggaatcgatggcggtgacggcc<br>gctccctatatcggttggctgtacacgaccgccgaaaagacacagcaaacagcgatccaagccagggcggc<br>agcgctggccttcgagcaagcatacgcaatgaccctgccgccaccggtggtagcggccaaccggatacagc<br>tgctagcactgatcgcgacgaacttcttcggccagaacactgcggcgatcgcggccaccgaggcacagtac<br>gccgagatgtgggcccaggacgccgccgcgatgtacggttacgccaccgcctcagcggctgcggccctgct<br>gacaccgttctccccgccgcggcagaccaccaacccggccggctgacc**gagctc**atgtccacgcaacgacc<br>gaggcactccggtattcgggctgttggcccctacgcatgggccggccgatgtggtcggataggcaggtggg<br>gggtgcaccaggaggcgatgatgaatctagcgatatggcacccgcgcaaggtgcaatccgccaccatctat<br>caggtgaccgatcgctcgcacgacgggcgcacagcacgggtgcctggtgacgagatcactagcaccgtgtc<br>cggttggttgtcggagttgggcacccaaagcccgttggccgatgagcttgcgcgtgcggtgcggatcggcg<br>actggcccgctgcgtacgcaatcggtgagcacctgtccgttgagattgccgttgcggtc**aagctt**gcatgc<br>aaaacggtgacgttgaccgtcgacggaaccgcgatgcgggtgaccacgatgaaatcgcgggtgatcgacat<br>cgtcgaagagaacgggttctcagtcgacgaccgcgacgacctgtatcccgcggccggcgtgcaggtccatg<br>acgccgacaccatcgtgctgcggcgtagccgtccgctgcagatctcgctggatggtcacgacgctaagcag<br>gtgtggacgaccgcgtcgacggtggacgaggcgctggcccaactcgcgatgaccgacacggcgccggccgc<br>ggcttctcgcgccagccgcgtcccgctgtccgggatggcgctaccggtcgtcagcgccaagacggtgcagc<br>tcaacgacggcgggttggtgcgcacggtgcacttgccggcccccaatgtcgcggggctgctgagtgcggcc<br>ggcgtgccgctgttgcaaagcgaccacgtggtgcccgccgcgacggccccgatcgtcgaaggcatgcagat<br>ccaggtgacccgcaatcggatcaagaaggtcaccgagcggctgccgctgccgccgaacgcgcgtcgtgtcg<br>aggacccggagatgaacatgagccgggaggtcgtcgaagacccgggggttccggggacccaggatgtgacg<br>ttcgcggtagctgaggtcaacggcgtcgagaccggccgtttgcccgtcgccaacgtcgtggtgaccccggc<br>ccacgaagccgtggtgcgggtgggcaccaagcccggtaccgaggtgcccccggtgatcgacggaagcatct<br>gggacgcgatcgccggctgtgaggccggtggcaactgggcgatcaacaccggcaacgggtattacggtggt<br>gtgcagtttgaccagggcacctgggaggccaacggcgggctgcggtatgcaccccgcgctgacctcgccac<br>ccgcgaagagcagatcgccgttgccgaggtgacccgactgcgtcaaggttggggcgcctggccggtatgtg<br>ctgcacgagcgggtgcgcgctga<br>(SEQ ID NO: 60)<br>MVSTYRSPDRAWQALADGTRRAIVERLAHGPLAVGELARDLPVSRPAVSQHLKVLKTARLVCDRPAGTRRV<br>YQLDPTGLAALRTDLDRFWTRALTGYAQLIDSEGDDTGSMTENLTVQPERLGVLASHHDNAAVDASSGVEA<br>AAGLGESVAITHGPYCSQFNDTLNVYLTAHNALGSSLHTAGVDLAKSLRIAAKIYSEADEAWRKAIDGLFT<br>EFMDFALLPPEVNSARMYTGPGAGSLLAAAGGWDSLAAELATTAEAYGSVLSGLAALHWRGPAAESMAVTA<br>APYIGWLYTTAEKTQQTAIQARAAALAFEQAYAMTLPPPVVAANRIQLLALIATNFFGQNTAAIAATEAQY<br>AEMWAQDAAAMYGYATASAAAALLTPFSPPRQTTNPAGLTELMSTQRPRHSGIRAVGPYAWAGRCGRIGRW<br>GVHQEAMMNLAIWHPRKVQSATIYQVTDRSHDGRTARVPGDEITSTVSGWLSELGTQSPLADELARAVRIG<br>DWPAAYAIGEHLSVEIAVAVKLACKTVTLTVDGTAMRVTTMKSRVIDIVEENGFSVDDRDDLYPAAGVQVH<br>DADTIVLRRSRPLQISLDGHDAKQVWTTASTVDEALAQLAMTDTAPAAASRASRVPLSGMALPVVSAKTVQ<br>LNDGGLVRTVHLPAPNVAGLLSAAGVPLLQSDHVVPAATAPIVEGMQIQVTRNRIKKVTERLPLPPNARRV<br>EDPEMNMSREVVEDPGVPGTQDVTFAVAEVNGVETGRLPVANVVVTPAHEAVVRVGTKPGTEVPPVIDGSI<br>WDAIAGCEAGGNWAINTGNGYYGGVQFDQGTWEANGGLRYAPRADLATREEQIAVAEVTRLRQGWGAWPVC<br>AARAGAR<br>(SEQ ID NO: 61) |
| M | atgacggaaaacttgaccgtccagcccgagcgtctcggtgtactggcgtcgcaccatgacaacgcggcggt<br>cgatgcctcctcgggcgtcgaagctgccgctggcctaggcgaatctgtggcgatcactcacggtccgtact<br>gctcacagttcaacgacacgttaaatgtgtacttgactgcccacaatgccctgggctcgtccttgcatacg<br>gccggtgtcgatctcgccaaaagtcttcgaattgcggcgaagatatatagcgaggccgacgaagcgtggcg<br>caaggctatcgacgggttgtttacc**ggattc**atgtccacgcaacgaccgaggcactccggtattcgggctg<br>ttggcccctacgcatgggccggccgatgtggtcggataggcaggtgggggtgcaccaggaggcgatgatg<br>aatctagcgatatggcacccgcgcaaggtgcaatccgccaccatctatcaggtgaccgatcgctcgcacga<br>cgggcgcacagcacgggtgcctggtgacgagatcactagcaccgtgtccggttggttgtcggagttgggca<br>cccaaagcccgttggccgatgagcttgcgcgtgcggtgcggatcggcgactggcccgctgcgtacgcaatc<br>ggtgagcacctgtccgttgagattgccgttgcggtc**gaattc**gcatgcaaaacggtgacgttgaccgtcga<br>cggaaccgcgatgcgggtgaccacgatgaaatcgcgggtgatcgacatcgtcgaagagaacgggttctcag |

TABLE 2-continued

| Construct | nucleotide sequence<br>amino acid sequence |
|---|---|
| | tcgacgaccgcgacgacctgtatcccgcggccggcgtgcaggtccatgacgccgacaccatcgtgctgcgg<br>cgtagccgtccgctgcagatctcgctggatggtcacgacgctaagcaggtgtggacgaccgcgtcgacggt<br>ggacgaggcgctggcccaactcgcgatgaccgacacggcgccggccgcggcttctcgcgccagccgcgtcc<br>cgctgtccgggatggcgctaccggtcgtcagcgccaagacggtgcagctcaacgacggcgggttggtgcgc<br>acggtgcacttgccggcccccaatgtcgcggggctgctgagtgcggccggcgtgccgctgttgcaaagcga<br>ccacgtggtgcccgccgcgacggccccgatcgtcgaaggcatgcagatccaggtgacccgcaatcggatca<br>agaaggtcaccgagcggctgccgctgccgccgaacgcgcgtcgtgtcgaggacccggagatgaacatgagc<br>cgggaggtcgtcgaagacccggggg ttccggggacccaggatgtgacgttcgcggtagctgaggtcaacgg<br>cgtcgagaccggccgtttgcccgtcgccaacgtcgtggtgaccccggcccacgaagccgtggtgcgggtgg<br>gcaccaagcccggtaccgaggtgcccccggtgatcgacggaagcatctgggacgcgatcgccggctgtgag<br>gccggtggcaactgggcgatcaacaccggcaacgggtattacggtggtgtgcagtttgaccagggcacctg<br>ggaggccaacggcgggctgcggtatgcaccccgcgctgacctcgccacccgcgaagagcagatcgccgttg<br>ccgaggtgacccgactgcgtcaaggttggggcgcctggccggtatgtgctgcacgagcgggtgcgcgc**gag**<br>**ctc**atggatttcgcactgttaccaccggaagtcaactccgcccggatgtacaccggccctggggcaggatc<br>gctgttggctgccgcgggcggctgggattcgctggccgccgagttggccaccacagccgaggcatatggat<br>cggtgctgtccggactggccgccttgcattggcgtggaccggcagcggaatcgatggcggtgacggccgct<br>ccctatatcggttggctgtacacgaccgccgaaaagacacagcaaacagcgatccaagccagggcggcagc<br>gctggccttcgagcaagcatacgcaatgaccctgccgccaccggtggtagcggccaaccggatacagctgc<br>tagcactgatcgcgacgaacttcttcggccagaacactgcggcgatcgcggccaccgaggcacagtacgcc<br>gagatgtgggcccaggacgccgccgcgatgtacggttacgccaccgcctcagcggctgcggccctgctgac<br>accgttctccccgccgcggcagaccaccaacccggccggcctgacc**aagctt**atggtgtccacttacagat<br>caccggatcgcgcttggcaggcgctggcggacggcactcgccgggccatcgtggagcggctggcgcacggc<br>ccgctggccgtcggcgagttggcccgcgacctgcccgtcagccgacccgcggtgtcacagcacctcaaagt<br>gctcaagaccgccaggctggtgtgcgaccgccccgcgggaacacgccgcgtctaccagctcgacccgacag<br>gccttgcggcattgcgcaccgacctcgaccggttctggacacgcgccctgactggctacgcgcagctcatc<br>gactccgaaggagacgacacataa<br>(SEQ ID NO: 62)<br>MTENLTVQPERLGVLASHHDNAAVDASSGVEAAAGLGESVAITHGPYCSQFNDTLNVYLTAHNALGSSLHT<br>AGVDLAKSLRIAAKIYSEADEAWRKAIDGLFTGFMSTQRPRHSGIRAVGPYAWAGRCGRIGRWGVHQEAMM<br>NLAIWHPRKVQSATIYQVTDRSHDGRTARVPGDEITSTVSGWLSELGTQSPLADELARAVRIGDWPAAYAI<br>GEHLSVEIAVAVEFACKTVTLTVDGTAMRVTTMKSRVIDIVEENGFSVDDRDDLYPAAGVQVHDADTIVLR<br>RSRPLQISLDGHDAKQVWTTASTVDEALAQLAMTDTAPAAASRASRVPLSGMALPVVSAKTVQLNDGGLVR<br>TVHLPAPNVAGLLSAAGVPLLQSDHVVPAATAPIVEGMQIQVTRNRIKKVTERLPLPPNARRVEDPEMNMS<br>REVVEDPGVPGTQDVTFAVAEVNGVETGRLPVANVVVTPAHEAVVRVGTKPGTEVPPVIDGSIWDAIAGCE<br>AGGNWAINTGNGYYGGVQFDQGTWEANGGLRYAPRADLATREEQIAVAEVTRLRQGWGAWPVCAARAGARE<br>LMDFALLPPEVNSARMYTGPGAGSLLAAAGGWDSLAAELATTAEAYGSVLSGLAALHWRGPAAESMAVTAA<br>PYIGWLYTTAEKTQQTAIQARAAALAFEQAYAMTLPPPVVAANRIQLLALIATNFFGQNTAAIAATEAQYA<br>EMWAQDAAAMYGYATASAAAALLTPFSPPRQTTNPAGLTKLMVSTYRSPDRAWQALADGTRRAIVERLAHG<br>PLAVGELARDLPVSRPAVSQHLKVLKTARLVCDRPAGTRRVYQLDPTGLAALRTDLDRFWTRALTGYAQLI<br>DSEGDDT<br>(SEQ ID NO: 63) |
| N | atggcattttcccggccgggcttgccggtggagtacctgcaggtgccgtcgccgtcgatgggccgtgacat<br>caaggtccaattccaaagtggtggtgccaactcgcccgccctgtacctgctcgacggcctgcgcgcgcagg<br>acgacttcagcggctgggacatcaacaccccggcgttcgagtggtacgaccagtcgggcctgtcggtggtc<br>atgccggtgggtggccagtcaagcttctactccgactggtaccagcccgcctgcggcaaggccggttgcca<br>gacttacaagtgggagaccttcctgaccagcgagctgccggggtggctgcaggccaacaggcacgtcaagc<br>ccaccggaagcgccgtcgtcggtctttcgatggctgcttcttcggcgctgacgctggcgatctatcacccc<br>cagcagttcgtctacgcgggagcgatgtcgggcctgttggacccctcccaggcgatgggtcccaccctgat<br>cggcctggcgatgggtgacgctggcggctacaaggcctccgacatgtggggcccgaaggaggacccggcgt<br>ggcagcgcaacgacccgctgttgaacgtcgggaagctgatcgccaacaacacccgcgtctgggtgtactgc<br>ggcaacggcaagccgtcggatctgggtggcaacaacctgccggccaagttcctcgagggcttcgtgcggac<br>cagcaacatcaagttccaagacgcctacaacgccggtggcggccacaacggcgtgttcgacttcccggaca<br>gcggtacgcacagctgggagtactggggcgcgcagctcaacgctatgaagcccgacctgcaacgggcactg<br>ggtgccacgcccaacaccgggcccgcgccccagggcgccatgttctcccggccggggctgccggtcgagta<br>cctgcaggtgccgtcgccgtcgatgggccgcgacatcaaggttcagttccagagcggtgggaacaactcac<br>ctgcggtttatctgctcgacggcctgcgcgcccaagacgactacaacggctgggatatcaacaccccggcg<br>ttcgagtggtactaccagtcgggactgtcgatagtcatgccggtcggcgggcagtccagcttctacagcga<br>ctggtacagcccggcctgcggtaaggctggctgccagacttacaagtgggaaaccttcctgaccagcgagc<br>tgccgcaatggttgtccgccaacagggccgtgaagcccaccggcagcgctgcaatcggcttgtcgatggcc<br>ggctcgtcggcaatgatcttggccgcctaccacccccagcagttcatctacgccggctcgctgtcggccct<br>gctggacccctctcaggggatggggcctagcctgatcggcctcgcgatgggtgacgccggcggttacaagg<br>ccgcagacatgtggggtccctcgagtgacccggcatgggagcgcaacgaccctacgcagcagatccccaag<br>ctggtcgcaaacaacacccggctatgggtttattgcgggaacggcaccccgaacgagttgggcggtgccaa<br>catacccgccgagttcttggagaacttcgttcgtagcagcaacctgaagttccaggatgcgtacaacgccg<br>cgggcgggcacaacgccgtgttcaacttcccgcccaacggcacgcacagctgggagtactggggcgctcag<br>ctcaacgccatgaagggtgacctgcagagttcgttaggcgccggcatgcgtgctaccgttgggcttgtgga<br>ggcaatcggaatccgagaactaagacagcacgcatcgcgatacctcgcccgggttgaagccggcgaggaac<br>ttggcgtcaccaacaaaggaagacttgtggcccgactcatcccggtgcaggccgcggagcgttctcgcgaa<br>gcctgattgaatcaggtgtcctgattccggctcgtcgtccacaaaaccttctcgacgtcaccgccgaaccg<br>gcgcgcggccgcaagcgcaccctgtccgatgttctcaacgaaatgcgcgacgagcagtga<br>(SEQ ID NO: 64)<br>MAFSRPGLPVEYLQVPSPSMGRDIKVQFQSGGANSPALYLLDGLRAQDDFSGWDINTPAFEWYDQSGLSVV<br>MPVGGQSSFYSDWYQPACGKAGCQTYKWETFLTSELPGWLQANRHVKPTGSAVVGLSMAASSALTLAIYHP<br>QQFVYAGAMSGLLDPSQAMGPTLIGLAMGDAGGYKASDMWGPKEDPAWQRNDPLLNVGKLIANNTRVWVYC<br>GNGKPSDLGGNNLPAKFLEGFVRTSNIKFQDAYNAGGGHNGVFDFPDSGTHSWEYWGAQLNAMKPDLQRAL<br>GATPNTGPAPQGAFSRPGLPVEYLQVPSPSMGRDIKVQFQSGGNNSPAVYLLDGLRAQDDYNGWDINTPAF |

TABLE 2-continued

| Construct | nucleotide sequence<br>amino acid sequence |
|---|---|
| | EWYYQSGLSIVMPVGGQSSFYSDWYSPACGKAGCQTYKWETFLTSELPQWLSANRAVKPTGSAAIGLSMAG<br>SSAMILAAYHPQQFIYAGSLSALLDPSQGMGPSLIGLAMGDAGGYKAADMWGPSSDPAWERNDPTQQIPKL<br>VANNTRLWVYCGNGTPNELGGANIPAEFLENFVRSSNLKFQDAYNAAGGHNAVFNFPPNGTHSWEYWGAQL<br>NAMKGDLQSSLGAGAAARATVGLVEAIGIRELRQHASRYLARVEAGEELGVTNKGRLVARLIPVQAAERSR<br>EALIESGVLIPARRPQNLLDVTAEPARGRKRTLSDVLNEMRDEQ<br>(SEQ ID NO: 65) |
| O | atgaccaccgcacgcgacatcatgaacgcaggtgtgacctgtgttggcgaacacgagacgctaaccgctgc<br>cgctcaatacatgcgtgagcacgacatcggcgcgttgccgatctgcggggacgacgaccggctgcacggca<br>tgctcaccgaccgcgacattgtgatcaaaggcctggctgcgggcctagacccgaataccgccacggctggc<br>gagttggcccgggacagcatctactacgtcgatgcgaacgcaagcatccaggagatgctcaacgtcatgga<br>agaacatcaggtccgccgtgttccggtcatctcagagcaccgcttggtcggaatcgtcaccgaagccgaca<br>tcgcccgacacctgcccgagcacgccattgtgcagttcgtcaaggcaatctgctcgcccatggccctcgcc<br>agcatgatcgccacaacccgcgatcgtgaaggagccaccatgatcacgtttaggctgcgcttgccgtgccg<br>gacgatactgcgggtgttcagccgcaatccgctggtgcgtgggacggatcgactcgaggcggtcgtcatgc<br>tgctggccgtcacggtctcgctgctgactatcccgttcgccgccgcggccggcaccgcagtccaggattcc<br>cgcagccacgtctatgcccaccaggcccagacccgccatcccgcaaccgcgaccgtgatcgatcacgaggg<br>ggtgatcgacagcaacacgaccgccacgtcagcgccgccgcgcacgaagatcaccgtgcctgcccgatggg<br>tcgtgaacggaatagaacgcagcggtgaggtcaacgcgaagccgggaaccaaatccggtgaccgcgtcggc<br>atttgggtcgacagtgccggtcagctggtcgatgaaccagctccgccggcccgtgccattgcggatgcggc<br>cctggccgccttgggactctggttgagcgtcgccgcggttgcgggcgccctgctggcgctcactcgggcga<br>ttctgatccgcgttcgcaacgccagttggcaacacgacatcgacagcctgttctgcacgcagcggtga<br>(SEQ ID NO: 66)<br>MTTARDIMNAGVTCVGEHETLTAAAQYMREHDIGALPICGDDDRLHGMLTDRDIVIKGLAAGLDPNTATAG<br>ELARDSIYYVDANASIQEMLNVMEEHQVRRVPVISEHRLVGIVTEADIARHLPEHAIVQFVKAICSPMALA<br>SMIATTRDREGATMITFRLRLPCRTILRVFSRNPLVRGTDRLEAVVMLLAVTVSLLTIPFAAAAGTAVQDS<br>RSHVYAHQAQTRHPATATVIDHEGVIDSNTTATSAPPRTKITVPARWVVNGIERSGEVNAKPGTKSGDRVG<br>IWVDSAGQLVDEPAPPARAIADAALAALGLWLSVAAVAGALLALTRAILIRVRNASWQHDIDSLFCTQR<br>(SEQ ID NO: 67) |
| P | atggcgtcagggaggcatcggaaaccaactacaagcaatgtatctgttgccaagattgctttcaccggcgc<br>agttcttggaggtggcggaattgccatggctgcccaggcaacagccgctacagatggagagtgggatcagg<br>tggctcgatgtgagtctggtggcaactggtctatcaacactgggaacgggtatcttggcggcttgcaattt<br>actcagagcacttgggctgcccacggagggggtgaatttgctcctagcgcgcagctggcctcccgcgagca<br>gcagatcgctgtgggagagagggtgttggccacacagggaagaggtgcctggcctgtctgtggccgcggac<br>tcagtaatgctacccctagggaggtgctgcccgcctcagccgctatggacgctccactggatgctgccgcc<br>gtgaatggcgagccagctccgctggcacccccacctgcagaccccgctcccccagtcgagctggcggcaaa<br>cgacctgcccgcacctctcggagaaccacttcctgcagcgcctgccgatccagctccacctgctgatttgg<br>ctcccccgctcccgccgatgtagcccctccggtcgagttggctgtgaatgacctgccggcacctctgggc<br>gagcccctcccagccgctccggccgaccctgcccctcctgctgatctggcaccacccgctcctgccgacct<br>cgccccacccgccccagcagacctggctccaccagcgcctgcggatcttgccccgcctgttgagctggctg<br>tcaacgatcttcctgcgcctcttggagagcccctgcccgctgctccagccgaactcgcaccaccggcagat<br>ctggctcccgcctctgccgatcttgcacctcccgcaccggcggacttggcacctccagcaccagcagaact<br>ggctccccctgcgccggctgacctggcccctccagcagccgttaatgagcaaaccgcaccaggggaccagc<br>cggctacggcaccaggtggaccggtggggctggccaccgacctggagctgcctgagccggatccccaacca<br>gctgatgctcccccacctggcgacgtaactgaggccccagctgaaacgccccaggtcagtaacatcgctta<br>cacaaagaaactgtggcaggcaattagggctcaggacgtgtgtgggaacgacgccctggacagcttggccc<br>aaccgtacgtgatcggtatgcacccccctccccgctgatcatggtcgcagtcgctgtaaccgccaccccatt<br>tcacctctcagccttattgggaatgcgtctgctacaagtggcgacatgtctagtatgacaaggattgctaa<br>gcccctcatcaaaagtgcgatggctgccggtctggtaacagcatccatgagcttgtccaccgcagtggctc<br>acgctgggccttccccgaactgggatgccgtcgcccagtgcgagtcaggcggcaattgggccgcaaatacc<br>ggtaacggtaagtatggaggactgcagtttaaacctgcaacttgggccgcctttggaggagtgggtaatcc<br>tgcagctgcttctagagaacagcagattgccgtggctaaccgcgttctcgcggagcagggtctggacgcct<br>ggccgacctgtggcgccgcatcaggtttgccgatcgcgttgtggtcaaagcccgccagggaatcaagcaga<br>ttatcaatgagatcatctgggccggaatacaggcaagcatccctagaatgactcctgggcttctgacaacc<br>gctggcgctgggaggcccagggataggtgcgcccggatcgtttgtaccgtattcatagagaccgccgtggt<br>cgcgacaatgttcgtggctctcttgggcttgagcaccattagctctaaggccgatgatatagattgggatg<br>ctattgctcaatgcgaatccggtgggaactgggccgctaataccggaaatgggctctacggcggactgcag<br>atcagccaggctacatgggatagcaacggaggagtcgggtcccctgccgctgcatccccgcaacagcaaat<br>cgaggtggccgataacatcatgaaaacccagggacccggagcctggcccaaatgtagctcatgtagccaag<br>gagatgcgccctcggttcactgacgcacatcctcaccttcctcgccgcggaaaccggagggtgctctggca<br>gccgggacgactga<br>(SEQ ID NO: 68)<br>MSGRHRKPTTSNVSVAKIAFTGAVLGGGGIAMAAQATAATDGEWDQVARCESGGNWSINTGNGYLGGLQFT<br>QSTWAAHGGGEFAPSAQLASREQQIAVGERVLATQGRGAWPVCGRGLSNATPREVLPASAAMDAPLDAAAV<br>NGEPAPLAPPPADPAPPVELAANDLPAPLGEPLPAAPADPAPPADLAPPAPADVAPPVELAVNDLPAPLGE<br>PLPAAPADPAPPADLAPPAPADLAPPAPADLAPPAPADLAPPVELAVNDLPAPLGEPLPAAPAELAPPADL<br>APASADLAPPAPADLAPPAPAELAPPAPADLAPPAAVNEQTAPGDQPATAPGGPVGLATDLELPEPDPQPA<br>DAPPPGDVTEAPAETPQVSNIAYTKKLWQAIRAQDVCGNDALDSLAQPYVIGVHPLPADHGRSRCNRHPIS<br>PLSLIGNASATSGDMSSMTRIAKPLIKSAMAAGLVTASMSLSTAVAHAGPSPNWDAVAQCESGGNWAANTG<br>NGKYGGLQFKPATWAAFGGVGNPAAASREQQIAVANRVLAEQGLDAWPTCGAASGLPIALWSKPAQGIKQI<br>INEIIWAGIQASIPRMTPGLLTTAGAGRPRDRCARIVCTVFIETAVVATMFVALLGLSTISSKADDIDWDA<br>IAQCESGGNWAANTGNGLYGGLQISQATWDSNGGVGSPAAASPQQQIEVADNIMKTQGPGAWPKCSSCSQG<br>DAPLGSLTHILTFLAAETGGCSGSRDD<br>(SEQ ID NO: 69) |

TABLE 2-continued

| Construct | nucleotide sequence<br>amino acid sequence |
|---|---|
| Q | atggcatgcaaaacggtgacgttgaccgtcgacggaaccgcgatgcgggtgaccacgatgaaatcgcgggt<br>gatcgacatcgtcgaagagaacgggttctcagtcgacgaccgcgacgacctgtatcccgcggccggcgtgc<br>aggtccatgacgccgacaccatcgtgctgcggcgtagccgtccgctgcagatctcgctggatggtcacgac<br>gctaagcaggtgtggacgaccgcgtcgacggtggacgaggcgctggcccaactcgcgatgaccgacacggc<br>gccggccgcggcttctcgcgccagccgcgtcccgctgtccgggatggcgctaccggtcgtcagcgccaaga<br>cggtgcagctcaacgacggcgggttggtgcgcacggtgcacttgccggcccccaatgtcgcggggctgctg<br>agtgcggccggcgtgccgctgttgcaaagcgaccacgtggtgcccgccgcgacggccccgatcgtcgaagg<br>catgcagatccaggtgacccgcaatcggatcaagaaggtcaccgagcggctgccgctgccgccgaacgcgc<br>gtcgtgtcgaggacccggagatgaacatgagccgggaggtcgtcgaagacccggggggttccggggacccag<br>gatgtgacgttcgcggtagctgaggtcaacggcgtcgagaccggccgtttgcccgtcgccaacgtcgtggt<br>gaccccggcccacgaagccgtggtgcgggtgggcaccaagcccggtaccgaggtgcccccggtgatcgacg<br>gaagcatctgggacgcgatcgccggctgtgaggccggtggcaactgggcgatcaacaccggcaacgggtat<br>tacggtggtgtgcagtttgaccagggcacctgggaggccaacggcgggctgcggtatgcaccccgcgctga<br>cctcgccacccgcgaagagcagatcgccgttgccgaggtgacccgactgcgtcaaggttggggcgcctggc<br>cggtatgtgctgcacgagcgggtgcgcgc**ggatcc**atgtccacgcaacgaccgaggcactccggtattcgg<br>gctgttggcccctacgcatgggccggccgatgtggtcggataggcaggtggggggtgcaccaggaggcgat<br>gatgaatctagcgatatggcacccgcgcaaggtgcaatccgccaccatctatcaggtgaccgatcgctcgc<br>acgacgggcgcacagcacgggtgcctggtgacgagatcactagcaccgtgtccggttggttgtcggagttg<br>ggcacccaaagcccgttggccgatgagcttgcgcgtgcggtgcggatcggcgactggcccgctgcgtacgc<br>aatcggtgagcacctgtccgttgagattgccgttgcggtc**gaattc**atggatttcgcactgttaccaccgg<br>aagtcaactccgcccggatgtacaccggccctggggcaggatcgctgttggctgccgcgggcggctgggat<br>tcgctggccgccgagttggccaccacagccgaggcatatggatcggtgctgtccggactggccgccttgca<br>ttggcgtggaccggcagcggaatcgatggcggtgacggccgctccctatatcggttggctgtacacgaccg<br>ccgaaaagacacagcaaacagcgatccaagccagggcggcagcgctggccttcgagcaagcatacgcaatg<br>accctgccgccaccggtggtagcggccaaccggatacagctgctagcactgatcgcgacgaacttcttcgg<br>ccagaacactgcggcgatcgcggccaccgaggcacagtacgccgagatgtgggcccaggacgccgccgcga<br>tgtacggttacgccaccgcctcagcggctgcggccctgctgacaccgttctccccgccgcggcagaccacc<br>aacccggccggcctgacc**gagctc**gtgtccacttacagatcaccggatcgcgcttggcaggcgctggcgga<br>cggcactcgccgggccatcgtggagcggctggcgcacggcccgctggccgtcggcgagttggcccgcgacc<br>tgcccgtcagccgacccgcggtgtcacagcacctcaaagtgctcaagaccgccaggctggtgtgcgaccgc<br>cccgcgggaacacgccgcgtctaccagctcgacccgacaggccttgcggcattgcgcaccgacctcgaccg<br>gttctggacacgcgccctgactggctacgcgcagctcatcgactccgaaggagacgacaca**aagctt**atga<br>cggaaaacttgaccgtccagcccgagcgtctcggtgtactggcgtcgcaccatgacaacgcggcggtcgat<br>gcctcctcgggcgtcgaagctgccgctggcctaggcgaatctgtggcgatcactcacggtccgtactgctc<br>acagttcaacgacacgttaaatgtgtacttgactgcccacaatgccctgggctcgtccttgcatacggccg<br>gtgtcgatctcgccaaaagtcttcgaattgcggcgaagatatatagcgaggccgacgaagcgtggcgcaag<br>gctatcgacgggttgtttacctga<br>(SEQ ID NO: 70)<br>MACKTVTLTVDGTAMRVTTMKSRVIDIVEENGFSVDDRDDLYPAAGVQVHDADTIVLRRSRPLQISLDGHD<br>AKQVWTTASTVDEALAQLAMTDTAPAAASRASRVPLSGMALPVVSAKTVQLNDGGLVRTVHLPAPNVAGLL<br>SAAGVPLLQSDHVVPAATAPIVEGMQIQVTRNRIKKVTERLPLPPNARRVEDPEMNMSREVVEDPGVPGTQ<br>DVTFAVAEVNGVETGRLPVANVVVTPAHEAVVRVGTKPGTEVPPVIDGSIWDAIAGCEAGGNWAINTGNGY<br>YGGVQFDQGTWEANGGLRYAPRADLATREEQIAVAEVTRLRQGWGAWPVCAARAGARGSMSTQRPRHSGIR<br>AVGPYAWAGRCGRIGRWGVHQEAMMNLAIWHPRKVQSATIYQVTDRSHDGRTARVPGDEITSTVSGWLSEL<br>GTQSPLADELARAVRIGDWPAAYAIGEHLSVEIAVAVEFMDFALLPPEVNSARMYTGPGAGSLLAAAGGWD<br>SLAAELATTAEAYGSVLSGLAALHWRGPAAESMAVTAAPYIGWLYTTAEKTQQTAIQARAAALAFEQAYAM<br>TLPPPVVAANRIQLLALIATNFFGQNTAAIAATEAQYAEMWAQDAAAMYGYATASAAAALLTPFSPPRQTT<br>NPAGLTELVSTYRSPDRAWQALADGTRRAIVERLAHGPLAVGELARDLPVSRPAVSQHLKVLKTARLVCDR<br>PAGTRRVYQLDPTGLAALRTDLDRFWTRALTGYAQLIDSEGDDTKLMTENLTVQPERLGVLASHHDNAAVD<br>ASSGVEAAAGLGESVAITHGPYCSQFNDTLNVYLTAHNALGSSLHTAGVDLAKSLRIAAKIYSEADEAWRK<br>AIDGLFT<br>(SEQ ID NO: 71) |
| R | atgtccacgcaacgaccgaggcactccggtattcgggctgttggcccctacgcatgggccggccgatgtgg<br>tcggataggcaggtggggggtgcaccaggaggcgatgatgaatctagcgatatggcacccgcgcaaggtgc<br>aatccgccaccatctatcaggtgaccgatcgctcgcacgacgggcgcacagcacgggtgcctggtgacgag<br>atcactagcaccgtgtccggttggttgtcggagttgggcacccaaagcccgttggccgatgagcttgcgcg<br>tgcggtgcggatcggcgactggcccgctgcgtacgcaatcggtgagcacctgtccgttgagattgccgttg<br>cggtc**ggatc**atggatttcgcactgttaccaccggaagtcaactccgcccggatgtacaccggccctgggg<br>caggatcgctgttggctgccgcgggcggctgggattcgctggccgccgagttggccaccacagccgaggca<br>tatggatcggtgctgtccggactggccgccttgcattggcgtggaccggcagcggaatcgatggcggtgac<br>ggccgctccctatatcggttggctgtacacgaccgccgaaaagacacagcaaacagcgatccaagccaggg<br>cggcagcgctggccttcgagcaagcatacgcaatgaccctgccgccaccggtggtagcggccaaccggata<br>cagctgctagcactgatcgcgacgaacttcttcggccagaacactgcggcgatcgcggccaccgaggcaca<br>gtacgccgagatgtgggcccaggacgccgccgcgatgtacggttacgccaccgcctcagcggctgcggccc<br>tgctgacaccgttctccccgccgcggcagaccaccaacccggccggcctgacc**gaattc**atggcatgcaaa<br>acggtgacgttgaccgtcgacggaaccgcgatgcgggtgaccacgatgaaatcgcgggtgatcgacatcgt<br>cgaagagaacgggttctcagtcgacgaccgcgacgacctgtatcccgcggccggcgtgcaggtccatgacg<br>ccgacaccatcgtgctgcggcgtagccgtccgctgcagatctcgctggatggtcacgacgctaagtcaggt<br>gtggacgaccgcgtcgacggtggacgaggcgctggcccaactcgcgatgaccgacacggcgccggccgcgg<br>cttctcgcgccagccgcgtcccgctgtccgggatggcgctaccggtcgtcagcgccaagacggtgcagctc<br>aacgacggcgggttggtgcgcacggtgcacttgccggcccccaatgtcgcggggctgctgagtgcggccgg<br>cgtgccgctgttgcaaagcgaccacgtggtgcccgccgcgacggccccgatcgtcgaaggcatgcagatcc<br>aggtgacccgcaatcggatcaagaaggtcaccgagcggctgccgctgccgccgaacgcgcgtcgtgtcgag<br>gacccggagatgaacatgagccgggaggtcgtcgaagacccggggggttccggggacccaggatgtgacgtt<br>cgcggtagctgaggtcaacggcgtcgagaccggccgtttgcccgtcgccaacgtcgtggtgaccccggccc<br>acgaagccgtggtgcgggtgggcaccaagcccggtaccgaggtgcccccggtgatcgacggaagcatctgg |

TABLE 2-continued

| Construct | nucleotide sequence<br>amino acid sequence |
|---|---|
| | gacgcgatcgccggctgtgaggccggtggcaactgggcgatcaacaccggcaacgggtattacggtggtgt<br>gcagtttgaccagggcacctgggaggccaacggcgggctgcggtatgcaccccgcgctgacctcgccaccc<br>gcgaagagcagatcgccgttgccgaggtgacccgactgcgtcaaggttggggcgcctggccggtatgtgct<br>gcacgagcgggtgcgcgc**gagctc**gtgtccacttacagatcaccggatcgcgcttggcaggcgctggcgga<br>cggcactcgccgggccatcgtggagcggctggcgcacggcccgctggccgtcggcgagttggcccgcgacc<br>tgcccgtcagccgacccgcggtgtcacagcacctcaaagtgctcaagaccgccaggctggtgtgcgaccgc<br>cccgcgggaacacgccgcgtctaccagctcgacccgacaggccttgcggcattgcgcaccgacctcgaccg<br>gttctggacacgcgccctgactggctacgcgcagctcatcgactccgaaggagacgacaca**aagctt**atga<br>cggaaaacttgaccgtccagcccgagcgtctcggtgtactggcgtcgcaccatgacaacgcggcggtcgat<br>gcctcctcgggcgtcgaagctgccgctggcctaggcgaatctgtggcgatcactcacggtccgtactgctc<br>acagttcaacgacacgttaaatgtgtacttgactgcccacaatgccctgggctcgtccttgcatacggccg<br>gtgtcgatctcgccaaaagtcttcgaattgcggcgaagatatatagcgaggccgacgaagcgtggcgcaag<br>gctatcgacgggttgtttacctga<br>(SEQ ID NO: 72)<br>MSTQRPRHSGIRAVGPYAWAGRCGRIGRWGVHQEAMMNLAIWHPRKVQSATIYQVTDRSHDGRTARVPGDE<br>ITSTVSGWLSELGTQSPLADELARAVRIGDWPAAYAIGEHLSVEIAVAVGFMDFALLPPEVNSARMYTGPG<br>AGSLLAAAGGWDSLAAELATTAEAYGSVLSGLAALHWRGPAAESMAVTAAPYIGWLYTTAEKTQQTAIQAR<br>AAALAFEQAYAMTLPPPVVAANRIQLLALIATNFFGQNTAAIAATEAQYAEMWAQDAAAMYGYATASAAAA<br>LLTPFSPPRQTTNPAGLTEFMACKTVTLTVDGTAMRVTTMKSRVIDIVEENGFSVDDRDDLYPAAGVQVHD<br>ADTIVLRRSRPLQISLDGHDAKQVWTTASTVDEALAQLAMTDTAPAAASRASRVPLSGMALPVVSAKTVQL<br>NDGGLVRTVHLPAPNVAGLLSAAGVPLLQSDHVVPAATAPIVEGMQIQVTRNRIKKVTERLPLPPNARRVE<br>DPEMNMSREVVEDPGVPGTQDVTFAVAEVNGVETGRLPVANVVVTPAHEAVVRVGTKPGTEVPPVIDGSIW<br>DAIAGCEAGGNWAINTGNGYYGGVQFDQGTWEANGGLRYAPRADLATREEQIAVAEVTRLRQGWGAWPVCA<br>ARAGARELVSTYRSPDRAWQALADGTRRAIVERLAHGPLAVGELARDLPVSRPAYSQHLKVLKTARLVCDR<br>PAGTRRVYQLDPTGLAALRTDLDRFWTRALTGYAQLIDSEGDDTKLMTENLTVQPERLGVLASHHDNAAVD<br>ASSGVEAAAGLGESVAITHGPYCSQFNDTLNVYLTAHNALGSSLHTAGVDLAKSLRIAAKIYSEADEAWRK<br>AIDGLFT<br>(SEQ ID NO: 73) |
| S | atgtccacgcaacgaccgaggcactccggtattcgggctgttggcccctacgcatgggccggccgatgtgg<br>tcggataggcaggtgggggtgcaccaggaggcgatgatgaatctagcgatatggcacccgcgcaaggtgc<br>aatccgccaccatctatcaggtgaccgatcgctcgcacgacgggcgcacagcacgggtgcctggtgacgag<br>atcactagcaccgtgtccggttggttgtcggagttgggcacccaaagcccgttggccgatgagcttgcgcg<br>tgcggtgcggatcggcgactggcccgctgcgtacgcaatcggtgagcacctgtccgttgagattgccgttg<br>cggtc**ggattc**atggatttcgcactgttaccaccggaagtcaactccgcccggatgtacaccggccctggg<br>gcaggatcgctgttggctgccgcgggcggctgggattcgctggccgccgagttggccaccacagccgaggc<br>atatggatcggtgctgtccggactggccgccttgcattggcgtggaccggcagcggaatcgatggcggtga<br>cggccgctccctatatcggttggctgtacacgaccgccgaaaagacacagcaaacagcgatccaagccagg<br>gcggcagcgctggccttcgagcaagcatacgcaatgaccctgccgccaccggtggtagcggccaaccggat<br>acagctgctagcactgatcgcgacgaacttcttcggccagaacactgcggcgatcgcggccaccgaggcac<br>agtacgccgagatgtgggcccaggacgccgccgcgatgtacggttacgccaccgcctcagcggctgcggcc<br>ctgctgacaccgttctccccgccgcggcagaccaccaacccggccggcctgacc**gaattc**gtgtccactta<br>cagatcaccggatcgcgcttggcaggcgctggcggacggcactcgccgggccatcgtggagcggctggcgc<br>acggcccgctggccgtcggcgagttggcccgcgacctgcccgtcagccgacccgcggtgtcacagcacctc<br>aaagtgctcaagaccgccaggctggtgtgcgaccgccccgcgggaacacgccgcgtctaccagctcgaccc<br>gacaggccttgcggcattgcgcaccgacctcgaccggttctggacacgcgccctgactggctacgcgcagc<br>tcatcgactccgaaggagacgacaca**gagctc**atgacggaaaacttgaccgtccagcccgagcgtctcggt<br>gtactggcgtcgcaccatgacaacgcggcggtcgatgcctcctcgggcgtcgaagctgccgctggcctagg<br>cgaatctgtggcgatcactcacggtccgtactgctcacagttcaacgacacgttaaatgtgtacttgactg<br>cccacaatgccctgggctcgtccttgcatacggccggtgtcgatctcgccaaaagtcttcgaattgcggcg<br>aagatatatagcgaggccgacgaagcgtggcgcaaggctatcgacgggttgtttacc**aagctt**atggcatg<br>caaaacggtgacgttgaccgtcgacggaaccgcgatgcgggtgaccacgatgaaatcgcgggtgatcgaca<br>tcgtcgaagagaacgggttctcagtcgacgaccgcgacgacctgtatcccgcggccggcgtgcaggtccat<br>gacgccgacaccatcgtgctgcggcgtagccgtccgctgcagatctcgctggatggtcacgacgctaagca<br>ggtgtggacgaccgcgtcgacggtggacgaggcgctggcccaactcgcgatgaccgacacggcgccggccg<br>cggcttctcgcgccagccgcgtcccgctgtccgggatggcgctaccggtcgtcagcgccaagacggtgcag<br>ctcaacgacggcgggttggtgcgcacggtgcacttgccggcccccaatgtcgcggggctgctgagtgcggc<br>cggcgtgccgctgttgcaaagcgaccacgtggtgcccgccgcgacggccccgatcgtcgaaggcatgcaga<br>tccaggtgacccgcaatcggatcaagaaggtcaccgagcggctgccgctgccgccgaacgcgcgtcgtgtc<br>gaggacccggagatgaacatgagccgggaggtcgtcgaagacccgggggttccggggacccaggatgtgac<br>gttcgcggtagctgaggtcaacggcgtcgagaccggccgtttgcccgtcgccaacgtcgtggtgaccccgg<br>cccacgaagccgtggtgcgggtgggcaccaagcccggtaccgaggtgcccccggtgatcgacggaagcatc<br>tgggacgcgatcgccggctgtgaggccggtggcaactgggcgatcaacaccggcaacgggtattacggtgg<br>tgtgcagtttgaccagggcacctgggaggccaacggcgggctgcggtatgcaccccgcgctgacctcgcca<br>cccgcgaagagcagatcgccgttgccgaggtgacccgactgcgtcaaggttggggcgcctggccggtatgt<br>gctgcacgagcgggtgcgcgctga<br>(SEQ ID NO: 74)<br>MSTQRPRHSGIRAVGPYAWAGRCGRIGRWGVHQEAMMNLAIWHPRKVQSATIYQVTDRSHDGRTARVPGDE<br>ITSTVSGWLSELGTQSPLADELARAVRIGDWPAAYAIGEHLSVEIAVAVGFMDFALLPPEVNSARMYTGPG<br>AGSLLAAAGGWDSLAAELATTAEAYGSVLSGLAALHWRGPAAESMAVTAAPYIGWLYTTAEKTQQTAIQAR<br>AAALAFEQAYAMTLPPPVVAANRIQLLALIATNFFGQNTAAIAATEAQYAEMWAQDAAAMYGYATASAAAA<br>LLTPFSPPRQTTNPAGLTEFVSTYRSPDRAWQALADGTRRAIVERLAHGPLAVGELARDLPVSRPAVSQHL<br>KVLKTARLVCDRPAGTRRVYQLDPTGLAALRTDLDRFWTRALTGYAQLIDSEGDDTELMTENLTVQPERLG<br>VLASHHDNAAVDASSGVEAAAGLGESVAITHGPYCSQFNDTLNVYLTAHNALGSSLHTAGVDLAKSLRIAA<br>KIYSEADEAWRKAIDGLFTKLMACKTVTLTVDGTAMRVTTMKSRVIDIVEENGFSVDDRDDLYPAAGVQVH<br>DADTIVLRRSRPLQISLDGHDAKQVWTTASTVDEALAQLAMTDTAPAAASRASRVPLSGMALPVVSAKTVQ<br>LNDGGLVRTVHLPAPNVAGLLSAAGVPLLQSDHVVPAATAPIVEGMQIQVTRNRIKKVTERLPLPPNARRV |

TABLE 2-continued

| Construct | nucleotide sequence<br>amino acid sequence |
|---|---|
| | EDPEMNMSREVVEDPGVPGTQDVTFAVAEVNGVETGRLPVANVVVTPAHEAVVRVGTKPGTEVPPVIDGSI<br>WDAIAGCEAGGNWAINTGNGYYGGVQFDQGTWEANGGLRYAPRADLATREEQIAVAEVTRLRQGWGAWPVC<br>AARAGAR<br>(SEQ ID NO: 75) |

Any Mtb antigen, including any Mtb antigen within any of the fusion proteins described herein, can have an amino acid sequence that is 100%, or from 70% to 99.9%, identical to the particular amino acid sequence listed in Tables 1 and 2. The amino acid sequence of any individual Mtb antigen, including any Mtb antigen within any of the fusion proteins described herein, can be at least 70%, at least 75%, at least 80%, at least 85%, at least 90%, at least 95%, at least 96%, at least 97%, at least 98%, or at least 99% identical to the particular amino acid sequence listed in Tables 1 and 2. Identity or similarity with respect to an amino acid or nucleotide sequence is defined herein as the percentage of amino acid residues (or nucleotide residues as the case may be) in the particular Mtb antigen that are identical (i.e., same residue) with the amino acid or nucleotide sequence for the Mtb antigen shown in Tables 1 and 2, after aligning the sequences and introducing gaps, if necessary, to achieve the maximum percent sequence identity. Percent sequence identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Any amino acid number calculated as a % identity can be rounded up or down, as the case may be, to the closest whole number.

Any Mtb antigen, including any Mtb antigen within any of the fusion proteins described herein, can be fragments of the particular amino acid sequence listed in Table 1. The amino acid sequence of any individual Mtb antigen, including any Mtb antigen within any of the fusion proteins described herein, can be missing consecutive amino acids constituting at least 20%, at least 15%, at least 10%, at least 5%, at least 4%, at least 3%, at least 2%, or at least 1%, of the particular amino acid sequence listed in Table 1. The omitted consecutive amino acids may be from the C-terminus or N-terminus portion of the antigen. Alternately, the omitted consecutive amino acids may be from the internal portion of the antigen, thus retaining at least its C-terminus and N-terminus amino acids of the antigen.

Any Mtb antigen, including any Mtb antigen within any of the fusion proteins described herein, can have one or more amino acid additions, deletions, or substitutions compared to the particular amino acid sequence listed in Table 1. Any individual Mtb antigen, including any Mtb antigen within any of the fusion proteins described herein, can have at least one, at least two, at least three, at least four, at least five, at least six, at least seven, at least eight, at least nine, at least ten, at least eleven, or at least twelve amino acid additions, deletions, or substitutions compared to the particular amino acid sequence listed in Table 1. Any individual Mtb antigen, including any Mtb antigen within any of the fusion proteins described herein, can have one, two, three, four, five, six, seven, eight, nine, ten, eleven, or twelve amino acid additions, deletions, or substitutions compared to the particular amino acid sequence listed in Table 1. The amino acid additions, deletions, or substitutions can take place at any amino acid position within the Mtb antigen.

Where a particular Mtb antigen, including any Mtb antigen within any of the fusion proteins described herein, comprises at least one or more substitutions, the substituted amino acid(s) can each be, independently, any naturally occurring amino acid or any non-naturally occurring amino acid. Thus, a particular Mtb antigen may comprise one or more amino acid substitutions that are naturally occurring amino acids and/or one or more amino acid substitutions that are non-naturally occurring amino acids. Individual amino acid substitutions are selected from any one of the following: 1) the set of amino acids with nonpolar sidechains, for example, Ala, Cys, Ile, Leu, Met, Phe, Pro, Val; 2) the set of amino acids with negatively charged side chains, for example, Asp, Glu; 3) the set of amino acids with positively charged sidechains, for example, Arg, His, Lys; and 4) the set of amino acids with uncharged polar sidechains, for example, Asn, Cys, Gln, Gly, His, Met, Phe, Ser, Thr, Trp, Tyr, to which are added Cys, Gly, Met and Phe. Substitutions of a member of one class with another member of the same class are contemplated herein. Naturally occurring amino acids include, for example, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Non-naturally occurring amino acids include, for example, norleucine, omithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Briefly, these procedures involve chemically activating a suppressor tRNA with a non-naturally occurring amino acid residue followed by in vitro transcription and translation of the RNA.

The Mtb antigens, including any Mtb antigen within any of the fusion proteins described herein, which are modified as described herein retain their ability to elicit an immune response against *Mycobacterium tuberculosis*. That is, modification of a particular Mtb antigen, including any Mtb antigen within any of the fusion proteins described herein, will still allow the resultant Mtb antigen, or fusion protein comprising the same, to elicit an immune response against *Mycobacterium tuberculosis*.

The present disclosure also provides nucleic acid molecules encoding any of the fusion proteins described herein that comprise at least three *Mycobacterium tuberculosis* (Mtb) antigens. The nucleic acid molecules described herein and in Tables 1 and 2 are representative. The specific sequences recited in Table 1 are simply one example of a nucleic acid molecule that can encode a particular Mtb antigen within a fusion protein. One skilled in the art having knowledge of the genetic code can routinely prepare and design a plethora of nucleic acid molecules encoding the same Mtb antigen. The length and nucleotide content of any particular nucleic acid molecule is dictated by the desired amino acid sequence of the encoded Mtb antigen. The nucleic acid molecule sequences shown in Tables 1 and 2 are DNA, although RNA nucleic acid molecules are also contemplated.

The present disclosure also provides vectors encoding any of the Mtb antigens, including Mtb antigens within any of the fusion proteins described herein, including any of the modified versions described herein. The vector can be capable of expressing an Mtb antigen in the cell of a mammal in a quantity effective to elicit an immune response in the mammal. The vector can be recombinant. The vector can comprise heterologous nucleic acid encoding the antigen. The vector can be a plasmid. In some embodiments, the plasmid is a DNA plasmid, such as a pVAX backbone vector. The vector can be useful for transfecting cells with nucleic acid encoding an Mtb antigen, which the transformed host cell is cultured and maintained under conditions wherein expression of the antigen takes place.

In some embodiments, coding sequences can be optimized for stability and high levels of expression. In some instances, codons are selected to reduce secondary structure formation of the RNA such as that formed due to intramolecular bonding.

In some embodiments, the vectors can comprise regulatory elements for gene expression of the coding sequences of the nucleic acid. The regulatory elements can be a promoter, an enhancer an initiation codon, a stop codon, or a polyadenylation signal. In some embodiments, the vector can comprise heterologous nucleic acid encoding an Mtb antigen and can further comprise an initiation codon, which is upstream of the antigen coding sequence, and a stop codon, which is downstream of the antigen coding sequence. The initiation and termination codon are in frame with the antigen coding sequence.

The vector can also comprise a promoter that is operably linked to the antigen coding sequence. The promoter operably linked to the Mtb antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter, or the like. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Representative examples of promoters include the bacteriophage T7 promoter, bacteriophage T3 promoter, SP6 promoter, lac operator-promoter, tac promoter, mycobacterial Hsp60 promoter, SV40 late promoter, SV40 early promoter, RSV-LTR promoter, CMV IE promoter, SV40 early promoter or SV40 late promoter and the CMV IE promoter.

The vector can also comprise a polyadenylation signal, which can be downstream of the antigen coding sequence. The polyadenylation signal can be a SV40 polyadenylation signal, LTR polyadenylation signal, CMV polyadeylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the consensus BoNT-A, BoNT-B, BoNT-E, and BoNT-F antigen sequences. The enhancer can be necessary for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The vector can also comprise a regulatory sequence, which can be well suited for gene expression in a mammalian or human cell into which the vector is administered. The consensus coding sequence can comprise a codon, which can allow more efficient transcription of the coding sequence in the host cell.

The vector can be pSE420 (Invitrogen, San Diego, Calif.) or pET28b (EMD Millipore, Billerca, Mass.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989).

In some embodiments, the vector is a viral vector. Suitable viral vectors include, but are not limited to, an adenovirus vector, an adeno-associated virus vector, a poxvirus vector (such as, for example, vaccinia virus vector), a paramyxovirus vector, a fowlpox virus vector, an attenuated yellow fever vectors (such as, for example, YFV-17D), an alphavirus vector, a retrovirus vector (such as, for example, lentivirus vector), a Sendai virus vector, and cytomegalovirus (CMV) vector. Suitable adenovirus vectors include, but are not limited to, adenovirus 4, adenovirus 5, chimpanzee adenovirus 3, chimpanzee adenovirus 63, and chimpanzee adenovirus 68. A suitable vaccinia virus vector includes, but is not limited to, modified vaccinia Ankara (MVA). Suitable paramyxovirus vectors include, but are not limited to, modified parainfluenza virus (PIV2) and recombinant human parainfluenza virus (rHPIV2). Suitable CMV vectors include, but are not limited to, Rhesus Macaque CMV (RhCMV) vectors and Human CMV (HCMV) vectors. In some embodiments, the vector is present within a composition comprising a pharmaceutically acceptable carrier. One skilled in the art is readily familiar with numerous vectors, many of which are commercially available.

In some embodiments, the vector is a non-viral vector. In some embodiments, the non-viral vector is RNA, such as mRNA. In some embodiments, the mRNA is protamine-complexed mRNA, wherein the Mtb antigen or fusion protein is encoded by the mRNA, and the protamine complexes contribute a strong immunostimulatory signal. An exemplary mRNA vector platform is RNActive® (CureVac Inc).

The present disclosure also provides host cells comprising any of the nucleic acid molecules or vectors disclosed herein. The host cells can be used, for example, to express the Mtb antigens, or fragments of thereof. The Mtb antigens, or fragments thereof, can also be expressed in cells in vivo. The host cell that is transformed (for example, transfected) to produce the Mtb antigens, or fragments of thereof can be an immortalised mammalian cell line, such as those of lymphoid origin (for example, a myeloma, hybridoma, trioma or quadroma cell line). The host cell can also include normal lymphoid cells, such as B-cells, that have been immortalized by transformation with a virus (for example, the Epstein-Barr virus).

In some embodiments, the host cells include, but are not limited to: bacterial cells, such as *E. coli, Caulobacter crescentus, Streptomyces species*, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda* (for example, Sf9 and Sf21 cell lines, and expresSF™ cells (Protein Sciences Corp., Meriden, Conn., USA)), *Drosophila* S2 cells, and *Trichoplusia* in High Five® Cells (Invitrogen, Carlsbad, Calif., USA); and mammalian cells, such as COS1 and COS7 cells, Chinese hamster ovary (CHO) cells, NS0 myeloma cells, NIH 3T3 cells, 293 cells, Procell92S, perC6, HEPG2 cells, HeLa cells, L cells, HeLa, MDCK, HEK293, WI38, murine ES cell lines (for example, from strains 129/SV, C57/BL6, DBA-1, 129/SVJ), K562, Jurkat cells, and BW5147. Other useful mammalian cell lines are well known and readily available from the American Type Culture Collection ("ATCC") (Manassas, Va., USA) and the National Institute of General Medical Sciences (NIGMS) Human Genetic Cell Repository at the Coriell Cell Repositories (Camden, N.J., USA). In some embodiments, the cell is a recombinant BCG. These cell types are only representative and are not meant to be an exhaustive list.

Among other considerations, some of which are described above, a host cell strain may be chosen for its ability to process the expressed Mtb antigens, or fragment thereof, in the desired fashion. Post-translational modifications of the polypeptide include, but are not limited to, glycosylation, acetylation, carboxylation, phosphorylation, lipidation, and acylation, and it is an aspect of the present disclosure to provide Mtb antigens thereof with one or more of these post-translational modifications.

In some embodiments, the recombinant BCG has been genetically engineered to express a functional endosomalytic protein that is bioactive at pH values near neutrality (e.g. about pH 6-8 or about 6.5 to 7.5). The endosomalytic protein is active within Mycobacteria-containing endosomes, which typically have an internal pH near neutrality. The activity of the endosomalytic protein produced by the rBCG results in disruption of the endosome, permitting the rBCG to escape from the endosome and into the cytoplasm of the cell. In some embodiments, the endosomalytic protein that is introduced into the rBCG by genetic engineering is Perfringolysin 0 (PfoA) from *Clostridium perfringens* or a mutant thereof, such as $PfoA_{G137Q}$, as described in WO 2007/058663.

In some embodiments, the Mycobacteria are attenuated, as exemplified by BCG. However, those of skill in the art will recognize that other attenuated and nonattenuated Mycobacteria exist which would also be suitable for use herein. Examples of additional types of Mycobacteria include, but are not limited to, *M. tuberculosis* strain CDC1551, *M. tuberculosis* strain Beijing, *M. tuberculosis* strain H37Ra (ATCC #:25177), *M. tuberculosis* strain H37Rv (ATCC #:25618), *M. bovis* (ATCC #:19211 and 27291), *M. fortuitum* (ATCC #:15073), *M. smegmatis* (ATCC #:12051 and 12549), *M. intracellulare* (ATCC #:35772 and 13209), *M. kansasii* (ATCC #:21982 and 35775) *M. avium* (ATCC #:19421 and 25291), *M. gallinarum* (ATCC #:19711), *M. vaccae* (ATCC #:15483 and 23024), *M. leprae* (ATCC #:), *M. marianum* (ATCC #:11566 and 11567), and *M. microtti* (ATCC #:11152).

Examples of attenuated *Mycobacterium* strains include, but are not restricted To, *M. tuberculosis* pantothenate auxotroph strain, *M. tuberculosis* rpoV mutant strain, *M. tuberculosis* leucine auxotroph strain, BCG Danish strain (ATCC #35733), BCG Japanese strain (ATCC #35737), BCG Chicago strain (ATCC #27289), BCG Copenhagen strain (ATCC #: 27290), BCG Pasteur strain (ATCC #: 35734), BCG Glaxo strain (ATCC #: 35741), BCG Connaught strain (ATCC #35745), BCG Montreal (ATCC #35746), BCG1331 strain, BCG Tokyo strain, BCG Moreau strain, BCG-Pasteur Aeras, and BCG Moscow strain.

In some embodiments, the cell comprising the one or more vector(s) is present within a composition comprising a pharmaceutically acceptable carrier.

In some embodiments, the Mtb antigen, or fragment thereof, is labeled with a detectable marker. Detectable markers include, but are not limited to, radioactive isotopes (such as $P^{32}$ and $S^{35}$), enzymes (such as horseradish peroxidase, chloramphenicol acetyltransferase (CAT), β-galactosidase (β-gal), and the like), fluorochromes, chromophores, colloidal gold, dyes, and biotin. The labeled Mtb antigens, or fragments thereof, can be used to carry out diagnostic procedures in a variety of cell or tissue types. For imaging procedures, in vitro or in vivo, the Mtb antigens can be labeled with additional agents, such as NMR contrasting agents, X-ray contrasting agents, or quantum dots. Methods for attaching a detectable agent to polypeptides are known in the art. The Mtb antigens can also be attached to an insoluble support (such as a bead, a glass or plastic slide, or the like).

In some embodiments, the Mtb antigens, or fragment thereof, can be conjugated to a therapeutic agent including, but not limited to, radioisotopes (such as $^{111}In$ or $^{90}Y$), toxins (such as tetanus toxoid or ricin), toxoids, and chemotherapeutic agents.

In some embodiments, the Mtb antigens, or fragments thereof, can be conjugated to an imaging agent. Imaging agents include, for example, a labeling moiety (such as biotin, fluorescent moieties, radioactive moieties, histidine tag or other peptide tags) for easy isolation or detection.

The present disclosure also provides compositions comprising at least two or three *Mycobacterium tuberculosis* (Mtb) antigens. In some embodiments, the at least two or three Mtb antigens are not present in a fusion protein. In some embodiments, the at least two or three Mtb antigens are in the form of a protein and not nucleic acid molecules encoding the Mtb antigens.

In some embodiments, the Mtb antigen is Rv1009, Rv3136, Rv3615c, Rv2628, Rv2034, Rv3136 N-terminus, Ag85A, Ag85B (also known as Rv1886c), Rv3407, Rv1733, Rv2626c, RpfA, RpfC, or RpfD. In some embodiments, the composition comprises at least two Mtb antigens. In some embodiments, the composition comprises Rv1733 and Rv2626c Mtb antigens. In some embodiments, the composition comprises at least three Mtb antigens. In some embodiments, the composition comprises Rv1009, Rv3615c, and Rv3136 Mtb antigens. In some embodiments, the composition comprises Rv1009, Rv2034, and Rv3136 Mtb antigens. In some embodiments, the composition comprises Ag85A, Ag85B, and Rv3407 Mtb antigens. In some embodiments, the composition comprises RpfA, RpfC, and RpfD Mtb antigens. In some embodiments, the composition comprises at least four Mtb antigens. In some embodiments, the composition comprises Rv1009, Rv2628, Rv3615c, and Rv3136 Mtb antigens. In some embodiments, the composition comprises Rv1009, Rv3615c, Rv2034, and Rv2628 Mtb antigens. In some embodiments, the composition comprises Rv2034, Rv3615c, Rv2628, and Rv3136 Mtb antigens. In some embodiments, the composition comprises at least five Mtb antigens. In some embodiments, the composition comprises Rv1009, Rv2034, Rv2628, Rv3615c, and Rv3136 Mtb antigens. In some embodiments, the composition comprises Rv1009, Rv3136Nt, Rv2628, Rv2034, and Rv3615c Mtb antigens. In some embodiments, the composition further comprises a pharmaceutically acceptable carrier.

The present disclosure also provides compositions comprising at least two or three *Mycobacterium tuberculosis* (Mtb) antigens, wherein the composition comprises at least one nucleic acid molecule encoding at least one of the Mtb antigens. In some embodiments, the composition comprises one Mtb antigen in protein form and one or two nucleic acid molecules encoding two Mtb antigens. In some embodiments, the composition comprises two Mtb antigens in protein form, optionally as a fusion protein, and one nucleic acid molecule encoding one Mtb antigen. Thus, the present composition is a mixture of a protein Mtb antigen(s) and nucleic acid molecule(s) encoding an Mtb antigen(s).

In some embodiments, at least two Mtb antigens are encoded by one or more nucleic acid molecules within one or more vectors. In some embodiments, the one or more vectors is one or more viral vectors. In some embodiments, the one or more viral vectors are any one or more of an adenovirus vector, an adeno-associated virus vector, a poxvirus vector (such as, for example, vaccinia virus vector), a paramyxovirus vector, a fowlpox virus vector, an attenuated yellow fever vectors (such as, for example, YFV-17D), an alphavirus vector, a retrovirus vector (such as, for example, lentivirus vector), a Sendai virus vector, and CMV vector. In some embodiments, the adenovirus vector is adenovirus 4, adenovirus 5, chimpanzee adenovirus 3, chimpanzee adenovirus 63, or chimpanzee adenovirus 68. In some embodiments, the vaccinia virus vector is MVA. In some embodiments, the paramyxovirus vector is PIV2 or rHPIV2. In some embodiments, the CMV vector is a RhCMV vector of an HCMV vector. In some embodiments, the vector is present within a composition comprising a pharmaceutically acceptable carrier. In some embodiments, the at least two Mtb antigens are encoded by a single nucleic acid molecule within the same expression vector as a fusion protein. In some embodiments, the one or more vectors is a non-viral vector. In some embodiments, the non-viral vector is RNA, such as mRNA. In some embodiments, the mRNA is protamine-complexed mRNA. An exemplary mRNA vector platform is RNActive® (CureVac Inc).

In some embodiments, where a rBCG is used as the vehicle to deliver the Mtb antigens, or fusion proteins, or nucleic acids and or vectors comprising or encoding the same, expression of all or part of the Dos R regulon is not up-regulated in the rBCG. In some embodiments, one or more of the following Dos R regulon antigens are not up-regulated in the rBCG: Rv1738, Rv2623, Rv2031c, Rv2032, Rv2626c, Rv2005c, Rv3127, Rv1733c, Rv1996, Rv2628c, Rv0079, Rv3130c, Rv3131, Rv1813c, Rv2006, Rv2029c, Rv2627c, Rv2030c, Rv3132c, and Rv2629. In some embodiments, the rBCG does not comprise up-regulation of: 1) one or more Mtb antigens, including "classical" Mtb antigens such as 85A, 85B and TB 10.4; and 2) at least one Mtb resuscitation antigen selected from Rv0867c, Rv1009, Rv1884c, Rv2389c, Rv2450c, Rv0288, Rv1009, Rv0685, Rv0824c, Rv1349, Rv2744c, Rv3347c, Rv1130, and Rv1169c. In some embodiments, the rBCG does not include the expression of the following combinations: classical antigens Rv1886c, Rv3804c; resuscitation antigens Rv0867c, Rv1884c, Rv2389c; and Mtb-specific antigen Rv3407. In some embodiments, the rBCG does not include the expression of the following combination: Rv3804c, Rv1886c, and Rv3407, or in addition with Rv3133c, and with the combination of Rv0867c, Rv1884c, and Rv2389c. In some embodiments, the rBCG does not include the expression of the following combination: TB10.4, Ag85B, Ag85A, and Rv3407. In some embodiments, the cell is not a rBCG.

The present disclosure also provides compositions comprising any one or more of the fusion proteins, Mtb antigens, nucleic acid molecules encoding Mtb antigens, including fusion proteins thereof, cells, and/or vectors and a pharmaceutically acceptable carrier. Compositions include, for example, pharmaceutical compositions. A pharmaceutically acceptable carrier refers to at least one component of a pharmaceutical preparation that is normally used for administration of active ingredients. As such, a carrier can contain any pharmaceutical excipient used in the art and any form of vehicle for administration. Carriers include, but are not limited to, phosphate buffered saline, physiological saline, water, citrate/sucrose/Tween formulations and emulsions such as, for example, oil/water emulsions.

The compositions can also include an active therapeutic agent and a variety of other pharmaceutically acceptable components. See Remington's Pharmaceutical Science (15th ed., Mack Publishing Company, Easton, Pa. (1980)). The desired form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents include, but are not limited to, distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include acacia, methylcellulose, sodium carboxymethylcellulose, polyvinylpyrrolidone (Povidone™), hydroxypropyl methylcellulose, sucrose, starch, and ethylcellulose. Lubricants that can be used include magnesium stearates, stearic acid, silicone fluid, talc, waxes, oils, and colloidal silica. Additional excipients include, for example, colorants, taste-masking agents, solubility aids, suspension agents, compressing agents, enteric coatings, sustained release aids, and the like.

In some embodiments, the compositions can be administered in the form of a depot injection or implant preparation, which can be formulated in such a manner as to permit a sustained release. An exemplary composition comprises any one or more of the compositions described herein formulated in aqueous buffer.

In some embodiments, liquid formulations of a pharmaceutical composition for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. Liquid formulations of pharmaceutical compositions can also include solutions, emulsions, syrups and elixirs containing, together with the active compound(s), wetting agents, sweeteners, and coloring and flavoring agents. Various liquid and powder formulations of the pharmaceutical compositions can be prepared by conventional methods for inhalation into the lungs of the mammal to be treated.

In some embodiments, liquid formulations of a pharmaceutical composition for injection can comprise various carriers such as vegetable oils, dimethylacetamide, dimethylformamide, ethyl lactate, ethyl carbonate, isopropyl myristate, ethanol, polyols such as, for example, glycerol, propylene glycol, liquid polyethylene glycol, and the like. In some embodiments, the composition includes a citrate/sucrose/tween carrier. For intravenous injections, water soluble versions of the compositions can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. A suitable insoluble form of the composition can be prepared and administered as a suspension in an aqueous base or a pharmaceutically acceptable oil base, such as an ester of a long chain fatty acid such as, for example, ethyl oleate.

The compositions can be, for example, injectable solutions, aqueous suspensions or solutions, non-aqueous suspensions or solutions, solid and liquid oral formulations, salves, gels, ointments, intradermal patches, creams, aerosols, lotions, tablets, capsules, sustained release formulations, and the like. In some embodiments, for topical applications, the pharmaceutical compositions can be formulated in a suitable ointment. In some embodiments, a topical semi-solid ointment formulation typically comprises a concentration of the active ingredient from about 1 to 20%, or from 5 to 10%, in a carrier, such as a pharmaceutical cream base. Some examples of formulations of a composition for topical use include, but are not limited to, drops, tinctures, lotions, creams, solutions, and ointments containing the active ingredient and various supports and vehicles.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect (see Langer, Science, 1990, 249, 1527 and Hanes, Advanced Drug Delivery Reviews, 1997, 28, 97). A sterile injectable preparation such as, for example, a sterile injectable aqueous or oleaginous suspension can also be prepared. This suspension may be formulated according to techniques known in the art using suitable dispersing, wetting, and suspending agents. In some embodiments, the pharmaceutical composition can be delivered in a microencapsulation device so as to reduce or prevent a host immune response against the protein.

In some embodiments, any of the Mtb antigens, constructs, vectors, or cells described herein, or compositions comprising the same, can be combined into a single therapeutic or prophylactic regimen. For example, in some embodiments, an antigen matched BCG can be combined or used with a recombinant protein vaccine.

In some embodiments, any of the Mtb antigens, constructs, vectors, or cells described herein, or compositions comprising the same, can be administered to a mammal as an aerosol. In some embodiments, the aerosol inocula comprises saline. Conventional aerosol delivery devices include, but are not limited to, a pressurized metered dose inhaler (pMDI) and a dry power inhaler (DPI), both of which deliver a dry powder formulation, and nebulizers such as the PARI eFlow device, which delivers an aqueous dose as a fine mist. In some embodiments, the aerosol delivery device is a Pari eFlow portable electronic aerosol delivery platform attached to a delivery mask. In some embodiments, the average particle size is from about 1 μm to about 10 μm, from about 1 μm to about 5 μm, from about 3 μm to about 5 μm, from about 4 μm to about 5 μm, or from about 3.9 μm to about 4.9 μm. In some embodiments, the aerosol is in a volume from about 0.1 ml to about 5 ml, from about 0.1 ml to about 2 ml, from about 0.1 ml to about 1.5 ml, from about 0.5 ml to about 1.5 ml, from about 0.5 ml to about 1.2 ml, from about 0.7 ml to about 1.2 ml, or about 1 ml.

Effective doses of the compositions of the present disclosure, for the treatment of a condition vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

In some embodiments, the compositions can be administered to a subject by injection intravenously, subcutaneously, intraperitoneally, intramuscularly, intramedullarily, intraventricularly, intraepidurally, intraarterially, intravascularly, intraarticularly, intrasynovially, intrasternally, intrathecally, intrahepatically, intraspinally, intratumorly, intracranially, enteral, intrapulmonary, transmucosal, intrauterine, sublingual, or locally at sites of inflammation or tumor growth by using standard methods. Alternately, the compositions can be administered to a subject by routes including oral, nasal, ophthalmic, rectal, or topical. The most typical route of administration is intravascular, subcutaneous, or intramuscular, although other routes can be effective. In some embodiments, compositions are administered as a sustained release composition or device, such as a Medipad™ device. The composition can also be administered via the respiratory tract, for example, using a dry powder inhalation device, nebulizer, or a metered dose inhaler. The composition can also be administered by traditional syringes, needleless injection devices, "microprojectile bombardment gone guns," or other physical methods such as electroporation ("EP"), "hydrodynamic method", or ultrasound.

In some embodiments, the composition can be administered to a subject by sustained release administration, by such means as depot injections of erodible implants directly applied during surgery or by implantation of an infusion pump or a biocompatible sustained release implant into the subject. Alternately, the composition can be administered to a subject by injectable depot routes of administration, such as by using 1-, 3-, or 6-month depot injectable or biodegradable materials and methods, or by applying to the skin of the subject a transdermal patch containing the composition, and leaving the patch in contact with the subject's skin, generally for 1 to 5 hours per patch.

In some embodiments, the compositions comprise about 1 nanogram to about 10 mg of nucleic acid. In some embodiments, the compositions comprise: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg.

In some embodiments, the compositions comprise about 5 nanograms to about 10 mg of nucleic acid molecule. In some embodiments, the compositions comprise about 25 nanograms to about 5 mg of nucleic acid molecule. In some embodiments, the compositions contain about 50 nanograms to about 1 mg of nucleic acid molecule. In some embodiments, the compositions contain about 0.1 to about 500 micrograms of nucleic acid molecule. In some embodiments, the compositions contain about 1 to about 350 micrograms of nucleic acid molecule. In some embodiments, the compositions contain about 5 to about 250 micrograms of nucleic acid molecule. In some embodiments, the compositions contain about 10 to about 200 micrograms of nucleic acid molecule. In some embodiments, the compositions contain about 15 to about 150 micrograms of nucleic acid molecule. In some embodiments, the compositions contain about 20 to about 100 micrograms of nucleic acid molecule. In some embodiments, the compositions contain about 25 to about 75 micrograms of nucleic acid molecule. In some embodiments, the compositions contain about 30 to about 50 micrograms of nucleic acid molecule. In some embodiments, the compositions contain about 35 to about 40 micrograms of nucleic acid molecule. In some embodiments, the compositions contain about 100 to about 200 micrograms of nucleic acid molecule. In some embodiments, the compositions comprise about 10 to about 100 micrograms of nucleic acid molecule. In some embodiments, the compositions comprise about 20 to about 80 micrograms of nucleic acid molecule. In some embodiments, the compositions comprise about 25 to about 60 micrograms of nucleic acid molecule. In some embodiments, the compositions comprise about 30 nanograms to about 50 micrograms of nucleic acid molecule. In some embodiments, the compositions comprise about 35 nanograms to about 45 micrograms of nucleic acid molecule. In some embodiments, the compositions contain about 0.1 to about 500 micrograms of nucleic acid molecule. In some embodiments, the compositions contain about 1 to about 350 micrograms of nucleic acid molecule. In some embodiments, the compositions contain about 25 to about 250 micrograms of nucleic acid molecule. In some embodiments, the compositions contain about 100 to about 200 micrograms of nucleic acid molecule.

In some embodiments, the delivery platforms described herein can be used either in a single administration alone or in combinations as matched antigen prime-boost approaches. In addition, the use of these antigens in a single vector system, which is envisioned to be used as an antigen matched prime for a boost with any of the modalities above, including protein, viral vectors, nucleic acids, or others. For example, the same Mtb antigen construct can be used as both the prime and the boost. In other embodiments, a first Mtb antigen construct can be used as the prime and a second different Mtb antigen construct can be used as the boost (i.e., heterologous prime-boost). In some embodiments, the prime is a DNA or RNA (such as mRNA) prime and the boost is a viral vector boost. In some embodiments, the prime is a viral vector prime and the boost is a DNA or RNA (such as mRNA) boost.

The compositions can be formulated according to the mode of administration to be used. In cases where compositions are injectable pharmaceutical compositions, they are sterile, pyrogen free and particulate free. An isotonic formulation can be used. Generally, additives for isotonicity can include sodium chloride, dextrose, mannitol, sorbitol and lactose. In some cases, isotonic solutions such as phosphate buffered saline are suitable. Stabilizers include gelatin and albumin. In some embodiments, a vasoconstriction agent is added to the formulation.

The compositions can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freund's incomplete adjuvant, LPS analog including monophosphoryl lipid A, muramyl peptides, quinone analogs, vesicles such as squalene and squalane, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more suitably, the poly-L-glutamate is present in the composition at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalane, and hyaluronic acid can also be used administered in conjunction with the genetic construct. In some embodiments, the plasmid compositions can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. In some embodiments, the transfection facilitating agent is a polyanion, polycation, including poly-L-glutamate (LGS), or lipid. Concentration of the transfection agent in the composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1a, MIP-1p, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The present disclosure also provides kits comprising any of the Mtb antigens, fragments thereof, fusion proteins, nucleic acid molecules, vectors, or cells, described herein. The kit can include, for example, container(s), package(s) or dispenser(s) along with labels and instructions for administration or use.

The present disclosure also provides methods of eliciting an immune response against *Mycobacterium tuberculosis* in a mammal comprising administering to the mammal an immunologically sufficient amount of one or more fusion proteins comprising at least two or three *Mycobacterium tuberculosis* (Mtb) antigens. Any of the fusion proteins described herein can be administered. In some embodiments, the fusion protein comprises at least three Mtb antigens. In some embodiments, the fusion protein comprises at least four Mtb antigens. In some embodiments, the fusion protein comprises at least five Mtb antigens.

The present disclosure also provides methods of eliciting an immune response against *Mycobacterium tuberculosis* in a mammal comprising administering to the mammal an immunologically sufficient amount of a composition comprising at least two or three *Mycobacterium tuberculosis* (Mtb) antigens, and a pharmaceutically acceptable carrier. Any of the compositions comprising two or more Mtb antigens can be administered. In some embodiments, the composition comprises at least three Mtb antigens. In some embodiments, the composition comprises at least four Mtb antigens. In some embodiments, the composition comprises at least five Mtb antigens.

The present disclosure also provides methods of eliciting an immune response against *Mycobacterium tuberculosis* in a mammal comprising administering to the mammal an immunologically sufficient amount of a composition comprising at least two or three *Mycobacterium tuberculosis* (Mtb) antigens, and a pharmaceutically acceptable carrier; wherein the composition comprises at least one nucleic acid molecule encoding at least one of the Mtb antigens. Any of the compositions comprising a mixture of one or more Mtb antigen proteins and one of more nucleic acid molecules encoding one or more Mtb antigens described herein can be administered.

The fusion proteins and compositions described herein can be used to treat or prevent tuberculosis. In some embodiments, the method comprises administering to a human a therapeutically- or prophylactically-effective amount of any of the fusion proteins or compositions described herein such that the tuberculosis infection is diminished or prevented.

In some embodiments, the subject being treated will have been previously diagnosed as having tuberculosis. Such subjects will, thus, have been diagnosed as being in need of such treatment. Alternately, the treatment may be intended to prevent a tuberculosis infection in a subject that does not yet have tuberculosis or to a subject that is travelling to an area where tuberculosis is prevalent.

Treatment of a subject suffering from tuberculosis can be monitored using standard methods. Some methods entail determining a baseline value, for example, of an antibody level or profile in a subject, before administering a dosage of agent, and comparing this with a value for the profile or level after treatment. A significant increase such as, for example, greater than the typical margin of experimental error in repeat measurements of the same sample, expressed as one standard deviation from the mean of such measurements in value of the level or profile signals a positive treatment outcome (i.e., that administration of the agent has achieved a desired response). If the value for immune response does not change significantly, or decreases, a negative treatment outcome is indicated.

In other embodiments, a control value such as a mean and standard deviation, of level or profile is determined for a control population. Typically the individuals in the control population have not received prior treatment. Measured values of the level or profile in a subject after administering a therapeutic agent are then compared with the control value. A significant increase relative to the control value, such as greater than one standard deviation from the mean, signals a positive or sufficient treatment outcome. A lack of significant increase or a decrease signals a negative or insufficient treatment outcome. Administration of the therapeutic is generally continued while the level is increasing relative to the control value. As before, attainment of a plateau relative to control values is an indicator that the administration of treatment can be discontinued or reduced in dosage and/or frequency.

In other embodiments, a control value of the level or profile, such as a mean and standard deviation, is determined from a control population of individuals who have undergone treatment with a therapeutic agent and whose levels or profiles have plateaued in response to treatment. Measured values of levels or profiles in a subject are compared with the control value. If the measured level in a subject is not significantly different, such as by more than one standard deviation, from the control value, treatment can be discontinued. If the level in a subject is significantly below the control value, continued administration of agent is warranted. If the level in the subject persists below the control value, then a change in treatment may be indicated.

In other embodiments, a subject who is not presently receiving treatment but has undergone a previous course of treatment is monitored for antibody levels or profiles to determine whether a resumption of treatment is required. The measured level or profile in the subject can be compared with a value previously achieved in the subject after a previous course of treatment. A significant decrease relative to the previous measurement, such as greater than a typical margin of error in repeat measurements of the same sample, is an indication that treatment can be resumed. Alternately, the value measured in a subject can be compared with a control value (mean plus standard deviation) determined in a population of subjects after undergoing a course of treatment. Alternately, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level, such as more than a standard deviation, is an indicator that treatment should be resumed in a subject.

In some methods, a baseline measurement of antibody to a given antigen in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline, such as 50%, 25% or 10%, administration of a further dosage of antigen is administered. In some embodiments, peak or subsequent measured levels less background are compared with reference levels previously determined to constitute a beneficial prophylactic or therapeutic treatment regime in other subjects. If the measured antibody level is significantly less than a reference level, such as less than the mean minus one standard deviation of the reference value in population of subjects benefiting from treatment, administration of an additional dosage of antigen is indicated.

In some embodiments, the subject(s) that can be treated by the above-described methods is an animal, including mammals and non-mammals. Suitable mammals, include, but are not limited to, humans, non-human primates, rodents (including rats, mice, hamsters and guinea pigs) cow, horse, sheep, badger, opossum, goat, pig, dog and cat. In most instances, the mammal is a human. In some embodiments, the non-mammal is a fish. Immunization of animals with any one or more of the vaccines described herein can prevent zoonotic transmission (i.e., transition of a disease, such as TB, from an animal to a human).

The present disclosure also provides fusion proteins for use in the preparation of a medicament for treating or preventing a *Mycobacterium tuberculosis* infection, wherein the fusion protein comprises at least two or three *Mycobacterium tuberculosis* (Mtb) antigens.

The present disclosure also provides fusion proteins for use in treating or preventing a *Mycobacterium tuberculosis* infection, wherein the fusion protein comprises at least two or three *Mycobacterium tuberculosis* (Mtb) antigens.

The present disclosure also provides uses of a fusion protein in the preparation of a medicament for treating or preventing a *Mycobacterium tuberculosis* infection, wherein the fusion protein comprises at least two or three *Mycobacterium tuberculosis* (Mtb) antigens.

The present disclosure also provides uses of a fusion protein in treating or preventing a *Mycobacterium tuberculosis* infection, wherein the fusion protein comprises at least two or three *Mycobacterium tuberculosis* (Mtb) antigens.

The present disclosure also provides compositions for use in the preparation of a medicament for treating or preventing a *Mycobacterium tuberculosis* infection, wherein the composition comprises at least two or three *Mycobacterium tuberculosis* (Mtb) antigens, and a pharmaceutically acceptable carrier.

The present disclosure also provides compositions for use in treating or preventing a *Mycobacterium tuberculosis* infection, wherein the composition comprises at least two or three *Mycobacterium tuberculosis* (Mtb) antigens, and a pharmaceutically acceptable carrier.

The present disclosure also provides uses of a composition in the preparation of a medicament for treating or preventing a *Mycobacterium tuberculosis* infection, wherein the composition comprises at least two or three *Mycobacterium tuberculosis* (Mtb) antigens, and a pharmaceutically acceptable carrier.

The present disclosure also provides uses of a composition in treating or preventing a *Mycobacterium tuberculosis* infection, wherein the composition comprises at least two or three *Mycobacterium tuberculosis* (Mtb) antigens, and a pharmaceutically acceptable carrier.

The present disclosure also provides compositions for use in the preparation of a medicament for treating or preventing a *Mycobacterium tuberculosis* infection, wherein the composition comprises at least two or three *Mycobacterium tuberculosis* (Mtb) antigens, and a pharmaceutically acceptable carrier, wherein the composition comprises at least one nucleic acid molecule encoding at least one of the Mtb antigens.

The present disclosure also provides compositions for use in treating or preventing a *Mycobacterium tuberculosis* infection, wherein the composition comprises at least two or three *Mycobacterium tuberculosis* (Mtb) antigens, and a pharmaceutically acceptable carrier, wherein the composition comprises at least one nucleic acid molecule encoding at least one of the Mtb antigens.

The present disclosure also provides uses of a composition in the preparation of a medicament for treating or preventing a *Mycobacterium tuberculosis* infection, wherein the composition comprises at least two or three *Mycobacterium tuberculosis* (Mtb) antigens, and a pharmaceutically acceptable carrier, wherein the composition comprises at least one nucleic acid molecule encoding at least one of the Mtb antigens.

The present disclosure also provides uses of a composition in treating or preventing a *Mycobacterium tuberculosis* infection, wherein the composition comprises at least two or three *Mycobacterium tuberculosis* (Mtb) antigens, and a pharmaceutically acceptable carrier, wherein the composition comprises at least one nucleic acid molecule encoding at least one of the Mtb antigens.

The present disclosure also provides any of the fusion proteins described herein, or any of the compositions described herein, or any of the cells described herein, or any of the vectors described herein, or any of the methods described herein, or any of the uses described herein, substantially as described with reference to the accompanying examples and/or figures.

Embodiment 1

A composition or fusion protein comprising at least three *Mycobacterium tuberculosis* (Mtb) antigens, wherein the Mtb antigens are chosen from Rv1009, Rv3136, Rv3615c, Rv2628, Rv2034, and Rv3136 N-terminus.

Embodiment 2

The composition or fusion protein according to embodiment 1 wherein Rv1009 comprises the amino acid sequence set forth in SEQ ID NO:2 or SEQ ID NO:4.

Embodiment 3

The composition or fusion protein according to embodiment 1 wherein Rv1009 is encoded by a nucleotide sequence set forth in SEQ ID NO:1 or SEQ ID NO:3.

Embodiment 4

The composition or fusion protein according to embodiment 1 wherein Rv3136 comprises the amino acid sequence set forth in SEQ ID NO:8.

Embodiment 5

The composition or fusion protein according to embodiment 1 wherein Rv3136 is encoded by a nucleotide sequence set forth in SEQ ID NO:5, SEQ ID NO:6, or SEQ ID NO:7.

Embodiment 6

The composition or fusion protein according to embodiment 1 wherein Rv3615c comprises the amino acid sequence set forth in SEQ ID NO:11.

Embodiment 7

The composition or fusion protein according to embodiment 1 wherein Rv3615c is encoded by a nucleotide sequence set forth in SEQ ID NO:9 or SEQ ID NO:10.

Embodiment 8

The composition or fusion protein according to embodiment 1 wherein Rv2628 comprises the amino acid sequence set forth in SEQ ID NO:14.

Embodiment 9

The composition or fusion protein according to embodiment 1 wherein Rv2628 is encoded by a nucleotide sequence set forth in SEQ ID NO:12 or SEQ ID NO:13.

Embodiment 10

The composition or fusion protein according to embodiment 1 wherein Rv2034 comprises the amino acid sequence set forth in SEQ ID NO:16.

Embodiment 11

The composition or fusion protein according to embodiment 1 wherein Rv2034 is encoded by a nucleotide sequence set forth in SEQ ID NO:15.

Embodiment 12

The composition or fusion protein according to embodiment 1 wherein Rv3136Nt comprises the amino acid sequence set forth in SEQ ID NO:18.

Embodiment 13

The composition or fusion protein according to embodiment 1 wherein Rv3136Nt is encoded by a nucleotide sequence set forth in SEQ ID NO:17.

Embodiment 14

The composition or fusion protein according to any one of embodiments 1 to 13 comprising at least four *Mycobacterium tuberculosis* (Mtb) antigens.

Embodiment 15

The composition or fusion protein according to any one of embodiments 1 to 13 comprising at least five *Mycobacterium tuberculosis* (Mtb) antigens.

Embodiment 16

The composition or fusion protein according to embodiment 1 comprising: Rv1009, Rv3615c, and Rv3136 Mtb antigens; Rv1009, Rv2034, and Rv3136 Mtb antigens; Rv1009, Rv3615c, and Rv3136 Mtb antigens; Rv1009, Rv2628, Rv3615c, and Rv3136 Mtb antigens; Rv1009, Rv3615c, Rv2034, and Rv2628 Mtb antigens; Rv2034, Rv3615c, Rv2628, and Rv3136 Mtb antigens; Rv1009, Rv2034, Rv2628, Rv3615c, and Rv3136 Mtb antigens; Rv1009, Rv3136Nt, Rv2628, Rv2034, and Rv3615c Mtb antigens; or Rv2034, Rv3615c, Rv3136Nt, Rv2628, and Rv1009 Mtb antigens.

Embodiment 17

The composition or fusion protein according to embodiment 16 wherein: Rv1009 comprises the amino acid sequence set forth in SEQ ID NO:2 or SEQ ID NO:4; Rv3136 comprises the amino acid sequence set forth in SEQ ID NO:8; Rv3615c comprises the amino acid sequence set forth in SEQ ID NO:11; Rv2628 comprises the amino acid sequence set forth in SEQ ID NO:14; Rv2034 comprises the amino acid sequence set forth in SEQ ID NO:16; and Rv3136Nt comprises the amino acid sequence set forth in SEQ ID NO:18.

Embodiment 18

The composition or fusion protein according to embodiment 16 wherein: Rv1009 is encoded by a nucleotide sequence set forth in SEQ ID NO:1 or SEQ ID NO:3; Rv3136 is encoded by a nucleotide sequence set forth in SEQ ID NO:5, SEQ ID NO:6, or SEQ ID NO:7; Rv3615c is encoded by a nucleotide sequence set forth in SEQ ID NO:9 or SEQ ID NO:10; Rv2628 is encoded by a nucleotide sequence set forth in SEQ ID NO:12 or SEQ ID NO:13; Rv2034 is encoded by a nucleotide sequence set forth in SEQ ID NO:15; and Rv3136Nt is encoded by a nucleotide sequence set forth in SEQ ID NO:17.

Embodiment 19

The fusion protein according to embodiment 1 comprising: Rv1009-Rv3615c-Rv3136; Rv1009-Rv2034-Rv3136; Rv1009-Rv2628-Rv3615c-Rv3136; Rv1009-Rv2034-Rv2628-Rv3615c-Rv3136; Rv2034-Rv1009-Rv3136; Rv3136-Rv2034-Rv1009; Rv1009-Rv3615c-Rv2034-Rv2628; Rv3615c-Rv2034-Rv2628-Rv1009; Rv2034-Rv3615c-Rv2628-Rv3136; Rv3136-Rv2628-Rv3615c-Rv2034; Rv1009-Rv3136Nt-Rv2628-Rv2034-Rv3615c; Rv2034-Rv3615c-Rv3136Nt-Rv2628-Rv1009; Rv3615c-Rv2628-Rv1009-Rv3136Nt-Rv2034; Rv1009-Rv2628-Rv3136Nt-Rv2034-Rv3615c; Rv2628-Rv3136Nt-Rv1009-Rv2034-Rv3615c; or Rv2628-Rv3136Nt-Rv2034-Rv3615c-Rv1009.

Embodiment 20

The fusion protein according to embodiment 19 wherein: Rv1009 comprises the amino acid sequence set forth in SEQ ID NO:2 or SEQ ID NO:4; Rv3136 comprises the amino acid sequence set forth in SEQ ID NO:8; Rv3615c comprises the amino acid sequence set forth in SEQ ID NO:11; Rv2628 comprises the amino acid sequence set forth in SEQ ID NO:14; Rv2034 comprises the amino acid sequence set forth in SEQ ID NO:16; and Rv3136Nt comprises the amino acid sequence set forth in SEQ ID NO:18.

Embodiment 21

The fusion protein according to embodiment 19 wherein: Rv1009 is encoded by a nucleotide sequence set forth in SEQ ID NO:1 or SEQ ID NO:3; Rv3136 is encoded by a nucleotide sequence set forth in SEQ ID NO:5, SEQ ID NO:6, or SEQ ID NO:7; Rv3615c is encoded by a nucleotide sequence set forth in SEQ ID NO:9 or SEQ ID NO:10; Rv2628 is encoded by a nucleotide sequence set forth in SEQ ID NO:12 or SEQ ID NO:13; Rv2034 is encoded by a nucleotide sequence set forth in SEQ ID NO:15; and Rv3136Nt is encoded by a nucleotide sequence set forth in SEQ ID NO:17.

Embodiment 22

The fusion protein according to embodiment 19 wherein: Rv1009-Rv3615c-Rv3136 comprises the amino acid sequence set forth in SEQ ID NO:39; Rv1009-Rv2034-Rv3136 comprises the amino acid sequence set forth in SEQ ID NO:41; Rv1009-Rv2628-Rv3615c-Rv3136 comprises the amino acid sequence set forth in SEQ ID NO:43; Rv1009-Rv2034-Rv2628-Rv3615c-Rv3136 comprises the amino acid sequence set forth in SEQ ID NO:45; Rv2034-Rv1009-Rv3136 comprises the amino acid sequence set forth in SEQ ID NO:47; Rv3136-Rv2034-Rv1009 comprises the amino acid sequence set forth in SEQ ID NO:49; Rv1009-Rv3615c-Rv2034-Rv2628 comprises the amino acid sequence set forth in SEQ ID NO:51; Rv3615c-Rv2034-Rv2628-Rv1009 comprises the amino acid sequence set forth in SEQ ID NO:53; Rv2034-Rv3615c-Rv2628-Rv3136 comprises the amino acid sequence set forth in SEQ ID NO:55; Rv3136-Rv2628-Rv3615c-Rv2034 comprises the amino acid sequence set forth in SEQ ID NO:57; Rv1009-Rv3136Nt-Rv2628-Rv2034-Rv3615c comprises the amino acid sequence set forth in SEQ ID NO:59; Rv2034-Rv3615c-Rv3136Nt-Rv2628-Rv1009 comprises the amino acid sequence set forth in SEQ ID NO:61; Rv3615c-Rv2628-Rv1009-Rv3136Nt-Rv2034 comprises the amino acid sequence set forth in SEQ ID NO:63; Rv1009-Rv2628-Rv3136Nt-Rv2034-Rv3615c comprises the amino acid sequence set forth in SEQ ID NO:71; Rv2628-Rv3136Nt-Rv1009-Rv2034-Rv3615c comprises the amino acid sequence set forth in SEQ ID NO:73; and Rv2628-Rv3136Nt-Rv2034-Rv3615c-Rv1009 comprises the amino acid sequence set forth in SEQ ID NO:75.

Embodiment 23

The fusion protein according to embodiment 19 wherein: Rv1009-Rv3615c-Rv3136 is encoded by a nucleotide sequence set forth in SEQ ID NO:38; Rv1009-Rv2034-Rv3136 is encoded by a nucleotide sequence set forth in SEQ ID NO:40; Rv1009-Rv2628-Rv3615c-Rv3136 is encoded by a nucleotide sequence set forth in SEQ ID NO:42; Rv1009-Rv2034-Rv2628-Rv3615c-Rv3136 is encoded by a nucleotide sequence set forth in SEQ ID NO:44; Rv2034-Rv1009-Rv3136 is encoded by a nucleotide sequence set forth in SEQ ID NO:46; Rv3136-Rv2034-Rv1009 is encoded by a nucleotide sequence set forth in SEQ ID NO:48; Rv1009-Rv3615c-Rv2034-Rv2628 is encoded by a nucleotide sequence set forth in SEQ ID NO:50; Rv3615c-Rv2034-Rv2628-Rv1009 is encoded by a nucleotide sequence set forth in SEQ ID NO:52; Rv2034-Rv3615c-Rv2628-Rv3136 is encoded by a nucleotide sequence set forth in SEQ ID NO:54; Rv3136-Rv2628-Rv3615c-Rv2034 is encoded by a nucleotide sequence set forth in SEQ ID NO:56; Rv1009-Rv3136Nt-Rv2628-Rv2034-Rv3615c is encoded by a nucleotide sequence set forth in SEQ ID NO:58; Rv2034-Rv3615c-Rv3136Nt-Rv2628-Rv1009 is encoded by a nucleotide sequence set forth in SEQ ID NO:60; Rv3615c-Rv2628-Rv1009-Rv3136Nt-Rv2034 is encoded by a nucleotide sequence set forth in SEQ ID NO:62; Rv1009-Rv2628-Rv3136Nt-Rv2034-Rv3615c is encoded by a nucleotide sequence set forth in SEQ ID NO:70; Rv2628-Rv3136Nt-Rv1009-Rv2034-Rv3615c is encoded by a nucleotide sequence set forth in SEQ ID NO:72; and Rv2628-Rv3136Nt-Rv2034-Rv3615c-Rv1009 is encoded by a nucleotide sequence set forth in SEQ ID NO:74.

Embodiment 24

A composition or fusion protein comprising at least two *Mycobacterium tuberculosis* (Mtb) antigens, wherein the Mtb antigens are Rv1733 and Rv2626c.

Embodiment 25

The composition or fusion protein according to embodiment 24 wherein Rv1733 comprises the amino acid sequence set forth in SEQ ID NO:29.

Embodiment 26

The composition or fusion protein according to embodiment 24 wherein Rv1733 is encoded by a nucleotide sequence set forth in SEQ ID NO:28.

Embodiment 27

The composition or fusion protein according to embodiment 24 wherein Rv2626c comprises the amino acid sequence set forth in SEQ ID NO:31.

Embodiment 28

The composition or fusion protein according to embodiment 24 wherein Rv2626c is encoded by a nucleotide sequence set forth in SEQ ID NO:30.

Embodiment 29

The fusion protein according to embodiment 24 comprising Rv1733-Rv2626c.

Embodiment 30

The fusion protein according to embodiment 29 wherein: Rv1733 comprises the amino acid sequence set forth in SEQ ID NO:29; and Rv2626c comprises the amino acid sequence set forth in SEQ ID NO:31.

Embodiment 31

The fusion protein according to embodiment 29 wherein: Rv1733 is encoded by a nucleotide sequence set forth in SEQ ID NO:28; and Rv2626c is encoded by a nucleotide sequence set forth in SEQ ID NO:30.

Embodiment 32

The fusion protein according to embodiment 29 wherein Rv1733-Rv2626c comprises the amino acid sequence set forth in SEQ ID NO:67

Embodiment 33

The fusion protein according to embodiment 29 wherein Rv1733-Rv2626c is encoded by a nucleotide sequence set forth in SEQ ID NO:66.

Embodiment 34

A composition or fusion protein comprising at least three *Mycobacterium tuberculosis* (Mtb) antigens, wherein the Mtb antigens are chosen from Ag85A, Ag85B, Rv3407, RpfA, RpfC, and Rpm.

Embodiment 35

The composition or fusion protein according to embodiment 34 wherein Ag85A comprises the amino acid sequence set forth in SEQ ID NO:20.

Embodiment 36

The composition or fusion protein according to embodiment 34 wherein Ag85A is encoded by a nucleotide sequence set forth in SEQ ID NO:19.

Embodiment 37

The composition or fusion protein according to embodiment 34 wherein Ag85B comprises the amino acid sequence set forth in SEQ ID NO:24 or SEQ ID NO:25.

Embodiment 38

The composition or fusion protein according to embodiment 34 wherein Ag85B is encoded by a nucleotide sequence set forth in SEQ ID NO:21, SEQ ID NO:22, or SEQ ID NO:23.

Embodiment 39

The composition or fusion protein according to embodiment 34 wherein Rv3407 comprises the amino acid sequence set forth in SEQ ID NO:27.

Embodiment 40

The composition or fusion protein according to embodiment 34 wherein Rv3407 is encoded by a nucleotide sequence set forth in SEQ ID NO:26.

Embodiment 41

The composition or fusion protein according to embodiment 34 wherein RpfA comprises the amino acid sequence set forth in SEQ ID NO:33.

Embodiment 42

The composition or fusion protein according to embodiment 34 wherein RpfA is encoded by a nucleotide sequence set forth in SEQ ID NO:32.

Embodiment 43

The composition or fusion protein according to embodiment 34 wherein RpfC comprises the amino acid sequence set forth in SEQ ID NO:35.

Embodiment 44

The composition or fusion protein according to embodiment 34 wherein RpfC is encoded by a nucleotide sequence set forth in SEQ ID NO:34.

Embodiment 45

The composition or fusion protein according to embodiment 34 wherein Rpm comprises the amino acid sequence set forth in SEQ ID NO:37.

Embodiment 46

The composition or fusion protein according to embodiment 34 wherein Rpm is encoded by a nucleotide sequence set forth in SEQ ID NO:36.

Embodiment 47

The composition or fusion protein according to embodiment 34 comprising: Ag85A, Ag85B, and Rv3407 Mtb antigens; or RpfA, RpfC, and Rpm Mtb antigens.

Embodiment 48

The composition or fusion protein according to embodiment 47 wherein: Ag85A comprises the amino acid sequence set forth in SEQ ID NO:20; Ag85B comprises the amino acid sequence set forth in SEQ ID NO:24 or SEQ ID NO:25; Rv3407 comprises the amino acid sequence set forth in SEQ ID NO:27; RpfA comprises the amino acid sequence set forth in SEQ ID NO:33; RpfC comprises the amino acid sequence set forth in SEQ ID NO:35; and Rpm comprises the amino acid sequence set forth in SEQ ID NO:37.

Embodiment 49

The composition or fusion protein according to embodiment 47 wherein: Ag85A is encoded by a nucleotide sequence set forth in SEQ ID NO:19; Ag85B is encoded by a nucleotide sequence set forth in SEQ ID NO:21, SEQ ID NO:22, or SEQ ID NO:23; Rv3407 is encoded by a nucleotide sequence set forth in SEQ ID NO:26; RpfA is encoded by a nucleotide sequence set forth in SEQ ID NO:32; RpfC is encoded by a nucleotide sequence set forth in SEQ ID NO:34; and RpfD is encoded by a nucleotide sequence set forth in SEQ ID NO:36.

Embodiment 50

The fusion protein according to embodiment 34 comprising: Ag85A-Ag85B-Rv3407; or RpfA-RpfC-RpfD.

Embodiment 51

The fusion protein according to embodiment 50 wherein: Ag85A comprises the amino acid sequence set forth in SEQ ID NO:20; Ag85B comprises the amino acid sequence set forth in SEQ ID NO:24 or SEQ ID NO:25; Rv3407 comprises the amino acid sequence set forth in SEQ ID NO:27; RpfA comprises the amino acid sequence set forth in SEQ ID NO:33; RpfC comprises the amino acid sequence set forth in SEQ ID NO:35; and RpfD comprises the amino acid sequence set forth in SEQ ID NO:37.

Embodiment 52

The fusion protein according to embodiment 50 wherein: Ag85A is encoded by a nucleotide sequence set forth in SEQ ID NO:19; Ag85B is encoded by a nucleotide sequence set forth in SEQ ID NO:21, SEQ ID NO:22, or SEQ ID NO:23; Rv3407 is encoded by a nucleotide sequence set forth in SEQ ID NO:26; RpfA is encoded by a nucleotide sequence set forth in SEQ ID NO:32; RpfC is encoded by a nucleotide sequence set forth in SEQ ID NO:34; and RpfD is encoded by a nucleotide sequence set forth in SEQ ID NO:36.

Embodiment 53

The fusion protein according to embodiment 50 wherein: Ag85A-Ag85B-Rv3407 comprises the amino acid sequence set forth in SEQ ID NO:65; and RpfA-RpfC-RpfD comprises the amino acid sequence set forth in SEQ ID NO:69.

Embodiment 54

The fusion protein according to embodiment 50 wherein: Ag85A-Ag85B-Rv3407 is encoded by a nucleotide sequence set forth in SEQ ID NO:64; RpfA-RpfC-RpfD is encoded by a nucleotide sequence set forth in SEQ ID NO:68.

Embodiment 55

A pharmaceutical composition comprising the composition or fusion protein according to any one of embodiments 1 to 54 and a pharmaceutically acceptable carrier.

Embodiment 56

A vector encoding the fusion protein according to any one of embodiments 1 to 54.

Embodiment 57

The vector according to embodiment 56 which is a viral vector.

Embodiment 58

The vector according to embodiment 57 wherein the viral vector is chosen from an adenovirus vector, an adeno-associated virus vector, a poxvirus vector, a paramyxovirus vector, a fowlpox virus vector, an attenuated yellow fever vector, an alphavirus vector, a retrovirus vector, a Sendai virus vector, and a CMV vector.

Embodiment 59

The vector according to embodiment 58 wherein the adenovirus vector is adenovirus 4, adenovirus 5, chimpanzee adenovirus 3, chimpanzee adenovirus 63, or chimpanzee adenovirus 68.

Embodiment 60

The vector according to embodiment 58 wherein the poxvirus vector is vaccinia virus vector.

Embodiment 61

The vector according to embodiment 60 wherein the vaccinia virus vector is a modified vaccinia Ankara (MVA).

Embodiment 62

The vector according to embodiment 58 wherein the retrovirus vector is a lentivirus vector.

Embodiment 63

The vector according to embodiment 58 wherein the CMV vector is a RhCMV vector or a HCMV vector.

Embodiment 64

The vector according to embodiment 58 wherein the paramyxovirus vector is PIV2 or rHPIV2.

Embodiment 65

The vector according to embodiment 56 which is a non-viral vector.

Embodiment 66

The vector according to embodiment 65 wherein the non-viral vector is mRNA.

Embodiment 67

A cell comprising the vector according to any one of embodiments 56 to 66.

Embodiment 68

The cell according to embodiment 67 which is a recombinant BCG.

Embodiment 69

A method of eliciting an immune response against *Mycobacterium tuberculosis* in a mammal comprising administering to the mammal an immunologically sufficient amount of the composition or fusion protein according to any one of embodiments 1 to 54.

Embodiment 70

A method of eliciting an immune response against *Mycobacterium tuberculosis* in a mammal comprising administering to the mammal an immunologically sufficient amount of the composition according to embodiment 55.

Embodiment 71

A method of eliciting an immune response against *Mycobacterium tuberculosis* in a mammal comprising administering to the mammal an immunologically sufficient amount of the vector according to any one of embodiments 56 to 66.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: Cloning, Overexpression and Purification of Fusion Proteins

Preparation of the Antigen Cassette and its Variants as Fusion Proteins

Cloning:

To clone Rv1009-Rv3615c-Rv3136, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv1009-Rv2034-Rv3136, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv1009-Rv2628-Rv3615c-Rv3136, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv1009-Rv2034-Rv2628-Rv3615c-Rv3136, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv2034-Rv1009-Rv3136, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv3136-Rv2034-Rv1009, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv1009-Rv3615c-Rv2034-Rv2628, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv3615c-Rv2034-Rv2628-Rv1009, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv2034-Rv3615c-Rv2628-Rv3136, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct.

To clone Rv3136-Rv2628-Rv3615c-Rv2034, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv1009-Rv3136Nt-Rv2628-Rv2034-Rv3615c, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv1009-Rv3136Nt-Rv2628-Rv2034-Rv3615c, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv2034-Rv3615c-Rv3136Nt-Rv2628-Rv1009, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv3615c-Rv2628-Rv1009-Rv3136Nt-Rv2034, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv1009-Rv2628-Rv3136Nt-Rv2034-Rv3615c, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv2628-Rv3136N-Rv1009-Rv2034-Rv3615c, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct. The DNA and amino acid sequences of fusions show Rv1009 minus its N-terminal signal sequence.

To clone Rv2628-Rv3136Nt-Rv2034-Rv3615c-Rv1009, the genes encoding the protein antigens were PCR amplified from Mtb H37Rv using primers that added restriction sites. Rv1009 was amplified without the N-terminal signal sequence. The amplified genes were cloned into the pET28b vector (Novagen) via the indicated restriction enzyme sites, creating N-terminal 6×His-tagged fusion proteins. The genes were cloned with no spacer sequences, only the restriction enzyme sites between each gene. The pET28b constructs were cloned in *E. coli* cloning strains, screened by restriction digest and sequenced to verify each construct.

The DNA and amino acid sequences of fusions show Rv1009 minus its N-terminal signal sequence.

Expression:

The plasmids encoding the fusion proteins were transformed into *E. coli* BL21 (Novagen) and T7 Express (New England Biolabs). Multiple colonies of each fusion construct were picked and grown overnight shaking at 37° C. in Tryptic Soy Broth (TSB) (Sigma). Overnight cultures were diluted 1:100 in TSB and grown shaking at 37° C. to OD600=0.6. Cultures were induced with 1 mM IPTG and grown shaking at 37° C. for 3 hours. Induced and uninduced aliquots of each culture were run on 4-12% Bis/Tris SDS-PAGE gels to verify induction of the fusion proteins. Colonies expressing each of the fusion proteins were frozen in TSB+20% glycerol at −80° C. as research stocks.

Purification of Fusion Proteins:

Ten ml cultures were inoculated from glycerol stocks of the fusion constructs and grown overnight shaking at 37° C. The overnight cultures were diluted 1:100 in 250 ml TSB and grown shaking at 37° C. to OD600=0.6. Cultures were induced with 1 mM IPTG and grown shaking at 37° C. for 3 hours. An aliquot of the induced sample was run on a 4-12% Bis/Tris SDS-PAGE gel to confirm induction of the protein. The induced culture was centrifuged at 6,000×g for 10 m and pellets were frozen at −80° C. Pellets were thawed and resuspended in 10 ml BPER buffer (Thermo Scientific), and an aliquot was taken for testing (lysate). Lysozyme (20 U/ml) and DNase I (25 U/ml) were added to help complete cell lysis. The lysed cells were centrifuged at 12,000×g for 10 minutes and the supernatant was collected (soluble fraction). The insoluble pellet was resuspended in 10 ml BPER buffer and a 100 μl aliquot was removed (insoluble fraction). The cells in the resuspended pellet were diluted with 10 ml 10% BPER buffer and the suspension was centrifuged at 12,000×g for 10 minutes. The supernatant was discarded and the pellet was washed again with 10 ml 10% BPER buffer 3 more times. The lysate, soluble and insoluble fractions and washes were run on a 4-12% Bis/Tris SDS-PAGE gel to confirm expression and determine the subcellular localization of the protein. The fusion proteins were found localized to the insoluble pellet in inclusion bodies. The insoluble pellet was resuspended in 10 ml denaturing binding buffer (DBB) (8 M urea, 92 mM $Na_2HPO_4$, 7 mM $NaH_2PO_4$, 10 mM Tris) pH 7.8. The inclusion bodies were lysed by sonication, and the lysate was cleared of debris by centrifugation at 12,000×g for 20 minutes.

Proteins were purified by column purification. Five (5) ml of HisPur Cobalt resin (Thermo Scientific) was equilibrated with DBB and incubated with 5 ml of cleared lysate. The mixture was rocked at room temperature for 90 minutes. The lysate/resin mixture was then loaded on a 30 ml column and washed with 25 volumes of denaturing wash buffer (8 M urea, 25 mM $Na_2HPO_4$, 75 mM $NaH_2PO_4$, 10 mM Tris, 12 mM sodium deoxycholate, pH 7.8). His-tagged protein was eluted from the Co+ column by eluting with elution buffer (8 M urea, 10 mM Tris, 5% glycerol) pH 8.0 with 50, 100, 350, 500, and 1000 mM imidazole. Eluted proteins were run on a 4-12% Bis/Tris SDS-PAGE gel and clean fractions were dialyzed stepwise from 8M urea, 10 mM Tris, 5% glycerol to 10 mM Tris, 5% glycerol. Dialyzed protein was analyzed by SDS-PAGE for purity, western blot for the presence of each antigen, and was assayed for the presence of residual endotoxin. Pure samples with <0.25 U endotoxin/ml were aliquoted and frozen at −80° C.

Example 2: Mouse Immunogenicity and Efficacy

The immunogenicity and efficacy of an antigen-matched recombinant BCG (422M, which overexpresses Ag85B, Ag85A, and Rv3407) with a recombinant protein vaccine (rBARv; comprised of Ag85B, Ag85A, and Rv3407) combined with the adjuvant PIKA was examined. At Week 0, mice were immunized in the scruff of the neck with approximately $2\times10^6$ CFU of BCG or 422M. At Weeks 6 and 8, mice received booster immunizations of 1 μg of rBARv with 100 μg of PIKA adjuvant in PBS, also administered subcutaneously in the scruff of the neck.

Immunogenicity: Two weeks following the final vaccination, a subset of mice were sacrificed and splenocytes were harvested for use in an ELISpot assay. As shown in FIG. 1, vaccination with both rBARv and 422M induced moderate immune responses against both Ag85B and Ag85A. In addition, a combination of 422M and BARv induced a potent immune response.

Figure 2:
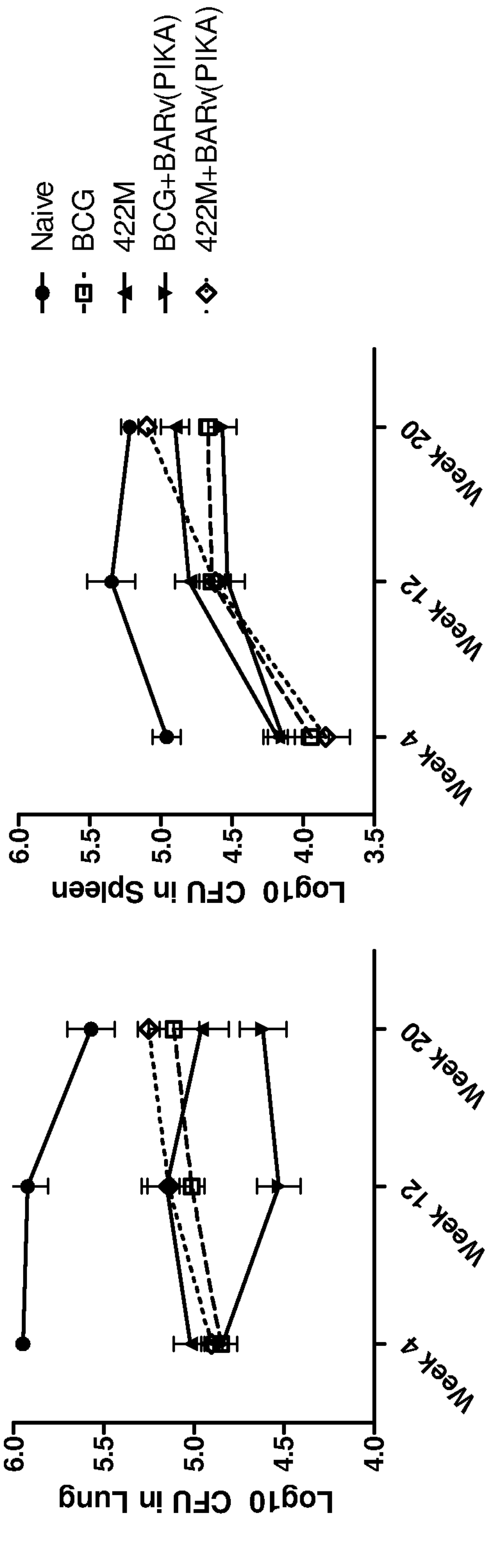
FIG. 2 shows mouse efficacy data for a recombinant protein form of the Ag85B, Ag85A, Rv3407 construct and a recombinant BCG encoding the same.

Efficacy: Four weeks after the final immunization, a subset of mice (15) from the naïve, BCG, 422M, BCG+BARv and 422M+BARv groups were challenged with 50 to 100 CFU of Mtb HN878. At Weeks 4, 12, and 20 post-challenge, five mice per group were sacrificed and the bacterial burden was evaluated in both lungs and spleen (see, FIG. 2). At each time point, vaccinated mice showed a significant degree of protection compared to naïve mice. However, the only group that demonstrated a significant increase in protection relative to BCG was the BCG+BARv group at week 12.

Example 3: Mouse Immunogenicity

Figure 3:
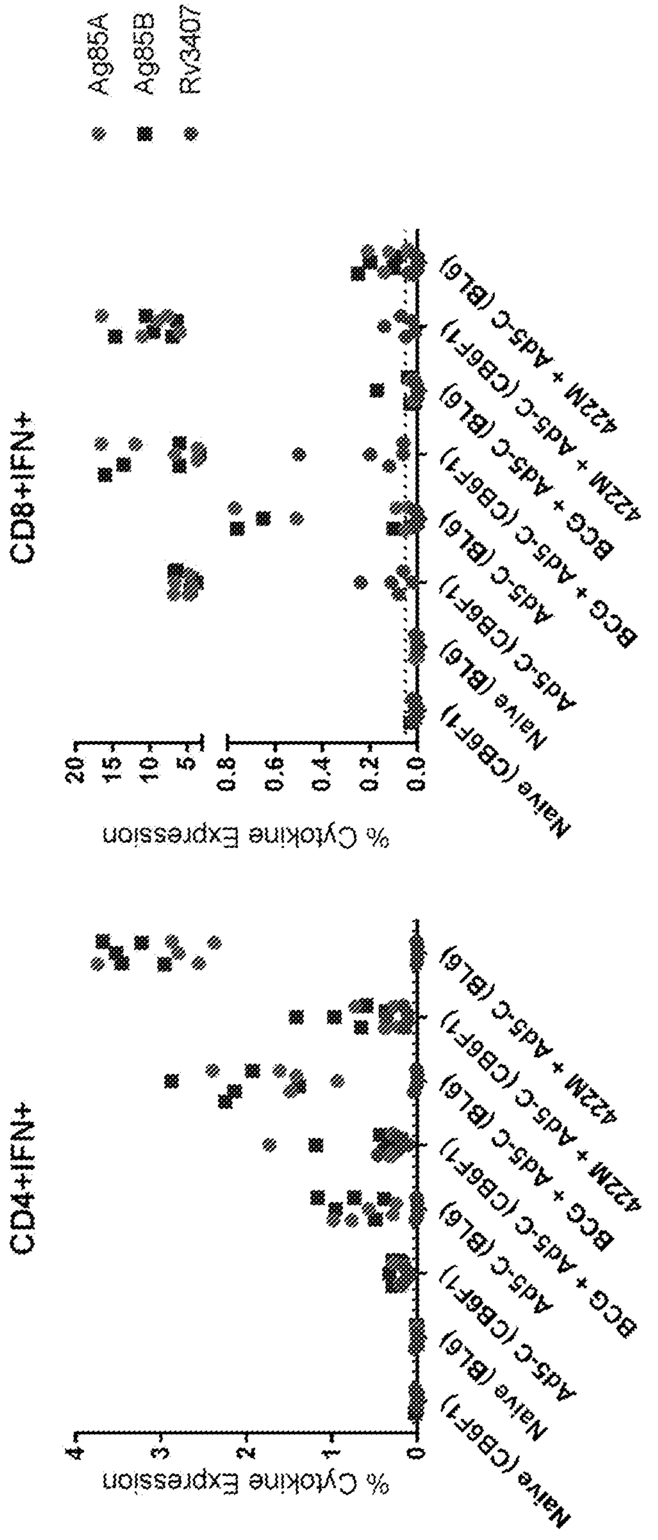
FIG. 3 shows mouse immunogenicity data for an Ad5 encoding the Ag85B, Ag85A, Rv3407 antigens and a with a recombinant BCG.

The immunogenicity of an antigen-matched recombinant BCG (422M; which overexpresses Ag85B, Ag85A, and Rv3407) with a recombinant adenovirus serotype 5 (Ad5-C; encoding Ag85B, Ag85A, and Rv3407) was examined. This study was performed in two strains of mice commonly used in TB research (C57BL/6 mice (BL6) and CB6F1 mice). At Week 0, mice were immunized in the scruff of the neck with approximately $2\times10^6$ CFU of BCG or 422M. At week 6, mice were vaccinated with $1\times10^9$ viral particles of Ad5-C. At week 8, mice were sacrificed and the splenocytes were harvested for use in an intracellular cytokine staining assay. As shown above in FIG. 3, immunization with Ad5-C induced potent T cell responses that can be significantly enhanced with a BCG or rBCG prime. Similar immunogenicity data has been observed for PanAd, Ad4, and ChAd63 (data not shown).

Example 4: Mouse Immunogenicity

Figure 4:
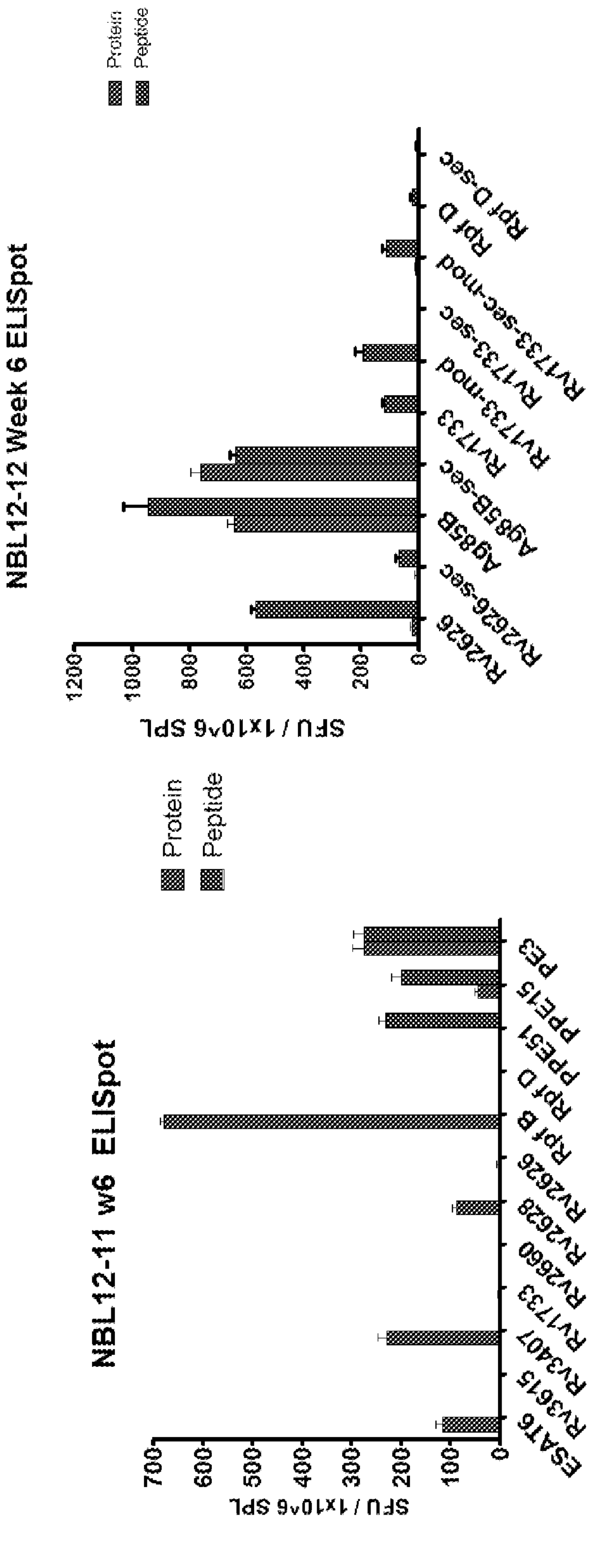
FIG. 4 shows mouse immunogenicity data for several Mtb antigens generated using DNA vaccine constructs.

The immunogenicity of several Mtb antigens delivered as plasmid DNA (pVAX backbone) were examined in two studies two studies (NBL12-11 and NBL12-12). NBL12-12 included modifications of certain antigens, including addition of a secretory leader sequence (sec) or removal of a transmembrane domain (mod). Mice were immunized with individual antigens at weeks 0, 2, and 4. At week 6, mice were sacrificed and the splenocytes were harvested for use in ELISpot assays. In some instances a) where peptide was not available, protein was used for stimulation, and b) if both were available, both were used. The strongest responders included Ag85B, PPE51, and Rv2626 (see, FIG. 4). Modest responses were also detected against ESAT6, Rv3407, Rv2628, PPE15, and PE3 (see, FIG. 4).

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A composition comprising an adjuvant, *Mycobacterium tuberculosis* (Mtb) antigen Rv2034, and at least two Mtb antigens chosen from Rv1009, Rv3136, Rv3615c, Rv2628, and Rv3136 N-terminus wherein the composition does not comprise a fusion protein.

2. The composition according to claim 1 wherein:

Rv1009 comprises the amino acid sequence set forth in SEQ ID NO:2 or SEQ ID NO:4;

Rv3136 comprises the amino acid sequence set forth in SEQ ID NO:8;

Rv3615c comprises the amino acid sequence set forth in SEQ ID NO:11;

Rv2628 comprises the amino acid sequence set forth in SEQ ID NO:14;

Rv2034 comprises the amino acid sequence set forth in SEQ ID NO:16; or

Rv3136 N-terminus comprises the amino acid sequence set forth in SEQ ID NO:18.

3. The composition according to claim 1 wherein:

Rv1009 is encoded by a nucleotide sequence set forth in SEQ ID NO:1 or SEQ ID NO:3;

Rv3136 is encoded by a nucleotide sequence set forth in SEQ ID NO:5, SEQ ID NO:6, or SEQ ID NO:7;

Rv3615c is encoded by a nucleotide sequence set forth in SEQ ID NO:9 or SEQ ID NO:10;

Rv2628 is encoded by a nucleotide sequence set forth in SEQ ID NO:12 or SEQ ID NO:13;

Rv2034 is encoded by a nucleotide sequence set forth in SEQ ID NO:15; or

Rv3136 N-terminus is encoded by a nucleotide sequence set forth in SEQ ID NO:17.

4. The composition according to claim 1 comprising at least four or five *Mycobacterium tuberculosis* (Mtb) antigens.

5. The composition according to claim 1, wherein the at least two Mtb antigens comprise:

Rv1009, Rv3615c, and Rv3136 Mtb antigens;

Rv1009, and Rv3136 Mtb antigens;

Rv1009, Rv2628, Rv3615c, and Rv3136 Mtb antigens;

Rv1009, Rv3615c, and Rv2628 Mtb antigens;

Rv3615c, Rv2628, and Rv3136 Mtb antigens;

Rv1009, Rv2628, Rv3615c, and Rv3136 Mtb antigens;

Rv2034, Rv3615c, Rv3136 N-terminus, Rv2628, and Rv1009 Mtb antigens.

6. The composition according to claim 5 wherein:

Rv1009 comprises the amino acid sequence set forth in SEQ ID NO:2 or SEQ ID NO:4;

Rv3136 comprises the amino acid sequence set forth in SEQ ID NO:8;

Rv3615c comprises the amino acid sequence set forth in SEQ ID NO:11;

Rv2628 comprises the amino acid sequence set forth in SEQ ID NO:14;

Rv2034 comprises the amino acid sequence set forth in SEQ ID NO:16; and

Rv3136 N-terminus comprises the amino acid sequence set forth in SEQ ID NO:18.

7. The composition according to claim 5 wherein:

Rv1009 is encoded by a nucleotide sequence set forth in SEQ ID NO:1 or SEQ ID NO:3;

Rv3136 is encoded by a nucleotide sequence set forth in SEQ ID NO:5, SEQ ID NO:6, or SEQ ID NO:7;

Rv3615c is encoded by a nucleotide sequence set forth in SEQ ID NO:9 or SEQ ID NO:10;

Rv2628 is encoded by a nucleotide sequence set forth in SEQ ID NO:12 or SEQ ID NO:13;

Rv2034 is encoded by a nucleotide sequence set forth in SEQ ID NO:15; and

Rv3136 N-terminus is encoded by a nucleotide sequence set forth in SEQ ID NO:17.

8. A pharmaceutical composition comprising the composition according to claim 1 and a pharmaceutically acceptable carrier.

9. A method of eliciting an immune response against *Mycobacterium tuberculosis* in a mammal comprising administering to the mammal an immunologically sufficient amount of the composition according to claim 1.

10. The method of claim 9 wherein the composition is administered to the mammal in the form of an aerosol.

11. The composition according to claim 1, wherein the composition is emulsified or encapsulated in polylactide, polyglycolide, or copolymer.

12. The composition according to claim 1, wherein the adjuvant is selected from the group consisting of α-interferon, β-interferon, γ-interferon, platelet derived growth factor, TNFα, TNFβ, GM-CSF, epidermal growth factor, cutaneous T-cell attracting chemokine, epithelial thymus-expressed chemokine, mucosae-associate epithelial chemokine, IL-1, IL-2, IL-4, IL-5, IL-6, IL-10, IL-12, IL-15, IL-18, IL-28, MHC, CD80 and CD86.

13. The composition according to claim 1, wherein the adjuvant is PIKA.

* * * * *